(12) United States Patent
Bishop et al.

(10) Patent No.: US 10,130,463 B2
(45) Date of Patent: Nov. 20, 2018

(54) TRANSLUMENALLY IMPLANTABLE HEART VALVE WITH FORMED IN PLACE SUPPORT

(71) Applicant: DIRECT FLOW MEDICAL, INC., Santa Rosa, CA (US)

(72) Inventors: Gordon B. Bishop, Santa Rosa, CA (US); Do Uong, Santa Rosa, CA (US); Randall T. Lashinski, Santa Rosa, CA (US)

(73) Assignee: DFM, LLC, Incline Village, NV (US)

( * ) Notice: Subject to any disclaimer, the term of this patent is extended or adjusted under 35 U.S.C. 154(b) by 0 days.

(21) Appl. No.: 15/061,743

(22) Filed: Mar. 4, 2016

(65) Prior Publication Data

US 2016/0317291 A1   Nov. 3, 2016

Related U.S. Application Data

(63) Continuation of application No. 12/976,671, filed on Dec. 22, 2010, now Pat. No. 9,308,360, which is a
(Continued)

(51) Int. Cl.
*A61F 2/24* (2006.01)
*A61M 29/02* (2006.01)
(Continued)

(52) U.S. Cl.
CPC .......... *A61F 2/2409* (2013.01); *A61F 2/2418* (2013.01); *A61F 2/2427* (2013.01); *A61M 29/02* (2013.01); *A61F 2002/485* (2013.01); *A61F 2220/005* (2013.01); *A61F 2220/0008* (2013.01); *A61F 2220/0016* (2013.01); *A61F 2220/0058* (2013.01);
(Continued)

(58) Field of Classification Search
CPC ..................................... A61F 2/82; A61F 2/24
See application file for complete search history.

(56) References Cited

U.S. PATENT DOCUMENTS 3,416,562 A    12/1968  Freeman et al.
3,657,744 A     4/1972  Ersek
(Continued)

FOREIGN PATENT DOCUMENTS

CA    2609201    12/2006
DE    2700531     4/1985
(Continued)

OTHER PUBLICATIONS

U.S. Appl. No. 09/496,231, filed Feb. 1, 2000, Hubbell.
(Continued)

*Primary Examiner* — Matthew Schall
(74) *Attorney, Agent, or Firm* — Knobbe, Martens, Olson & Bear LLP

(57) ABSTRACT

A cardiovascular prosthetic valve, the valve comprising an inflatable cuff comprising at least one inflatable channel that forms, at least in part, an inflatable structure, and a valve coupled to the inflatable cuff, the valve configured to permit flow in a first axial direction and to inhibit flow in a second axial direction opposite to the first axial direction, the valve comprising a plurality of tissue supports that extend generally in the axial direction and that are flexible and/or movable throughout a range in a radial direction.

4 Claims, 105 Drawing Sheets

Related U.S. Application Data continuation of application No. 12/197,172, filed on Aug. 22, 2008, now abandoned.

(60) Provisional application No. 60/957,691, filed on Aug. 23, 2007.

(51) Int. Cl.
    *A61M 25/00*     (2006.01)
    *A61M 25/09*     (2006.01)
    *A61F 2/48*      (2006.01)

(52) U.S. Cl.
    CPC .............. *A61F 2220/0066* (2013.01); *A61F 2220/0075* (2013.01); *A61F 2230/008* (2013.01); *A61F 2230/0078* (2013.01); *A61F 2250/0003* (2013.01); *A61F 2250/0059* (2013.01); *A61M 2025/0081* (2013.01); *A61M 2025/0096* (2013.01); *A61M 2025/09008* (2013.01); *A61M 2025/09175* (2013.01)

(56) References Cited

U.S. PATENT DOCUMENTS

| | | |
|---|---|---|
| 3,671,979 A | 6/1972 | Moulopoulos |
| 3,714,671 A | 2/1973 | Edwards et al. |
| 4,035,849 A | 7/1977 | Angell et al. |
| 4,056,854 A | 11/1977 | Boretos et al. |
| 4,106,129 A | 8/1978 | Carpentier et al. |
| 4,183,102 A | 1/1980 | Guiset |
| 4,192,020 A | 3/1980 | Davis et al. |
| 4,213,207 A | 7/1980 | Wilson |
| 4,221,548 A | 9/1980 | Child |
| 4,316,503 A | 2/1982 | Kurachi et al. |
| 4,339,831 A | 7/1982 | Johnson |
| 4,592,340 A | 6/1986 | Boyles |
| 4,612,011 A | 9/1986 | Kautzky |
| 4,652,263 A | 3/1987 | Herweck et al. |
| 4,662,885 A | 5/1987 | DiPisa, Jr. |
| 4,727,873 A | 3/1988 | Mobin-Uddin |
| 4,750,488 A | 6/1988 | Wuchinich et al. |
| 4,750,901 A | 6/1988 | Molteno |
| 4,781,682 A | 11/1988 | Patel |
| 4,787,899 A | 11/1988 | Lazarus |
| 4,817,600 A | 4/1989 | Herms et al. |
| 4,819,751 A | 4/1989 | Shimada et al. |
| 4,827,911 A | 5/1989 | Broadwin et al. |
| 4,872,874 A | 10/1989 | Taheri |
| 4,892,541 A | 1/1990 | Alonso |
| 4,922,902 A | 5/1990 | Wuchinich et al. |
| 4,931,047 A | 6/1990 | Broadwin et al. |
| 4,955,856 A | 9/1990 | Phillips |
| 4,960,424 A | 10/1990 | Grooters |
| 4,994,077 A | 2/1991 | Dobben |
| 5,015,227 A | 5/1991 | Broadwin et al. |
| 5,026,383 A | 6/1991 | Nobles |
| 5,032,128 A | 7/1991 | Alonso |
| 5,119,148 A | 6/1992 | Anderson et al. |
| 5,149,150 A | 9/1992 | Davis |
| 5,151,105 A | 9/1992 | Kwan-Gett |
| 5,163,897 A | 11/1992 | Persky |
| 5,163,953 A | 11/1992 | Vince |
| 5,167,628 A | 12/1992 | Boyles |
| 5,207,695 A | 5/1993 | Trout, III |
| 5,269,784 A | 12/1993 | Mast |
| 5,330,528 A | 7/1994 | Lazim |
| 5,332,402 A | 7/1994 | Teitelbaum |
| 5,360,444 A | 11/1994 | Kusuhara |
| 5,370,685 A | 12/1994 | Stevens |
| 5,370,691 A | 12/1994 | Samson |
| 5,397,351 A | 3/1995 | Pavcnik et al. |
| 5,411,552 A | 5/1995 | Andersen et al. |
| 5,423,851 A | 6/1995 | Samuels |
| 5,441,515 A | 8/1995 | Khosravi et al. |
| 5,443,499 A | 8/1995 | Schmitt |
| 5,449,385 A | 9/1995 | Religa et al. |
| 5,500,014 A | 3/1996 | Quijano et al. |
| 5,506,193 A | 4/1996 | Cederbaum et al. |
| 5,534,024 A | 7/1996 | Rogers et al. |
| 5,554,180 A | 9/1996 | Turk |
| 5,554,185 A | 9/1996 | Block et al. |
| 5,578,034 A | 11/1996 | Estes |
| 5,616,149 A | 4/1997 | Barath |
| 5,618,299 A | 4/1997 | Khosravi et al. |
| 5,649,978 A | 7/1997 | Samson |
| 5,690,570 A | 11/1997 | Chang et al. |
| 5,697,968 A | 12/1997 | Rogers et al. |
| 5,817,102 A | 10/1998 | Johnson et al. |
| 5,824,052 A | 10/1998 | Khosravi et al. |
| 5,824,053 A | 10/1998 | Khosravi et al. |
| 5,840,081 A | 11/1998 | Andersen et al. |
| 5,848,964 A | 12/1998 | Samuels |
| 5,855,601 A | 1/1999 | Bessler et al. |
| 5,871,537 A | 2/1999 | Holman et al. |
| 5,957,949 A | 9/1999 | Leonhardt et al. |
| 5,980,570 A | 11/1999 | Simpson |
| 6,007,575 A | 12/1999 | Samuels et al. |
| 6,027,525 A | 2/2000 | Suh et al. |
| 6,090,139 A | 7/2000 | Lemelson |
| 6,090,140 A | 7/2000 | Gabbay |
| 6,102,944 A | 8/2000 | Huynh et al. |
| 6,110,201 A | 8/2000 | Quijano et al. |
| 6,117,106 A | 9/2000 | Wasicek et al. |
| 6,126,007 A | 10/2000 | Kari et al. |
| 6,156,062 A | 12/2000 | McGuinness |
| 6,162,245 A | 12/2000 | Jayaraman |
| 6,165,215 A | 12/2000 | Rottenberg et al. |
| 6,168,614 B1 | 1/2001 | Andersen et al. |
| 6,196,996 B1 | 3/2001 | Teirstein |
| 6,221,096 B1 | 4/2001 | Aiba et al. |
| 6,280,412 B1 | 8/2001 | Pedersen et al. |
| 6,299,637 B1 | 10/2001 | Shaolian et al. |
| 6,309,399 B1 | 10/2001 | Barbut et al. |
| 6,312,462 B1 | 11/2001 | McDermott et al. |
| 6,312,465 B1 | 11/2001 | Griffin et al. |
| 6,319,276 B1 | 11/2001 | Holman et al. |
| 6,331,191 B1 | 12/2001 | Chobotov |
| 6,358,250 B1 | 3/2002 | Orbay |
| 6,364,882 B1 | 4/2002 | Orbay |
| 6,371,970 B1 | 4/2002 | Khosravi et al. |
| 6,371,983 B1 | 4/2002 | Lane |
| 6,395,019 B2 | 5/2002 | Chobotov |
| 6,395,026 B1 | 5/2002 | Aboul-Hosn et al. |
| 6,409,759 B1 | 6/2002 | Peredo |
| 6,425,916 B1 | 7/2002 | Garrison et al. |
| 6,440,164 B1 | 8/2002 | Dimatteo et al. |
| 6,458,153 B1 | 10/2002 | Bailey et al. |
| 6,458,156 B1 | 10/2002 | Wan et al. |
| 6,471,723 B1 | 10/2002 | Ashworth et al. |
| 6,482,228 B1 | 11/2002 | Norred |
| 6,494,909 B2 | 12/2002 | Greenhalgh |
| 6,503,272 B2 | 1/2003 | Duerig et al. |
| 6,508,833 B2 | 1/2003 | Pavcnik et al. |
| 6,517,515 B1 | 2/2003 | Eidenschink |
| 6,540,782 B1 | 4/2003 | Snyders |
| 6,544,291 B2 | 4/2003 | Taylor |
| 6,562,069 B2 | 5/2003 | Cai et al. |
| 6,572,652 B2 | 6/2003 | Shaknovich |
| 6,582,462 B1 | 6/2003 | Andersen et al. |
| 6,602,280 B2 | 8/2003 | Chobotov |
| 6,602,286 B1 | 8/2003 | Strecker |
| 6,629,987 B1 | 10/2003 | Gambale et al. |
| 6,645,160 B1 | 11/2003 | Heesch |
| 6,676,698 B2 | 1/2004 | McGuckin, Jr. et al. |
| 6,682,543 B2 | 1/2004 | Barbut et al. |
| 6,692,512 B2 | 2/2004 | Jang |
| 6,692,523 B2 | 2/2004 | Holman et al. |
| 6,719,788 B2 | 4/2004 | Cox |
| 6,719,789 B2 | 4/2004 | Cox |
| 6,733,525 B2 | 5/2004 | Yang et al. |
| 6,736,845 B2 | 5/2004 | Marquez et al. |
| 6,755,811 B1 | 6/2004 | Constantz |
| 6,761,733 B2 | 7/2004 | Chobotov et al. |
| 6,764,494 B2 | 7/2004 | Menz et al. |

(56) References Cited

U.S. PATENT DOCUMENTS

| | | |
|---|---|---|
| 6,767,362 B2 | 7/2004 | Schreck |
| 6,769,434 B2 | 8/2004 | Liddicoat et al. |
| 6,776,604 B1 | 8/2004 | Chobotov et al. |
| 6,790,230 B2 | 9/2004 | Beyersdorf et al. |
| 6,827,735 B2 | 12/2004 | Greenberg |
| 6,835,188 B2 | 12/2004 | Samson et al. |
| 6,875,212 B2 | 4/2005 | Shaolian et al. |
| 6,890,353 B2 | 5/2005 | Cohn et al. |
| 6,896,690 B1 | 5/2005 | Lambrecht et al. |
| 6,921,414 B2 | 7/2005 | Klumb et al. |
| 6,936,057 B1 | 8/2005 | Nobles |
| 6,945,957 B2 | 9/2005 | Freyman |
| 6,949,122 B2 | 9/2005 | Adams et al. |
| 6,958,212 B1 | 10/2005 | Hubbell et al. |
| 6,974,476 B2 | 12/2005 | McGuckin, Jr. et al. |
| 6,989,027 B2 | 1/2006 | Allen et al. |
| 6,994,093 B2 | 2/2006 | Murphy et al. |
| 7,018,406 B2 | 3/2006 | Seguin et al. |
| 7,037,334 B1 | 5/2006 | Hlavka et al. |
| 7,052,410 B2 | 5/2006 | Cameron |
| 7,052,487 B2 | 5/2006 | Cohn et al. |
| 7,066,951 B2 | 6/2006 | Chobotov |
| 7,077,844 B2 | 7/2006 | Michelson |
| 7,077,862 B2 | 7/2006 | Vidlund et al. |
| 7,081,129 B2 | 7/2006 | Chobotov |
| 7,090,693 B1 | 8/2006 | Chobotov et al. |
| 7,101,395 B2 | 9/2006 | Tremulis et al. |
| 7,108,715 B2 | 9/2006 | Lawrence-Brown et al. |
| 7,112,219 B2 | 9/2006 | Vidlund et al. |
| 7,125,464 B2 | 10/2006 | Chobotov et al. |
| 7,147,660 B2 | 12/2006 | Chobotov et al. |
| 7,147,661 B2 | 12/2006 | Chobotov et al. |
| 7,150,758 B2 | 12/2006 | Kari et al. |
| 7,178,978 B2 | 2/2007 | Argentine et al. |
| 7,182,756 B2 | 2/2007 | Saeed et al. |
| 7,186,264 B2 | 3/2007 | Liddicoat et al. |
| 7,192,441 B2 | 3/2007 | Sherry |
| 7,201,772 B2 | 4/2007 | Schwammenthal et al. |
| 7,217,287 B2 | 5/2007 | Wilson et al. |
| 7,252,682 B2 | 8/2007 | Seguin |
| 7,255,711 B2 | 8/2007 | Holman et al. |
| 7,273,481 B2 | 9/2007 | Lombardo et al. |
| 7,276,078 B2 | 10/2007 | Spenser et al. |
| 7,309,340 B2 | 12/2007 | Fallin et al. |
| 7,320,704 B2 | 1/2008 | Lashinski et al. |
| 7,329,279 B2 | 2/2008 | Haug et al. |
| 7,335,213 B1 | 2/2008 | Hyde et al. |
| 7,381,219 B2 | 6/2008 | Salahieh et al. |
| 7,429,269 B2 | 9/2008 | Schwammenthal et al. |
| 7,435,257 B2 | 10/2008 | Lashinski et al. |
| 7,442,204 B2 | 10/2008 | Schwammenthal et al. |
| 7,445,630 B2 | 11/2008 | Lashinski et al. |
| 7,445,631 B2 | 11/2008 | Salahieh et al. |
| 7,468,072 B2 | 12/2008 | Morsi |
| 7,491,230 B2 | 2/2009 | Holman et al. |
| 7,534,259 B2 | 5/2009 | Lashinski et al. |
| 7,534,261 B2 | 5/2009 | Friedman |
| 7,556,645 B2 | 7/2009 | Lashinski et al. |
| 7,556,646 B2 | 7/2009 | Yang et al. |
| 7,585,321 B2 | 9/2009 | Cribier |
| 7,615,071 B2 | 11/2009 | Chobotov |
| 7,628,805 B2 | 12/2009 | Bash et al. |
| 7,632,291 B2 | 12/2009 | Stephens et al. |
| 7,641,686 B2 | 1/2010 | Lashinski et al. |
| 7,658,762 B2 | 2/2010 | Lashinski et al. |
| 7,666,193 B2 | 2/2010 | Starksen et al. |
| 7,666,220 B2 | 2/2010 | Evans et al. |
| 7,678,217 B2 | 3/2010 | Chobotov et al. |
| 7,682,383 B2 | 3/2010 | Robin |
| 7,708,163 B2 | 5/2010 | Argentine |
| 7,712,606 B2 | 5/2010 | Salahieh et al. |
| 7,726,943 B2 | 6/2010 | Stommel |
| 7,731,741 B2 | 6/2010 | Eidenschink |
| 7,744,912 B1 | 6/2010 | Hubbell |
| 7,762,943 B2 | 7/2010 | Khairkhahan |
| 7,766,954 B2 | 8/2010 | Chobotov et al. |
| 7,780,726 B2 | 8/2010 | Seguin |
| 7,785,365 B2 | 8/2010 | Holman et al. |
| 7,799,068 B2 | 9/2010 | Holman et al. |
| 7,824,442 B2 | 11/2010 | Salahieh et al. |
| 7,837,727 B2 | 11/2010 | Goetz et al. |
| 7,846,203 B2 | 12/2010 | Cribier |
| 7,935,144 B2 | 5/2011 | Robin et al. |
| 8,002,826 B2 | 8/2011 | Seguin |
| 8,012,201 B2 | 9/2011 | Lashinski et al. |
| 8,016,877 B2 | 9/2011 | Seguin et al. |
| 8,052,750 B2 | 11/2011 | Tuval et al. |
| 8,057,540 B2 | 11/2011 | Cribier et al. |
| 8,070,805 B2 | 12/2011 | Vidlund et al. |
| 8,092,525 B2 | 1/2012 | Eliasen et al. |
| 8,133,213 B2 | 3/2012 | Lashinski |
| 8,136,659 B2 | 3/2012 | Salahieh et al. |
| 8,137,398 B2 | 3/2012 | Tuval et al. |
| 8,142,497 B2 | 3/2012 | Friedman |
| 8,167,932 B2 | 5/2012 | Bourang et al. |
| 8,197,534 B2 | 6/2012 | Brumleve et al. |
| 8,308,796 B2 | 11/2012 | Lashinski et al. |
| 8,313,525 B2 | 11/2012 | Tuval et al. |
| 8,348,995 B2 | 1/2013 | Tuval et al. |
| 8,348,996 B2 | 1/2013 | Tuval et al. |
| 8,377,118 B2 | 2/2013 | Lashinski et al. |
| 8,414,643 B2 | 4/2013 | Tuval et al. |
| 8,454,656 B2 | 6/2013 | Tuval |
| 8,556,881 B2 | 10/2013 | Lashinski |
| 8,562,663 B2 | 10/2013 | Mearns et al. |
| 8,568,477 B2 | 10/2013 | Lashinski et al. |
| 8,584,849 B2 | 11/2013 | McCaffrey |
| 8,647,381 B2 | 2/2014 | Essinger et al. |
| 9,308,360 B2 | 4/2016 | Bishop et al. |
| 9,433,501 B2 | 9/2016 | Perera et al. |
| 9,445,897 B2 | 9/2016 | Bishop et al. |
| 9,572,661 B2 | 2/2017 | Robin et al. |
| 9,603,708 B2 | 3/2017 | Robin et al. |
| 2001/0007956 A1 | 7/2001 | Letac et al. |
| 2001/0010017 A1 | 7/2001 | Letac et al. |
| 2001/0021872 A1 | 9/2001 | Bailey et al. |
| 2001/0044656 A1 | 11/2001 | Williamson, IV et al. |
| 2002/0082689 A1 | 6/2002 | Chinn |
| 2002/0095116 A1 | 7/2002 | Strecter |
| 2002/0096177 A1 | 7/2002 | Toti et al. |
| 2002/0123802 A1 | 9/2002 | Snyders |
| 2002/0151961 A1 | 10/2002 | Lashinski et al. |
| 2002/0151970 A1 | 10/2002 | Garrison et al. |
| 2002/0183838 A1 | 12/2002 | Liddicoat et al. |
| 2002/0183841 A1 | 12/2002 | Cohn et al. |
| 2003/0004537 A1 | 1/2003 | Boyle et al. |
| 2003/0014104 A1 | 1/2003 | Cribier |
| 2003/0023300 A1 | 1/2003 | Bailey et al. |
| 2003/0023303 A1 | 1/2003 | Palmaz et al. |
| 2003/0027332 A1 | 2/2003 | Lafrance et al. |
| 2003/0036795 A1 | 2/2003 | Andersen et al. |
| 2003/0040772 A1 | 2/2003 | Hyodoh et al. |
| 2003/0055492 A1 | 3/2003 | Shaolian et al. |
| 2003/0055495 A1 | 3/2003 | Pease et al. |
| 2003/0055496 A1 | 3/2003 | Cai et al. |
| 2003/0074045 A1 | 4/2003 | Buzzard et al. |
| 2003/0074058 A1 | 4/2003 | Sherry |
| 2003/0078654 A1 | 4/2003 | Taylor et al. |
| 2003/0083538 A1 | 5/2003 | Adams et al. |
| 2003/0083741 A1 | 5/2003 | Woo et al. |
| 2003/0093145 A1 | 5/2003 | Lawrence-Brown et al. |
| 2003/0109923 A1 | 6/2003 | Chinn et al. |
| 2003/0125793 A1 | 7/2003 | Vesely |
| 2003/0125797 A1 | 7/2003 | Chobotov et al. |
| 2003/0130730 A1 | 7/2003 | Cohn et al. |
| 2003/0130731 A1 | 7/2003 | Vidlund et al. |
| 2003/0153974 A1 | 8/2003 | Spenser et al. |
| 2003/0191527 A1 | 10/2003 | Shaknovich |
| 2003/0216802 A1 | 11/2003 | Chobotov |
| 2003/0220684 A1 | 11/2003 | Holman et al. |
| 2003/0225453 A1 | 12/2003 | Murch |
| 2003/0233022 A1 | 12/2003 | Vidlund et al. |
| 2003/0236568 A1 | 12/2003 | Hojeibane et al. |
| 2004/0003819 A1 | 1/2004 | St. Goar et al. |

(56) References Cited

U.S. PATENT DOCUMENTS

| | | |
|---|---|---|
| 2004/0030381 A1 | 2/2004 | Shu |
| 2004/0030382 A1 | 2/2004 | St. Goar et al. |
| 2004/0034320 A1 | 2/2004 | Burnett |
| 2004/0039436 A1 | 2/2004 | Spenser et al. |
| 2004/0039442 A1 | 2/2004 | St. Goar et al. |
| 2004/0059412 A1 | 3/2004 | Lytle et al. |
| 2004/0087975 A1 | 5/2004 | Lucatero et al. |
| 2004/0093060 A1 | 5/2004 | Seguin et al. |
| 2004/0116951 A1 | 6/2004 | Rosengart |
| 2004/0127979 A1 | 7/2004 | Wilson et al. |
| 2004/0148019 A1 | 7/2004 | Vidlund et al. |
| 2004/0148020 A1 | 7/2004 | Vidlund et al. |
| 2004/0167620 A1 | 8/2004 | Ortiz et al. |
| 2004/0176836 A1 | 9/2004 | Kari et al. |
| 2004/0186563 A1 | 9/2004 | Lobbi |
| 2004/0210304 A1 | 10/2004 | Seguin et al. |
| 2004/0225354 A1 | 11/2004 | Allen et al. |
| 2004/0225355 A1 | 11/2004 | Allen et al. |
| 2004/0236411 A1 | 11/2004 | Sarac et al. |
| 2004/0249413 A1 | 12/2004 | Allen et al. |
| 2004/0249452 A1 | 12/2004 | Adams et al. |
| 2004/0254600 A1 | 12/2004 | Zarbatany et al. |
| 2004/0260322 A1 | 12/2004 | Rudko et al. |
| 2004/0260389 A1 | 12/2004 | Case et al. |
| 2004/0260390 A1 | 12/2004 | Sarac et al. |
| 2005/0004654 A1 | 1/2005 | Khosravi et al. |
| 2005/0010285 A1 | 1/2005 | Lambrecht et al. |
| 2005/0021056 A1 | 1/2005 | St. Goar et al. |
| 2005/0021057 A1 | 1/2005 | St. Goar et al. |
| 2005/0021128 A1 | 1/2005 | Nakahama et al. |
| 2005/0033446 A1 | 2/2005 | Deem et al. |
| 2005/0055082 A1 | 3/2005 | Ben Muvhar et al. |
| 2005/0065550 A1 | 3/2005 | Starksen et al. |
| 2005/0090804 A1 | 4/2005 | Chobotov et al. |
| 2005/0090846 A1 | 4/2005 | Pedersen et al. |
| 2005/0107810 A1 | 5/2005 | Morales et al. |
| 2005/0131528 A1 | 6/2005 | Buscemit et al. |
| 2005/0137686 A1 | 6/2005 | Salahieh et al. |
| 2005/0137687 A1 | 6/2005 | Salahieh et al. |
| 2005/0137688 A1 | 6/2005 | Salahieh et al. |
| 2005/0137689 A1 | 6/2005 | Salahieh et al. |
| 2005/0137690 A1 | 6/2005 | Salahieh et al. |
| 2005/0137691 A1 | 6/2005 | Salahieh et al. |
| 2005/0137692 A1 | 6/2005 | Haug et al. |
| 2005/0137695 A1 | 6/2005 | Salahieh et al. |
| 2005/0137696 A1 | 6/2005 | Salahieh et al. |
| 2005/0137697 A1 | 6/2005 | Salahieh et al. |
| 2005/0137698 A1 | 6/2005 | Salahieh et al. |
| 2005/0137699 A1 | 6/2005 | Salahieh et al. |
| 2005/0137701 A1 | 6/2005 | Salahieh et al. |
| 2005/0143809 A1 | 6/2005 | Salahieh et al. |
| 2005/0158272 A1 | 7/2005 | Whirley et al. |
| 2005/0171593 A1 | 8/2005 | Whirley et al. |
| 2005/0203549 A1 | 9/2005 | Realyvasquez |
| 2005/0203614 A1 | 9/2005 | Forster et al. |
| 2005/0209674 A1 | 9/2005 | Kutscher et al. |
| 2005/0209687 A1 | 9/2005 | Sitzmann et al. |
| 2005/0222488 A1 | 10/2005 | Rahdert et al. |
| 2005/0222489 A1 | 10/2005 | Rahdert et al. |
| 2005/0228422 A1 | 10/2005 | Rahdert et al. |
| 2005/0251251 A1 | 11/2005 | Cribier |
| 2005/0267574 A1 | 12/2005 | Cohn et al. |
| 2005/0273160 A1 | 12/2005 | Lashinski et al. |
| 2005/0283231 A1 | 12/2005 | Haug et al. |
| 2006/0004442 A1 | 1/2006 | Spenser et al. |
| 2006/0020327 A1 | 1/2006 | Lashinski et al. |
| 2006/0020332 A1 | 1/2006 | Lashinski et al. |
| 2006/0020333 A1 | 1/2006 | Lashinski et al. |
| 2006/0020334 A1 | 1/2006 | Lashinski et al. |
| 2006/0025750 A1 | 2/2006 | Starksen et al. |
| 2006/0025787 A1 | 2/2006 | Morales et al. |
| 2006/0025854 A1 | 2/2006 | Lashinski et al. |
| 2006/0025855 A1 | 2/2006 | Lashinski et al. |
| 2006/0041306 A1 | 2/2006 | Vidlund et al. |
| 2006/0058872 A1 | 3/2006 | Salahieh et al. |
| 2006/0063970 A1 | 3/2006 | Raman et al. |
| 2006/0064058 A1 | 3/2006 | Coyle |
| 2006/0074485 A1 | 4/2006 | Realyvasquez |
| 2006/0088836 A1 | 4/2006 | Wohlgemuth et al. |
| 2006/0100699 A1 | 5/2006 | Vidlund et al. |
| 2006/0106449 A1 | 5/2006 | Ben Muvhar |
| 2006/0106450 A1 | 5/2006 | Ben Muvhar |
| 2006/0129025 A1 | 6/2006 | Levine et al. |
| 2006/0129051 A1 | 6/2006 | Rowe et al. |
| 2006/0129235 A1 | 6/2006 | Seguin et al. |
| 2006/0149135 A1 | 7/2006 | Paz |
| 2006/0149360 A1 | 7/2006 | Schwammenthal et al. |
| 2006/0173524 A1 | 8/2006 | Salahieh et al. |
| 2006/0178700 A1 | 8/2006 | Quinn |
| 2006/0178732 A1 | 8/2006 | Chobotov et al. |
| 2006/0190030 A1 | 8/2006 | To et al. |
| 2006/0195183 A1 | 8/2006 | Navia et al. |
| 2006/0206193 A1 | 9/2006 | Chobotov et al. |
| 2006/0212112 A1 | 9/2006 | Evans et al. |
| 2006/0217637 A1 | 9/2006 | Leiboff et al. |
| 2006/0222596 A1 | 10/2006 | Askari et al. |
| 2006/0224232 A1 | 10/2006 | Chobotov |
| 2006/0229717 A1 | 10/2006 | Cohn et al. |
| 2006/0235512 A1 | 10/2006 | Osborne et al. |
| 2006/0241656 A1 | 10/2006 | Starksen et al. |
| 2006/0252984 A1 | 11/2006 | Rahdert et al. |
| 2006/0253191 A1 | 11/2006 | Salahieh et al. |
| 2006/0259134 A1 | 11/2006 | Schwammenthal et al. |
| 2006/0271172 A1 | 11/2006 | Tehrani |
| 2006/0276874 A1 | 12/2006 | Wilson et al. |
| 2006/0276881 A1 | 12/2006 | Holman et al. |
| 2007/0005133 A1 | 1/2007 | Lashinski et al. |
| 2007/0010877 A1 | 1/2007 | Salahieh et al. |
| 2007/0027536 A1 | 2/2007 | Mihaljevic |
| 2007/0038293 A1 | 2/2007 | St. Goar et al. |
| 2007/0043435 A1 | 2/2007 | Seguin et al. |
| 2007/0050022 A1 | 3/2007 | Vidlund et al. |
| 2007/0055356 A1 | 3/2007 | Eidenschink |
| 2007/0093890 A1 | 4/2007 | Eliasen et al. |
| 2007/0118214 A1 | 5/2007 | Salahieh et al. |
| 2007/0142906 A1 | 6/2007 | Figulla et al. |
| 2007/0162107 A1 | 7/2007 | Haug et al. |
| 2007/0185566 A1 | 8/2007 | Khitin et al. |
| 2007/0185571 A1 | 8/2007 | Kapadia et al. |
| 2007/0203503 A1 | 8/2007 | Salahieh et al. |
| 2007/0203575 A1 | 8/2007 | Forster et al. |
| 2007/0213814 A1 | 9/2007 | Liddicoat et al. |
| 2007/0219630 A1 | 9/2007 | Chu |
| 2007/0244552 A1 | 10/2007 | Salahieh et al. |
| 2007/0255399 A1 | 11/2007 | Eliasen et al. |
| 2007/0265700 A1 | 11/2007 | Eliasen et al. |
| 2007/0270932 A1 | 11/2007 | Headley et al. |
| 2007/0282436 A1 | 12/2007 | Pinchuk |
| 2007/0293943 A1 | 12/2007 | Quinn |
| 2008/0015687 A1 | 1/2008 | Lashinski et al. |
| 2008/0039881 A1 | 2/2008 | Greenberg |
| 2008/0039923 A1 | 2/2008 | Taylor et al. |
| 2008/0039935 A1 | 2/2008 | Buch et al. |
| 2008/0071361 A1 | 3/2008 | Tuval et al. |
| 2008/0071362 A1 | 3/2008 | Tuval et al. |
| 2008/0071363 A1 | 3/2008 | Tuval et al. |
| 2008/0071366 A1 | 3/2008 | Tuval et al. |
| 2008/0071368 A1 | 3/2008 | Tuval et al. |
| 2008/0071369 A1 | 3/2008 | Tuval et al. |
| 2008/0109073 A1 | 5/2008 | Lashinski et al. |
| 2008/0125859 A1 | 5/2008 | Salahieh et al. |
| 2008/0125860 A1 | 5/2008 | Webler et al. |
| 2008/0188923 A1 | 8/2008 | Chu |
| 2008/0194905 A1 | 8/2008 | Walsh |
| 2008/0208329 A1 | 8/2008 | Bishop et al. |
| 2008/0215143 A1 | 9/2008 | Seguin |
| 2008/0234814 A1 | 9/2008 | Salahieh et al. |
| 2008/0243081 A1 | 10/2008 | Nance et al. |
| 2009/0043382 A1 | 2/2009 | Maurer et al. |
| 2009/0048668 A1 | 2/2009 | Wilson et al. |
| 2009/0054969 A1 | 2/2009 | Salahieh et al. |
| 2009/0054976 A1 | 2/2009 | Tuval et al. |
| 2009/0076598 A1 | 3/2009 | Salahieh et al. |
| 2009/0076600 A1 | 3/2009 | Quinn |

(56) References Cited

U.S. PATENT DOCUMENTS

| | | |
|---|---|---|
| 2009/0082857 A1 | 3/2009 | Lashinski et al. |
| 2009/0088836 A1 | 4/2009 | Bishop et al. |
| 2009/0099649 A1 | 4/2009 | Chobotov et al. |
| 2009/0131849 A1 | 5/2009 | Maurer et al. |
| 2009/0149949 A1 | 6/2009 | Quinn |
| 2009/0222084 A1 | 9/2009 | Friedman |
| 2009/0234443 A1 | 9/2009 | Ottma et al. |
| 2009/0264984 A1 | 10/2009 | Chobotov |
| 2009/0264997 A1 | 10/2009 | Salahieh et al. |
| 2009/0318949 A1 | 12/2009 | Ganpath et al. |
| 2009/0319029 A1 | 12/2009 | Evans et al. |
| 2010/0004728 A1 | 1/2010 | Rao et al. |
| 2010/0004730 A1 | 1/2010 | Benjamin et al. |
| 2010/0010623 A1 | 1/2010 | Lashinski et al. |
| 2010/0016942 A1 | 1/2010 | Chobotov et al. |
| 2010/0016943 A1 | 1/2010 | Chobotov |
| 2010/0016948 A1 | 1/2010 | Chobotov |
| 2010/0030204 A1 | 2/2010 | Stein et al. |
| 2010/0030327 A1 | 2/2010 | Chatel |
| 2010/0036360 A1 | 2/2010 | Herbowy et al. |
| 2010/0036485 A1 | 2/2010 | Seguin |
| 2010/0048987 A1 | 2/2010 | Khairkhahan |
| 2010/0076481 A1 | 3/2010 | Stephens et al. |
| 2010/0106087 A1 | 4/2010 | Evans et al. |
| 2010/0121434 A1 | 5/2010 | Paul et al. |
| 2010/0132892 A1 | 6/2010 | Chobotov et al. |
| 2010/0168844 A1 | 7/2010 | Toomes et al. |
| 2010/0185275 A1 | 7/2010 | Richter et al. |
| 2010/0234852 A1 | 9/2010 | Shinohara et al. |
| 2010/0256754 A1 | 10/2010 | Styrc |
| 2010/0292772 A1 | 11/2010 | Samuels |
| 2010/0324668 A1 | 12/2010 | Maurer et al. |
| 2011/0060407 A1 | 3/2011 | Ketai et al. |
| 2011/0066170 A1 | 3/2011 | Farnan |
| 2011/0066233 A1 | 3/2011 | Thornton et al. |
| 2011/0098802 A1 | 4/2011 | Braido et al. |
| 2011/0112625 A1 | 5/2011 | Ben-Muvhar et al. |
| 2011/0153009 A1 | 6/2011 | Navia et al. |
| 2011/0213460 A1 | 9/2011 | Lashinski et al. |
| 2011/0257733 A1 | 10/2011 | Dwork |
| 2011/0295354 A1 | 12/2011 | Bueche et al. |
| 2012/0016468 A1 | 1/2012 | Robin et al. |
| 2012/0022629 A1 | 1/2012 | Perera et al. |
| 2012/0078237 A1 | 3/2012 | Wang et al. |
| 2012/0226341 A1 | 9/2012 | Schreck et al. |
| 2012/0277855 A1 | 11/2012 | Lashinski et al. |
| 2013/0041458 A1 | 2/2013 | Lashinski |
| 2013/0297011 A1 | 11/2013 | Morris et al. |
| 2014/0107691 A1 | 4/2014 | Lashinski et al. |
| 2014/0163667 A1 | 6/2014 | Lashinski et al. |
| 2015/0094795 A1 | 4/2015 | Ginn et al. |
| 2016/0045311 A1 | 2/2016 | McCann et al. |
| 2016/0100963 A1 | 4/2016 | Aristizabal et al. |
| 2017/0156857 A1 | 6/2017 | Bishop et al. |
| 2017/0157376 A1 | 6/2017 | Lashinski et al. |
| 2017/0290660 A1 | 10/2017 | Robin et al. |
| 2017/0325943 A1 | 11/2017 | Robin et al. |

FOREIGN PATENT DOCUMENTS

| | | |
|---|---|---|
| DE | 195 46 692 | 12/1995 |
| DE | 199 07 646 | 2/1999 |
| EP | 0 275 535 | 7/1988 |
| EP | 2 241 284 | 10/2010 |
| JP | 59-005299 | 2/1984 |
| JP | 61-003499 | 2/1986 |
| JP | 2000-513248 | 10/2000 |
| JP | 2001-238900 | 9/2001 |
| JP | 2001-516616 | 10/2001 |
| JP | 2004-502499 | 1/2004 |
| JP | 2004-049772 | 2/2004 |
| JP | 2004-507317 | 3/2004 |
| JP | 2005-525172 | 8/2005 |
| WO | WO 91/017720 | 11/1991 |
| WO | WO 93/001768 | 2/1993 |
| WO | WO 96/002212 | 2/1996 |
| WO | WO 97/009947 | 3/1997 |
| WO | WO 97/030659 | 8/1997 |
| WO | WO 97/046177 | 11/1997 |
| WO | WO 98/043556 | 10/1998 |
| WO | WO 98/055047 | 12/1998 |
| WO | WO 99/039662 | 8/1999 |
| WO | WO 00/041652 | 7/2000 |
| WO | WO 00/042950 | 7/2000 |
| WO | WO 00/047139 | 8/2000 |
| WO | WO 00/051522 | 9/2000 |
| WO | WO 01/006959 | 2/2001 |
| WO | WO 01/049213 | 7/2001 |
| WO | WO 01/062189 | 8/2001 |
| WO | WO 01/064137 | 9/2001 |
| WO | WO 03/003949 | 1/2003 |
| WO | WO 03/011195 | 2/2003 |
| WO | WO 03/047468 | 6/2003 |
| WO | WO 03/053288 | 7/2003 |
| WO | WO 03/053289 | 7/2003 |
| WO | WO 03/063740 | 8/2003 |
| WO | WO 03/094799 | 11/2003 |
| WO | WO 03/096932 | 11/2003 |
| WO | WO 2005/087140 | 9/2005 |
| WO | WO 2005/107650 | 11/2005 |
| WO | WO 2006/116725 | 11/2006 |
| WO | WO 2006/127756 | 11/2006 |
| WO | WO 2006/133294 | 12/2006 |
| WO | WO 2009/144463 | 12/2009 |
| WO | WO 2010/008548 | 1/2010 |
| WO | WO 2010/117367 | 10/2010 |
| WO | WO 2011/033427 | 3/2011 |
| WO | WO 2011/035154 | 3/2011 |
| WO | WO 2011/105979 | 9/2011 |
| WO | WO 2011/146745 | 11/2011 |
| WO | WO 2012/023980 | 2/2012 |
| WO | WO 2012/023981 | 2/2012 |
| WO | WO 2012/024428 | 2/2012 |
| WO | WO 2013/165896 | 11/2013 |

OTHER PUBLICATIONS

Carabello, Blase, "Timing of Valve Replacement in Aortic Stenosis Moving Closer to Perfection," Circulation, 1997, vol. 95, pp. 2241-2243.

David et al., Aortic Valve Replacement with the Toronto SPV Bioprosthesis, The Journal of Heart Valve Disease, 1992, pp. 244-248, vol. 1(2), ICR Publishers.

Vyavahare et al., "Prevention of Bioprosthetic Heart Valve Calcification by Ethanol Preincubation," Circulation, Jan. 21, 1997, pp. 479-488, vol. 95(2), American Heart Association.

Internatioal Search Report and Written Opinion in PCT Application No. PCT/US2008/74104, dated Dec. 24, 2008.

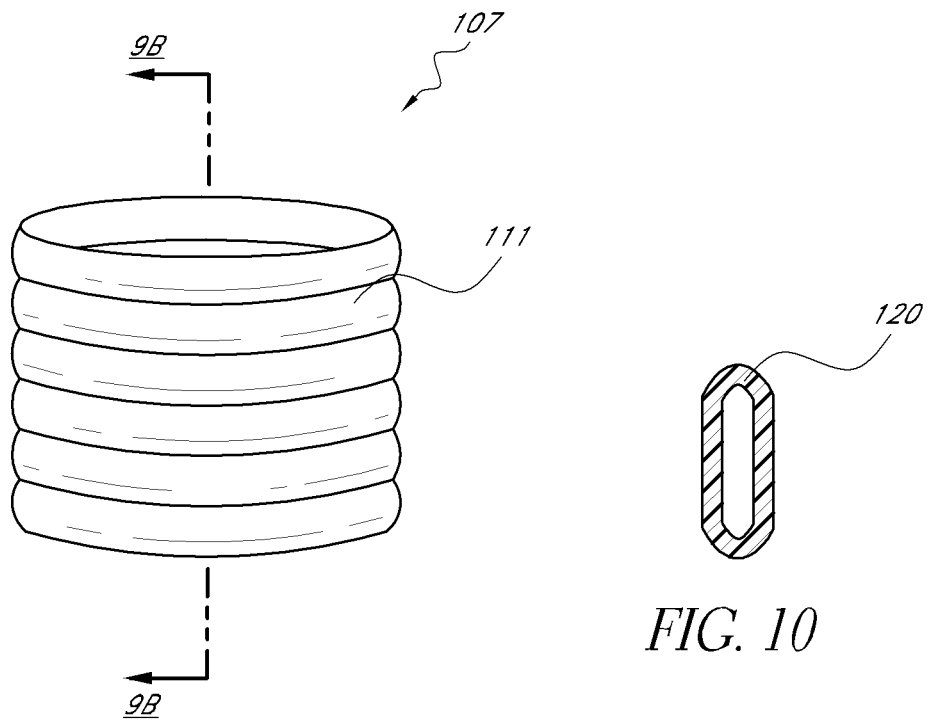
FIG. 10
FIG. 9A
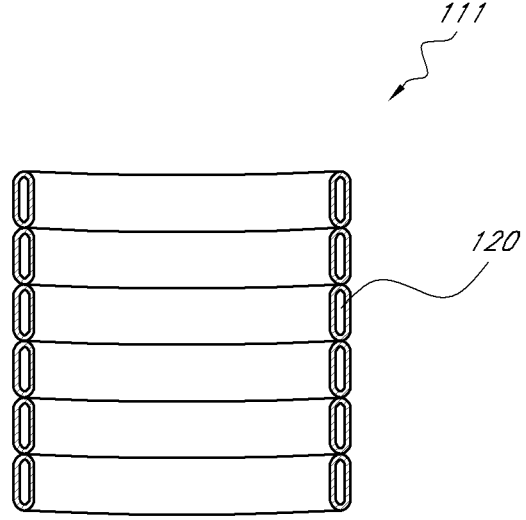
FIG. 9B

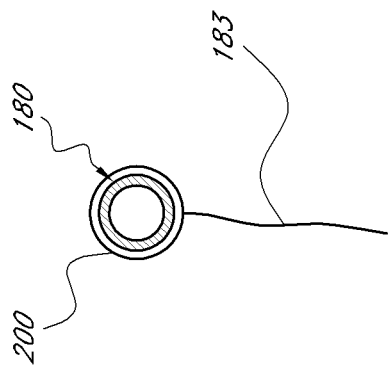
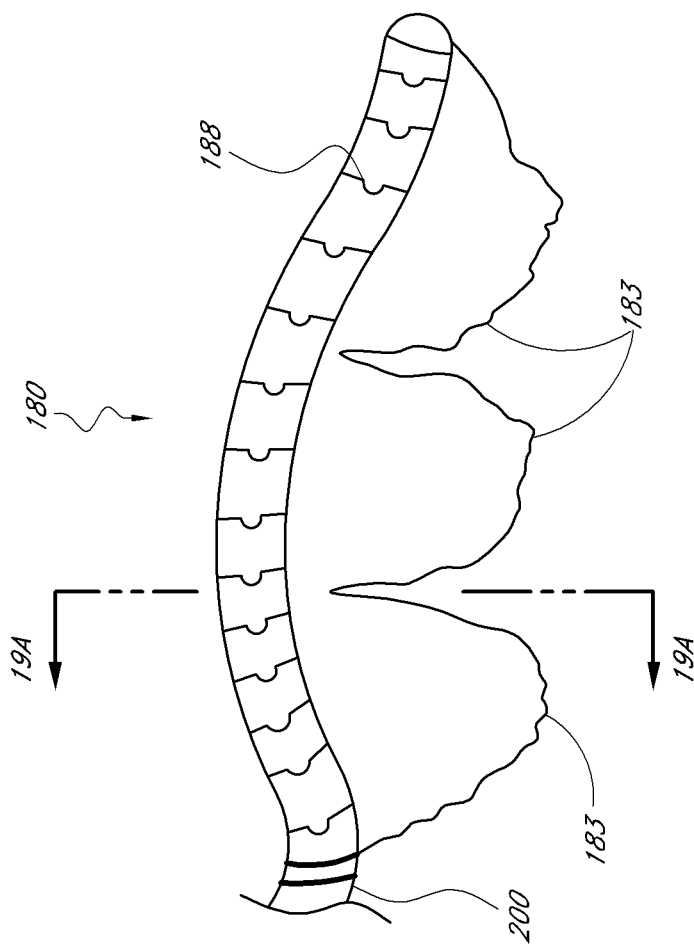
FIG. 19A
FIG. 19

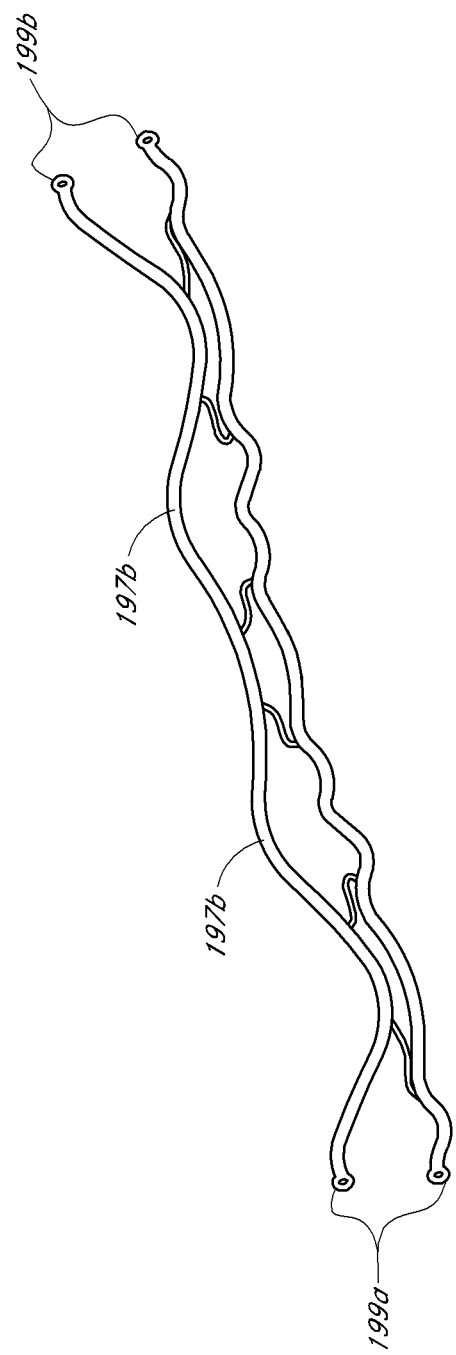

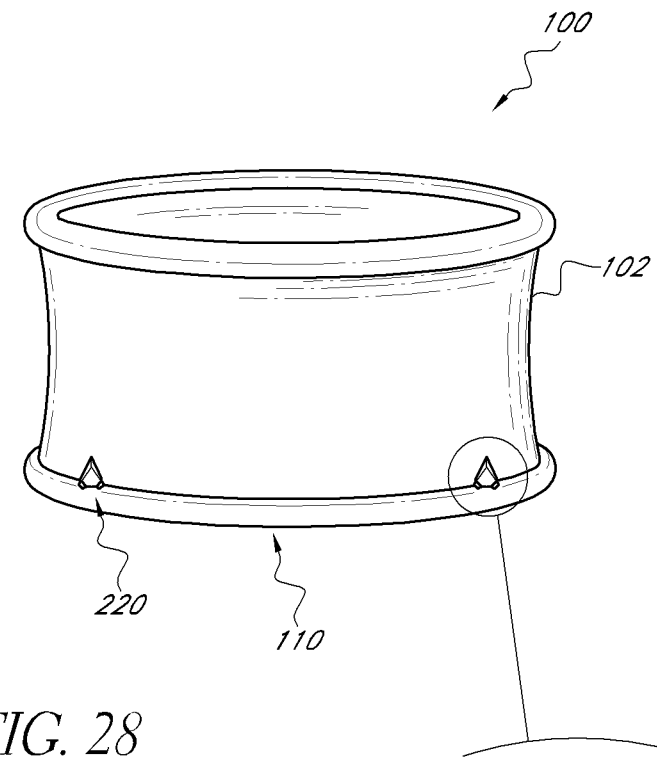
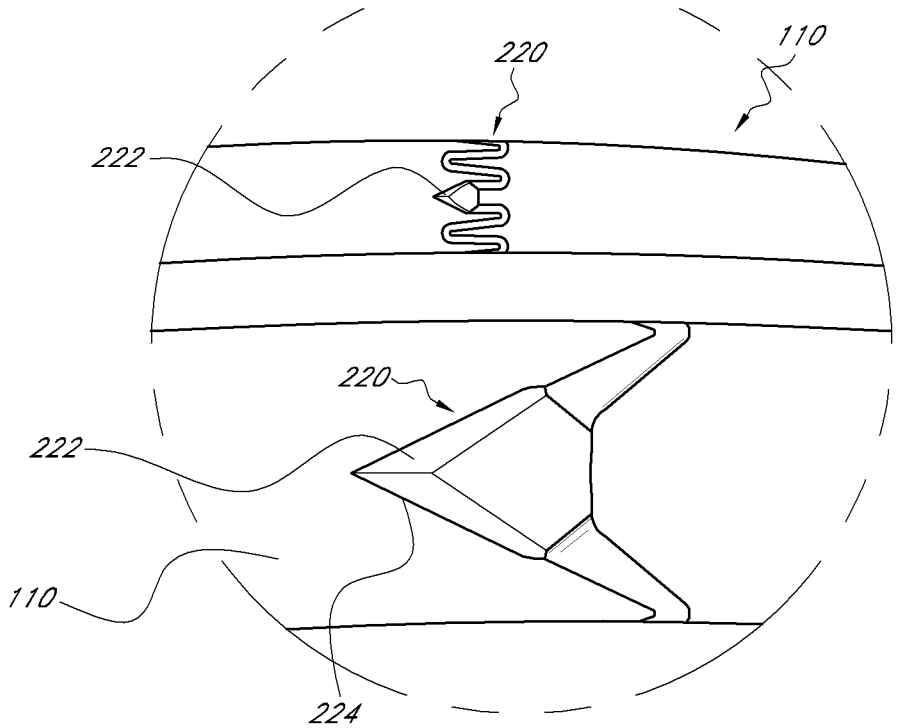
FIG. 28

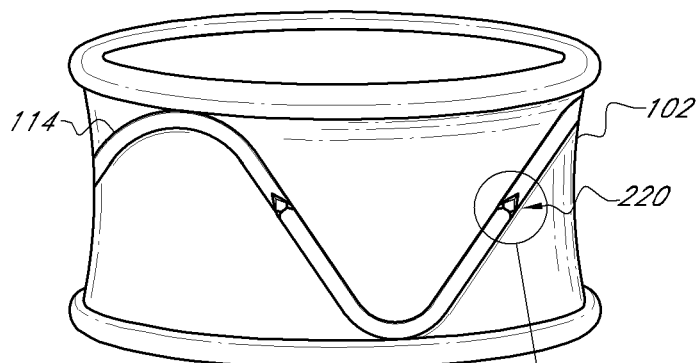
FIG. 29
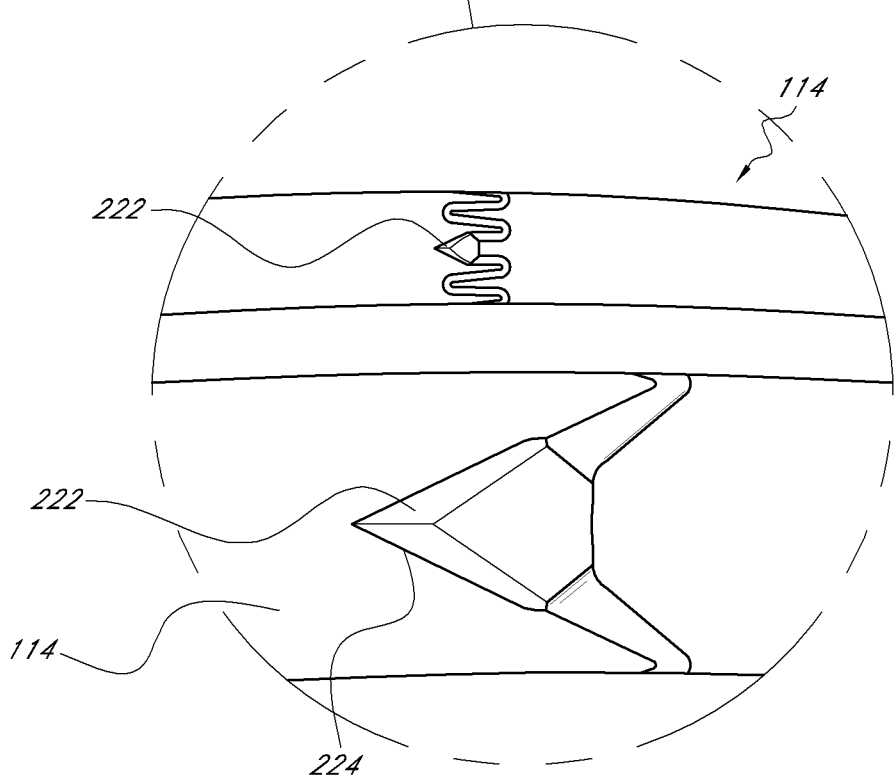

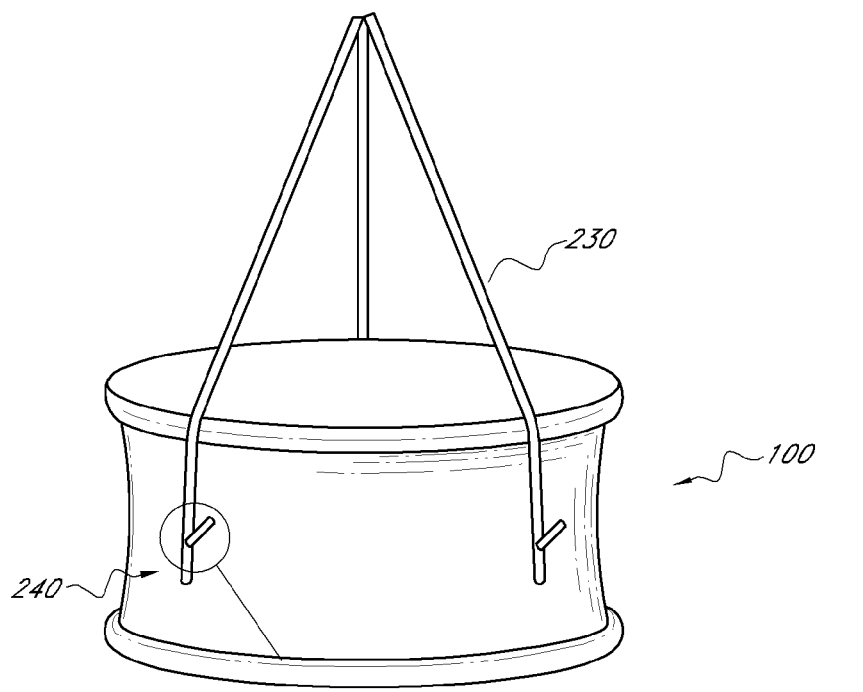
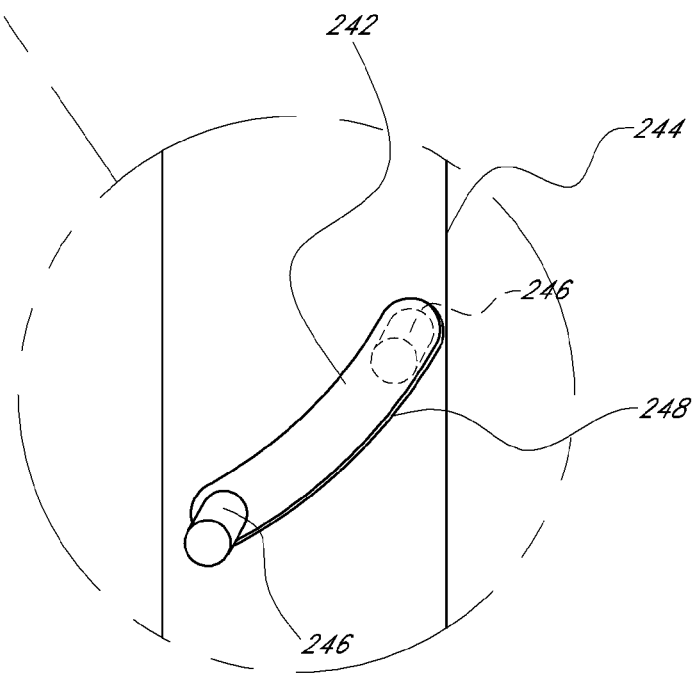
FIG. 30

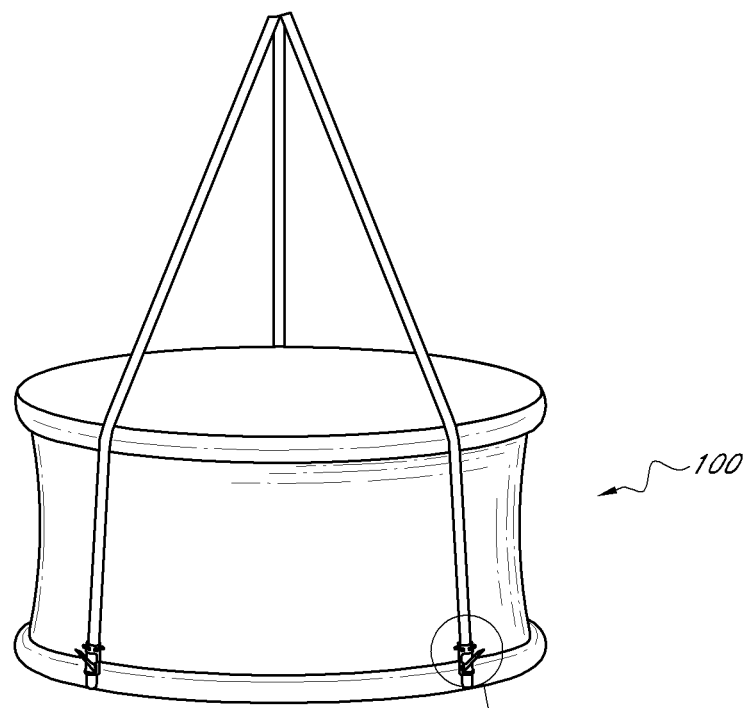
FIG. 32A
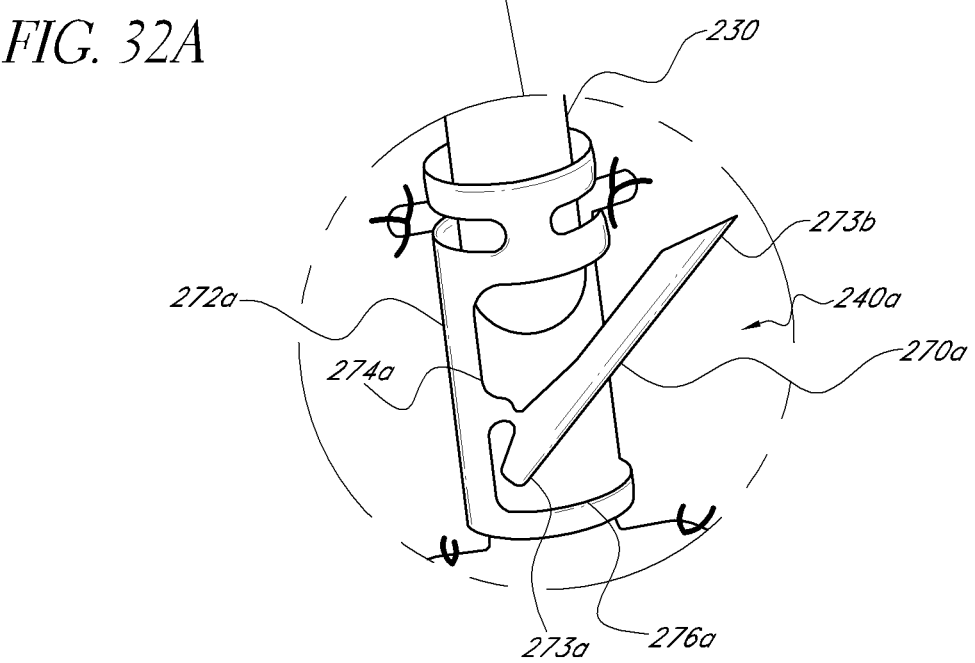

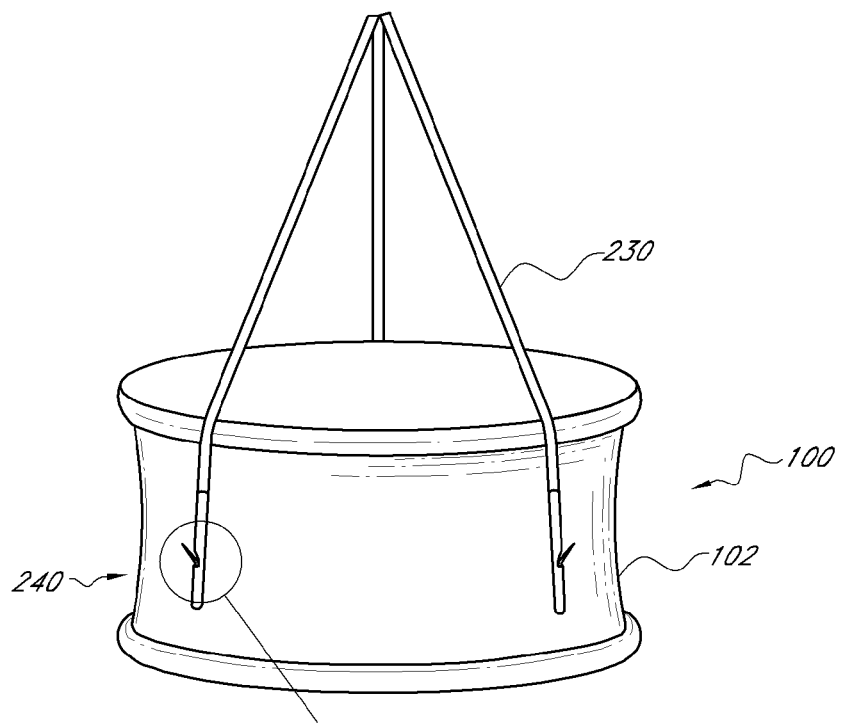
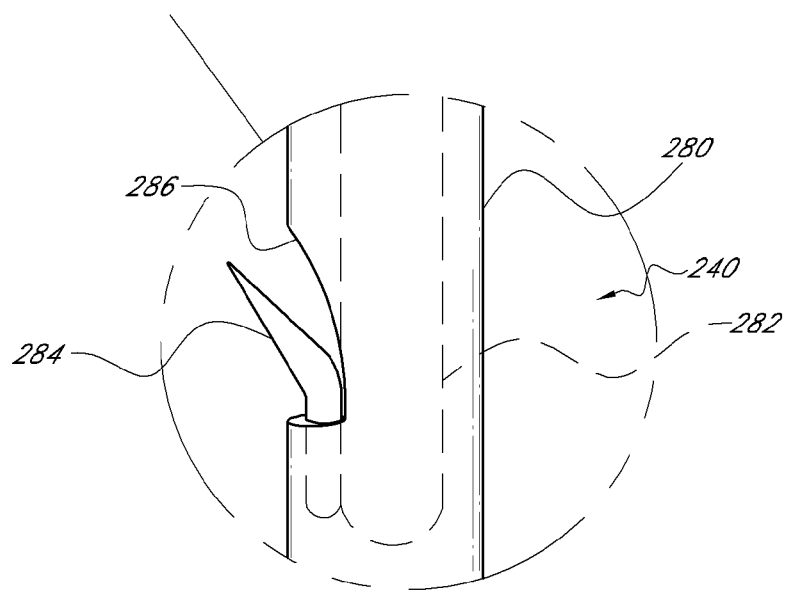
FIG. 33

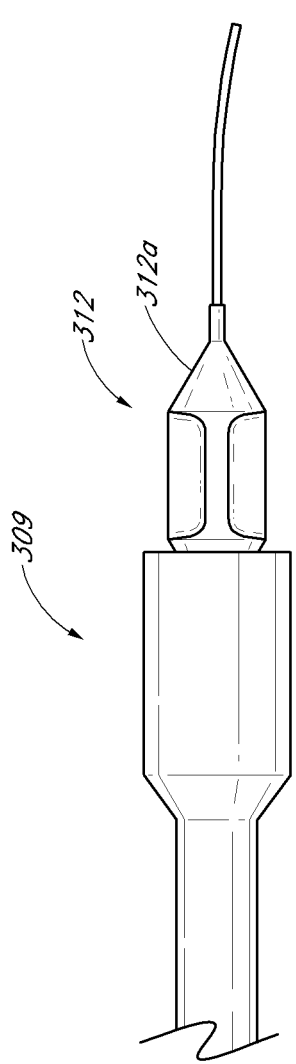
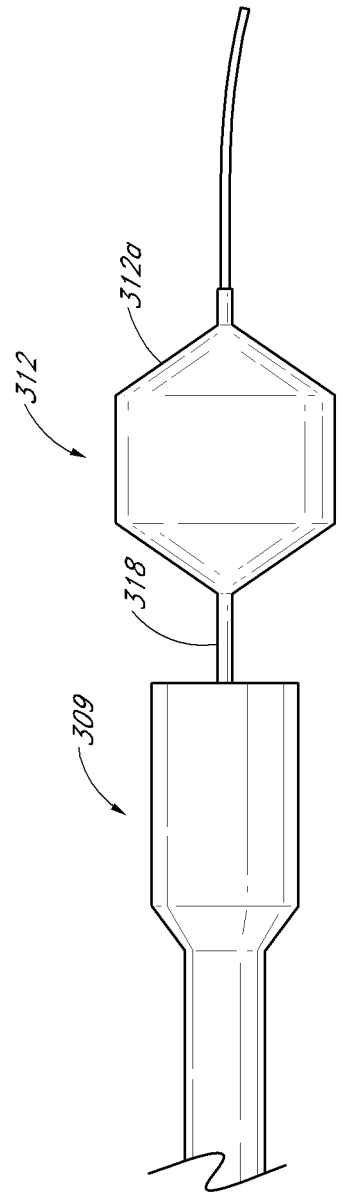
FIG. 35A
FIG. 35B

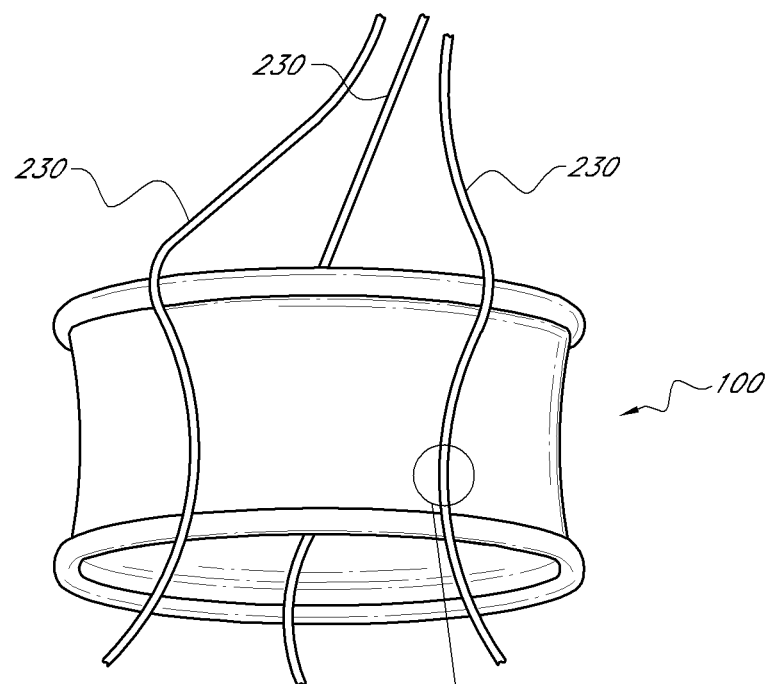
FIG. 44
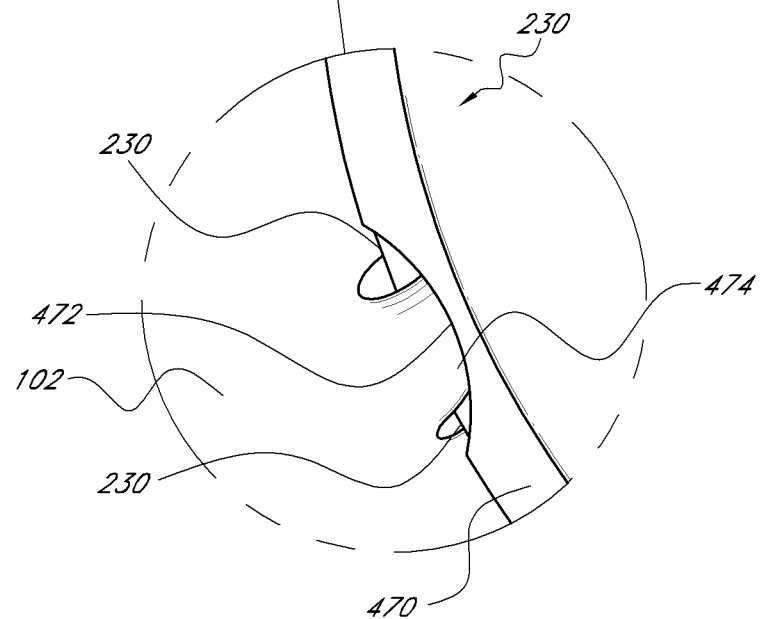

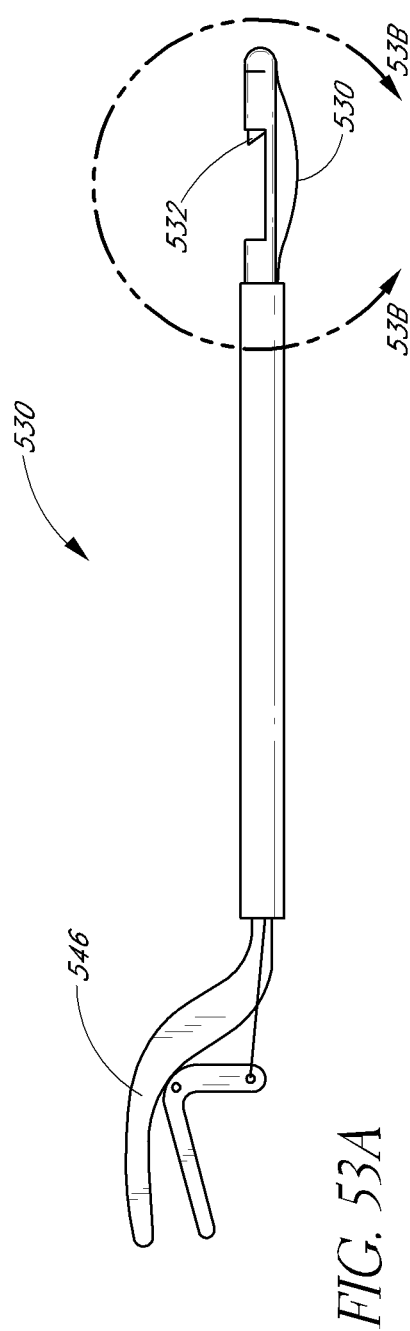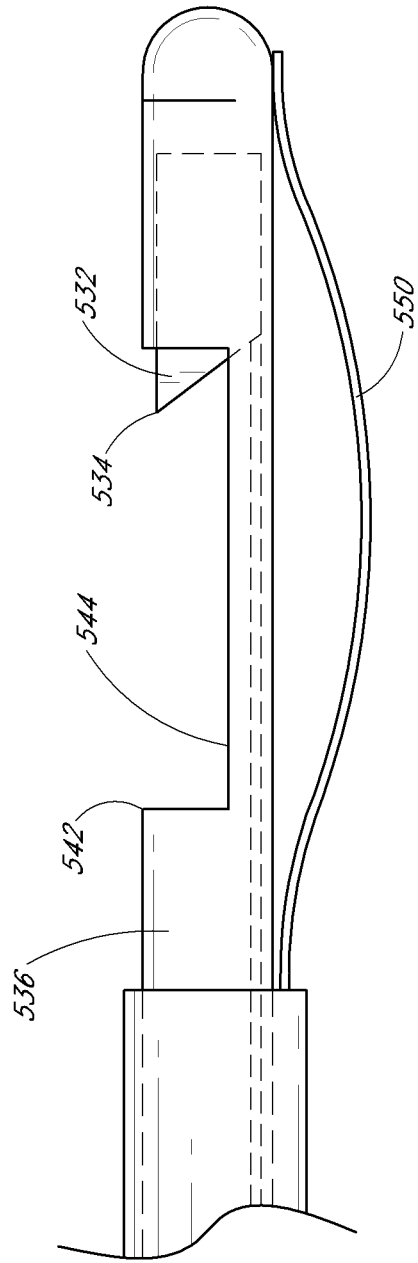

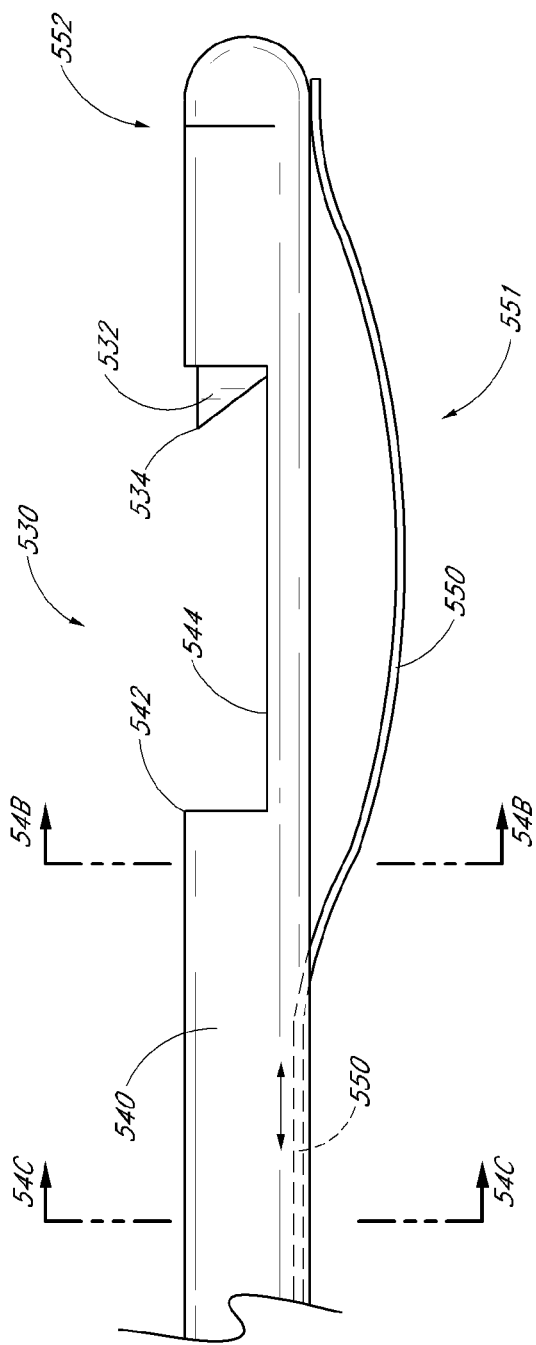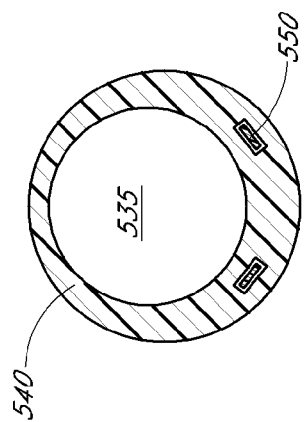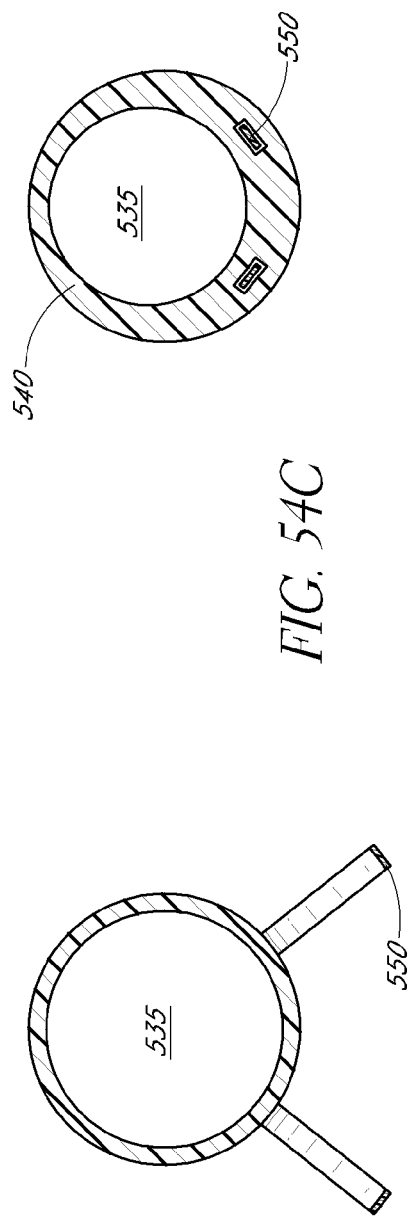

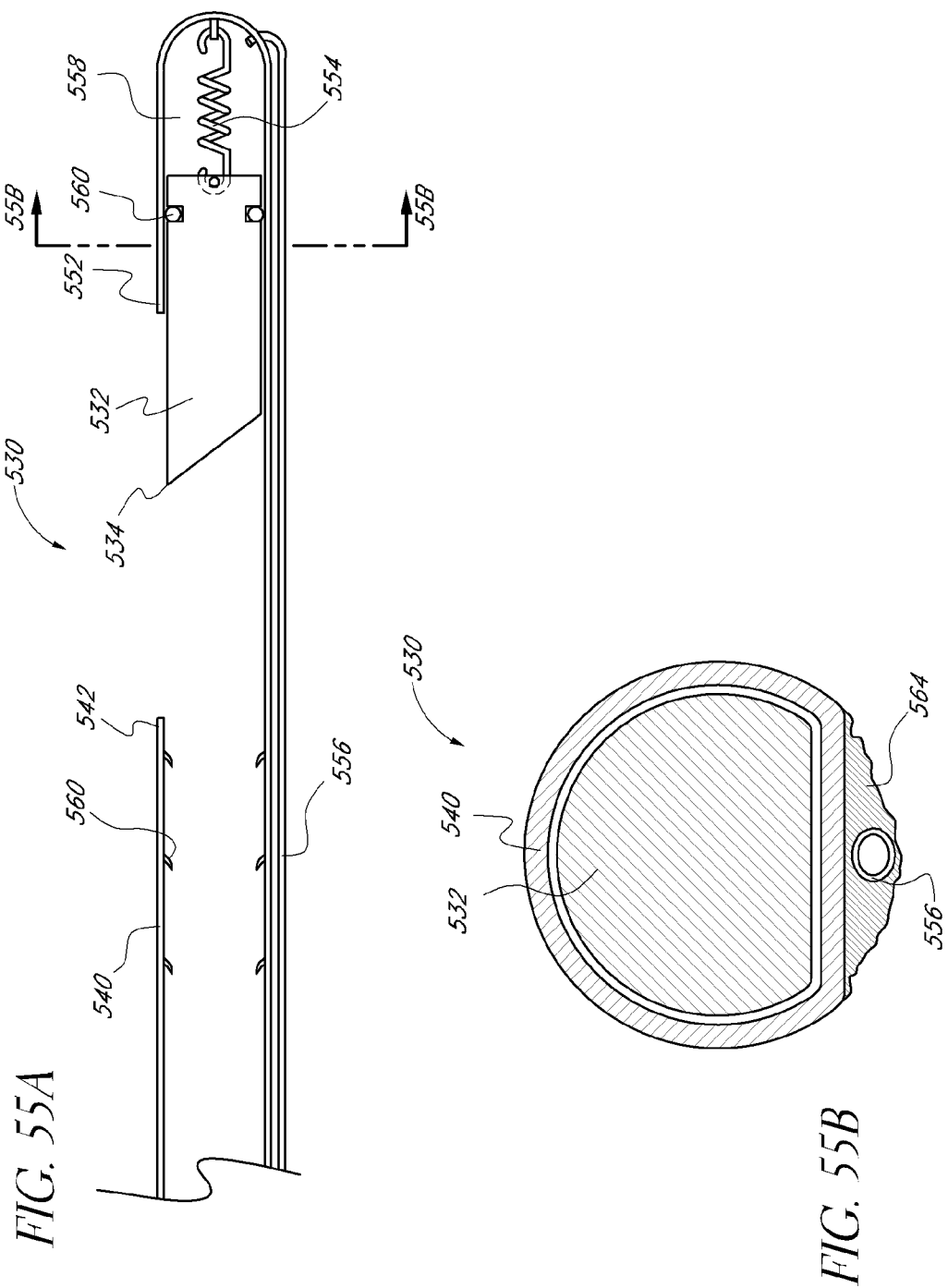

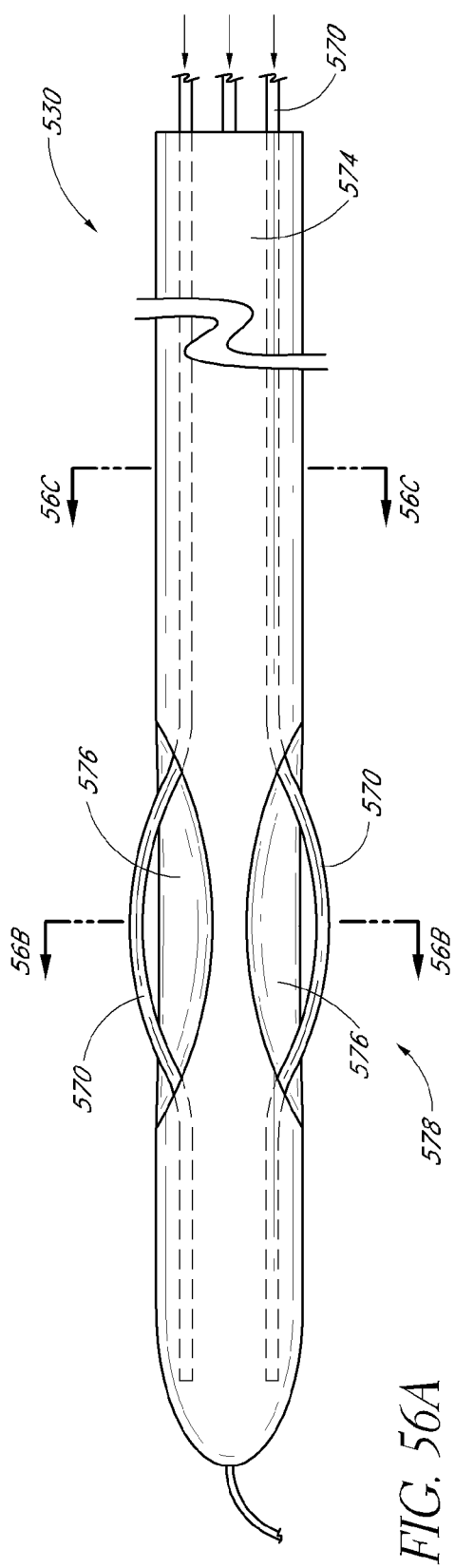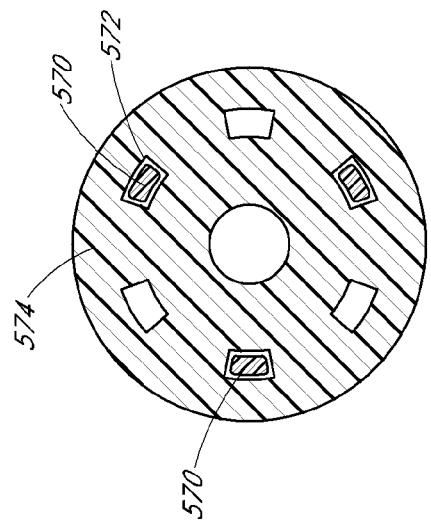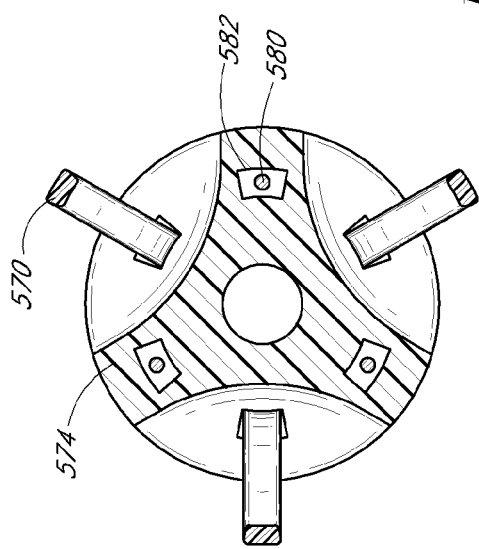
FIG. 56A
FIG. 56C
FIG. 56B

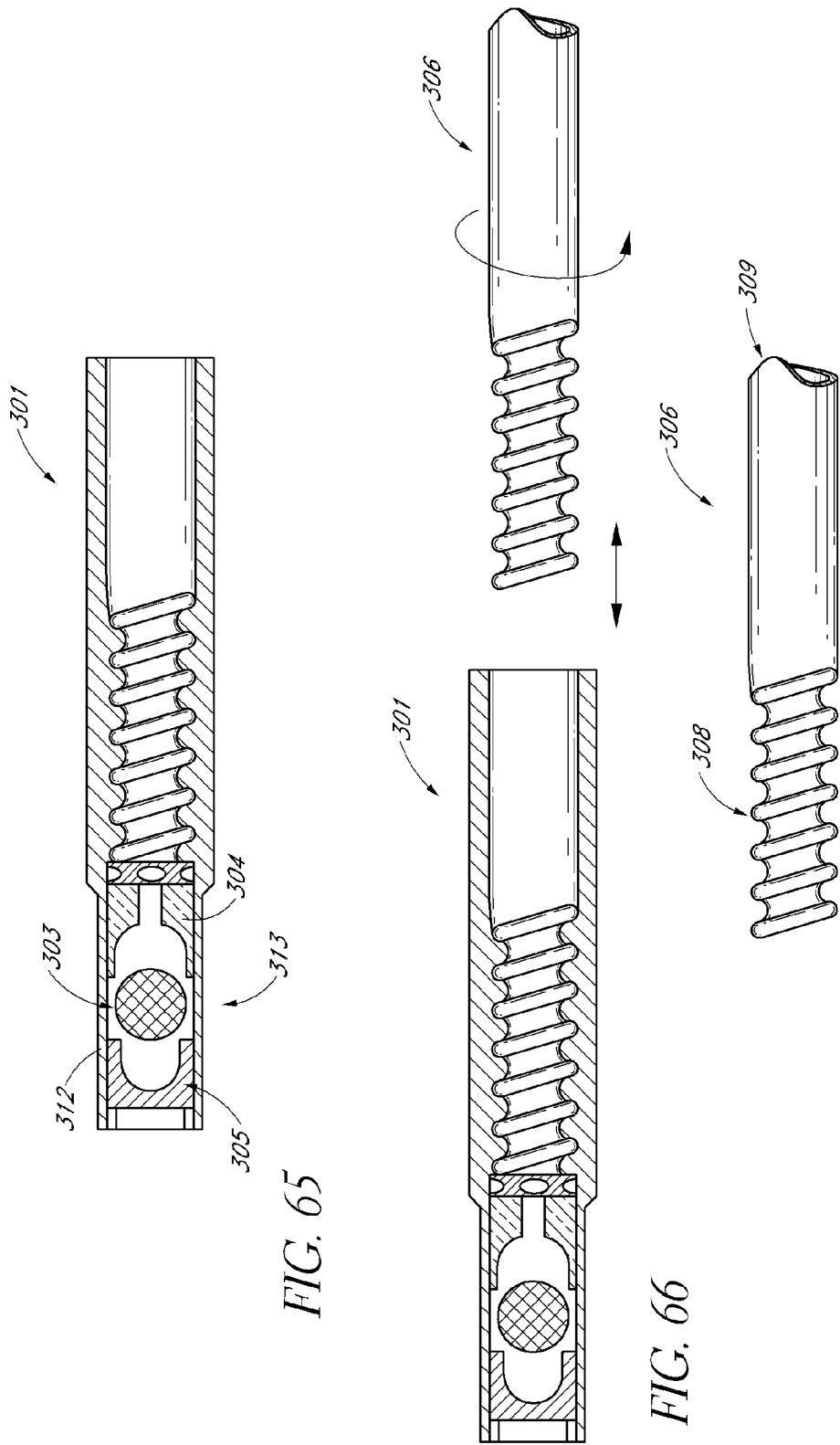

TRANSLUMENALLY IMPLANTABLE HEART VALVE WITH FORMED IN PLACE SUPPORT

CROSS-REFERENCE TO RELATED APPLICATIONS

This application is a continuation of U.S. patent application Ser. No. 12/976,671, filed Dec. 22, 2010, which is a continuation of U.S. patent application Ser. No. 12/197,172, filed Aug. 22, 2008, which claims priority to U.S. Provisional Application No. 60/957,691, filed Aug. 23, 2007, all of these applications are hereby incorporated by reference herein in their entirety.

BACKGROUND OF THE INVENTION

Field of the Invention

The present invention relates to medical methods and devices, and, in particular, to methods and devices for percutaneously implanting a stentless valve having a formed in place support structure.

Description of the Related Art

According to recent estimates, more than 79,000 patients are diagnosed with aortic and mitral valve disease in U.S. hospitals each year. More than 49,000 mitral valve or aortic valve replacement procedures are performed annually in the U.S., along with a significant number of heart valve repair procedures.

The circulatory system is a closed loop bed of arterial and venous vessels supplying oxygen and nutrients to the body extremities through capillary beds. The driver of the system is the heart providing correct pressures to the circulatory system and regulating flow volumes as the body demands. Deoxygenated blood enters heart first through the right atrium and is allowed to the right ventricle through the tricuspid valve. Once in the right ventricle, the heart delivers this blood through the pulmonary valve and to the lungs for a gaseous exchange of oxygen. The circulatory pressures carry this blood back to the heart via the pulmonary veins and into the left atrium. Filling of the left atrium occurs as the mitral valve opens allowing blood to be drawn into the left ventricle for expulsion through the aortic valve and on to the body extremities. When the heart fails to continuously produce normal flow and pressures, a disease commonly referred to as heart failure occurs.

Heart failure simply defined is the inability for the heart to produce output sufficient to demand. Mechanical complications of heart failure include free-wall rupture, septal-rupture, papillary rupture or dysfunction aortic insufficiency and tamponade. Mitral, aortic or pulmonary valve disorders lead to a host of other conditions and complications exacerbating heart failure further. Other disorders include coronary disease, hypertension, and a diverse group of muscle diseases referred to as cardiomyopothies. Because of this syndrome establishes a number of cycles, heart failure begets more heart failure.

Heart failure as defined by the New York Heart Association in a functional classification.

I. Patients with cardiac disease but without resulting limitations of physical activity. Ordinary physical activity does not cause undue fatigue, palpitation, dyspnea, or anginal pain.

II. Patient with cardiac disease resulting in slight limitation of physical activity. These patients are comfortable at rest. Ordinary physical activity results in fatigue, palpitation, dyspnea, or anginal pain.

III. Patients with cardiac disease resulting in marked limitation of physical activity. These patients are comfortable at rest. Less than ordinary physical activity causes fatigue palpitation, dyspnea, or anginal pain.

IV. Patients with cardiac disease resulting in inability to carry on any physical activity without discomfort. Symptoms of cardiac insufficiency or of the anginal syndrome may be present even at rest. If any physical activity is undertaken, discomfort is increased.

There are many styles of mechanical valves that utilize both polymer and metallic materials. These include single leaflet, double leaflet, ball and cage style, slit-type and emulated polymer tricuspid valves. Though many forms of valves exist, the function of the valve is to control flow through a conduit or chamber. Each style will be best suited to the application or location in the body it was designed for.

Bioprosthetic heart valves comprise valve leaflets formed of flexible biological material. Bioprosthetic valves or components from human donors are referred to as homografts and xenografts are from non-human animal donors. These valves as a group are known as tissue valves. This tissue may include donor valve leaflets or other biological materials such as bovine pericardium. The leaflets are sewn into place and to each other to create a new valve structure. This structure may be attached to a second structure such as a stent or cage or other prosthesis for implantation to the body conduit.

Implantation of valves into the body has been accomplished by a surgical procedure and has been attempted via percutaneous method such as a catheterization or delivery mechanism utilizing the vasculature pathways. Surgical implantation of valves to replace or repair existing valves structures include the four major heart valves (tricuspid, pulmonary, mitral, aortic) and some venous valves in the lower extremities for the treatment of chronic venous insufficiency. Implantation includes the sewing of a new valve to the existing tissue structure for securement. Access to these sites generally include a thoracotomy or a sternotomy for the patient and include a great deal of recovery time. An open-heart procedure can include placing the patient on heart bypass to continue blood flow to vital organs such as the brain during the surgery. The bypass pump will continue to oxygenate and pump blood to the body's extremities while the heart is stopped and the valve is replaced. The valve may replace in whole or repair defects in the patient's current native valve. The device may be implanted in a conduit or other structure such as the heart proper or supporting tissue surrounding the heart. Attachments methods may include suturing, hooks or barbs, interference mechanical methods or an adhesion median between the implant and tissue.

Although valve repair and replacement can successfully treat many patients with valvular insufficiency, techniques currently in use are attended by significant morbidity and mortality. Most valve repair and replacement procedures require a thoracotomy, usually in the form of a median sternotomy, to gain access into the patient's thoracic cavity. A saw or other cutting instrument is used to cut the sternum longitudinally, allowing the two opposing halves of the anterior or ventral portion of the rib cage to be spread apart. A large opening into the thoracic cavity is thus created, through which the surgical team may directly visualize and operate upon the heart and other thoracic contents. Alternatively, a thoracotomy may be performed on a lateral side of the chest, wherein a large incision is made generally parallel to the ribs, and the ribs are spread apart and/or removed in the region of the incision to create a large enough opening to facilitate the surgery.

Surgical intervention within the heart generally requires isolation of the heart and coronary blood vessels from the remainder of the arterial system, and arrest of cardiac function. Usually, the heart is isolated from the arterial system by introducing an external aortic cross-clamp through a sternotomy and applying it to the aorta to occlude the aortic lumen between the brachiocephalic artery and the coronary ostia. Cardioplegic fluid is then injected into the coronary arteries, either directly into the coronary ostia or through a puncture in the ascending aorta, to arrest cardiac function. The patient is placed on extracorporeal cardiopulmonary bypass to maintain peripheral circulation of oxygenated blood.

Since surgical techniques are highly invasive and in the instance of a heart valve, the patient must be put on bypass during the operation, the need for a less invasive method of heart valve replacement has long been recognized. At least as early as 1972, the basic concept of suturing a tissue aortic valve to an expandable cylindrical "fixation sleeve" or stent was disclosed. See U.S. Pat. No. 3,657,744 to Ersek. Other early efforts were disclosed in U.S. Pat. No. 3,671,979 to Mouloupolos and U.S. Pat. No. 4,056,854 to Boretos, relating to prosthetic valves carried by an expandable valve support delivered via catheter for remote placement. More recent iterations of the same basic concept were disclosed, for example, in patents such as U.S. Pat. Nos. 5,411,552, 5,957,949, 6,168,614, and 6,582,462 to Anderson, et al., which relate generally to tissue valves carried by expandable metallic stent support structures which are crimped to a delivery balloon for later expansion at the implantation site.

In each of the foregoing systems, the tissue or artificial valve is first attached to a preassembled, complete support structure (some form of a stent) and then translumenally advanced along with the support structure to an implantation site. The support structure is then forceably enlarged or allowed to self expand without any change in its rigidity or composition, thereby securing the valve at the site.

Despite the many years of effort, and enormous investment of entrepreneurial talent and money, no stent based heart valve system has yet received regulatory approval, and a variety of difficulties remain. For example, stent based systems have a fixed rigidity even in the collapsed configuration, and have inherent difficulties relating to partial deployment, temporary deployment, removal and navigation.

Thus, a need remains for improvements over the basic concept of a stent based prosthetic valve. As disclosed herein a variety of significant advantages may be achieved by eliminating the stent and advancing the valve to the site without a support structure. Only later, the support structure is created in situ such as by inflating one or more inflatable chambers to impart rigidity to an otherwise highly flexible and functionless subcomponent.

SUMMARY OF THE INVENTION

In accordance with one aspect of present invention, there is provided an inflatable or formed in place support for a translumenally implantable heart valve, in which a plurality of tissue supports are flexible and/or movable throughout a range in a radial direction. As used herein, a radial direction is a direction which is transverse to the longitudinal axis of the flow path through the valve.

Further features and advantages of the present invention will become apparent from the detailed description of preferred embodiments which follows, when considered together with the attached drawings and claims.

BRIEF DESCRIPTION OF THE DRAWINGS

FIG. 9A is a front perspective view of another embodiment of an implant.

FIG. 9B is cross-sectional view taken through line 9B-9B of FIG. 9A.

FIG. 10 is an embodiment of a cross-section of an inflation channel.

FIG. 19 is a side view of an un-deployed non-inflatable valve implant.

FIG. 19A is a cross-sectional view taken at line 19A-19A of FIG. 19.

FIGS. 25A-C are side perspective views of a modified embodiment of a non-inflatable valve implant in an expanded, compressed and assembled configuration.

FIG. 28 is a side perspective view of another embodiment of an anchor for an implant valve.

FIG. 29 is a side perspective view of another embodiment of an anchor for an implant valve.

FIG. 30 is a side perspective view of another embodiment of an anchor for an implant valve.

FIG. 32A is a side perspective view of another embodiment of an anchor for an implant valve.

FIG. 33 is a side perspective view of another embodiment of an anchor for an implant valve.

FIGS. 35A and 35B are side views of a modified embodiment of the distal end of the deployment catheter of FIG. 35.

FIG. 44 is a side perspective view of an embodiment of connecting a control wire to a prosthetic valve implant.

FIG. 53A is a side view of an embodiment of an excise device.

FIG. 53B is a closer view of a portion of FIG. 53A.

FIG. 54A is a closer view of the distal end of the excise device of FIG. 53A.

FIG. 54B is a cross-sectional view taken through line 54B-54B of FIG. 53A.

FIG. 54C is a cross-sectional view taken through line 54C-54C of FIG. 53A.

FIG. 55A is a cross-sectional view of a distal end of another embodiment of an excise device.

FIG. 55B is a cross-sectional view taken through line 55B-55B of FIG. 55A.

FIG. 56A is a side view of a distal end of another embodiment of an excise device.

FIG. 56B is a cross-sectional view taken through line 56B-56B of FIG. 56A.

FIG. 56C is a cross-sectional view taken through line 56C-56C of FIG. 56A.

FIG. 65-68 are cross-sectional and side views of portions of the valve of FIG. 65.

DETAILED DESCRIPTION OF THE PREFERRED EMBODIMENTS

Figure 1:
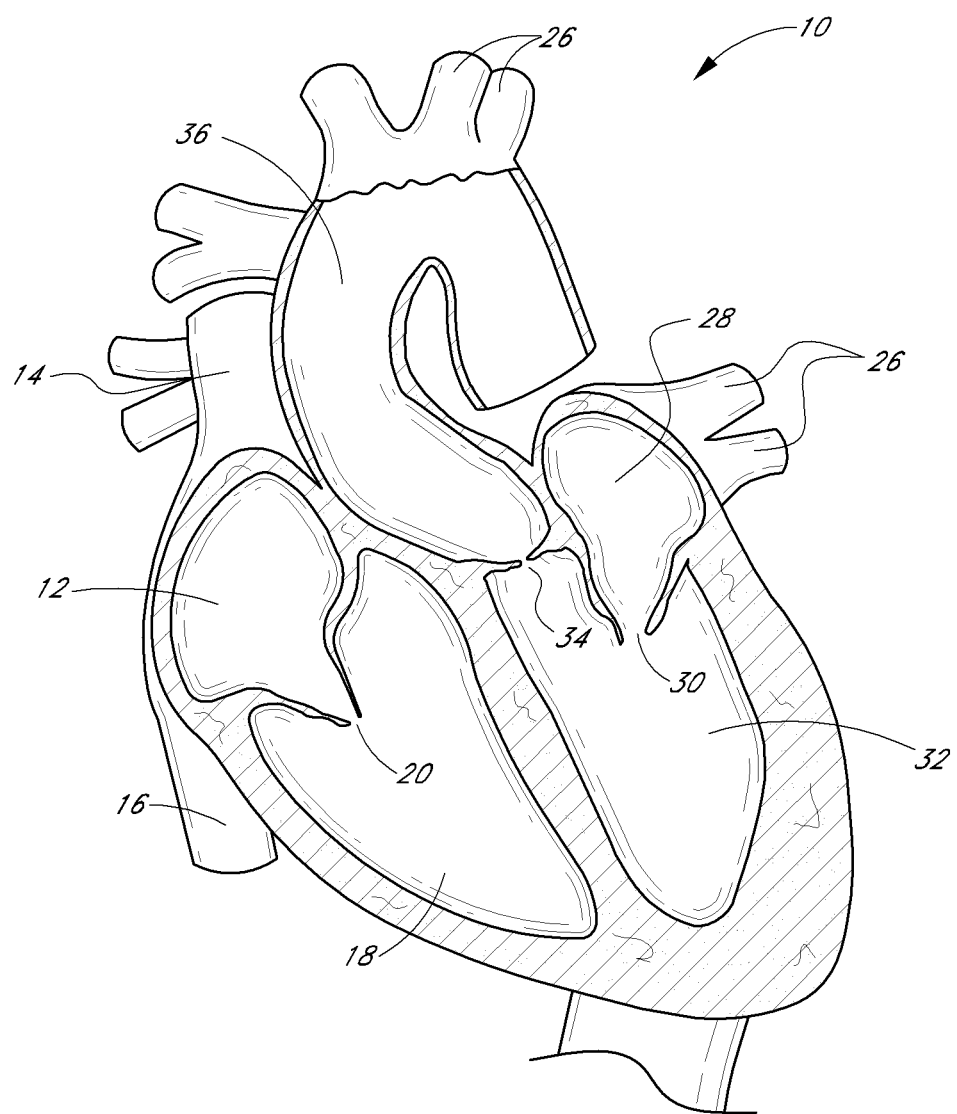
FIG. 1 is a cross-sectional schematic view of a heart and its major blood vessels.

FIG. 1 is a schematic cross-sectional illustration of the anatomical structure and major blood vessels of a heart 10. Deoxygenated blood is delivered to the right atrium 12 of the heart 10 by the superior and inferior vena cava 14, 16. Blood in the right atrium 12 is allowed into the right ventricle 18 through the tricuspid valve 20. Once in the right ventricle 18, the heart 10 delivers this blood through the pulmonary valve 22 to the pulmonary arteries 24 and to the lungs for a gaseous exchange of oxygen. The circulatory pressures carry this blood back to the heart via the pulmonary veins 26 and into the left atrium 28. Filling of the left atrium 28 occurs as the mitral valve 30 opens allowing blood to be drawn into the left ventricle 32 for expulsion through the aortic valve 34 and on to the body extremities through the aorta 36. When the heart 10 fails to continuously produce normal flow and pressures, a disease commonly referred to as heart failure occurs.

One cause of heart failure is failure or malfunction of one or more of the valves of the heart 10. For example, the aortic valve 34 can malfunction for several reasons. For example, the aortic valve 34 may be abnormal from birth (e.g., bicuspid, calcification, congenital aortic valve disease), or it could become diseased with age (e.g., acquired aortic valve disease). In such situations, it can be desirable to replace the abnormal or diseased valve 34.

Figure 2:
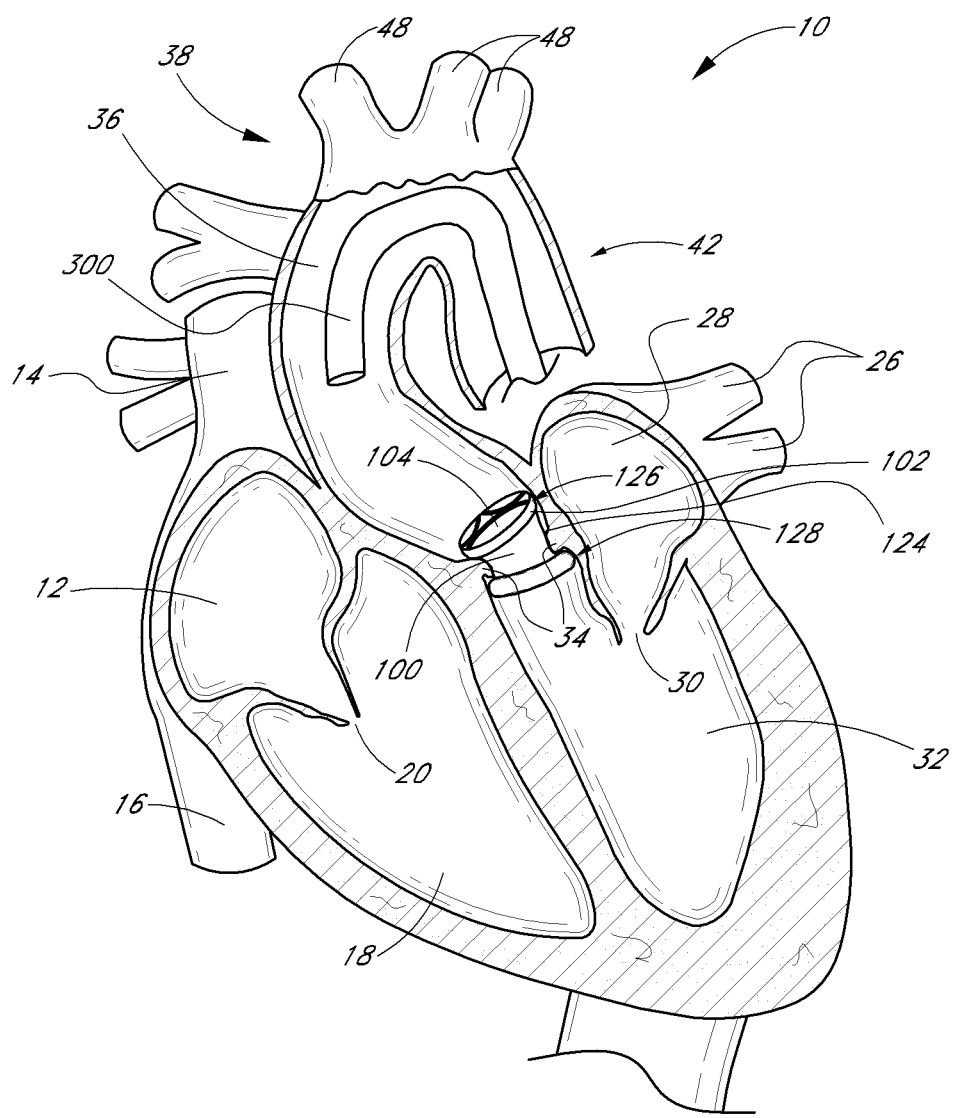
FIG. 2 is a partial cut-away view a left ventricle and aortic with an prosthetic aortic valve implant according to one embodiment of the present invention positioned therein.

FIG. 2 is a schematic illustration of the left ventricle 32, which delivers blood to the aorta 36 through the aortic valve 34. The aorta 36 comprises (i) the ascending aorta 38, which arises from the left ventricle 32 of the heart 10, (ii) the aortic arch 10, which arches from the ascending aorta 38 and (iii) the descending aorta 42 which descends from the aortic arch 40 towards the abdominal aorta (not shown). Also shown are the principal branches of the aorta 14, which include the innomate artery 44 that immediately divides into the right carotid artery (not shown) and the right subclavian artery (not shown), the left carotid 46 and the subclavian artery 48.

Inflatable Prosthetic Aortic Valve Implant

With continued reference to FIG. 2, a prosthetic aortic valve implant 100 in accordance with an embodiment of the present invention is shown spanning the native abnormal or diseased aortic valve 34, which has been partially removed as will be described in more detail below. The implant 100 and various modified embodiments thereof will be described in detail below. As will be explained in more detail below, the implant 100 is preferably delivered minimally invasively using an intravascular delivery catheter 200 or trans apical approach with a trocar.

In the description below, the present invention will be described primarily in the context of replacing or repairing an abnormal or diseased aortic valve 34. However, various features and aspects of methods and structures disclosed herein are applicable to replacing or repairing the mitral 30, pulmonary 22 and/or tricuspid 20 valves of the heart 10 as those of skill in the art will appreciate in light of the disclosure herein. In addition, those of skill in the art will also recognize that various features and aspects of the methods and structures disclosed herein can be used in other parts of the body that include valves or can benefit from the addition of a valve, such as, for example, the esophagus, stomach, ureter and/or vesice, biliary ducts, the lymphatic system and in the intestines.

In addition, various components of the implant and its delivery system will be described with reference to coordinate system comprising "distal" and "proximal" directions. In this application, distal and proximal directions refer to the deployment system 300, which is used to deliver the implant 100 and advanced through the aorta 36 in a direction opposite to the normal direction of blood through the aorta 36. Thus, in general, distal means closer to the heart while proximal means further from the heart with respect to the circulatory system.

With reference now to FIGS. 3A-D, the implant 100 of the illustrated embodiment generally comprises an inflatable cuff or body 102, which is configured to support a valve 104 (see FIG. 2) that is coupled to the cuff 102. As will be explained in more detail below, the valve 104 is configured to move in response to the hemodynamic movement of the blood pumped by the heart 10 between an "open" configuration where blood can throw the implant 100 in a first direction (labeled A in FIG. 3B) and a "closed" configuration whereby blood is prevented from back flowing through the valve 104 in a second direction B (labeled B in FIG. 3B).

In the illustrated embodiment, the cuff 102 comprises a thin flexible tubular material 106 such as a flexible fabric or thin membrane with little dimensional integrity. As will be explained in more detail below, the cuff 102 can be changed preferably, in situ, to a support structure to which other components (e.g., the valve 104) of the implant 100 can be secured and where tissue ingrowth can occur. Uninflated, the cuff 102 is preferably incapable of providing support. In one embodiment, the cuff 102 comprises Dacron, PTFE, ePTFE, TFE or polyester fabric 106 as seen in conventional devices such as surgical stented or stent less valves and annuloplasty rings. The fabric 106 thickness may range from about 0.002 inches to about 0.020 inches of an inch depending upon material selection and weave. Weave density may also be adjusted from a very tight weave to prevent blood from penetrating through the fabric 106 to a looser weave to allow tissue to grow and surround the fabric 106 completely.

Additional compositions and configurations of the cuff 102 will be described in more detail below.

Figure 3A:
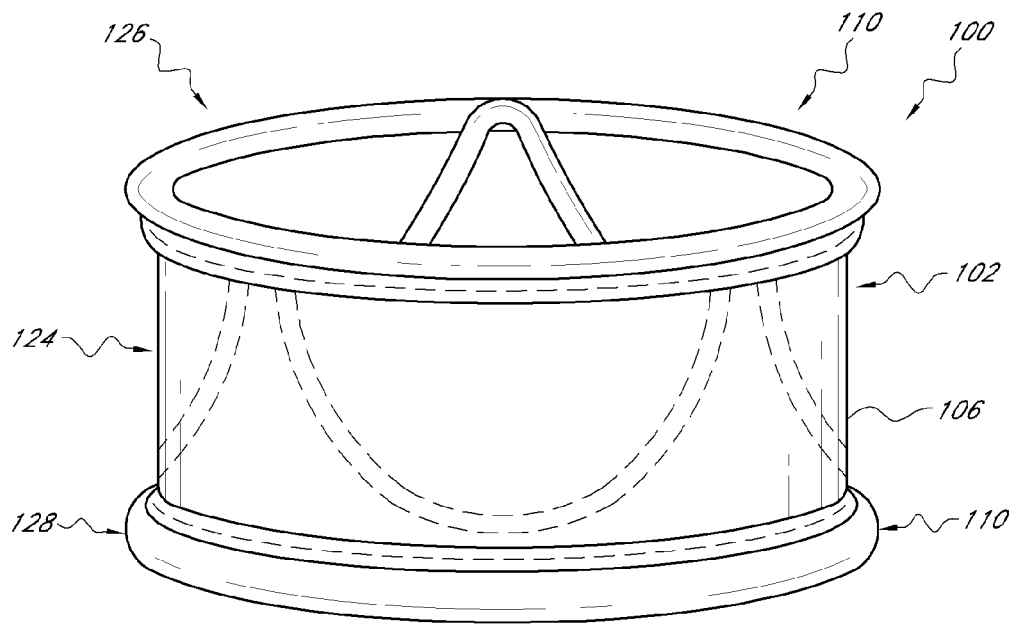
FIG. 3A is a front perspective view of the implant of FIG. 2.
Figure 3B:
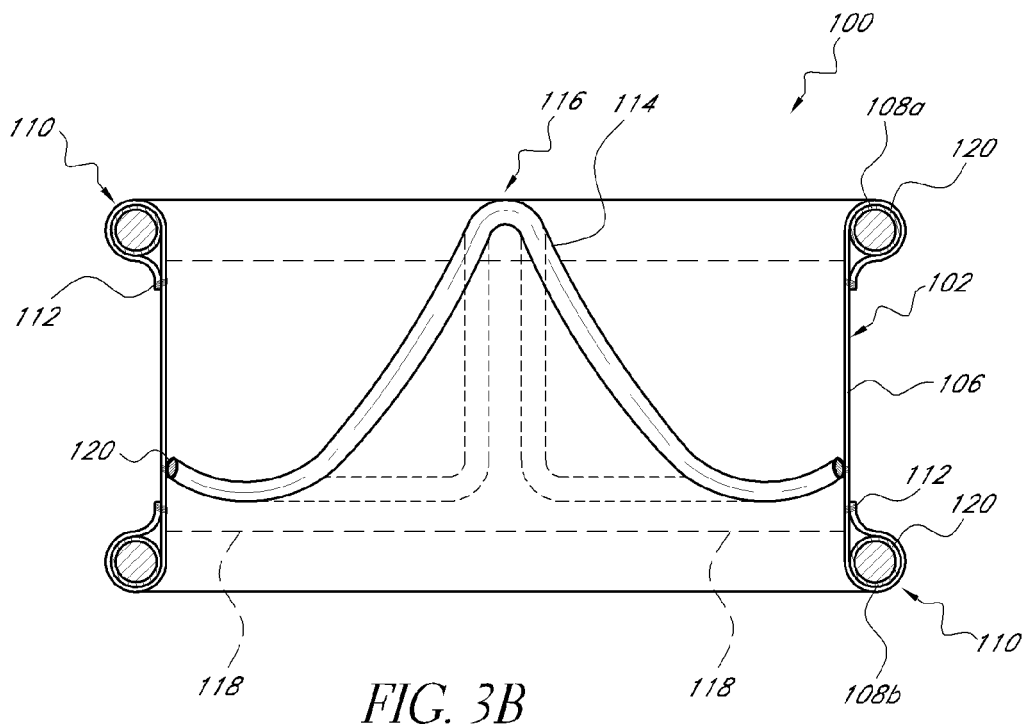
FIG. 3B is a cross-sectional side view of the implant of FIG. 3A.
Figure 3C:
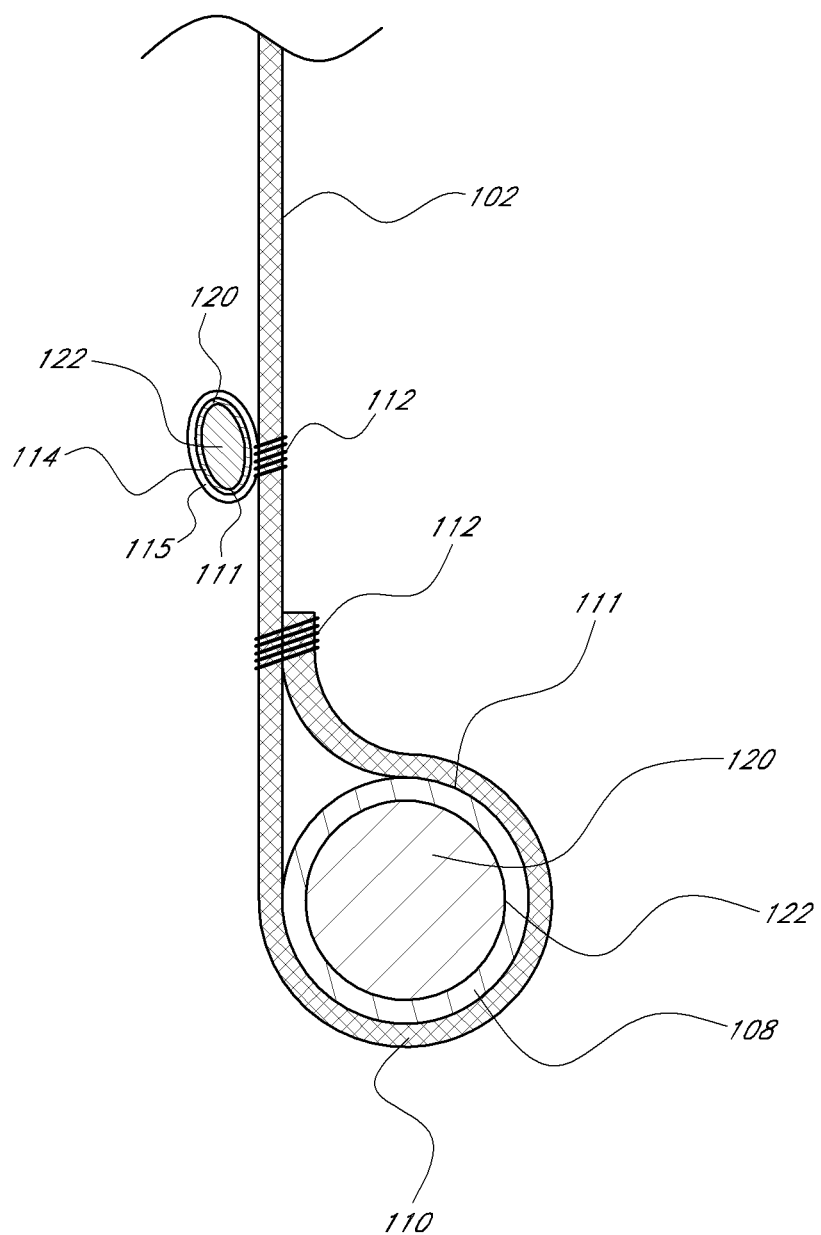
FIG. 3C is an enlarged cross-sectional view of a lower portion of FIG. 3B.
Figure 3D:
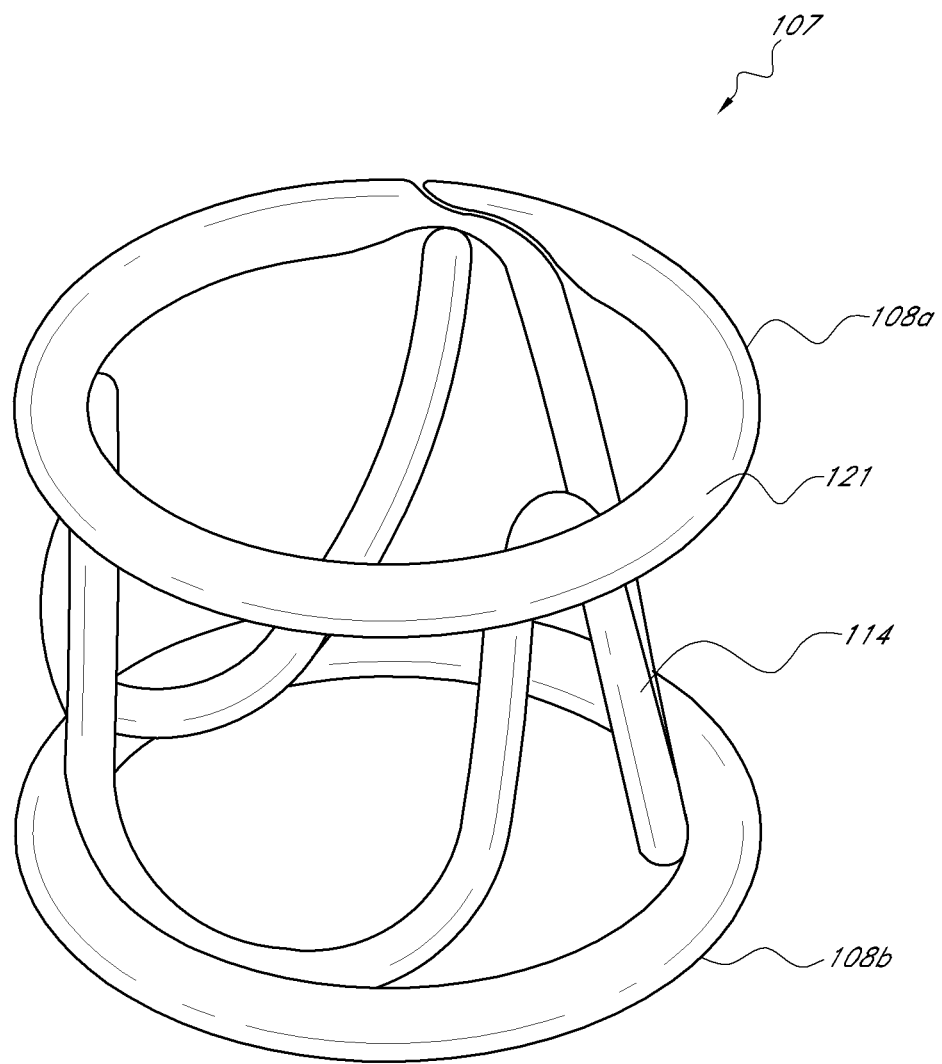
FIG. 3D is a front perspective view of an inflatable support structure of the implant of FIG. 3A.

With continued reference to FIGS. 3B-3D, in the illustrated embodiment, the implant 100 includes an inflatable structure 107 that forms one or more of inflation channels 120, which in illustrated embodiment are formed in part by a pair of distinct balloon rings or toroids 108a, 108b. The rings 108a, 108b in this embodiment are positioned at the proximal and distal ends 126, 128 of the cuff 102. As will be explained below, the rings 108 can be secured to the body 102 in any of a variety of manners. With reference to FIG. 3C, in the illustrated embodiment, the rings 108 are secured within folds 110 formed at the proximal and distal ends 126, 128 of the cuff 102. The folds 110, in turn, are secured by sutures or stitches 112. See FIG. 3C.

The illustrated inflatable structure 107 also includes inflatable struts 114, which in the illustrated embodiment are formed from an annular zig-zag pattern having three proximal bends 116 and three distal bends 118. As best seen in FIG. 3C, the struts 114 can be secured to the cuff 102 within pockets 115 of cuff material by sutures 112. Of course, as will be explained in more detail, other embodiments other configurations can be can be used to secure the struts 114 to the fabric 106.

As mentioned above, the inflatable rings 108 and struts 114 form the inflatable structure 107, which, in turn, defines the inflation channels 120. The inflation channels 120 receive inflation media 122 to generally inflate the inflatable structure 107. When inflated, the inflatable rings and struts 108, 114 provide can provide structural support to the inflatable implant 100 and/or help to secure the implant 100 within the heart 10. Uninflated, the implant 100 is a generally thin, flexible shapeless assembly that is preferably uncapable of support and is advantageously able to take a small, reduced profile form in which it can be percutaneously inserted into the body. As will be explained in more detail below, in modified embodiments, the inflatable structure 107 may comprise any of a variety of configurations of inflation channels 120 that can be formed from other inflatable members in addition to or in the alternative to the inflatable rings 108 and struts 114 shown in FIGS. 3A and 3B. In addition, the inflatable media 122 and methods for inflating the inflatable structure 107 will be described in more detail below.

With particular reference to FIG. 3D, in the illustrated embodiment, the proximal ring 108a and struts 114 are joined such that the inflation channel 120 of the proximal ring 108a is in fluid communication with the inflation channel 120 of the struts 114. In contrast, the inflation channel 120 of the distal ring 108b is not in communication with the inflation channels 120 of the proximal ring 108a and struts 114. In this manner, the inflation channels of the (i) proximal ring 108a and struts 115 can be inflated independently from the (ii) distal ring 108b. As will be explained in more detail below, the two groups of inflation channels 120 are preferably connected to independent fluid delivery devices to facilitate the independent inflation. It should be appreciated that in modified embodiments the inflatable structure can include less (i.e., one common inflation channel) or more independent inflation channels. For example, in one embodiment, the inflation channels of the proximal ring 108a, struts 114 and distal ring 108b can all be in fluid communication with each other such that they can be inflated from a single inflation device. In another embodiment, the inflation channels of the proximal ring the proximal ring 108a, struts 114 and distal ring 108b can all be separated and therefore utilize three inflation devices.

With reference to FIG. 3B, in the illustrated embodiment, the proximal ring 108a has a cross-sectional diameter of about 0.090 inches. The struts have a cross-sectional diameter of about 0.060 inches. The distal ring 108b has a cross-sectional diameter of about 0.090 inches diameter.

In prior art surgically implanted valves, the valve generally includes a rigid inner support structure that is formed from polycarbonate, silicone or titanium wrapped in silicone and Dacron. These surgical valves vary in diameter for different patients due to the respective implantation site and orifice size. Generally the largest diameter implantable is the best choice for the patient. These diameters range from about 16 mm to 30 mm.

As mentioned above, the implant 100 allows the physician to deliver a valve via catheterization in a lower profile and a safer manner than currently available. When the implant 100 is delivered to the site via a delivery catheter 300, the implant 100 is a thin, generally shapeless assembly in need of structure and definition. At the implantation site, the inflation media 122 (e.g., a fluid or gas) may be added via a catheter lumen to the inflation channels 120 providing structure and definition to the implant 100. The inflation media 122 therefore comprises part of the support structure for implant 100 after it is inflated. The inflation media 122 that is inserted into the inflation channels 120 can be pressurized and/or can solidify in situ to provide structure to the implant 100. Additional details and embodiments of the implant 100, can be found in U.S. Pat. No. 5,554,185 to Block, the disclosure of which is expressly incorporated in its entirety herein by reference.

Figure 2A:
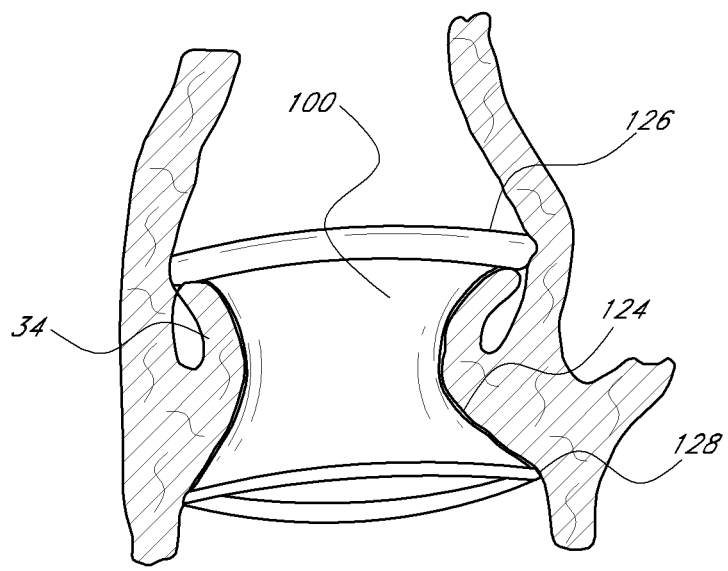
FIG. 2A is a side view of the implant of FIG. 2 positioned across a native aortic valve.

With reference to FIG. 2A, in the illustrated embodiment, the implant 100 has shape that can be viewed as a tubular member or hyperboloid shape where a waist 124 excludes the native valve or vessel 34 and proximally the proximal end 126 forms a hoop or ring to seal blood flow from re-entering the left ventricle 32 Distally, the distal end 128 also forms a hoop or ring to seal blood from forward flow through the outflow track. Between the two ends 126, 128, the valve 104 is mounted to the body 102 such that when inflated the implant 100 excludes the native valve 34 or extends over the former location of the native valve 34 and replaces its function. The distal end 128 should have an appropriate size and shape so that it does not interfere with the proper function of the mitral valve, but still secures the valve adequately. For example, there may be a notch, recess or cut out in the distal end 128 of the device to prevent mitral valve interference. The proximal end 126 is designed to sit in the aortic root. It is preferably shaped in such a way that it maintains good apposition with the wall of the aortic root. This prevents the device from migrating back into the ventricle 32. In some embodiments, the implant 100 is configured such that it does not extend so high that it interferes with the coronary arteries.

Any number of additional inflatable rings or struts may be between the proximal and distal end 126, 128. The distal end 126 of the implant 100 is preferably positioned within the left ventrical 34 and can utilize the aortic root for axial stabilization as it may have a larger diameter than the aortic lumen. This may lessen the need for hooks, barbs or an interference fit to the vessel wall. Since the implant 100 may be placed without the aid of a dilatation balloon for radial expansion, the aortic valve 34 and vessel may not have any duration of obstruction and would provide the patient with more comfort and the physician more time to properly place the device accurately. Since the implant 100 is not utilizing a support member with a single placement option as a plastically deformable or shaped memory metal stent does, the implant 100 may be movable and or removable if desired. This could be performed multiple times until the implant 100 is permanently disconnected from the delivery catheter 300 as will be explained in more detail below. In addition, the implant 100 can include features, which allow the implant 100 to be tested for proper function, sealing and sizing, before the catheter 300 is disconnected. When the disconnection occurs, a seal at the device may be required to maintain the fluid within the inflation channels 120. Devices for providing such a seal will be described in more detail below.

Figure 2B:
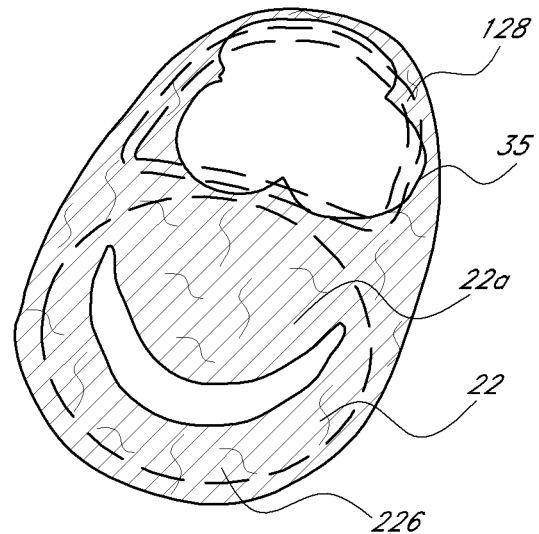
FIG. 2B is a schematic top illustration of a modified embodiment of an implant positioned across the aortic valve.
Figure 2C:
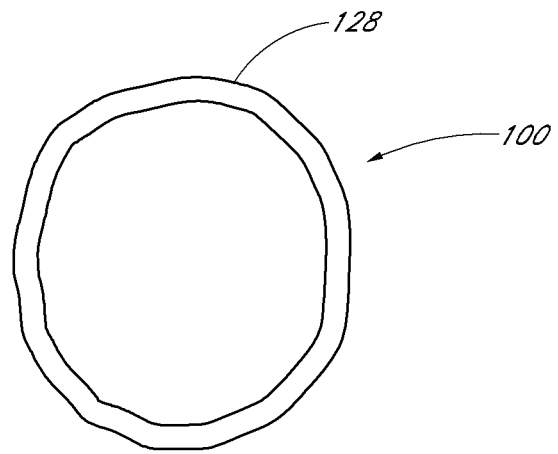
FIG. 2C is a schematic cross-sectional view of a modified embodiment of an implant.
Figure 2D:
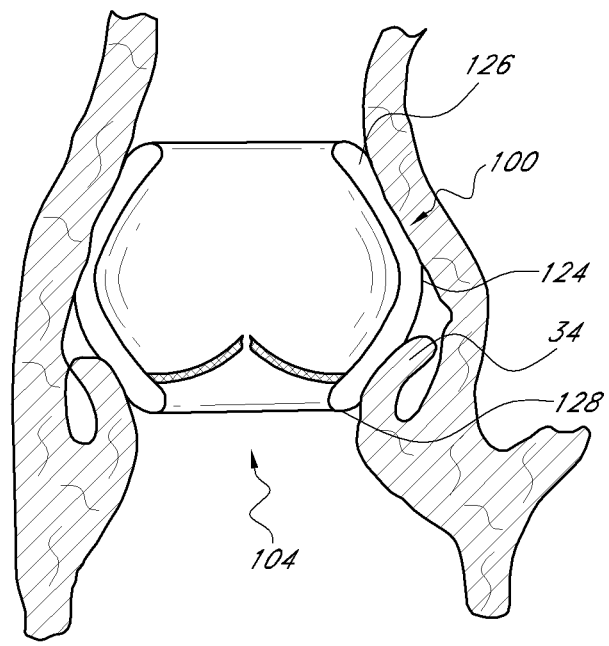
FIG. 2D is a side cross-sectional view of another embodiment of an implant positioned at the aortic valve.
Figure 2E:
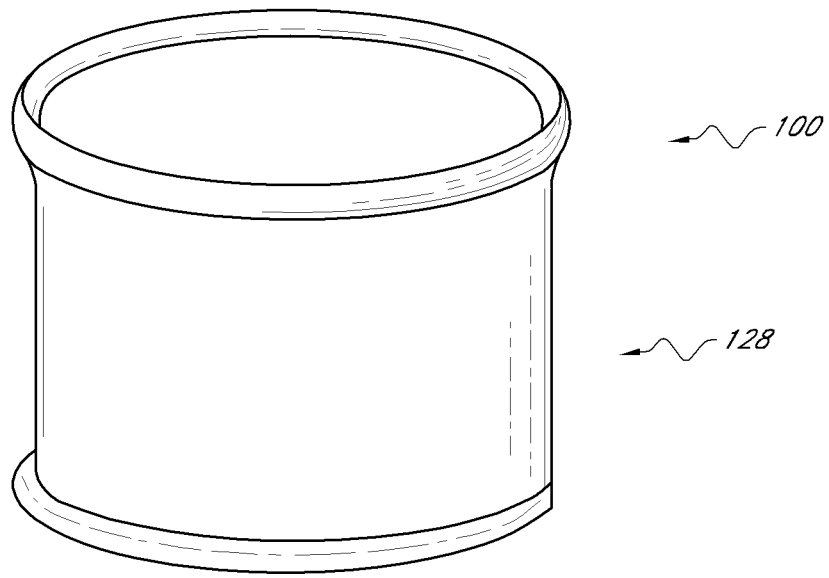
FIGS. 2E and 2F are side and bottom views of another embodiment of an implant.
Figure 2F:
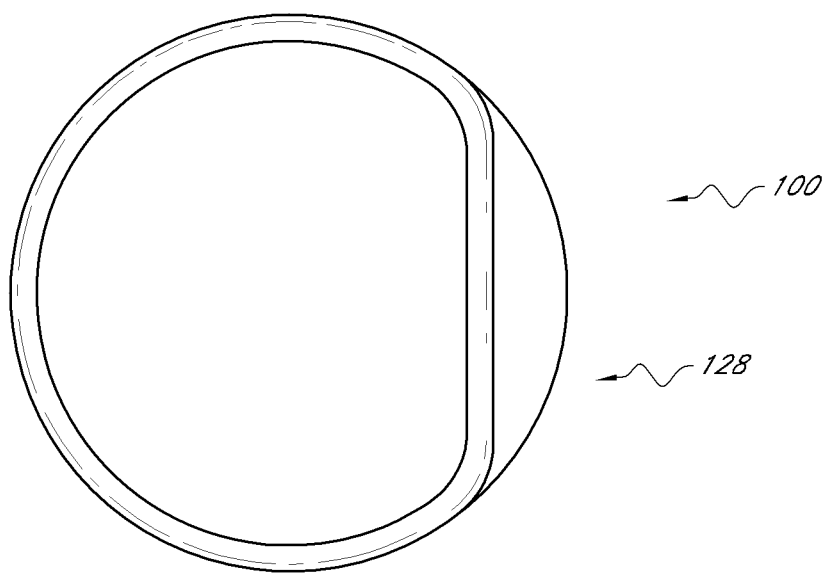
Figure 2G:
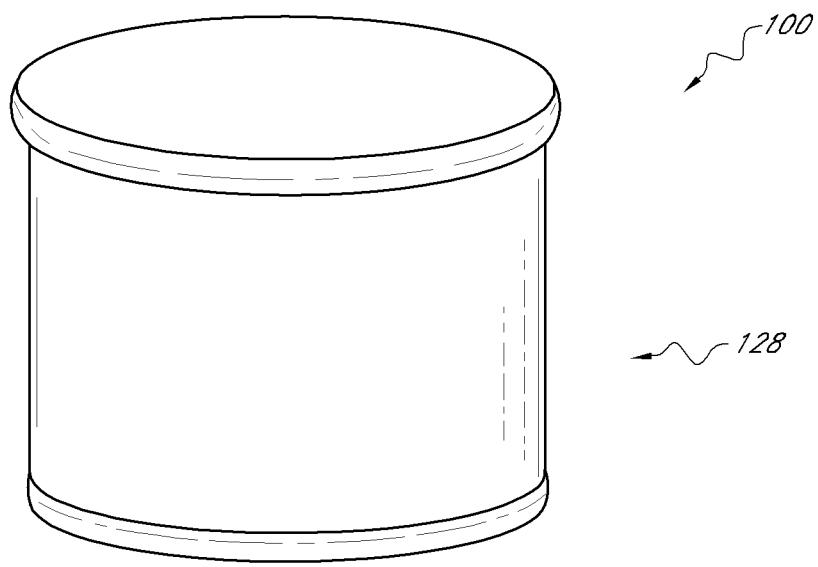
FIGS. 2G and 2H are side and bottom views of another embodiment of an implant.
Figure 2H:
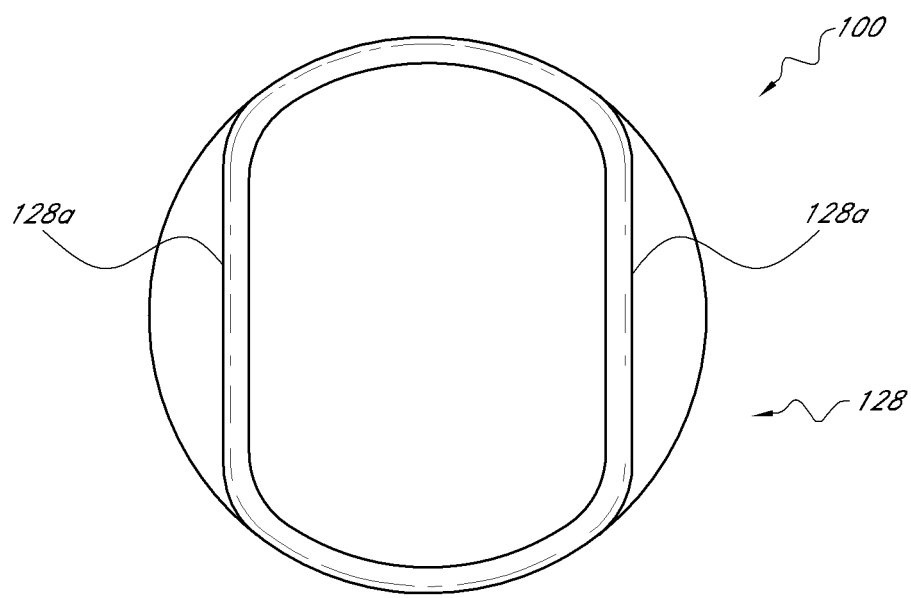

With reference to FIG. 2B, in a modified embodiment, the shape of the distal end 128 of the implant 100 can be configured so that the impact to the shape of the mitral valve annulus is minimized. This is particularly important in the implant 100 extends into or beyond the native annulus 35 and into the left ventrical 32 as shown in FIG. 2A. In general, the distal end 128 can be shaped so that the chordae and leaflet tissue from the mitral valve are not impacted or abraded by the implant 100 during their normal motion. In this manner, the implant 100 does not apply or only applies minimal pressure to the major conduction pathways of the heart. Several different embodiment of the valve 100 address these issues. In the embodiment shown in FIGS. 2B, 2E and 2F, the distal end 128 of the implant has of a "D" shaped cross section where the flat side of the "D" is positioned to correspond with the mitral valve 22 location. In another embodiment shown in FIG. 2C, the distal end 128 of the implant 100 has a generally elliptical cross section, where the minor axis of the ellipse extends generally from the mitral valve location to the septal wall. In yet another embodiment, the distal end 128 of the implant 100 contains feet or enlarged pads, designed to contact the native anatomy at the desired locations. For example, the desired locations are just below the annulus in the areas on either side of the mitral valve. The feet may be inflatable structures or separate mechanical structures such as deployable anchors may be made from materials such as stainless steel or nitinol. These anchors can deployed by the inflation media or a secondary system. FIGS. 2G and 2H illustrate an embodiment in which the distal end of the valve 100 has a pair of generally opposing flat sides 128a.

In yet another embodiment of the implant 100, the implant 100 is configured such that it does affect the mitral valve 22. In such an embodiment, the distal end 128 of the implant 100 has a protrusion or feature that pushes on the annulus of the mitral valve 22 from the aortic root or aortic valve annulus. In this way, mitral regurgitation is treated by pushing the anterior leaflet closer 22a to the posterior leaflet 22b and improving the coaptation of the valve. This feature can be a separate device from the implant 100 and/or it may be actuated by a secondary mechanism, or it may simply be a function of the shape of the implant 100.

In yet another modified embodiment the implant 100 (see FIG. 2D), for an aortic valve replacement application, the implant 100 uses both the top and bottom of the aortic root for securement. In this case, the axial force pushing the implant 100 away from the heart 10 is resisted by a normal force from the upper portion of the aortic root. A implant 100 designed to be implanted in this configuration can have a different configuration than an implant designed to anchor around the annulus (e.g., the implant 100 shown in FIG. 2A). For example, as shown in FIG. 2D, the implant 100 can have a cylindrical or partially spherical shape, where the diameter in the mid portion 124 of the device is larger than the diameter at the proximal or distal portions 126, 128. The valve 104 can be located in the distal portion 128 of the implant 100 below the coronary arteries, preferably in a supra-annular position but an intra-annular position would also be possible. Anchors (not shown) can also be used with a device of this configuration. The anchors preferably have a length of 1 to 4 mm and a diameter for 0.010 to 0.020 inches.

With reference back to FIGS. 3A and 3B, the body 102 may be made from many different materials such as Dacron, TFE, PTFE, ePTFE, woven metal fabrics, braided structures, or other generally accepted implantable materials. These materials may also be cast, extruded, or seamed together using heat, direct or indirect, sintering techniques, laser energy sources, ultrasound techniques, molding or thermoforming technologies. Since the body 102 generally surrounds the inflation lumens 120, which can be formed by separate members (e.g., rings 108), the attachment or encapsulation of these lumens 120 can be in intimate contact with the body material 106 or a loosely restrained by the surrounding material 106. These inflation lumens 120 can also be formed also by sealing the body material 106 to create an integral lumen from the body 102 itself. For example, by adding a material such as a silicone layer to a porous material such as Dacron, the fabric 106 can resist fluid penetration or hold pressures if sealed. Materials may also be added to the sheet or cylinder material to create a fluid tight barrier. However, in the illustrated embodiment of FIGS. 3A and 3B, the inflation lumens 120 are formed by balloons 111 (see FIG. 4C), which form the separate inflation components 108a, 108b, 122, which are, in turn, secured to the material 106.

Various shapes of the body 102 may be manufactured to best fit anatomical variations from person to person. As described above, these may include a simple cylinder, a hyperboloid, a device with a larger diameter in its mid portion and a smaller diameter at one or both ends, a funnel type configuration or other conforming shape to native anatomies. The shape of the implant 100 is preferably contoured to engage a feature of the native anatomy in such a way as to prevent the migration of the device in a proximal or distal direction. In one embodiment the feature that the device engages is the aortic root or aortic bulb 34 (see e.g., FIG. 2A), or the sinuses of the coronary arteries. In another embodiment the feature that the device engages is the native valve annulus, the native valve or a portion of the native valve. In certain embodiments, the feature that the implant 100 engages to prevent migration has a diametral difference between 1% and 10%. In another embodiment the feature that the implant 100 engages to prevent migration the diameter difference is between 5% and 40%. In certain embodiments the diameter difference is defined by the free shape of the implant 100. In another embodiment the diameter difference prevents migration in only one direction. In another embodiment. the diameter difference prevents migration in two directions, for example proximal and distal or retrograde and antigrade. Similar to surgical valves, the implant 100 will vary in diameter ranging from about 14 mm to about 30 mm and have a height ranging from about 10 mm to about 30 mm in the portion of the implant 100 where the leaflets of the valve 104 are mounted. Portions of the implant 100 intended for placement in the aortic root may have larger diameters preferably ranging from about 20 to about 45 mm Different diameters of valves will be required to replace native valves of various sizes. For different locations in the anatomy, different lengths of valves or anchoring devices will also be required. For example a valve designed to replace the native aortic valve needs to have a relatively short length because of the location of the coronary artery ostium (left and right arteries). A valve designed to replace or supplement a pulmonary valve could have significantly greater length because the anatomy of the pulmonary artery allows for additional length.

Figure 4:
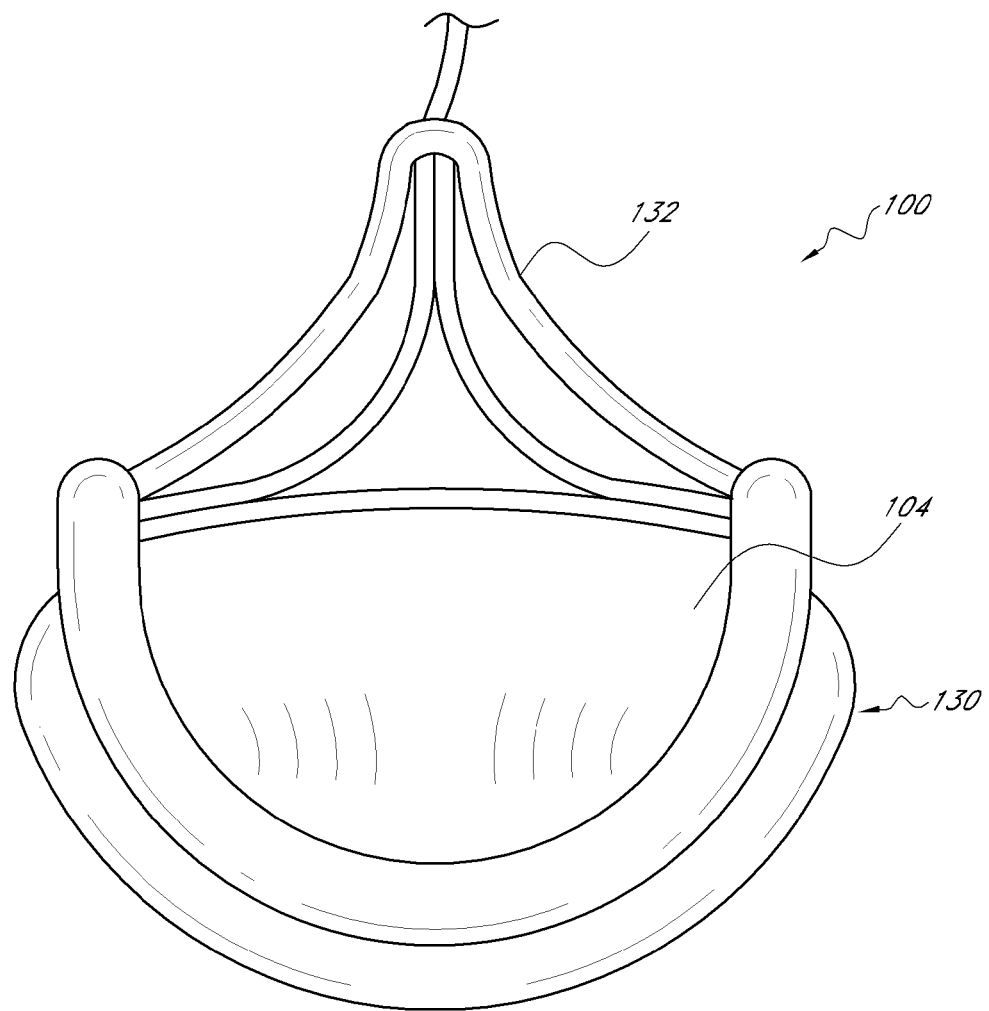
FIG. 4 is a front perspective view of a modified embodiment of an implant.

FIG. 4 illustrates a modified embodiment of the implant 100 in which the implant 100 includes a distal inflation ring 130 with three commissural inflatable supports posts 132, which are arranged in a manner similar to that described above. The valve 104 is supported by the distal inflation ring 130 and support posts 132. This shape is similar to a commercially available valve sold by Edwards Life Science under the trade name of Magna™ and many other commercially available surgical valves. However, the illustrated embodiment is advantageous because of the inflation channels (not shown) in the distal inflation ring 130 and supports posts 132. As described above, the inflation channels of the inflation ring 130 and support posts 132 can be in fluid connection or separated.

Other variations of inflatable valve shapes may include an implant 100 in which entire or substantially the entire cuff 102 forms an cylindrical pocket that is filled with fluid creating a cylinder shape with commissural supports defined by sinusoidal patterns cut from a cylindrical portion of the body 102. In such an embodiment, there may be a desire to seam or join the body 102 together at points or areas to provide passageways for fluid to flow or be restricted. This may also allow for wall definition of the body 102 defining a thickness of the cylinder. It may be desired to maintain a thin body wall allowing the largest area where blood or other fluids may pass through the valve. The wall thickness of the inflated implant 100 may vary from 0.010 to 0.100 of an inch depending upon construction, pressures and materials. There also may be a desire to vary the thickness of the cuff wall from distal to proximal or radially. This would allow for other materials such as fixed pericardial tissue or polymer valve materials to be joined to the wall where support is greatest, or allow the maximum effective orifice area in the area of the implant 100 its self. The implant 100 may be sealed fluid tight by glue, sewing, heat or other energy source sufficient to bond or fuse the body material together. There can be secondary materials added to the cuff for stiffness, support or definition. These may include metallic elements, polymer segments, composite materials.

Figure 5A:
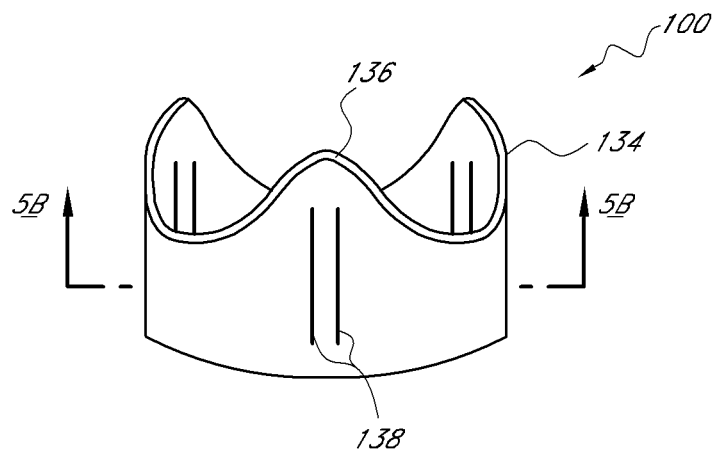
FIG. 5A is a front perspective view of another modified embodiment of an implant.
Figure 5B:
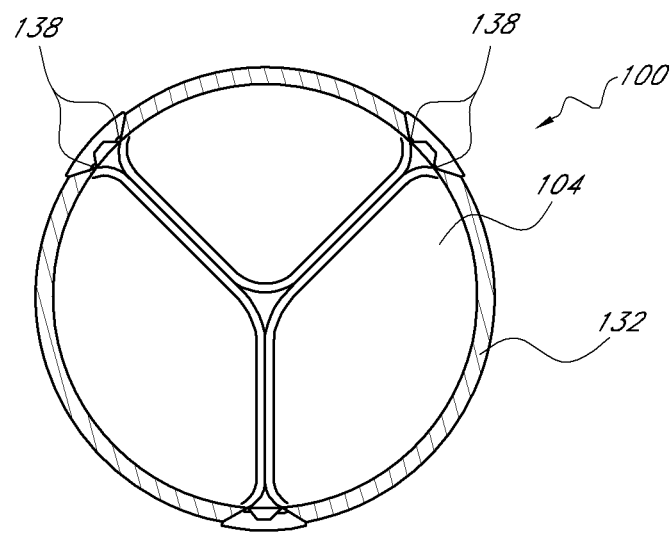
FIG. 5B is cross-sectional view taken through line 5B-5B of FIG. 5A

FIGS. 5A and 5B illustrate an example of such the embodiment described above. In the illustrated embodiment, the body 102 defines a generally sleeve shaped lumen 132. The top surface 134 of the body 102 is scalloped shaped. The peaks or commissars 136 of the top surface 134 are supported by elongated members 138 positioned within or along the outer surface of the body 102. The leaflets 104 are supported within the body 102 with its edges corresponding to the supported commissars 136. The members 138 can comprise metallic wire or laser-cut elements. These elements 138 may be attached by conventional techniques such as sewing, gluing or woven to the body 102. The elements 138 can range in cross section from round, oval, square or rectangular. Dimensionally they can have a width and or thickness from 0.002 to 0.030 inches. Materials for these elements 138 can be stainless steel, Nitinol, Cobalt-Chromium such as MP35N or other implant grade materials. These elements 138 can provide visualization under conventional imaging techniques such as fluoroscopy, echo, or ultrasound. Radiopaque markers may be desired to define the proximal and distal ends of the cuff and these markers may be materials such as gold, platinum iridium, or other materials that would provide an imaging element on body 102.

Figure 6:
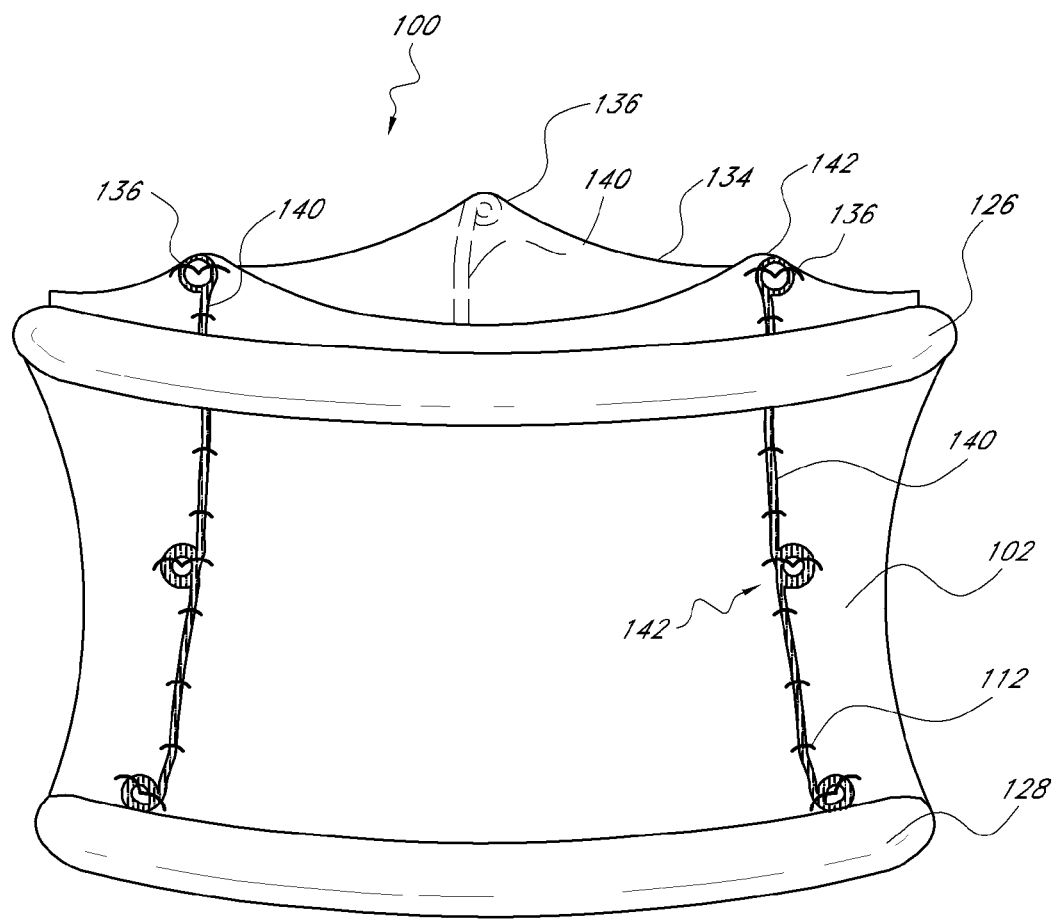
FIG. 6 is a front perspective view of another embodiment of an implant.

FIG. 6 illustrates another embodiment of the valve 100, which includes a body 102, with distal and proximal ends 126, 128 supported by rings (not shown) as described above. As compared to the embodiment of FIGS. 3A and 3B, in this embodiment, the inflatable struts 114 are replaced by elongated stiffening members 140. The stiffening members 140 can be positioned on the body 102 to generally correspond to the commissars 136 of a scalped to surface 134 as described above. The stiffening members 140 can be coupled to the body 102 in any of a variety of manners. In the illustrated embodiment, the stiffening member 140 are coupled to the body 102 through a combinations of sutures 112 and loops 142 that extend through the body 102.

The stiffening members 140 can be metallic wire, ribbon or tube. They may vary in thickness from 0.005 to 0.050 inches and taper or vary in thickness, width or diameter. As mentioned embodiment, the members 140 can be used to support the valve commissars 136, and/or define the height of the cuff or be attachment points for the deployment catheter. These members 140 may be sewn to or woven into the cuff material 106 through conventional techniques as described above and may be shaped with hoops to accept thread or wires. The members 140 may also be formed from a hypotube, allowing deployment control wires or a deployment control system as will be described below to pass through the stiffening wires or to attach to them. Other lengths of stiffening wires are also possible, in some instances a shorter wire may be preferred, either to allow a smaller profile, better conform to a calcified valve annulus, or to ensure positive engagement of an anchor. Short sections of stiffening wires may also be positioned in directions other than the axial direction. Positioning wires off axis may allow the valve to move more naturally relative to the native tissue, or prevent anchors from rotating and disengaging. The stiffening members 140 may be substantially straight pieces of wire.

Figure 7A:
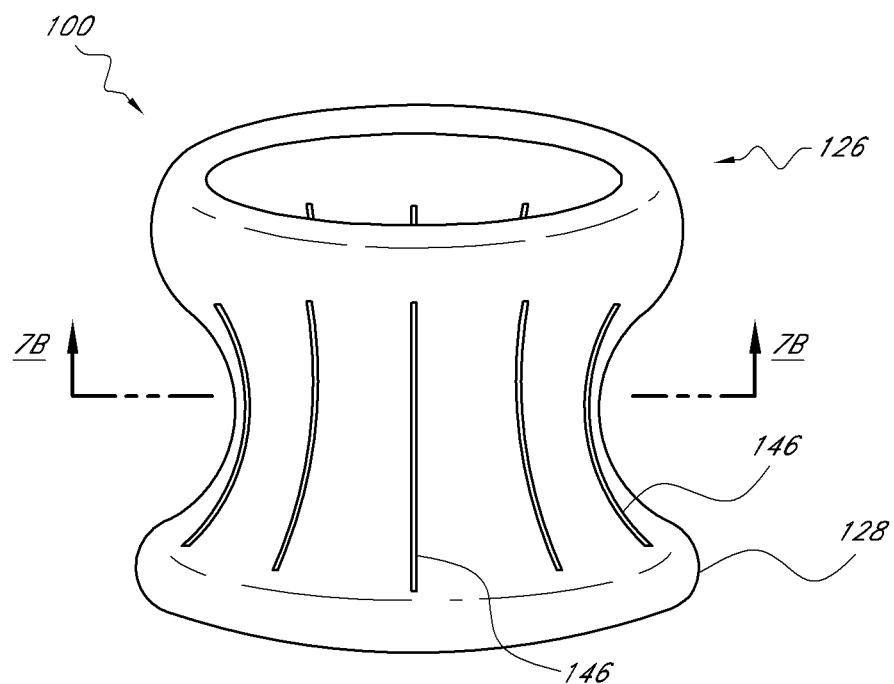
FIG. 7A is a front perspective view of another embodiment of an implant.
Figure 7B:
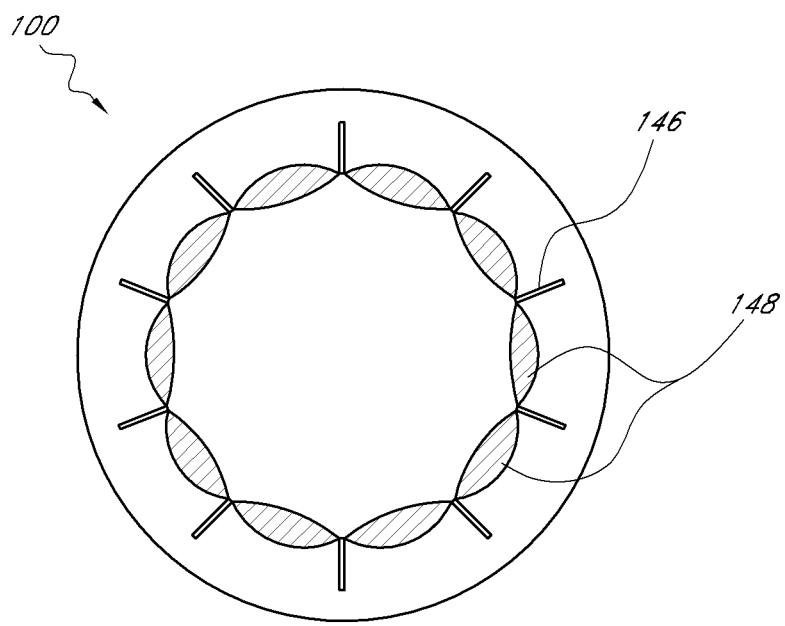
FIG. 7B is cross-sectional view taken through line 7B-7B of FIG. 7A.

FIGS. 7A and 7B illustrate yet another embodiment of the implant 100 in which substantially the entire body 102 is filled with fluid creating an hour glass shape. Between the proximal and distal ends 126, 128, the body 102 includes axially extending channels 46 which form axially extending lumens 48 for extending over the native valve or valve stem.

Figure 8A:
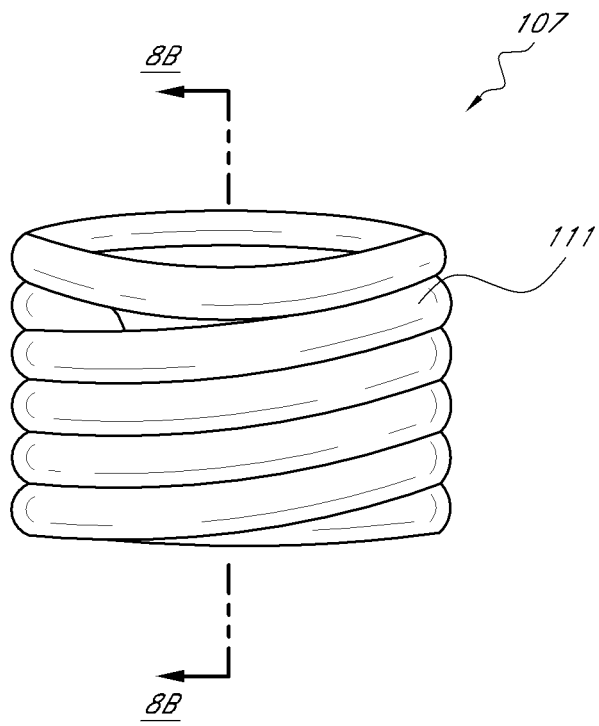
FIG. 8A is a front perspective view of another embodiment of an implant.
Figure 8B:
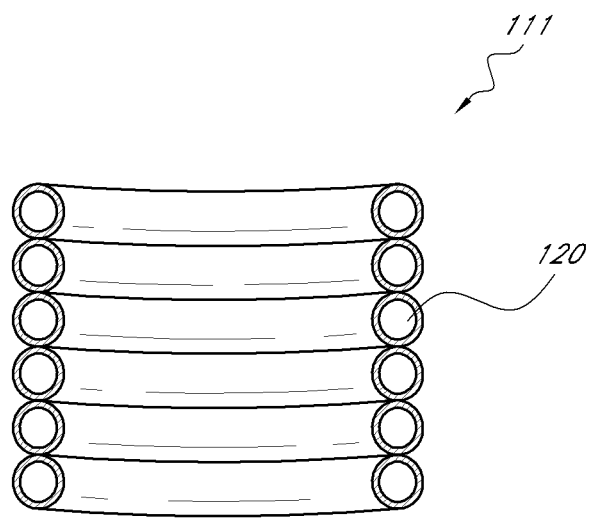
FIG. 8B is cross-sectional view taken through line 8B-8B of FIG. 8A

In the embodiments described herein, the inflation channels 120 may be configured such that they are of round (see FIG. 8A), oval, square (FIG. 10), rectangular (see FIG. 9B) or parabolic shape in cross section. Round cross sections may vary from 0.020-0.100 inches in diameter with wall thicknesses ranging from 0.0005-0.010 inches. Oval cross sections may have an aspect ratio of two or three to one depending upon the desired cuff thickness and strength desired. In embodiments in which the lumens 120 are formed by balloons 111, these lumens 120 can be constructed from conventional balloon materials such as nylon, polyethylene, PEEK, silicone or other generally accepted medical device material. They may be helically coiled into a cylinder shape creating a tube (see FIG. 8A) or looped radially to create a series of toroids (see FIG. 9A) or undulate (see FIG. 3C) to create a sinusoidal pattern to provide support both radially and axially. A combination of these patterns may be desired to best suit the patient and desired valve. For example, a combination of single a single toroid proximal and distal may be the preferred pattern however any number of toroids may be located between proximal and distal portions of the device to provide additional tissue and or calcium support throughout the height of the device.

Figure 11:
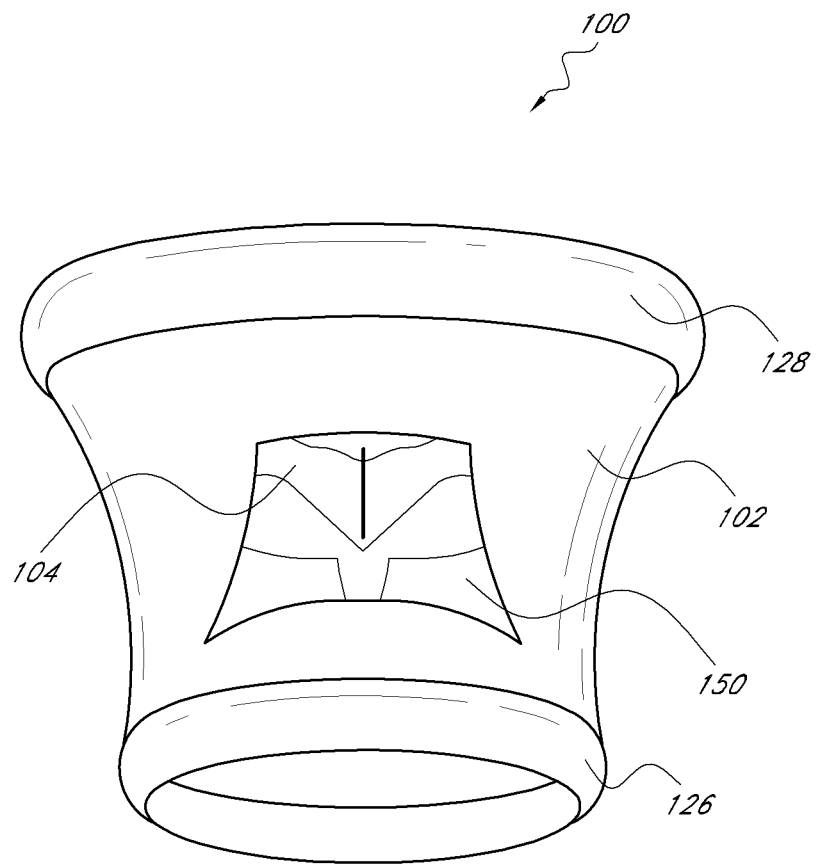
FIG. 11 is a front perspective view of another embodiment of an implant.
Figure 12:
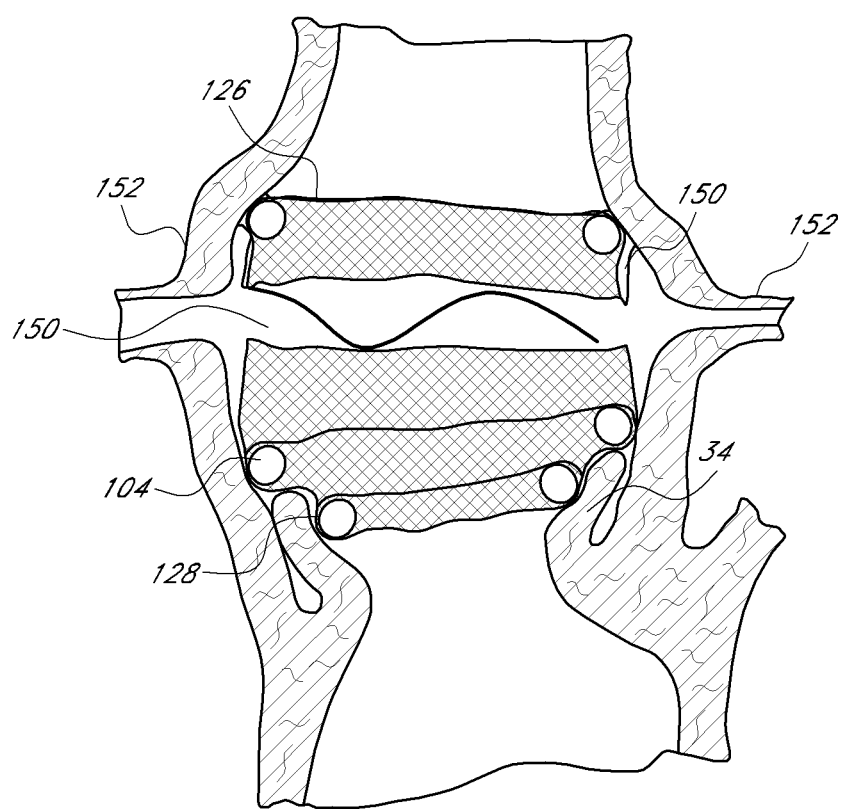
FIG. 12 is a cross-sectional side view of the implant of FIG. 11 positioned across an aortic valve.

With reference now to FIGS. 11 and 12, the implant 100 can include one or more windows 150 cut or otherwise formed in the body 102 of the valve 120 to supply blood to the coronary arteries 152. The number of windows 150 can range from one to twenty. In the illustrated embodiment, the windows 150 are generally located radially between the proximal and distal ends 126, 128. Depending upon the configuration of the implant 100, these windows 150 can be defined, at least in part, by inflation lumens, support structures such as metallic or polymer struts or be cut into the body material as a step in the manufacturing process. In one embodiment, the locations of the windows 150 is denoted by radio-opaque markers to ensure the proper orientation of the windows 150. In another embodiment, the rotational orientation of the implant 100 is controlled by the orientation that the implant 100 is loaded into the deployment catheter 300. In this embodiment, the deployment catheter 300 can have a preset curve or a preferred bending plane, oriented such that as the catheter 300 is delivered over the aortic arch or some other native anatomy, the implant 100 is oriented in the proper rotational position. The area of the windows 150 is preferably between about 1 square centimeter and about 6 square centimeters. In one embodiment, the area of the window 150 is between about 1.5 square centimeters and about 3 square centimeters. A larger sized window advantageously can permit some tolerance in the placement of the window 150 relative to the coronary ostia. Windows 150 may also be placed in a stent segment of a prosthetic valve.

In other embodiments configured for maintaining patent flow through the coronary arteries 152, the cuff 102 has an open mesh structure that allows patent flow in any orientation. The mesh structure is preferably sufficiently configured that not more than one or two of its threads or wires would cross an ostium at any position. It is also possible to access the coronary arteries with an angioplasty balloon and deform the mesh structure away from the ostium, provided that the mesh is manufactured from a plastically deformable material, such as stainless steel, or any of the biocompatible materials with similarly appropriate mechanical properties.

In order to visualize the position and orientation of the implant 100, portions of the body 102 would ideally be radio-opaque. Markers made from platinum gold or tantalum or other appropriate materials may be used. These may be used to identify critical areas of the valve that must be positioned appropriately, for example the valve commissures may need to be positioned appropriately relative to the coronary arteries for an aortic valve. Additionally during the procedure it may be advantageous to catheterize the coronary arteries using radio-opaque tipped guide catheters so that the ostia can be visualized. Special catheters could be developed with increased radio-opacity or larger than standard perfusion holes. The catheters could also have a reduced diameter in their proximal section allowing them to be introduced with the valve deployment catheter.

As mentioned above, during delivery, the body 102 is limp and flexible providing a compact shape to fit inside a delivery sheath. The body 102 is therefore preferably made form a thin, flexible material that is biocompatible and may aid in tissue growth at the interface with the native tissue. A few examples of material may be Dacron, ePTFE, PTFE, TFE, woven material such as stainless steel, platinum, MP35N, polyester or other implantable metal or polymer. As mentioned above with reference to FIG. 2, the body 102 may have a tubular or hyperboloid shape to allow for the native valve to be excluded beneath the wall of the cuff. Within this body 102 the inflation channels 120 can be connected to a catheter lumen for the delivery of an inflation media to define and add structure to the implant 100. As described above, these channels 120 can have any of a variety of configurations. In such configurations, the channels 120 may number from one to fifty and may have a single lumen communicating to all channels or separate lumens for communication separate channels or groups of channels. In one embodiment, the cuff or sleeve 102 contains 2 to 12 lumens, in another the cuff 102 contains 10 to 20 lumens. As described above, the channels 120 can be part of or formed by the sleeve 102 material 106 and/or be a separate component attached to the cuff such as balloon 111. The valve 104, which is configured such that a fluid, such as blood, may be allowed to flow in a single direction or limit flow in one or both directions, is positioned within the sleeve 102. The attachment method of the valve 104 to the sleeve 102 can be by conventional sewing, gluing, welding, interference or other means generally accepted by industry.

The cuff 102 would ideally have a diameter of between 15 and 30 mm and a length of between 6 to 70 mm. The wall thickness would have an ideal range from 0.01 mm to 2.00 mm. As described above, the cuff 102 may gain longitudinal support in situ from members formed by fluid channels or formed by polymer or solid structural elements providing axial separation. The inner diameter of the cuff 102 may have a fixed dimension providing a constant size for valve attachment and a predictable valve open and closure function. Portions of the outer surface of the cuff 102 may optionally be compliant and allow the implant 100 to achieve interference fit with the native anatomy.

Many embodiments of inflatable structure 107 shapes have been described above. In addition, as described above, the implant 100 can have various overall shapes (e.g., an hourglass shape to hold the device in position around the valve annulus, or the device may have a different shape to hold the device in position in another portion of the native anatomy, such as the aortic root). Regardless of the overall shape of the device, the inflatable channels 120 can be located near the proximal and distal ends 126, 128 of the implant 100, preferably forming a configuration that approximates a ring or toroid. These channels 120 may be connected by intermediate channels designed to serve any combination of three functions: (i) provide support to the tissue excluded by the implant 100, (ii) provide axial and radial strength and stiffness to the 100, and/or (iii) to provide support for the valve 104. The specific design characteristics or orientation of the inflatable structure 107 can be optimized to better serve each function. For example if an inflatable channel 120 were designed to add axial strength to the relevant section of the device, the channels 120 would ideally be oriented in a substantially axial direction. If an inflatable channel 120 were designed primarily to add radial strength to the relevant section of the device the channel would ideally be oriented generally circumferentially. In order to prevent tissue from extending between the inflatable channels the channels 120 should be spaced sufficiently close together to provide sufficient scaffolding.

Additionally depending on the manufacturing process used certain configurations may be preferred. For example a single spiraling balloon (see e.g., FIG. 8A) that forms the proximal, mid and distal inflation channels may be simplest to manufacture if a balloon is placed within a sewing cuff as described with referenced to FIG. 3C. FIG. 3D illustrates an embodiment that utilizes rings 108 and struts 114 that are positioned within folds 110 of the cuff 102.

Figure 13A:
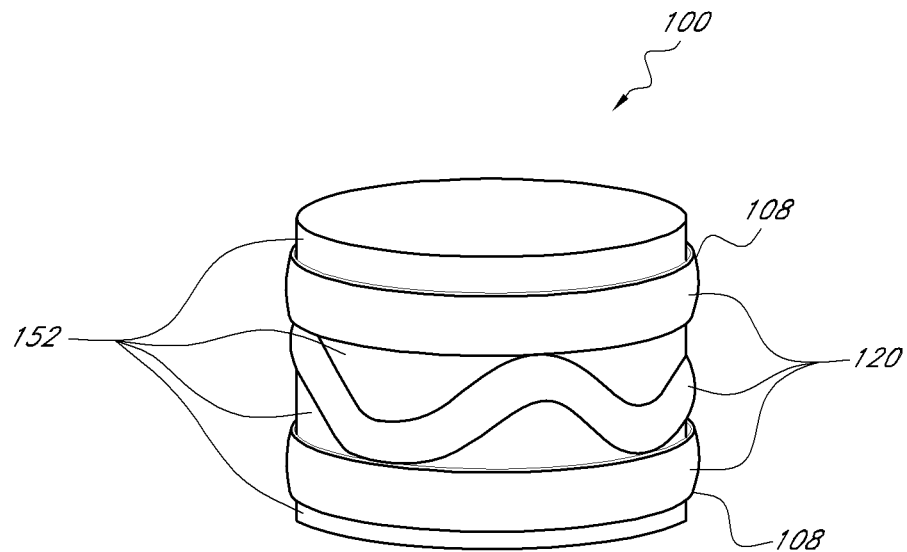
FIGS. 13A-D are front perspective views of three modified embodiments of a valve implant.
Figure 13B:
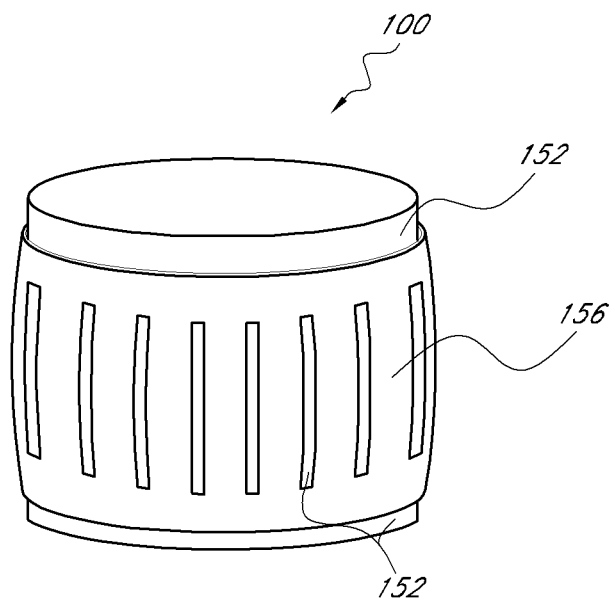
Figure 13C:
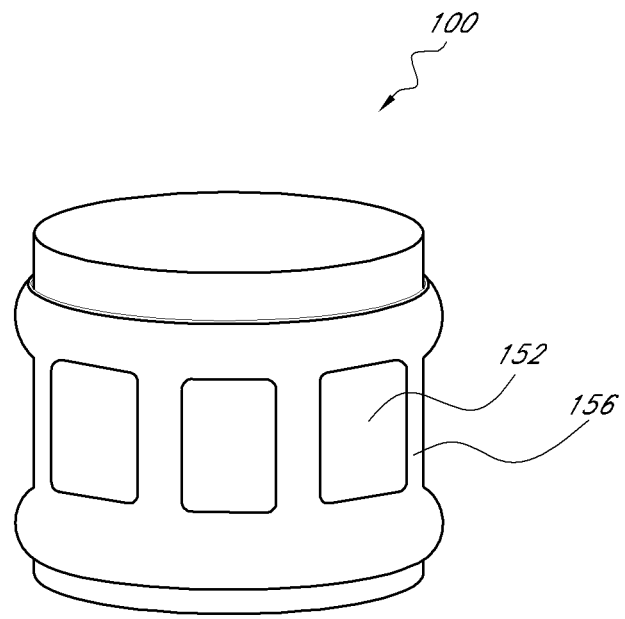

In other embodiments, the implant 100 is manufactured from multiple layers that are selectively fused together, then the inflation channels 120 are defined by the unfused or unjoined areas between fused areas 152. In this case any of a variety configurations of inflation channels 120 can be used. For example, as shown in FIG. 13A, the implant 100 can comprise distal and proximal rings 108 with undulating channels 120 positioned therebetween. FIG. 13B illustrates an embodiment in which the inflation 120 generally formed a cylinder with axially extending fused portions forming axially extending ribs 156. FIG. 13C is similar to the embodiment of FIG. 13B, however, the fused portions 152 are larger to form narrow ribs 156. In these embodiments, the inflation channels 120 are preferably configured so that the inflation media can flow into all of the channels without forming pockets of trapped air or pre inflation fluid.

The cuff 102 and inflation channels 120 of the implant 100 can be manufactured in a variety of ways. In one embodiment the cuff 102 is manufactured from a fabric, similar to those fabrics typically used in endovascular grafts or for the cuffs of surgically implanted prosthetic heart valves. The fabric is preferably woven into a tubular shape for some portions of the cuff 102. The fabric may also be woven into sheets. The yarn used to manufacture the fabric is preferably a twisted yarn, but monofilament or braided yarns may also be used. The useful range of yarn diameters is from approximately 0.0005 of an inch in diameter to approximately 0.005 of an inch in diameter. Depending on how tight the weave is made. Preferably, the fabric is woven with between about 50 and about 500 yarns per inch. In one embodiment, a fabric tube is woven with a 18 mm diameter with 200 yarns per inch or picks per inch. Each yarn is made of 20 filaments of a PET material. The final thickness of this woven fabric tube is 0.005 inches for the single wall of the tube. Depending on the desired profile of the implant 100 and the desired permeability of the fabric to blood or other fluids different weaves may be used. Any biocompatible material may be used to make the yarn, some embodiments include nylon and PET. Other materials or other combinations of materials are possible, including Teflon, floropolymers, polyimide, metals such as stainless steel, titanium, Nitinol, other shape memory alloys, alloys comprised primarily of a combinations of cobalt, chromium, nickel, and molybdenum. Fibers may be added to the yarn to increases strength or radiopacity, or to deliver a pharmaceutical agent. The fabric tube may also be manufactured by a braiding process.

The cut edges of the fabric are melted or covered with an adhesive material, or sutured over, in order to prevent the fabric from unraveling. Preferably the edges are melted during the cutting process, this can be accomplished using a hot-knife. The blade of the tool is heated and used to cut the material. By controlling temperature and feed rate as well as the geometry of the blade, the geometry of the cut edge is defined. In one embodiment the hot knife blade is 0.060 inches thick sharpened to a dull edge with a radius of approximately 0.010 inches. The blade is heated to approximately 400 degrees F. and used to cut through a Dacron fabric at a speed of about 20 inches per minute. Preferably the cutting parameters are adjusted so that the cut edge is sealed with a thin layer of melted fabric, where the melted area is small enough to remain flexible, and prevent cracking, but thick enough to prevent the fabric from unraveling. The diameter of the bead of melted fabric is preferably between 0.0007 and 0.0070 inches in diameter.

Two edges of a fabric may be sealed together by clamping the edges together to form a lap joint, and then melting the free edge. This may be accomplished with a flame, laser energy, a heated element that contacts the fabric, such as a hot-knife or a heating element that passes near the fabric, or a directed stream of a heated gas such as air. The bead of melted fabric joining the two edges is preferably between 0.0007 and 0.0070 inches in diameter.

The fabric is stitched, sutured, sealed, melted, glued or bonded together to form the desired shape of the implant 100. The preferred method for attaching portions of the fabric together is stitching. The preferred embodiment uses a polypropylene monofilament suture material, with a diameter of approximately 0.005 of an inch. The suture material may range from 0.001 to 0.010 inches in diameter. Larger suture materials may be used at higher stress locations such as where the valve commissures attach to the cuff. The suture material may be of any acceptable implant grade material. Preferably a biocompatible suture material is used such as polypropylene. Nylon and polyethylene are also commonly used suture materials. Other materials or other combinations of materials are possible, including Teflon, fluoropolymers, polyimides, metals such as stainless steel, titanium, Kevlar, Nitinol, other shape memory alloys, alloys comprised primarily of a combinations of cobalt, chromium, nickel, and molybdenum such as MP35N. Preferably the sutures are a monofilament design. Multi strand braided or twisted suture materials also may be used. Many suture and stitching patterns are possible and have been described in various texts. The preferred stitching method is using some type of lock stitch, of a design such that if the suture breaks in a portion of its length the entire running length of the suture will resist unraveling. And the suture will still generally perform its function of holding the layers of fabric together.

Figure 13D:
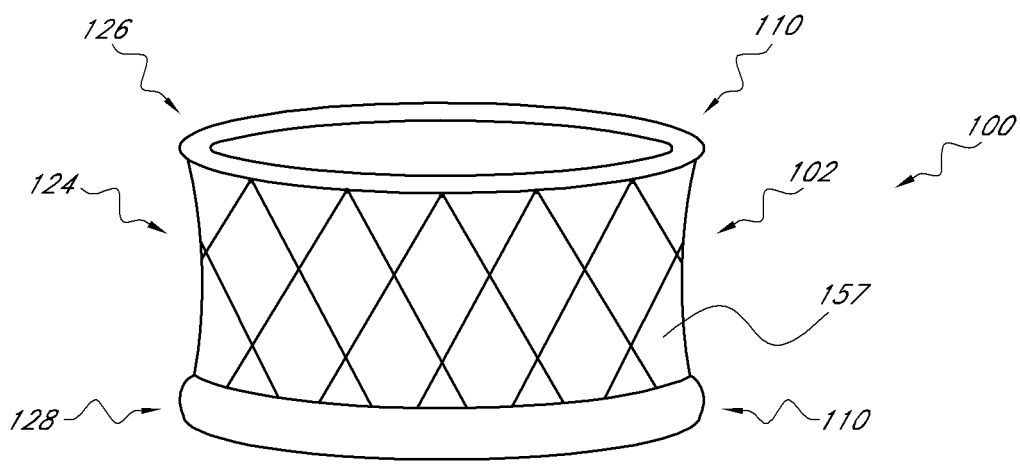

FIG. 13D illustrates another embodiment of an implant 100 in which an outer portion 156 of the cuff 102, which is in contact with the calcified annulus contains a material selected for its abrasion resistance. In one embodiment, the abrasion resistant material is a synthetic fiber such a Kevlar or other Aramid fiber. In another embodiment, the abrasion resistant material is a metal such as MP35N or stainless steel. In one embodiment, the fabric is woven entirely from the abrasion resistant material. In another embodiment, the fabric is woven from a combination of materials including an abrasion resistant material and a second material, designed to optimize other properties, such as tissue in-growth. The fibers of different materials may be twisted together into a single yarn, or multiple yarns of different materials may be woven together as the fabric is manufactured. Alternatively, an abrasion resistant layer may be added to the outside of the finished device or implanted first as a barrier or lattice to protect the valve device.

As mentioned above, the cuff 102 may be manipulated in several ways to form inflation channels 120. In many embodiments, the implant 100 is not provided with separate balloons 111, instead the fabric 106 of the cuff 102 itself can form the inflation channels 100. For example, in one embodiment two fabric tubes of a diameter similar to the desired final diameter of the implant 100 are place coaxial to each other. The two fabric tubes are stitched, fused, glued or otherwise coupled together in a pattern of channels 120 that is suitable for creating the geometry of the inflatable structure 107. In one embodiment the stitching pattern consists of a spiral connecting the two tubes. The spiral channel formed between the sutured areas becomes the inflation channel (see e.g., FIG. 8A). In another embodiment the two coaxial fabric tubes are actually a single tube folded over its self. In another embodiment, the tubes are sewn together in a pattern so that the proximal and distal ends of the fabric tubes form an annular ring or toroid. See e.g., FIG. 13C. In yet another embodiment of the design the middle section of the device contains one or more inflation channels shaped in a sinusoidal pattern. See e.g., FIG. 13A.

Figure 14:
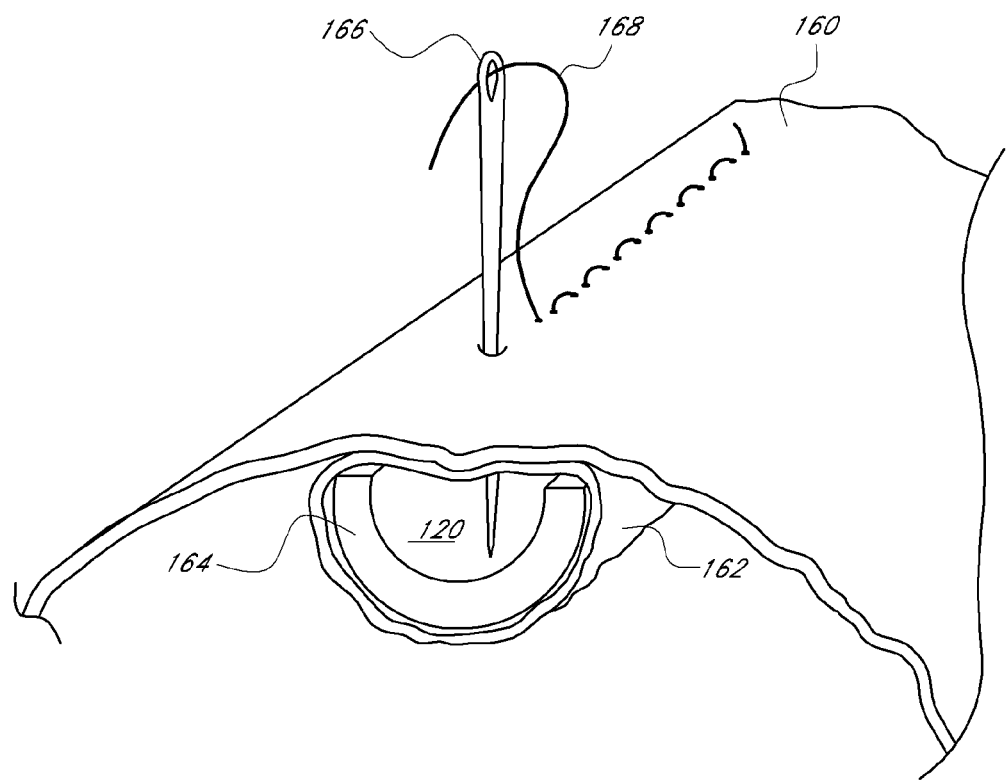
FIG. 14 is a side perspective view of a method of forming a lumen in an valve implant.

With reference to FIG. 14, in another embodiment, the implant 100 is formed from a single fabric tube 160 similar to the final diameter of the implant 100. Smaller fabric tubes 162 of a diameter suitable for an inflation channel are attached to the larger tube 160. The smaller tubes 162 can be attached to the inside or the outside of the larger tube 160 in any pattern desired to provide the inflatable structure 107 with the desired properties. In one embodiment, the tubes 162 are attached in a spiral pattern, in another embodiment the tubes 162 are attached in a sinusoidal pattern simulating the shape of the connection of the leaflet to the cuff. As shown in FIG. 14, an optional skived hypotube or similar component 164 can be positioned within the smaller tubes 162. The smaller tubes 162 can be sutured, glued, fused or otherwised coupled to the larger tube 160. In the illustrated embodiment, sutures 112 applied via a needle 166 and thread 168 to secure the smaller tube 162 to the larger tube 164.

In another embodiment, a single fabric tube similar to the final diameter of the prosthetic implant 100 is used. The ends or an end of the tube is turned inside out forming two layers of tube for a short length at one or both ends of the tube. The layers of tube are sewn or otherwise attached together to form a ring shaped inflation channel at the end of the tube in a manner similar to that shown in FIG. 3C. Alternatively the layers may be sewn together in a different pattern to form an inflation channel with a different shape such as a spiral or a sinusoid.

If a porous fabric is used for the cuff 102, it may be desired to use a liner (e.g., as shown in FIG. 14) or coating to prevent the inflation media from escaping from the inflation lumens 120. This portion of the fabric may be coated, filled or encapsulated in a polymer or other dealing agent to better seal the fabric. The entire fabric portion may be treated or, a specific portion of the fabric may be treated. The fabric may be treated before the cuff 102 is manufactured, or after the cuff 102 is manufactured. In one embodiment, the treatment is a polymer suspended in a solvent. After the solvent evaporates or is otherwise removed the polymer is left behind sealing the fabric. In another embodiment, the sealing agent is applied as a liquid or paste, and then cured by moisture, heat external energy, such as UV light, light of another wave length or a chemical reaction caused by mixing two or more components together. In another embodiment, the sealing agent is a silicone.

In the preferred embodiment, the fabric inflation channels contain a liner in a form of the balloons 111 as described with reference to FIGS. 3A-C. The balloon 111 preferably is a thin wall tube made from a biocompatible material. In one embodiment, the balloon 111 is blown from nylon tubing the tubing diameter is about 0.030 of an inch with a 0.005 inches wall thickness. The tubing is then necked to an outside diameter of approximately 0.020 inches the tubing is then placed inside a mold and pressurized to about 200 PSI the mold is then heated in the area where the balloon should be formed. The heating step may be accomplished using a stream of heated air at approximately 300 degrees F. The final diameter of the balloon in this embodiment is 0.060 inches at one portion of the balloon and 0.090 inches a second portion of the balloon. The total length of the balloon 111 is approximately 18 cm. The balloon 111 may be blown in a shape that conforms to the cuff, or the balloon may be shaped to conform to the cuff in a secondary step. Alternatively the liner may be a different shape than the fabric cuff, where the liner is larger than the fabric cuff, allowing the assembly to inflate to a size determined by the fabric.

Several embodiments of the inflatable prosthetic implant 100 described above utilize circular or ringed shaped balloon members 111. These balloons 111 can be manufactured using a glass tube bent in a helix. The balloon 111 is then blown inside the tube using methods similar to those used to manufacture balloons for angioplasty. For example, the glass mold may be heated using air, water, steam infrared elements and pressure and tension may be applied to blow the balloon to a specific diameter and length. Secondary processes may be added to "set" the balloon's shape by providing a second heating process to hold the balloon as it relaxes and ages. The balloons can be blown from many different materials; Nylon pebax and polyethylene are particularly suitable polymers. The balloon tubing is inserted through the mold, and sealed at one end. A knot tied in the tubing is sufficient for sealing. The other end of the tubing is connected to a pressure source, providing pressure in the range of 80 to 350 psi. The required pressure depends on the material and dimensions of the tubing. The balloon is then heated in a localized area, while tension is optionally applied to either end of the tubing. After the tubing expands to match the inside diameter of the glass mold, the heat source is advanced along the length of the mold, at a rate that allows the tubing to grow to match the inside diameter of the mold. The balloon and mold may then be cooled. One method for cooling is blowing compressed air over the mold. The balloon is then removed from the mold. Optionally a release agent may be used to facilitate this step. Acceptable mold release agents include silicone, Polyvinyl alcohol (PVA) and Polyethylene oxide (PEO) Additionally balloons may be produced by wrapping braiding or weaving a material such as EPTFE over a mandrel to produce a shape desired the material is then bonded to itself by a process such as sintering or gluing.

With reference back to FIGS. 3A-D, in a preferred embodiment, the implant 100 is manufactured from a single layer of woven fabric tube 106 of a diameter similar to the desired diameter of the finished prosthetic valve. The diameter of the tube 106 is approximately 1 inch. A length of tube 106 approximately 1.2 inches long is used. The ends of the tube 106 are cut using a hot knife to prevent the edges from unraveling. A second piece 115 of woven fabric tubing with a diameter of approximately 0.065 inches is cut to length of approximately 7 inches long using a hot-knife so that the edges of the tube 115 do not unravel. The smaller diameter tube 115 is then sewed to the middle portion of the inner diameter of the larger diameter fabric tube 106, in a shape producing three cusps near the top edge of the fabric tube 106. The cusps are located approximately 0.15 inches from the top edge of the fabric tube 106. The portion of the smaller tube 115 between the cusps is sewed to the middle section of the larger diameter tube, in approximately a 0.5 inches in radius. The bottom portion of the radius is positioned about 0.27 inches from the bottom edge of the larger diameter fabric tube 106. The bottom edge of the larger diameter fabric tube 106 is then folded inside out over its outside diameter. A suture 112 is placed through the two layers of the larger diameter fabric tube 106, located about 0.1 inches from the folded edge. This suture 112 is spaced approximately 0.05 inch from the cut edge of the fabric tube 106, and approximately 0.05 in from the lower edge of the radii formed from the attachment of the smaller diameter fabric tube 115.

Figure 15:
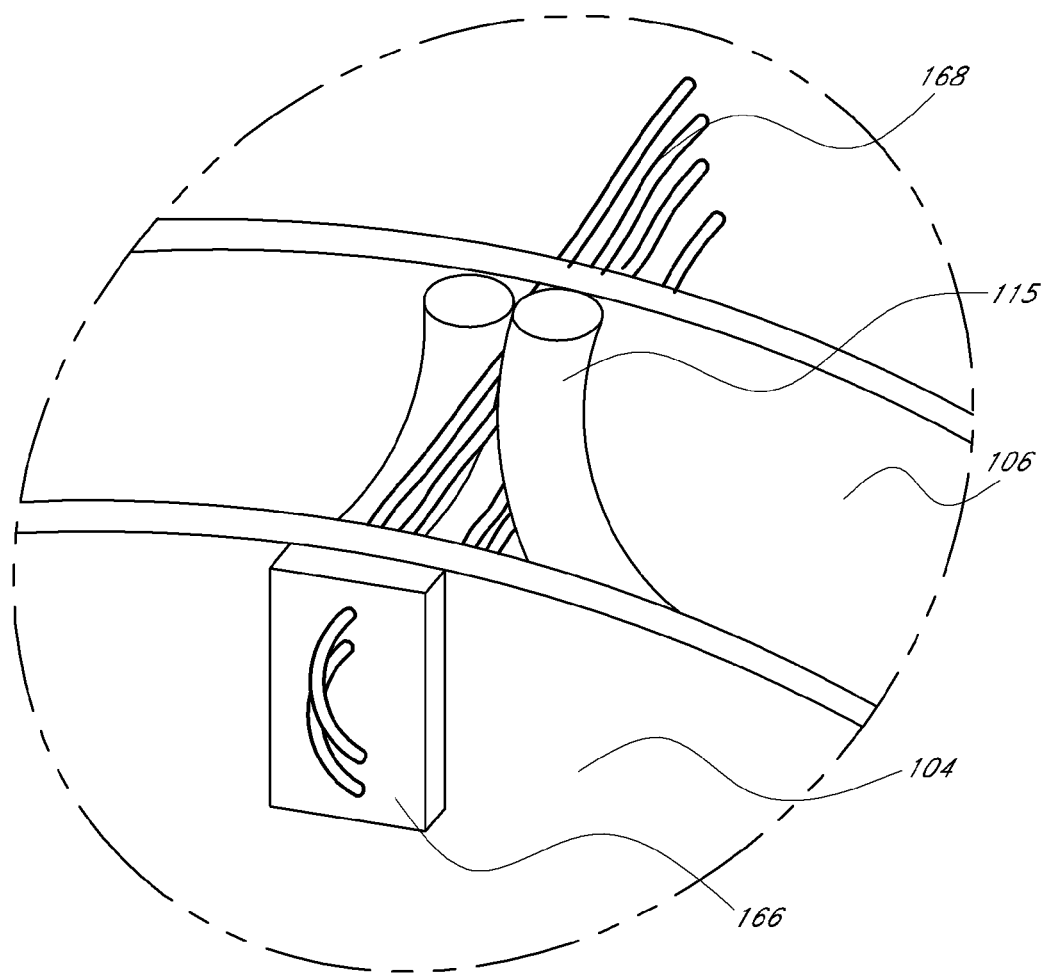
FIG. 15 is a top perspective view of a method of attaching a valve to a valve implant.

With reference to FIG. 15, in the embodiment of FIG. 3A-D, a tubular section of the valve 104 (preferably fixed pericardial tissue, of approximately 1 inches in diameter and 0.6 inches in length) is inserted into the inside diameter of the larger fabric tube 106. Small squares of fabric 166 approximately 0.08 inches by 0.18 inches are placed at each valve cusp inside the tubular section of pericardial tissue 104. Sutures 168 are passed through the square of fabric and the pericardial tissue 104, and then between two segments of the smaller diameter fabric tube 115 that form the cusp 116, and through the larger diameter fabric tube 106. In this manner, the top edge of the pericardial tissue tube is attached to the cuff 102 at the three locations that form the cusps 116 and valve commissures. The bottom edge of the pericardial tissue tube is then attached to the bottom edge of the cuff 102 by suturing the tissue in the location between the smaller fabric tube 115 and the suture that forms the bottom ring shaped inflation channel.

The balloon members 111 are then placed inside each channel formed by the cuff 102. See e.g. FIG. 3C. In another embodiment, the cuff 102 is manufactured from a nonporous polymer sheet or tube, or from polymer sheet or tube with minimal porosity, where a secondary sealing member such as a balloon is not required.

Figure 16A:
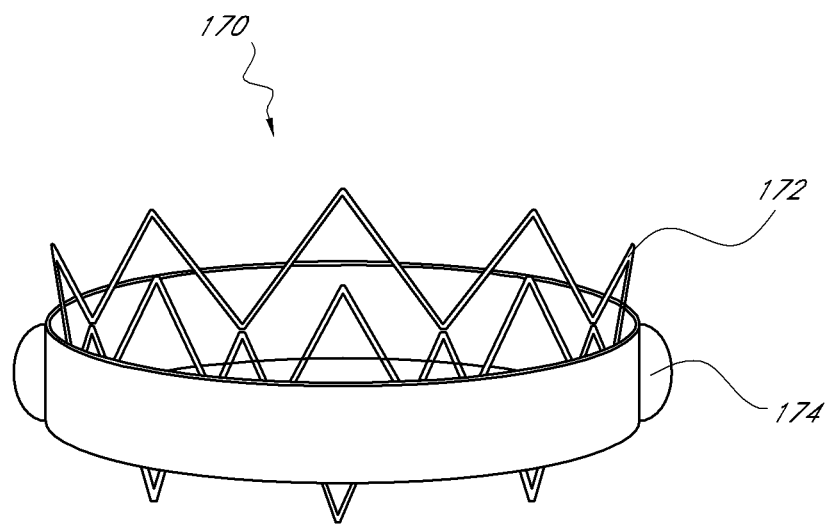
FIG. 16A-B are front perspective views of two modified embodiments of a valve implant.
Figure 16B:
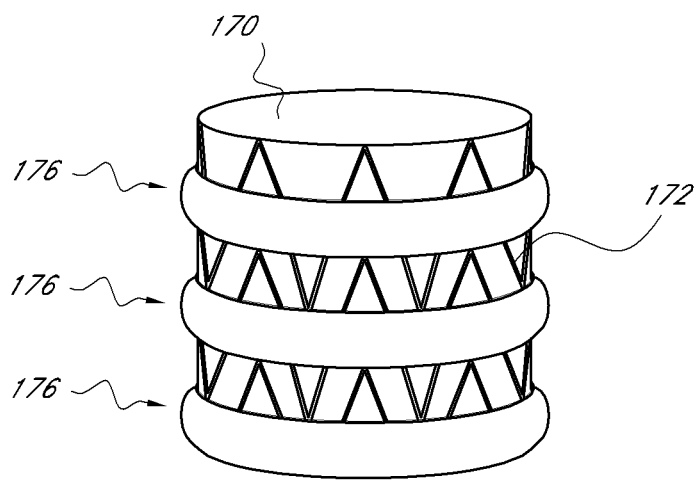

FIGS. 16A and 16B illustrate a modified embodiment a stented implant 170 that can be delivered percutaneously as described by Andersen in U.S. Pat. No. 6,168,614, which is hereby incorporated by reference herein. The implant 170 generally comprises a stent-like structure 172 that comprises a one or more elongated members arranged in an annular zig-zag pattern comprising proximal and distal bends to form a self-expandable stent. A valve 174 is coupled to the structure 172. The implant 170 can include one (FIG. 16A) or more (FIG. 16B) inflatible cuffs 176 configured in a manner as described above. The inflatable cuff 176 is configured to minimize or eliminate peri-valvular leaks. For example, the inflatable cuff 176 can be positioned on the implant 170 so that when it is in inflated it prevents or restricts fluid flow around the fixed edge of each leaflet of the valve 174. In the embodiment of FIG. 16A, the valve 170 includes a single circular cuff 174 attached to the outer surface of the stent 172 in a location where the fixed edge of the leaflets of the valve 174 are attached to the stent 172. After the stent 172 is expanded, the inflatable cuff 176 is filled with inflation media. The cuff 176 is inflated to a pressure adequate to seal the outer surface of the implant 170 to the native anatomy. A passive structure such as an O-ring that has no inflatable passage but does serve to form a seal between the vessel wall and the valve 174 could also be provided. In such an embodiment, the sealing structure is preferably made from a low durometer material or foam so that it can easily conform to the anatomy. A silicone or silicone foam can also be used to produce an adequate sealing member.

Another problem with an expandable stent based valve prosthesis is that if the stent is over-expanded the valve leaflets may not coapt. This results in a central leak, and an incompetent valve. In one embodiment, the inflatable sealing cuff 176 described above is designed so that if the operator detects a central leak the operator can inflate the cuff to a high pressure causing the stent 172 to decrease in diameter at the prosthetic valves annulus. The operator monitors any regurgant flow using an imaging technique such as echocardiography. Guided by this information the cuff 176 can be inflated to the minimum pressure that eliminates the leak. Using the minimum pressure insures that the maximum possible area is available for blood flow. This technique would allow for a reduction in the initial deployed diameter or a resizing of the structure to properly fit the implantation area.

Non-Inflatable Prosthetic Aortic Valve Implants

Figure 21A:
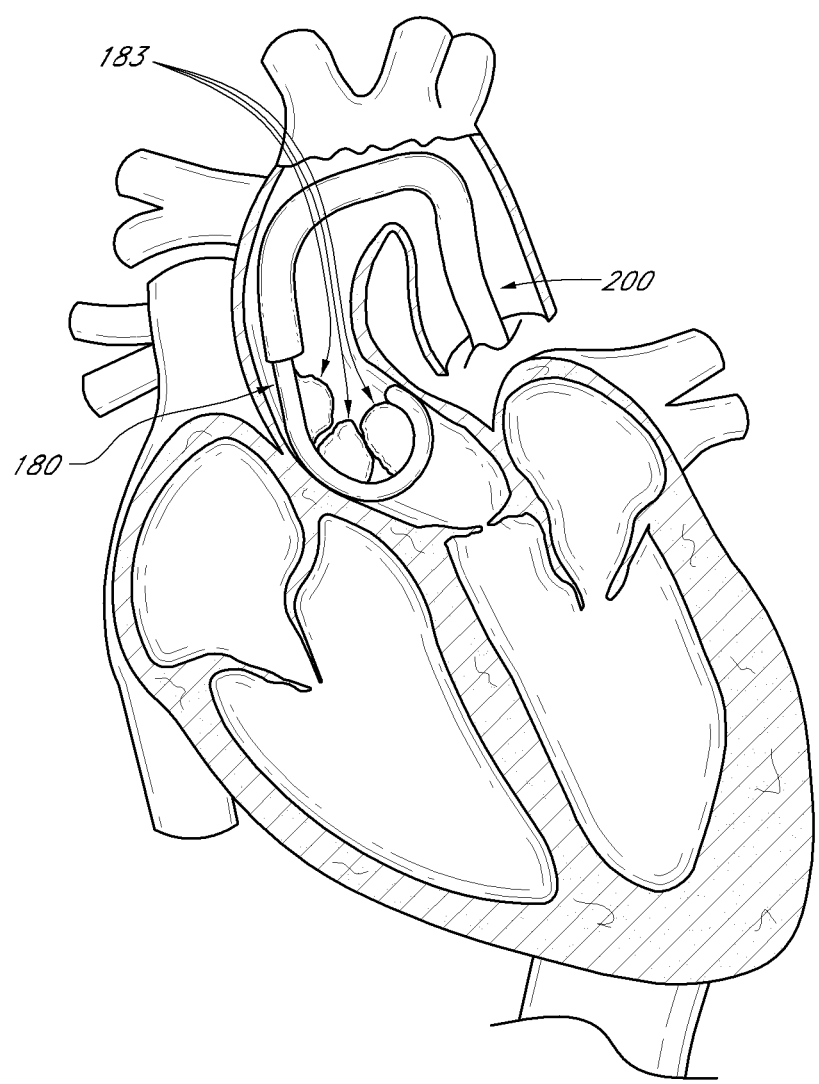
FIGS. 21A-B are time sequenced steps of deploying a non-inflatable valve implant
Figure 21B:
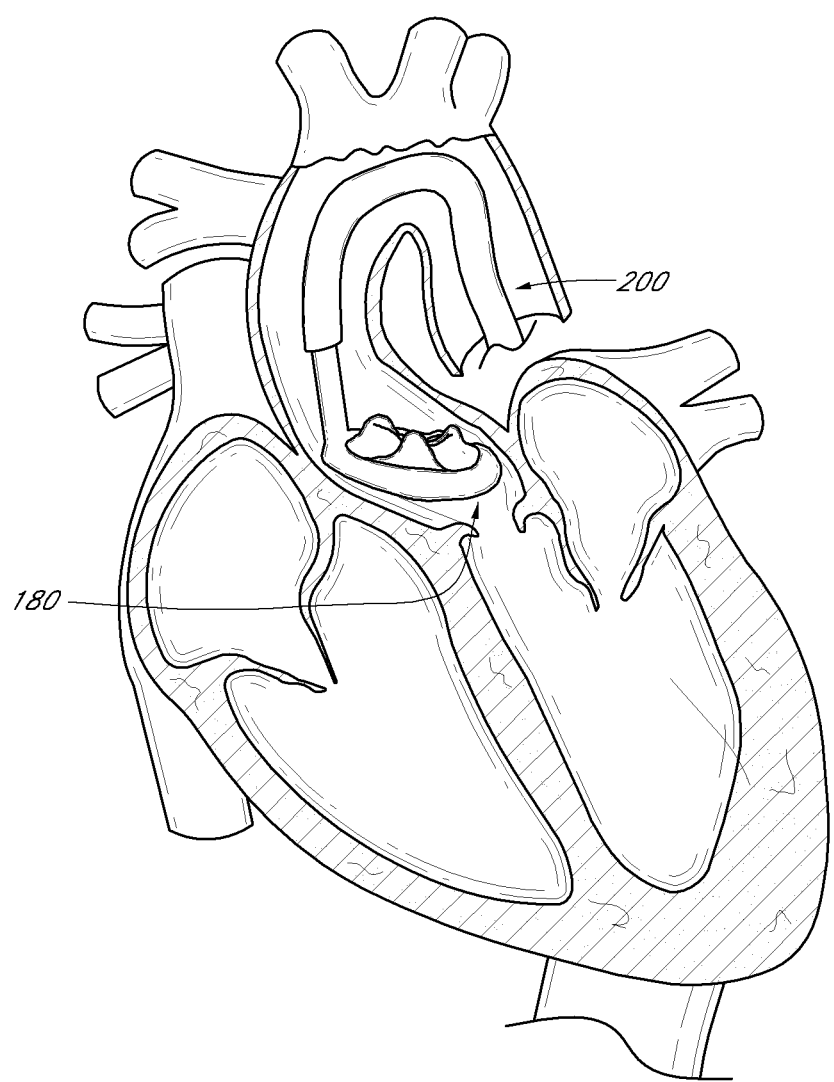

FIGS. 17A-20A illustrate another embodiment of a implant 180, which utilizes a different technique to secure a valve 182 at the implantation site. In this embodiment, the implant 180 comprises at least one member 184 that is attached to the valve 182 and provides the valve 182 shape as it is deployed into the body. In general, the member 184 forms a ring or annular shape when it is actuated and deployed. However, during delivery the member 184 is flexible and generally elongated with a reduced profile, while the leaflets 183 of the valve 182 are wrapped around the support member 184 (see FIGS. 20 and 20A) so as to pass through a delivery catheter. During deployment leaflets 183 of the valve 182 unwrap and take a second shape to form a seal with the vessel and function as a single direction gate for blood flow. See also FIGS. 21A and 21B which show the deployment of the valve 180 within the heart 10.

A latch or lock mechanism 181 maintains the tension in the wire or locks the distal end to a location near the proximal end. This tension mechanism may be driven from the handle through a tension wire, a hydraulic system, a rotational member to drive a screw. Furthermore the tensioning members may utilize a locking means to maintain the desired circular shape, such as a suture, an adhesive, or a mechanical snap together type lock actuated by the tension wire.

Figure 17A:
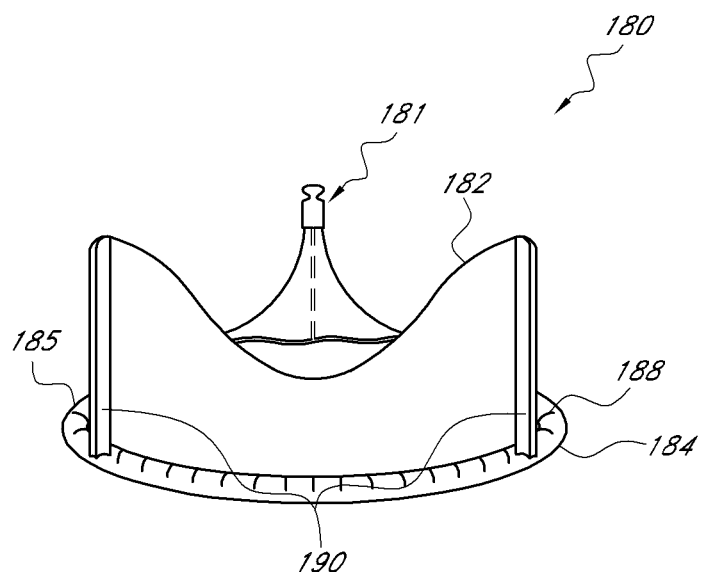
FIG. 17A-B are front perspective views of two modified embodiments of a non-inflatable valve implant.
Figure 17B:
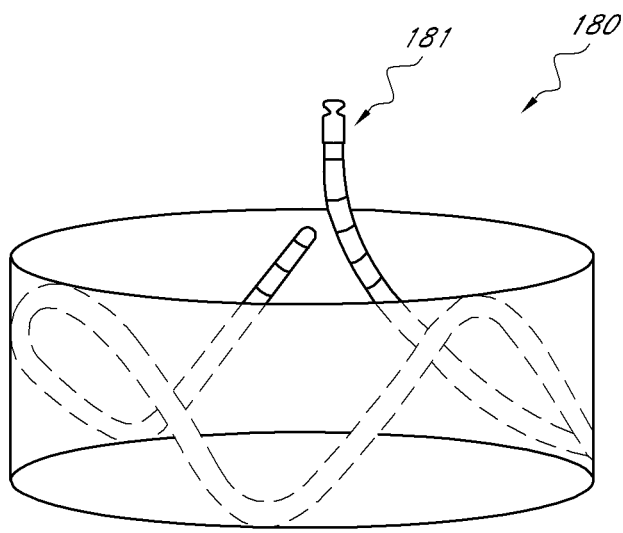
Figure 18A:
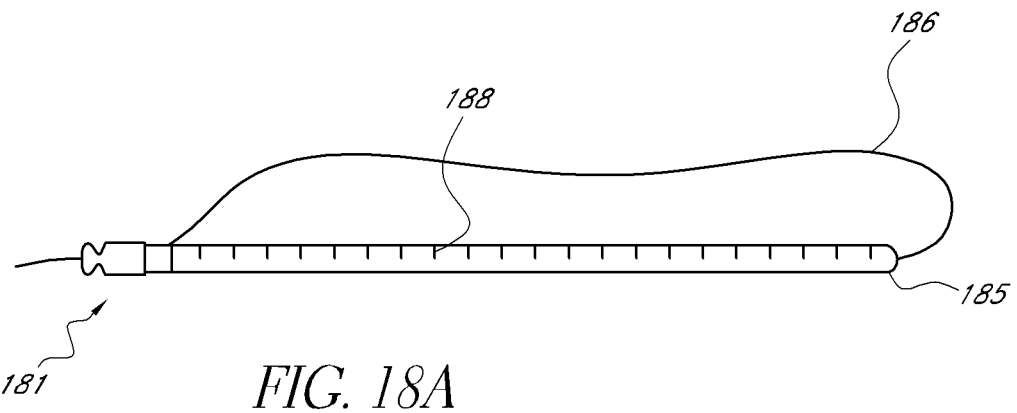
FIGS. 18A-C are time sequence steps of deploying a non-inflatable valve implant.
Figure 18B:
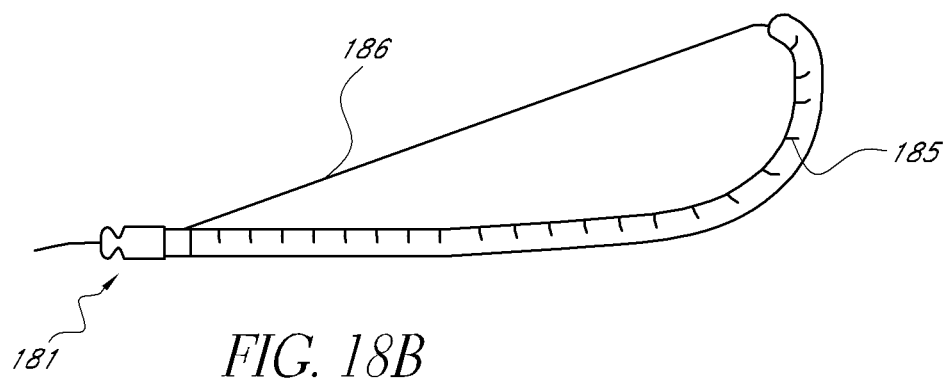
Figure 18C:
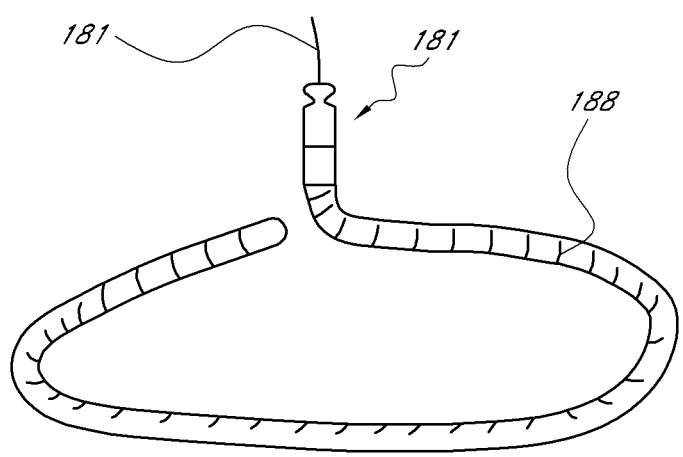

With initial reference to FIGS. 18A-C, in one embodiment the structure 184 or a portion of the structure, is manufactured from a stainless steel tube 185 with slots 188 cut on one side (e.g., as seen in Published Application number US 2002/0151961 A1, which is hereby incorporated by reference herein) to provide flexibility during delivery. A wire 186 located inside the tube is tensioned providing a bias to shape the device as determined by the patterning and width of the transverse slots 188 cut into the member 184. These slots 188 and tension wire 186 cause the device to form into a circular shape as shown in FIGS. 17A and 18C. In another embodiment, the slots 188 can be oriented such that the ring is three dimensional, possibly incorporating cusps or high points at the valve commissars as shown in FIG. 17B. Additionally, the member may incorporate integral struts 190 to support the commissars of the valve 182 as shown in FIG. 17A.

Figure 19B:
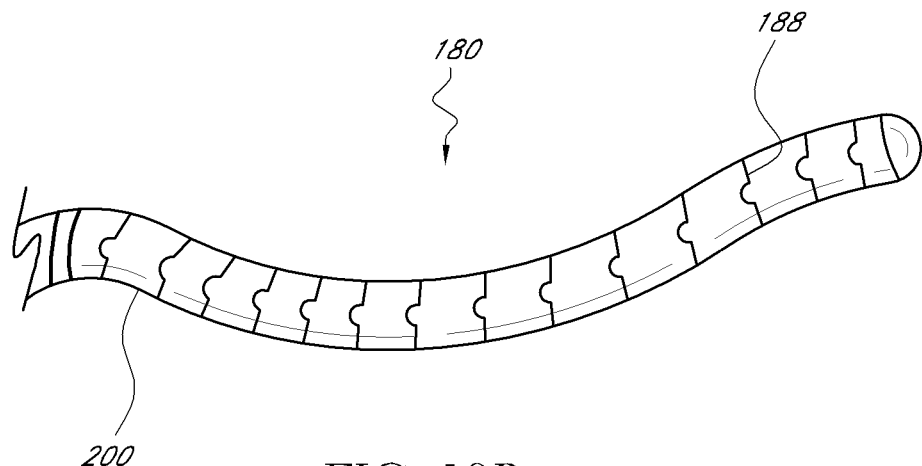
FIG. 19B is a side view of another embodiment of un-deployed non-inflatable valve implant.
Figure 19C:
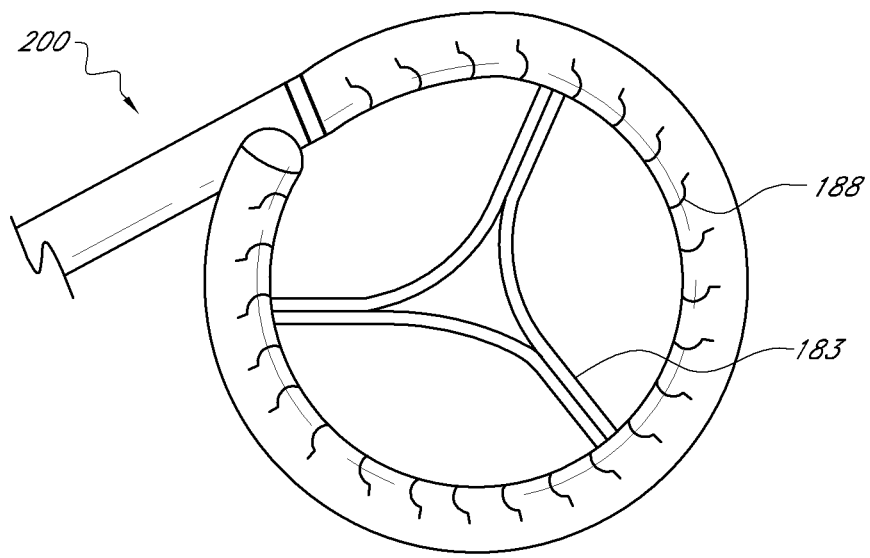
FIG. 19C is a top view of the valve implant of FIG. 19B in a deployed state.
Figure 20A:
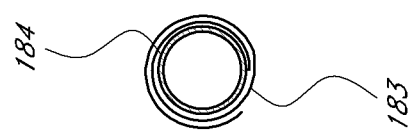
FIG. 20A is a cross-sectional view taken at line 20A-20A of FIG. 20.
Figure 20:
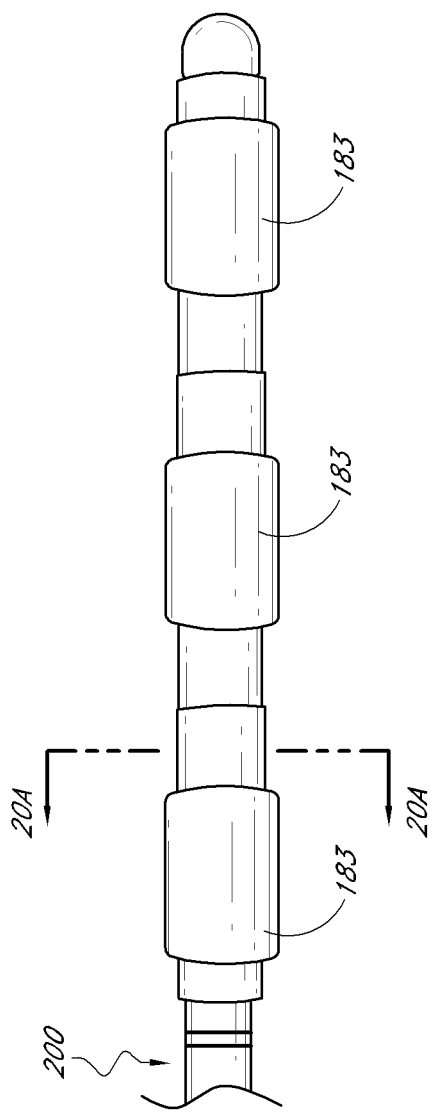
FIG. 20 is side view of another embodiment of an un-deployed non-inflatable valve.

FIGS. 19B and 19C illustrate an embodiment in which the slots 188 have a chevron type shape. The wire inside the device is tensioned providing a bias to shape the device as determined by the patterning and width of the transverse slots 188, causing the device to form into a circular shape as shown in FIG. 19C. In another embodiment, the slots 188 can be oriented such that the ring has a three dimensional shape when tensioned.

Figure 22A:
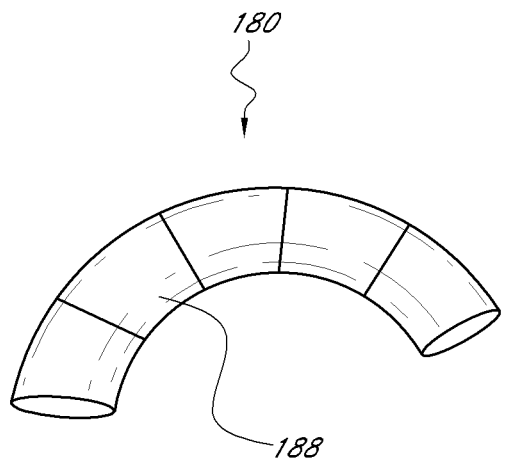
FIGS. 22A-B illustrate the deployment of a modified embodiment of a non-inflatable valve implant.
Figure 22B:
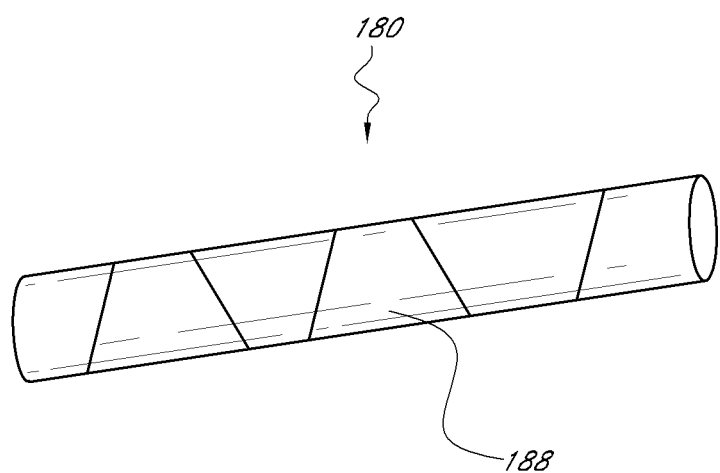

FIGS. 22A and type shape 22B illustrate a modified embodiment in which the member 180 is formed from elements 191 that are configured to provide the member 180 with a preformed shape as the member 180 is rotated. For example, as shown in the figures, the elements 191 may have a trapezoidal shape.

Figure 23:
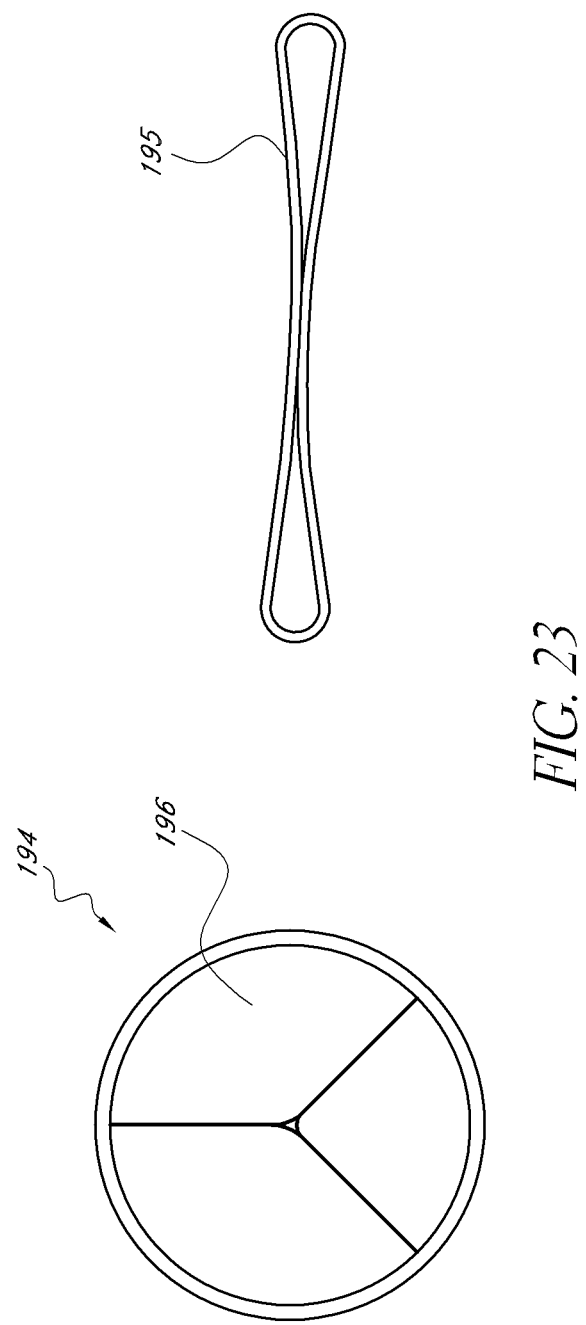
FIG. 23 are top views of a modified embodiment of a non-inflatable valve implant in an expanded and compressed configuration.
Figure 24B:
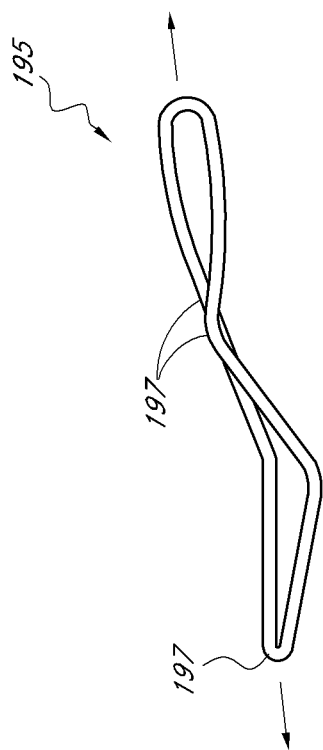
FIGS. 24A-B are side perspective views of a modified embodiment of a non-inflatable valve implant in an expanded and compressed configuration.
Figure 24A:
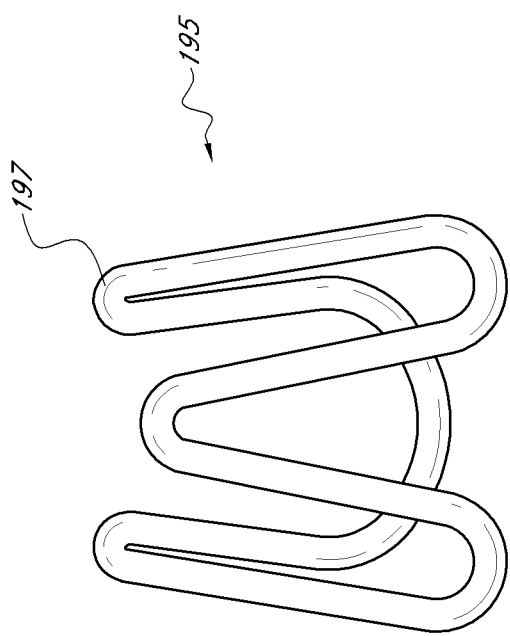

FIG. 23 illustrates an embodiment of an implant 194 in which the implant 194 comprises a ring 195. As shown, the device 194 can be constrained in a catheter by bending the ring 105 into an oval with a large aspect ratio. Once expelled from the catheter, the implant 194 would assume its free state of a circle or more round shape. A tissue valve 196 could be attached by conventional manners such as sewing or seaming the tissue together. FIGS. 24A and 24B illustrate a similar embodiment in which the ring 195 has an undeformed configuration that includes elongated members 197.

Figure 25A:
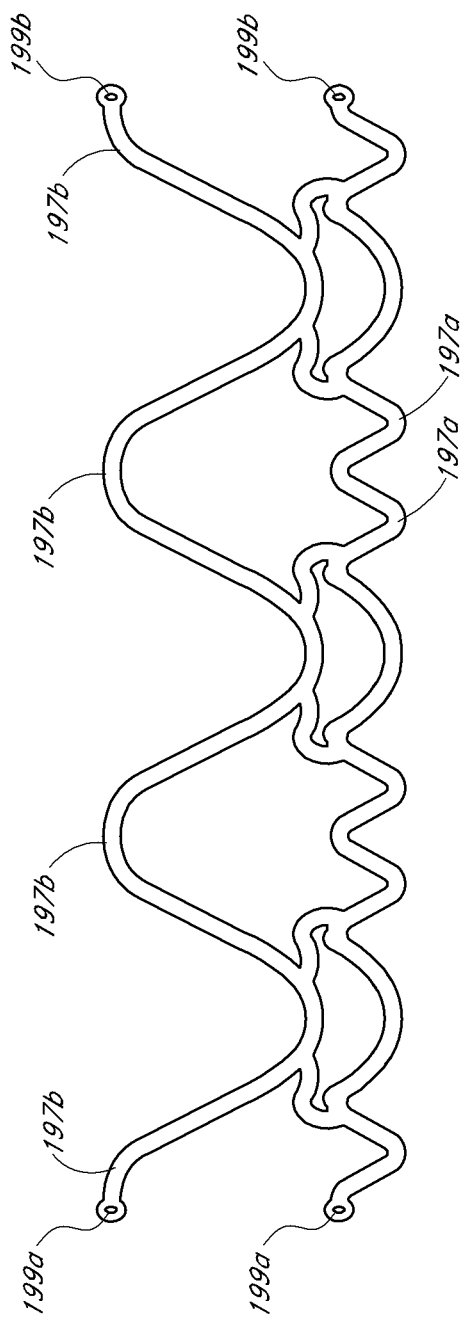
Figure 25C:
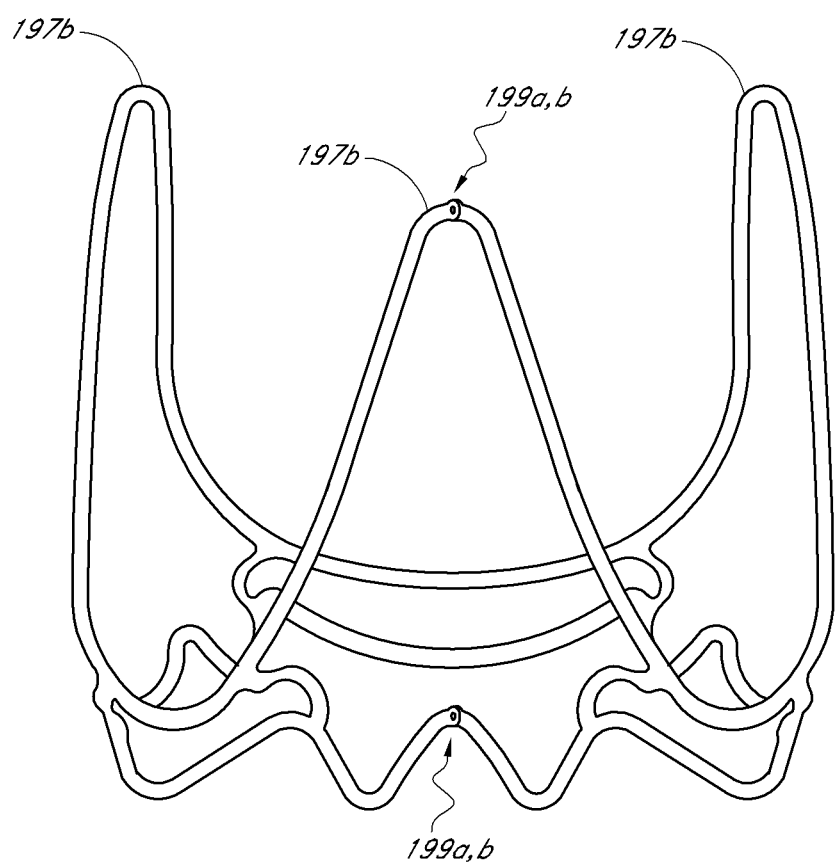

FIGS. 25A-C illustrate another modified embodiment in which the ring 195 needs to be assembled in situ. In this embodiment, the ring 195 comprises a series of distal and proximal bends 197a, 197b. As shown in FIG. 25B, the ring 195 can be elongated and compressed for delivery via a catheter. Once expelled from the catheter, the ring 195 is assembled by coupling together connection points 199a, 199b through the use of sutures etc.

In the embodiments described above with reference to FIGS. 17A-17C, the implant must be released or disconnected from a delivery catheter. Those of skill in the art will recognize in light of the disclosure herein that many different release disconnect methods are possible. For example if rotational motion is used to deploy the device, then a disconnect that can transmit torque is typically provided such as a threaded connection. In other embodiments, the device is pushed out of the catheter by a pusher element. In still other embodiments, a mechanical release mechanism such as a pin joint, unscrewing the device from the catheter delivery system, a tethered link such as a thread or wire, a fusible link as used in a GDC coil deployment, a cutting tool to sever an attachment of the device from the catheter, a threaded knot to tether the catheter to the device where the as the knot could be untied or cut, a hydraulic mechanism to deploy, expand or fracture a link between the catheter and the device.

Figure 25D:
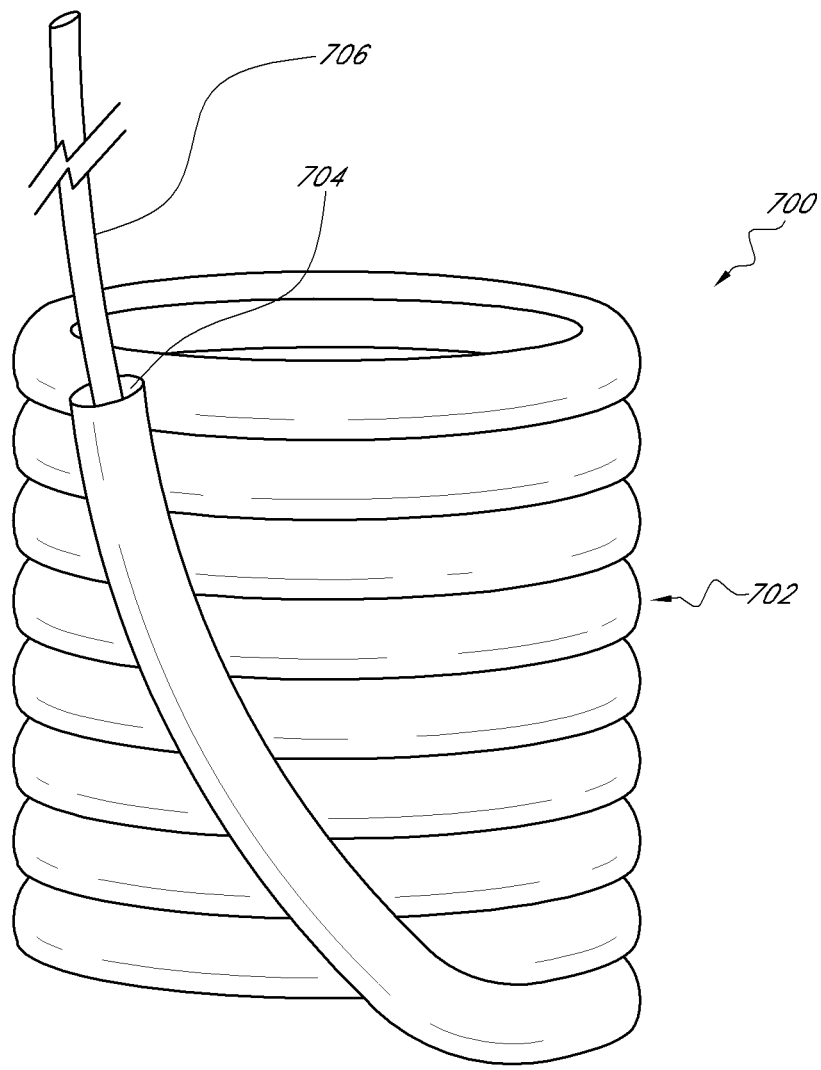
FIG. 25D is a side perspective view of another embodiment of a non-inflatable valve implant.

FIG. 25D illustrates another embodiment of a prosthesis 700. In this embodiment, the prosthesis 700 includes a flexible fabric cuff 702. The fabric cuff 702 includes one or more channels 704 where a permanent support structure 706 can later be located. In one embodiment, the permanent support structure is woven through the channels 704 that will later contain the support structure. In another embodiment, the support structure 706 is preloaded into the cuff in a flexible configuration. In one embodiment of use, a catheter contains at least one lumen through which the support structure can be advanced and the assembly can be fitted inside a retractable delivery sheath. The cuff 702 is delivered to the desired valve annulus, and the support structure 706 is advanced into a portion (e.g., a channel 704) of the device 700. This provides structure to the prosthesis 700 such that it can support a valve (not shown) that is coupled to the cuff 702, and allows it to be positioned in the native annulus and to function. In one embodiment, the support structure 706 is a wire. If the operator is satisfied with the size and position of the prosthesis 700 additional support structure may be added to stiffen or secure the prosthesis 700. After the prosthesis 700 is positioned the delivery catheter may optionally be withdrawn or disconnected, leaving, the valve cuff 702 and support structure 706 in place. Alternatively, the delivery catheter may be left in place for any length of time to allow later adjustment or removal of the prosthesis 700.

In the illustrated embodiment, the cuff 702 contains a spiral channel 704 allowing the delivery of a wire 706, which takes a helical shape after it is inserted into the cuff. The helix extends from the proximal end of the device 700 to the distal end of the valve with the individual coils spaced close together as shown in FIG. 25D.

The preferred wire material is Nitinol, although many other metals and polymers have suitable properties. Nitinol provides an advantage that its chemistry and thermal history can be used to tune the temperature at which it undergoes a phase change. By adjusting this transition temperature to fall at a temperature just below body temperature the support structure 706 can be delivered (e.g., within the cuff 702) with one set of mechanical properties and after delivery, and after the support structure 706 has equalized in temperature with the body, the support structure 706 assumes a second set of mechanical properties (e.g., shape). Other materials that undergo a phase change near body temperature, such as other shape memory alloys may provide similar benefits.

In one embodiment, the catheter that is attached to the channels 704 in the cuff 702 is preferably in an orientation that allows the wire 706 to be delivered with minimal friction making a minimum number of excessively sharp bends. The catheter may optionally include an inflation portion to allow an inflation media to temporarily act as a support structure during the process of positioning the prosthesis 700.

Figure 25E:
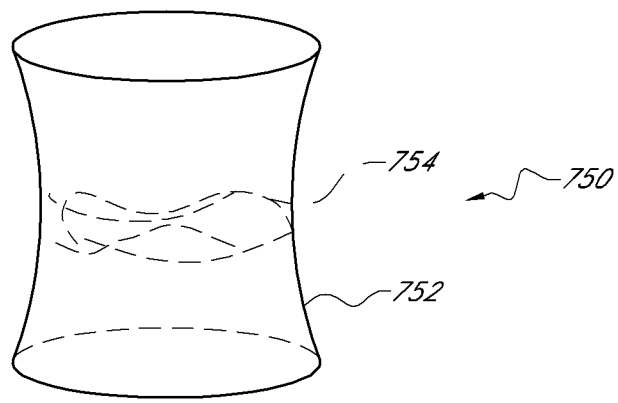
FIGS. 25E-F are side perspective views of another embodiment of a non-inflatable valve implant.
Figure 25F:
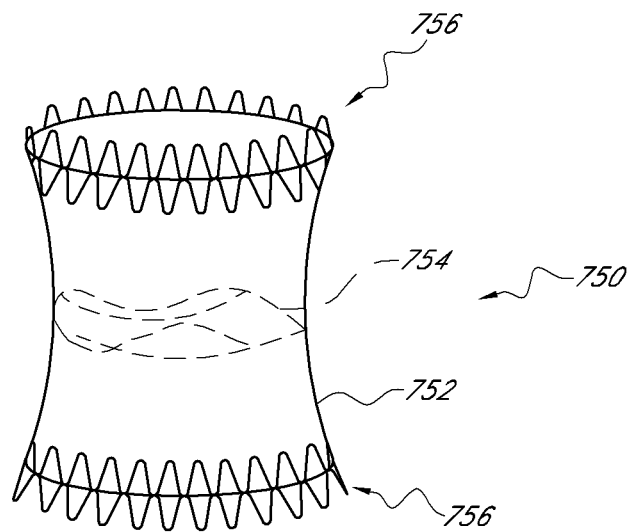

FIGS. 25E and 25F illustrate another embodiment of a prosthesis 750. In this embodiment, the prosthesis 750 includes a flexible fabric cuff 752, which can be coupled to a valve 754. As shown in FIG. 25E, the prosthesis 750 has a highly flexible shape in this configuration, which delivery within a catheter. Once the device 750 is positioned near the delivery site, the device 750 can be given structure through the use of one or more stents 756. The stents 756 can be self-expandable or balloon expandable. In the illustrated embodiment, the stents 756 are positioned generally at the proximal and distal ends of the device 750. The stents 756 provide structure to the prosthesis 750 such that it can support the valve 754 that is coupled to the cuff 752, and allows it to be positioned in the native annulus and to function.

Leaflet Subassembly

With reference back to the embodiments of FIGS. 1-16B, the valve 104 preferably is a tissue-type heart valve that includes a dimensionally stable, pre-aligned tissue leaflet subassembly. Pursuant to this construction, an exemplary tissue valve 104 includes a plurality of tissue leaflets that are templated and attached together at their tips to form a dimensionally stable and dimensionally consistent coapting leaflet subassembly. Then, in what can be a single process, each of the leaflets of the subassembly is aligned with and individually sewn the cuff 102, from the tip of one commissure uniformly, around the leaflet cusp perimeter, to the tip of an adjacent commissure. As a result, the sewed sutures act like similarly aligned staples, all of which equally take the loading force acting along the entire cusp of each of the pre-aligned, coapting leaflets. Once inflated, the cuff 102 supports the commissures with the inflation media and its respective pressure which will solidify and create a system similar to a stent structure. The resulting implant 100 thereby formed reduces stress and potential fatigue at the leaflet suture interface by distributing stress evenly over the entire leaflet cusp from commissure to commissure. This improved, dimensionally stable, reduced-stress assembly is operatively attached to the top of a previously prepared cloth-covered cuff 102 to clamp the tissue leaflet cusps on a load-distributing cloth seat formed by the top of the cloth-covered cuff without distorting the leaflets or disturbing their relative alignment and the resultant coaptation of their mating edges. Because the tissue leaflets experience lower, more evenly distributed stresses during operation, they are less likely to experience distortion in use. Thus, a more stable, long lived, functional closure or coaptation of the leaflets is provided by this even distribution of attachment forces.

A number of additional advantages result from the use of the implant 100 and the cuff 102 construction utilized therein. For example, for each key area of the cuff 102, the flexibility can be optimized or customized. If desired, the coapting tissue leaflet commissures can be made more or less flexible to allow for more or less deflection to relieve stresses on the tissue at closing or to fine tune the operation of the valve. Similarly, the base radial stiffness of the overall valve 100 structure can be increased or decreased by pressure or inflation media to preserve the roundness and shape of the valve 100.

Attachment of the valve 104 to the cuff 102 can be completed in any number of conventional methods including sewing, ring or sleeve attachments, gluing, welding, interference fits, bonding through mechanical means such as pinching between members. An example of these methods are described in Published Application from Huynh et al U.S. Pat. No. 6,102,944 or Lafrance et al 2003/0027332 or Peredo U.S. Pat. No. 6,409,759, which are hereby incorporated by reference herein. These methods are generally know and accepted in the valve device industry. As mentioned above, the cuff 102 may additionally house an inflation mold where the structure is formed within the body or the cuff made be the mold where the fluid is injected to create the support structure. The valve, whether it is tissue, engineered tissue, mechanical or polymer, may be attached before packaging or in the hospital just before implantation. Some tissue valves are native valves such as pig, horse, cow or native human valves. Most of which are suspended in a fixing solution such as Glutaraldehyde.

Although mechanical heart valves with rigid pivoting occluders or leaflets have the advantage of proven durability through decades of use, they are associated with blood clotting on or around the prosthetic valve. Blood clotting can lead to acute or subacute closure of the valve or associated blood vessel. For this reason, patients with implanted mechanical heart valves remain on anticoagulants for as long as the valve remains implanted. Anticoagulants impart a 3-5% annual risk of significant bleeding and cannot be taken safely by certain individuals.

Besides mechanical heart valves, heart valve prostheses can be constructed with flexible tissue leaflets or polymer leaflets. Prosthetic tissue heart valves can be derived from, for example, porcine heart valves or manufactured from other biological material, such as bovine or equine pericardium. Biological materials in prosthetic heart valves generally have profile and surface characteristics that provide laminar, nonturbulent blood flow. Therefore, intravascular clotting is less likely to occur than with mechanical heart valve prostheses.

Natural tissue valves can be derived from an animal species, typically mammalian, such as human, bovine, porcine canine, seal or kangaroo. These tissues can be obtained from, for example, heart valves, aortic roots, aortic walls, aortic leaflets, pericardial tissue such as pericardial patches, bypass grafts, blood vessels, human umbilical tissue and the like. These natural tissues are typically soft tissues, and generally include collagen containing material. The tissue can be living tissue, decellularized tissue or recellularized tissue.

Tissue can be fixed by crosslinking. Fixation provides mechanical stabilization, for example by preventing enzymatic degradation of the tissue. Glutaraldehyde or formaldehyde is typically used for fixation, but other fixatives can be used, such as other difunctional aldehydes, epoxides, genipin and derivatives thereof. Tissue can be used in either crosslinked or uncrosslinked form, depending on the type of tissue, use and other factors. Generally, if xenograft tissue is used, the tissue is crosslinked and/or decellularized.

The implants 100 can further include synthetic materials, such as polymers and ceramics. Appropriate ceramics include, for example, hydroxyapatite, alumina, graphite and pyrolytic carbon. Appropriate synthetic materials include hydrogels and other synthetic materials that cannot withstand severe dehydration. Heart valve prostheses can include synthetic polymers as well as purified biological polymers. These synthetic polymers can be woven or knitted into a mesh to form a matrix or similar structure. Alternatively, the synthetic polymer materials can be molded or cast into appropriate forms.

Appropriate synthetic polymers include without limitation polyamides (e.g., nylon), polyesters, polystyrenes, polyacrylates, vinyl polymers (e.g., polyethylene, polytetrafluoroethylene, polypropylene and polyvinyl chloride), polycarbonates, polyurethanes, poly dimethyl siloxanes, cellulose acetates, polymethyl methacrylates, ethylene vinyl acetates, polysulfones, nitrocelluloses and similar copolymers. Bioresorbable polymers can also be used such as dextran, hydroxyethyl starch, gelatin, derivatives of gelatin, polyvinylpyrolidone, polyvinyl alcohol, poly[N-(2-hydroxypropyl)methacrylamide], poly (hydroxy acids), poly (epsilon-caprolactone), polylactic acid, polyglycolic acid, poly(dimethyl glycolic acid), poly(hydroxy buterate), and similar copolymers. These synthetic polymeric materials can be woven or knitted into a mesh to form a matrix or substrate. Alternatively, the synthetic polymer materials can be molded or cast into appropriate forms.

Biological polymers can be naturally occurring or produced in vitro by fermentation and the like or by recombinant genetic engineering. Recombinant DNA technology can be used to engineer virtually any polypeptide sequence and then amplify and express the protein in either bacterial or mammalian cells. Purified biological polymers can be appropriately formed into a substrate by techniques such as weaving, knitting, casting, molding, extrusion, cellular alignment and magnetic alignment. Suitable biological polymers include, without limitation, collagen, elastin, silk, keratin, gelatin, polyamino acids, polysaccharides (e.g., cellulose and starch) and copolymers thereof.

A tissue-based valve prosthesis can maintain structural elements, such as leaflets, from its native form and/or structural elements can be incorporated into the prosthesis from the assembly of distinct pieces of tissue. For example, the valve prosthesis can be assembled from a porcine heart valve, from bovine pericardium or from a combination thereof. Porcine tissue valves, for example, the Toronto SPV® valve marketed by St. Jude Medical, Inc. St. Paul, Minn., can be implanted in the patient using the tools described herein. The Toronto SPV® valve is designed for implantation in an aortic heart valve position. See, for example, David et al., J. Heart Valve Dis. 1:244-248 (1992). It will be appreciated by those skilled in the art that the tools of the present invention are applicable to any valve, especially any tissue valve prosthesis, that is adapted for implanting in a patient.

A reinforcement may be placed along the inner surface of the valve commissure supports and/or scallops. In alternative embodiments, the reinforcement is placed on the outer surface of the valve, such as at the valve commissure supports. The reinforcement preferably includes apertures through which the fasteners extend or can be inserted. The reinforcements are thin strips of relatively strong material. The reinforcement can prevent or reduce damage to the prosthesis when the fasteners are inserted and after implantation of the heart valve prosthesis in the patient. The reinforcement, thus, can protect and support the commissure supports from potential damage generated by the presence of the fasteners. In alternative embodiments, the reinforcement is placed on the outside of the aorta such that the fastener pierces the reinforcement after passing through the prosthetic valve.

Tissue valves whether implanted surgically or percutaneously have a risk of calcification after implantation. To prevent or minimize the calcification several treatments have been employed before the tissue is fixed. Some strategies include treating the valves with ethanol, metallic salts, detergents, biophosphonates, coimplants of polymeric controlled release drug delivery systems, and covalent attachment of anticalcifying agents. In the preferred embodiment the valve tissue is treated in 40% to 80% ethanol for 20 to 200 hours before fixation in a buffered glutaraldehyde solution. The ethanol pretreatment may prevent calcification in the valve after implantation and serves to remove cholesterol and phospholipids from the tissue before fixation. (ref Prevention of Bioprosthetic Heart Valve Calcification by Ethanol Preincubation, Vyavahare et al)

Inflation Media

The inflatable structure 107 can be inflated using any of a variety of inflation media 122, depending upon the desired performance. In general, the inflation media can include a liquid such water or an aqueous based solution, a gas such as CO2, or a hardenable media which may be introduced into the cuff 102 at a first, relatively low viscosity and converted to a second, relatively high viscosity. Viscosity enhancement may be accomplished through any of a variety of known UV initiated or catalyst initiated polymerization reactions, or other chemical systems known in the art. The end point of the viscosity enhancing process may result in a hardness anywhere from a gel to a rigid structure, depending upon the desired performance and durability.

Useful inflation media generally include those formed by the mixing of multiple components and that have a cure time ranging from a few minutes to tens of minutes, preferably from about three and about twenty minutes. Such a material should be biocompatible, exhibit long-term stability (preferably on the order of at least ten years in vivo), pose as little an embolic risk as possible, and exhibit adequate mechanical properties, both pre and post-cure, suitable for service in the cuff of the present invention in vivo. For instance, such a material should have a relatively low viscosity before solidification or curing to facilitate the cuff and channel fill process. A desirable post-cure elastic modulus of such an inflation medium is from about 50 to about 400 psi—balancing the need for the filled body to form an adequate seal in vivo while maintaining clinically relevant kink resistance of the cuff. The inflation media ideally should be radiopaque, both acute and chronic, although this is not absolutely necessary.

Details of compositions suitable for use as an inflation medium in the present invention are described in greater detail in U.S. patent application Ser. No. 09/496,231 to Hubbell et al., filed Feb. 1, 2000 and entitled "Biomaterials Formed by Nucleophilic Addition Reaction to Conjugated Unsaturated Groups" and U.S. patent application Ser. No. 09/586,937 to Hubbell et al., filed Jun. 2, 2000 and entitled "Conjugate Addition Reactions for the Controlled Delivery of Pharmaceutically Active Compounds". The entirety of each of these patent applications is hereby incorporated herein by reference.

Below is listed one particular three-component medium. This medium comprises:

(1) polyethylene glycol diacrylate (PEGDA), present in a proportion ranging from about 50 to about 55 weight percent; specifically in a proportion of about 52 weight percent, (2) pentaerthyritol tetra 3(mercaptopropionate) (QT) present in a proportion ranging from about 22 to about 27 weight percent; specifically in a proportion of about 24 weight percent, and (3) glycylglycine buffer present in a proportion ranging from about 22 to about 27 weight percent; specifically in a proportion of about 24 weight percent.

Variations of these components and other formulations as described in copending U.S. patent application Ser. Nos. 09/496,231 and 09/586,937, both to Hubbell et al., may be used as appropriate. In addition, we have found PEGDA having a molecular weight ranging from about 350 to about 850 to be useful; PEGDA having a molecular weight ranging from about 440 to about 560 are particularly useful.

Radiopaque materials as previously discussed may be added to this 3-component system. We have found that adding radiopacifiers such as barium sulfate, tantalum powder, and soluble materials such as iodine compounds to the glycylglycine buffer is useful.

Applicants have found that triethanolamine in phosphate-buffered saline may be used as an alternative to glycylglycine buffer as the third component described above to form an alternative curable gel suitable for use in embodiments of the present invention.

An alternative to these three-component systems is a gel made via polymer precipitation from biocompatible solvents. Examples of such suitable polymers include ethylene vinyl alcohol and cellulose acetate. Examples of such suitable biocompatible solvents include dimethylsulfoxide (DMSO), n-methyl pyrrolidone (NMP) and others. Such polymers and solvents may be used in various combinations as appropriate.

Alternatively, various siloxanes may be used as inflation gels. Examples include hydrophilic siloxanes and polyvinyl siloxanes (such as STAR-VPS from Danville Materials of San Ramon, Calif. and various silicone products such as those manufactured by NuSil, Inc. of Santa Barbara, Calif.).

Other gel systems useful as an inflation medium or material for the present invention include phase change systems that gel upon heating or cooling from their initial liquid or thixotropic state. For example, materials such as n-isopropyl-polyacrylimide (NIPAM), BASF F-127 pluronic polyoxyamer, and polyethylene glycol (PEG) chemistries having molecular weights ranging between about 500 and about 1,200 are suitable.

Effective gels may also comprise thixotropic materials that undergo sufficient shear-thinning so that they may be readily injected through a conduit such as a delivery catheter but yet still are able to become substantially gel-like at zero or low shear rates when present in the various channels and cuffs of the present invention.

In the case of the three-component PEDGA-QT-glycylglycine formulation described above, a careful preparation and delivery protocol should be followed to ensure proper mixing, delivery, and ultimately clinical efficacy. Each of the three components is typically packaged separately in sterile containers such as syringes until the appropriate time for deploying the device. The QT and buffer (typically glycylglycine) are first continuously and thoroughly mixed, typically between their respective syringes for approximately two minutes. PEGDA is then mixed thoroughly with the resulting two-component mixture for approximately three minutes. This resulting three-component mixture is then ready for introduction into the cuff as it will cure into a gel having the desired properties within the next several minutes. Cure times may be tailored by adjusting the formulations, mixing protocol, and other variables according to the requirements of the clinical setting. Details of suitable delivery protocols for these materials are discussed in U.S. patent application Ser. No. 09/917,371 to Chobotov et al.

The post-cure mechanical properties of these gels may be highly tailorable without significant changes to the formulation. For instance, these gels may exhibit moduli of elasticity ranging from tens of psi to several hundred psi; the formulation described above exhibits moduli ranging from about 175 to about 250 psi with an elongation to failure ranging from about 30 to about 50 percent.

It may be helpful to add an inert biocompatible material to the inflation material. In particular, adding a fluid such as saline to the PEGDA-QT-glycylglycine formulation (typically after it has been mixed but before significant curing takes place) lowers the viscosity of the formulation and results in greater ease when injecting the formulation into cuffs and channels without sacrificing the desired physical, chemical, and mechanical properties of the formulation or its clinical efficacy. In the appropriate volume percentages, adding materials such as saline may also reduce the potential for the inflation material such as PEGDA-QT-glycylglycine to pose an embolic risk in case of spillage or leakage. Saline concentrations as a volume percentage of the final saline/three-component formulation combination may range from zero to as high as sixty percent or more; particularly suitable are saline concentrations ranging from about twenty to about forty percent. A saline volume concentration of about thirty percent to be most suitable. Alternatives to saline may include biocompatible liquids, including buffers such as glycylglycine.

In more general terms, it is desirable to use an inflation medium in which each of its components is biocompatible and soluble in blood. A biocompatible inflation medium is desirable so to manage any toxicity risk in the case the inflation medium were inadvertently released into the patient's vasculature. A soluble inflation medium is desirable so to manage any embolism risk if released into the vasculature. Such an inflation medium should not disperse nor gel or solidify if spilled into flowing blood before curing. In the event of a spill, the normal blood flow would then rapidly disperse the components and their concentration would fall below the level required for crosslinking and formation of a solid. These components would then be eliminated by the body through standard pathways without posing an embolic risk to the patient. Among the many possibilities of an inflation medium example in which all of the components are soluble in blood is the combination polyethylene glycol diacrylate, a thiolated polyethyleneamine, and a buffer.

As previously discussed, more than one type of inflation medium, or more than one variant of a single type of inflation medium may be used in a single graft to optimize the graft properties in the region in which it is disposed.

For example, in the cuffs 102 of the various embodiments of the present invention, the inflation material serves as a conformable sealing medium to provide a seal against the lumen wall. Desirable mechanical characteristics for the inflation medium in the proximal and distal cuffs would therefore include a low shear strength so to enable the cuff to deform around any luminal irregularities (such as calcified plaque asperities) and to conform to the luminal profile, as well as a high volumetric compressibility to allow the fill material to expand the cuffs as needed to accommodate any late lumen dilatation and maintain a seal.

Another inflation media that has proven especially useful is an epoxy based two part inflation media, where one part contains the reaction product of epichlorohydrin and bisphenol A, and Butaneddiol diglyceridyl ether. And where one part contains 2,2,4-trimethyl-1, 6-hexanediamine. Whereas the material may have a viscosity of about 100-200 cPs (@100 rpm/23 C) but most preferably they may be readily injected through a small lumen to be introduced to the implant from outside the body. The operating temperature range may be from about −55 to about +125 C but would be most advantageous at the body temperature of +37 C. Other properties may include a hardness of about 81 on the Shore D scale and a lap shear strength of 1,700 PSI. An example of this would be EPO-TEK 301 supplied by 14 Fortune Drive Billerica, Mass.

The mixed uncured inflation media preferably has a viscosity less than 2000 cps In one embodiment the epoxy based inflation media has a viscosity of 100-200 cps. In another embodiment the inflation media has a viscosity less than 1000 cps.

In one embodiment the inflation media contains a foaming agent. The foaming inflation media is beneficial because the foaming action can generate pressure within the inflatable portion of the device. Therefore less inflation media needs to be injected. Additionally any pressure loss from the disconnection process is compensated for by the foaming action of the inflation media. Many appropriate foaming medias are possible; one example is a urethane foam.

In another embodiment the balloon or inflation channel may be connected to the catheter on both ends. This allows the balloon to be preinflated with a nonsolidifying material such as a gas or liquid. If a gas is chosen $CO_2$ or helium are likely choices, these gasses are used to inflate intraortic balloon pumps. Preferably the preinflation media is radiopaque so that the balloon position can be determined by angiography. Contrast media typically used in interventional cardiology could be used to add sufficient radiopacity to most liquid preinflation medias. When it is desired to make the implant permanent and exchange the preinflation media for the permanent inflation media, the permanent inflation media is injected into the inflation channel through a first catheter connection. As the permanent inflation media is injected the preinflation media is expelled out a second catheter connection. The catheter connections are positioned in such a way that substantially all of the preinflation media is expelled as the permanent inflation media is injected. In one embodiment an intermediate inflation media is used to prevent entrapment of preinflation media in the permanent inflation media. In one embodiment the intermediate inflation media is a gas and the preinflation media is a liquid. In another embodiment the intermediate inflation media or preinflation media functions as a primer to aid the permanent inflation media to bond to the inner surface of the inflation channel. In another embodiment the preinflation media or the intermediate inflation media serves as a release agent to prevent the permanent inflation media from bonding to the inner surface of the inflation channel.

The permanent inflation media may have a different radiopacity than the preinflation media. A device that is excessively radiopaque tends to obscure other nearby features under angiography. During the preinflation step it may be desirable to visualize the inflation channel clearly, so a very radiopaque inflation media may be chosen. After the device is inflated with the permanent inflation media a less radiopaque inflation media may be preferred. The feature of lesser radiopacity is beneficial for visualization of proper valve function as contrast media is injected into the ventricle or the aorta.

Anchoring Mechanisms

In the embodiments described above, it may be necessary or desirable to incorporate an anchoring mechanism 220 into the cuff 102. The anchoring mechanism 220 can comprise any of a variety of anchors or barbs such as those that have been used extensively on interventional devices, such as grafts for the treatment of abdominal aortic aneurysms, atrial appendage closure devices and filters. Most of the traditional retention mechanisms used for percutaneously implantable valves rely on an interference fit between the implant and the vessel to provide a significant portion of the retention force, or to activate the retention means. However, in the case of a replacement mitral or aortic valve, it can be desirable to minimize the radial force at the valve annulus, because excessive dilation of either annulus may have a detrimental effect on the function of another other valve.

Figure 26:
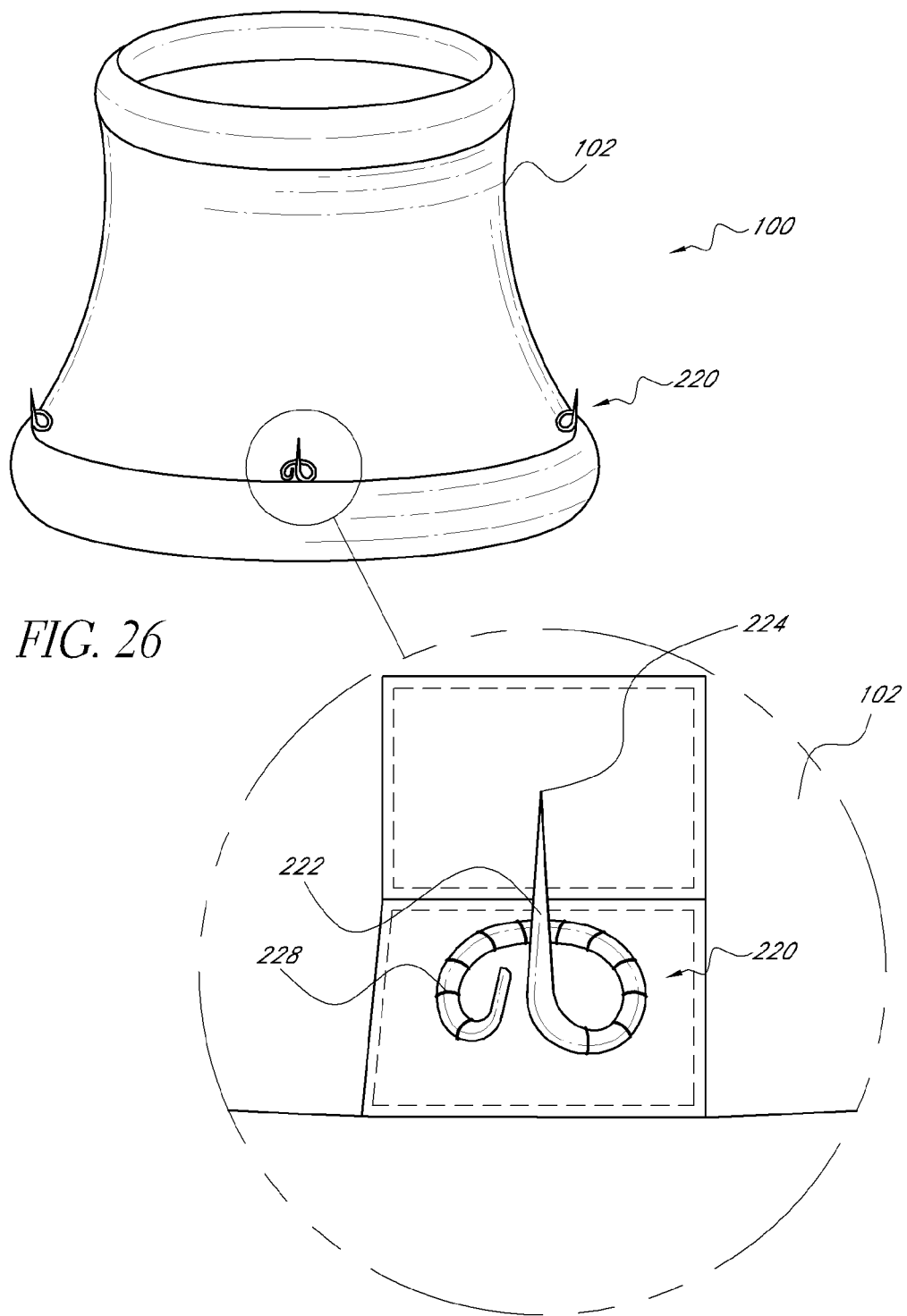
FIG. 26 is a side perspective view of an anchor for an implant valve.

With reference to FIG. 26, the anchoring mechanism 220 generally comprises a radially extending flange 222 that protrudes radially outward from the implant 100 to engage the tissue thus securing the implant 100 from migration. The radially extending flange 222 can include a sharpened tip 224 as shown in FIG. 26. With reference to the particular embodiment shown in FIG. 26, the anchor 220 can comprise a looped base 226 that is coupled to the cuff 102 by sutures 228. The base 226 can be sutured to a reinforced area 230 of the cuff 102. Of course, those of skill in the art will recognize in light of the disclosure herein various other configurations of the anchor 220 and the manner of securing the anchor 220 to the implant 100.

In another embodiment, the valve 100 is sutured to the native anatomy. For example, the valve 100 can include a sewing ring configured allow sutures to be easily attached to the implant 100. A percutaneous or minimally invasive sewing device can also be incorporated or used as a secondary procedure. This device would contain at least one needle remotely actuated to attach the valve 100 to the tissue, or to a second device previously implanted at the desired valve location. Other methods may utilize a balloon or other force mechanism to push or pull the suture into position. These needles can be made from metallic or polymer elements or utilize sutures that may be inserted through the anatomy. They would range in diameters from 0.002 inches to about 0.040 inches and may protrude into the anatomy from 0.005 inches to about 0.090 inches depending upon the anatomy.

Figure 27A:
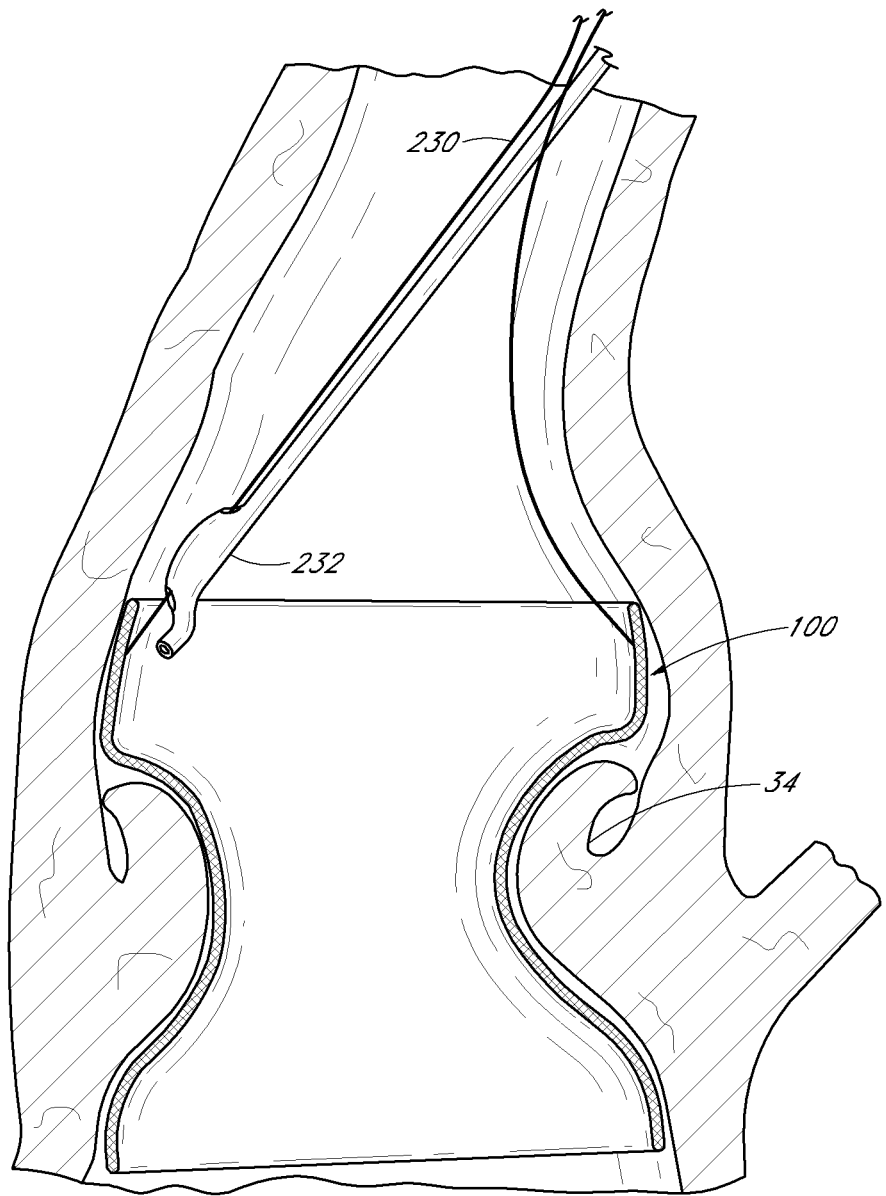
FIGS. 27A-C are time sequenced steps of securing an implant to the aorta with a staple or clip.
Figure 27B:
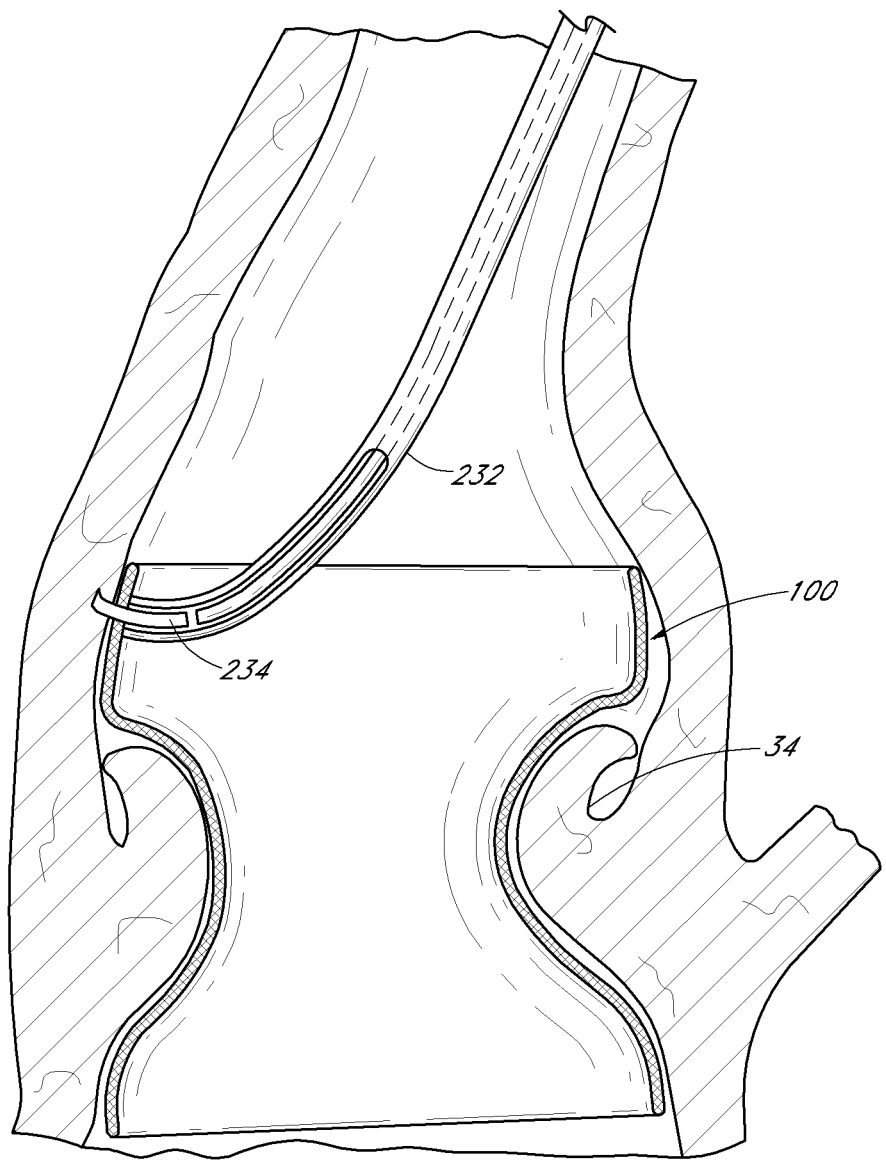
Figure 27C:
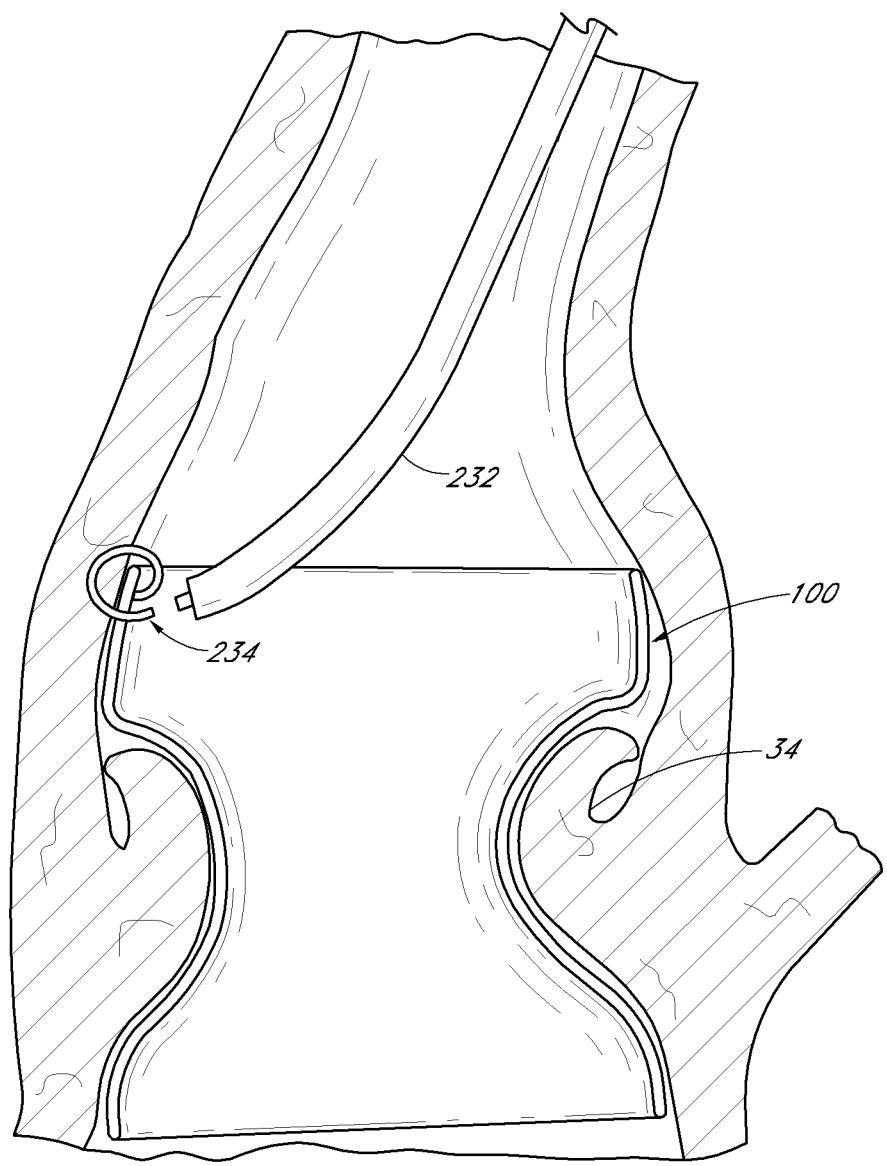
Figure 27D:
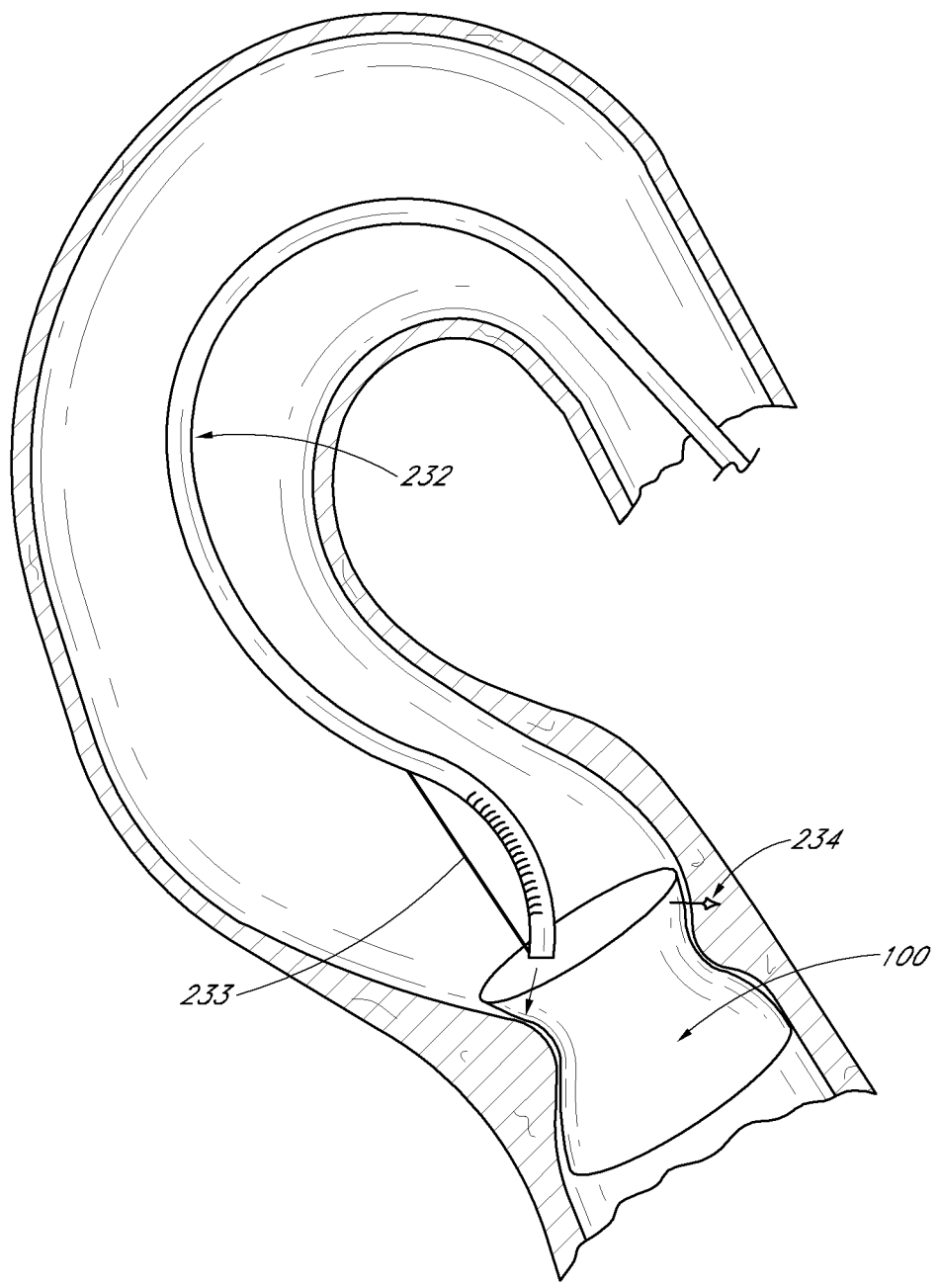
FIGS. 27D-E are side views of another embodiment of securing an implant to the aorta with a staple or clip.
Figure 27E:
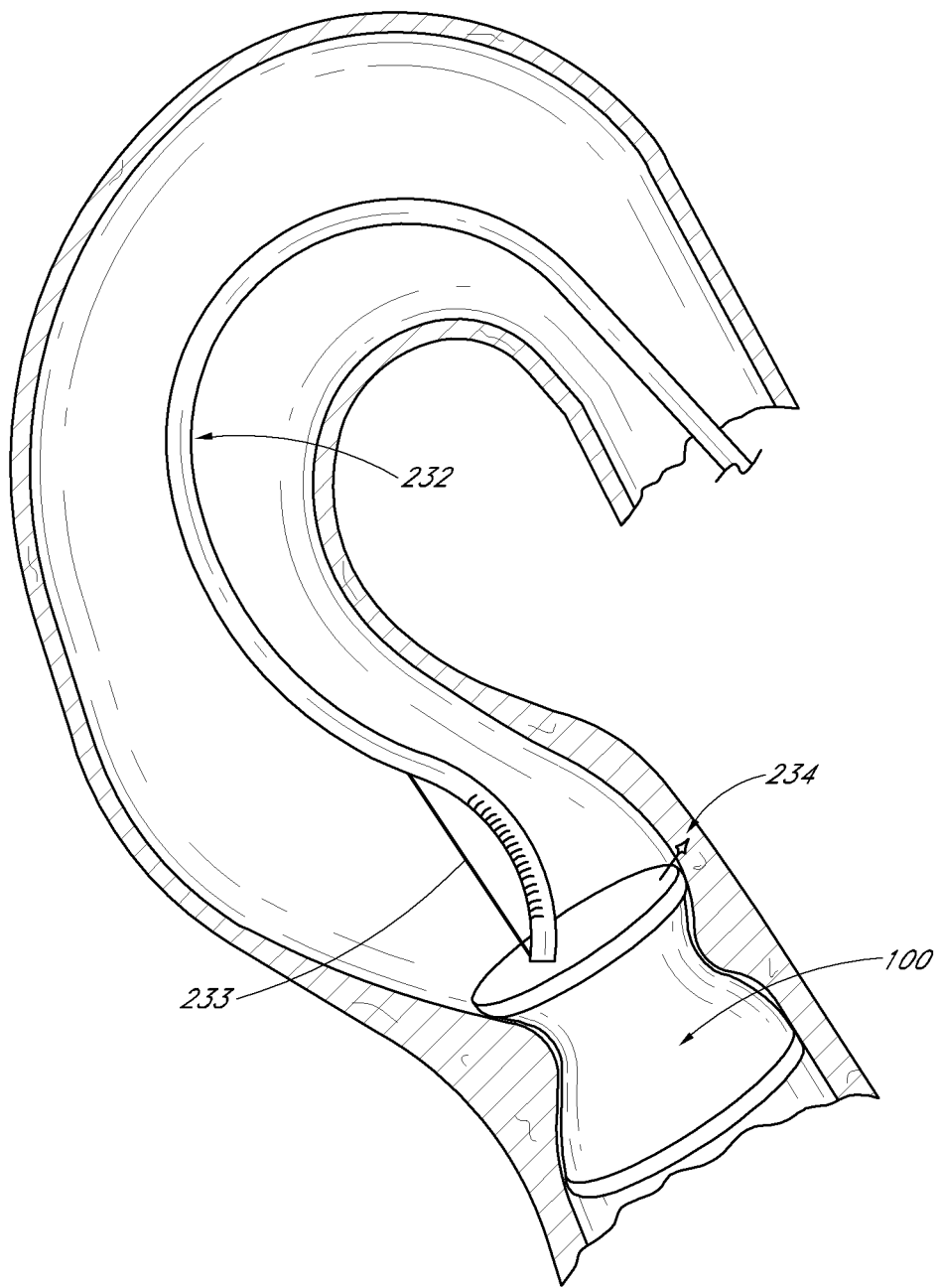

With reference to FIGS. 27A-C, in yet another embodiment, the valve 100 is stapled or clipped into place with a single or multiple detachable staples, clips, barbs or hooks. As shown in FIG. 27A, the valve 100 can be positioned over the native aortic valve 24. In this embodiment, the valve 100 is temporarily secured by control wires 230 as will be explained in more detail below. A surgically inserted or percutaneously insert tool 232 is positioned near the valve 100 and is used to insert clips 234 or other type of anchor around the annulus and allows them to engage the tissue and/or portion of the valve 100. The staples, clips, hooks or barbs could also be delivered percutaneously with a device that positions the staples, clips, hooks or barbs near or below to the native valve. These could be attached through a balloon, pull wire or other force mechanism to push or pull them into position. The tool 232 used to stapled in place the valve 100 can be similar to those used to connect the mitral valve leaflets together by the company E-Valve and described in US patent publication 2004/0087975 Lucatero, Sylvester et al, which is hereby incorporated by reference herein. FIGS. 27D and 27E illustrate an embodiment in which the tool 232 includes a tensioning wire 233, which has a distal end that is preferably coupled to the distal end of the device 232 and has a proximal end that extend through the device 232. By applying tension to the wire 233, the top of the too 232 can be bent towards the wall of the aorta as shown in FIGS. 27D and 27E.

In one embodiment wires similar to, the control wires 230 described in this application serve as guide wires over which the secondary anchoring catheter is delivered. This allows the precise placement of the anchors, staples, sutures etc. relative to the prosthesis, because the anchor catheter will follow the wire right to the desired anchor location. In one embodiment the anchor location is at the valve commissures. In another embodiment the anchor location is at the proximal end of the device. The anchor delivery catheter may consist of a multi lumen tube where one lumen serves to track over the wire and the second lumen or additional lumens deliver the anchor. In one embodiment the anchor is a screw which is actuated with a rotational motion and threaded through the prosthesis and in to the aortic wall. Other anchor designs described in this application may also be adapted to the anchor delivery catheter.

In another embodiment, an adhesive is used to secure the valve 100 to the tissue. For example, adhesives such as a fibrin glue or cyanoacrylate could be delivered percutaneously or surgically to attach the valve 100 to the tissue. A method for percutaneously delivering an adhesive includes channeling it through a tubular support member, which has openings around its outer surface to allow the adhesive to be released. The adhesive could be used in conjunction with other anchoring methods to ensure that no blood leaks around the valve 100. Adhesion enhancing surfaces can be provided, such as ePTFE patches or jackets, to promote cellular in-growth for long term anchoring.

With reference to FIG. 28, in another embodiment, a barb, anchor, hook or pin 220 is located within a fold 110 of the cuff 102. When the inflation channels 120 are not inflated, the flange 222 of the anchor 220 does not extend in a radial direction. As the inflation channels 120 in the cuff 102 are inflated and deployed, the anchor 220 is configured to unfold moving the flange 222 of the anchoring mechanism 220 into a radially protruding position. In such an embodiment, a section of the cuff 102 can be reinforced to inhibit the anchoring mechanism from puncturing the fabric or inflation passages 120 of the cuff 102. Preferably, the anchoring mechanism 220 is located so that the sharp end 224 of the anchor mechanism is designed to engage the tissue is not located near an inflation passage 120, and is oriented so that it is unlikely that the anchoring mechanism 220 could damage an inflation passage during normal use of the device. The anchor mechanism 220 could be attached to the cuff 102 in many ways, for example the end of the anchor mechanism 220 not intended to engage tissue could be sutured, glued or crimped to the cuff. In this case the sutured end of the anchor mechanism 220 can have a shape that prevents disengagement from the sutures. The anchor mechanism 220 may have holes through it, which the sutures pass through, or the anchor mechanism may be made from wire and shaped in a configuration that does not allow the disengagement of the sutures. One suitable pattern is a generally circle, or oval shape. Others would be apparent to one skilled in the art. FIG. 29 illustrated a modified embodiment in which the anchor mechanism is positioned on an inflatable strut. In yet another embodiment, the anchors 220 can be fixed to the device at or near the attachment point of the deployment control wires 230 to provide a solid engagement for each anchor, and to test the engagement of each anchor individually.

In the embodiment of FIGS. 28 and 29, the anchor 220 can comprise a laser cut tubular member attached to the inflation lumens such that they deploy and expand radially when inflated and provide an exposure to a point or hook 224. These expansion members could be cut from stainless steel and be plastically deformable or a super-elastic material such as Nitinol and recover as the inflation lumen is deflated thus hiding the point or hook from tissue exposure. It may be desirable to wrap these devices around the inflation lumen and attach them to the cuff for stability. A longer device may provide better stability since the forces would be spread out over a longer distance. A single device or multiple hooks may be required to anchor the cuff properly. The hooks 224 may be pointed either proximally or distally or in both directions if desired. The hooks 224 in these embodiments would preferably be bent from the axial direction between 40 and 95 degrees.

Figure 28A:
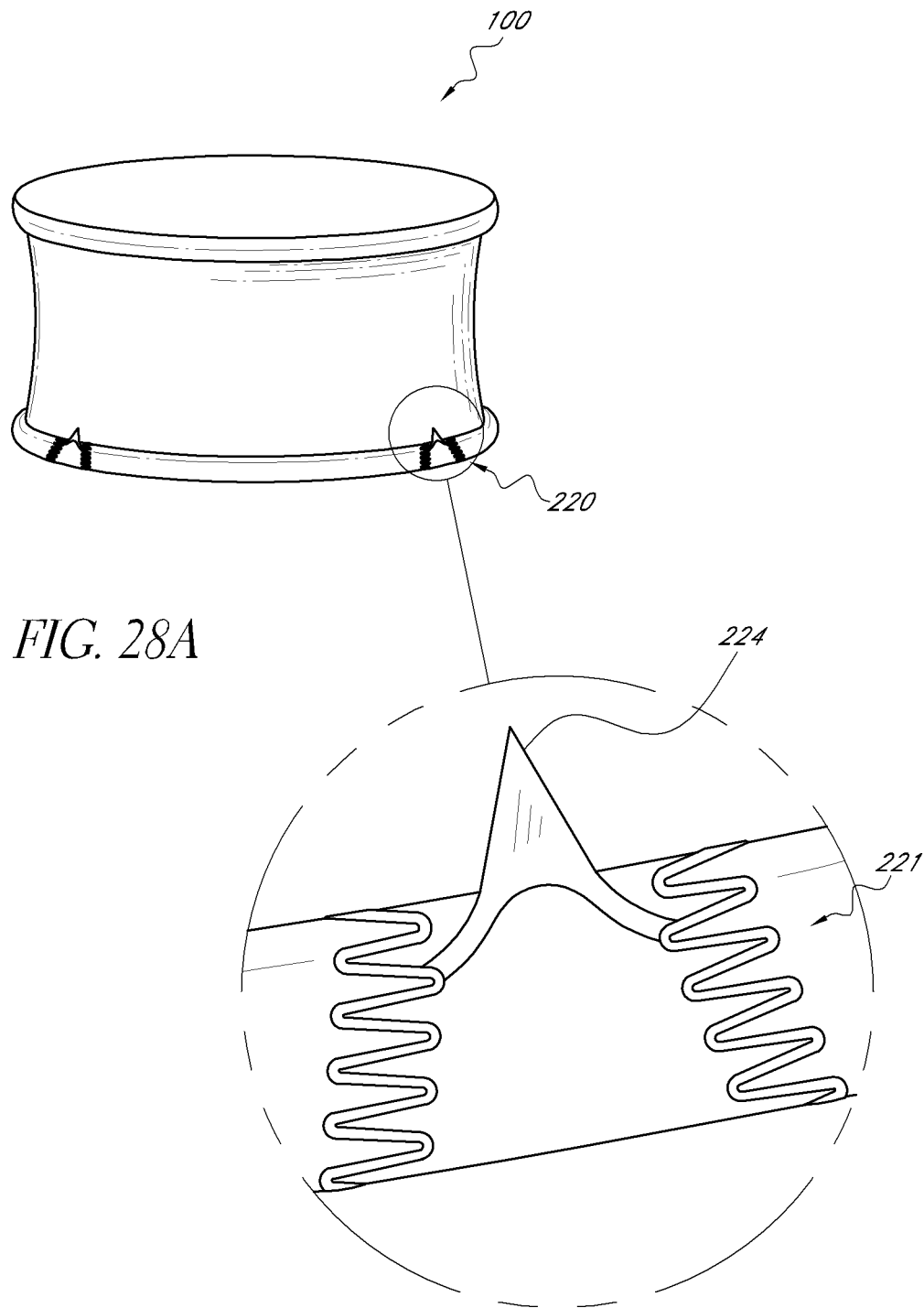
FIG. 28A is a side perspective view of another embodiment of an anchor for an implant valve.

FIG. 28A illustrates an other embodiment of an anchor 224. In this embodiment, the anchor is supported between a pair of annular stents 221 that are formed with proximal and distal bends in a generally sinusoidal pattern. The stents 221 can be wrapped around an inflation lumen as shown. In one embodiment, the hook 224 is moved into a radially extending position as the stents 221 are expanded by the inflation lumen.

In another embodiment, the distal and proximal ends 128, 126 of the implant 100 can be sized to provide an anchor functions For example, as described above with reference to FIG. 3A, the valve 100 can utilize a distal or proximal ends 128, 126 of larger diameter than the middle portion 124 of the valve 100. In a preferred embodiment, the implant 100 includes both an enlarged distal and an enlarged proximal ends 128, 126. This produces a device with an hourglass shape as shown in FIG. 2A. The enlarged sections 128, 126 of the valve 100 inhibit the device from migrating proximally or distally. It is also possible to shape the transitions of the implant 100 so that the cone shape produces a wedge effect in a desired location, thereby increasing the radial force. Alternatively it is possible to shape the transitions with a shallow angle so that the implant is shaped like a rivet and the radial force caused by the application of axial force is minimized. The axial force is applied to the implant by the pressure of the blood acting on the area of the implant. This axial force must be reacted by a normal force on the surface of the implant. The implant 100 can be designed so that the radial component of the normal force at any desired location is any desired ratio of the axial force.

For an implant 100 that utilizes an hourglass shape as described above, the orientation of the anchoring mechanisms 220 described above can be adapted from radially expandable applications can be reevaluated and reapplied. For example barbs could be placed on the most distal portion 128 of the hourglass shaped structure and the barbs would preferably be oriented approximately parallel to the axial direction. See e.g., Figure FIG. 28. During the deployment procedure, the implant can be pulled back into the annulus after the distal portion 128 inflated. An axial force is then applied by the inflation lumens 120 to the anchoring mechanism 220.

FIG. 30 illustrates an embodiment of an actuated anchoring mechanism 240. In this embodiment, a rod member 242 is coaxially positioned within a tube 244 positioned generally on the outer surface of the valve 100. A radially extending hook or barb 246 is attached to the rod member 242 and extends through a slot 248 formed in the tube 244. In a first position, the barb 246 extends generally against the outer surface of the valve 100. When the rod 242 is rotated, the barb 246 rotates away from the valve 100 to expose the barb 246 and form an anchor. When rotated back, the barb 246 would unexposed such that the valve 100 can be delivered or repositioned. In the illustrated embodiment, the rod member 242 is coupled to the control wire 230. The slot 248 forms a ramp or guide that promotes rotational movement and exposure of the barb 246 as the rod member 242 is axially moved within the tub 246. The mechanism could also be driven hydraulically by the inflation of the device.

Figure 30A:
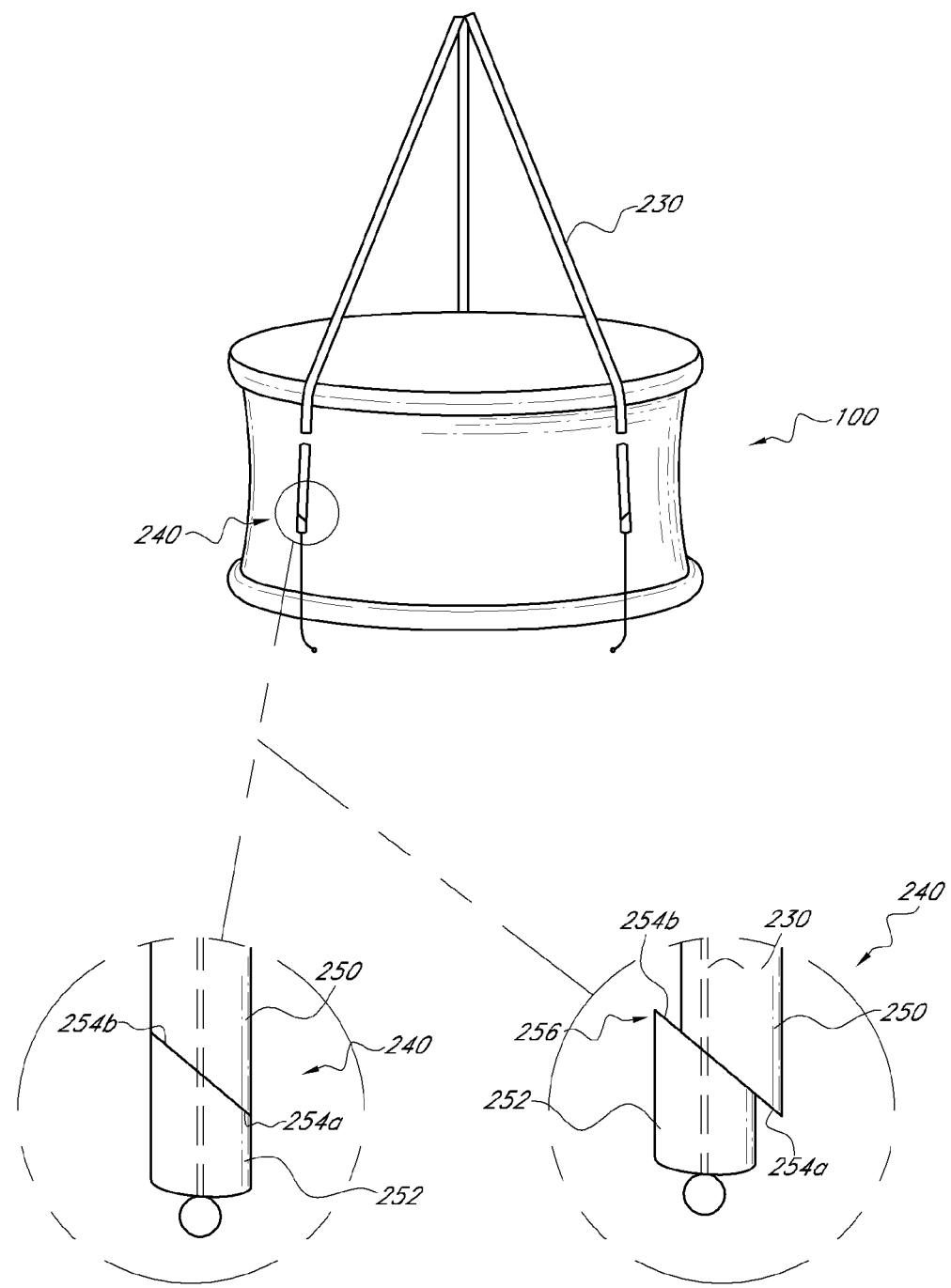
FIG. 30A is a side perspective view of another embodiment of an anchor for an implant valve in a deployed and un-deployed configuration.

FIG. 30A illustrates another embodiment of an actuated anchor mechanism 240. In this embodiment, the mechanism 240 comprises a proximal tube portion 250 and a distal tube portion 252, which interface at corresponding tapered faces 254a, 254b. By applying a force to the two sections of tube, the distal portion 252 moves both longitudinally and horizontally exposing a sharp section 256 of the lower portion 252 to the tissue wall. Once exposed and engaged to the wall of the tissue, the device could be locked by maintaining a force on control wire 230 or by using an interference fit such as a screw and nut to hold the device in place.

Figure 31:
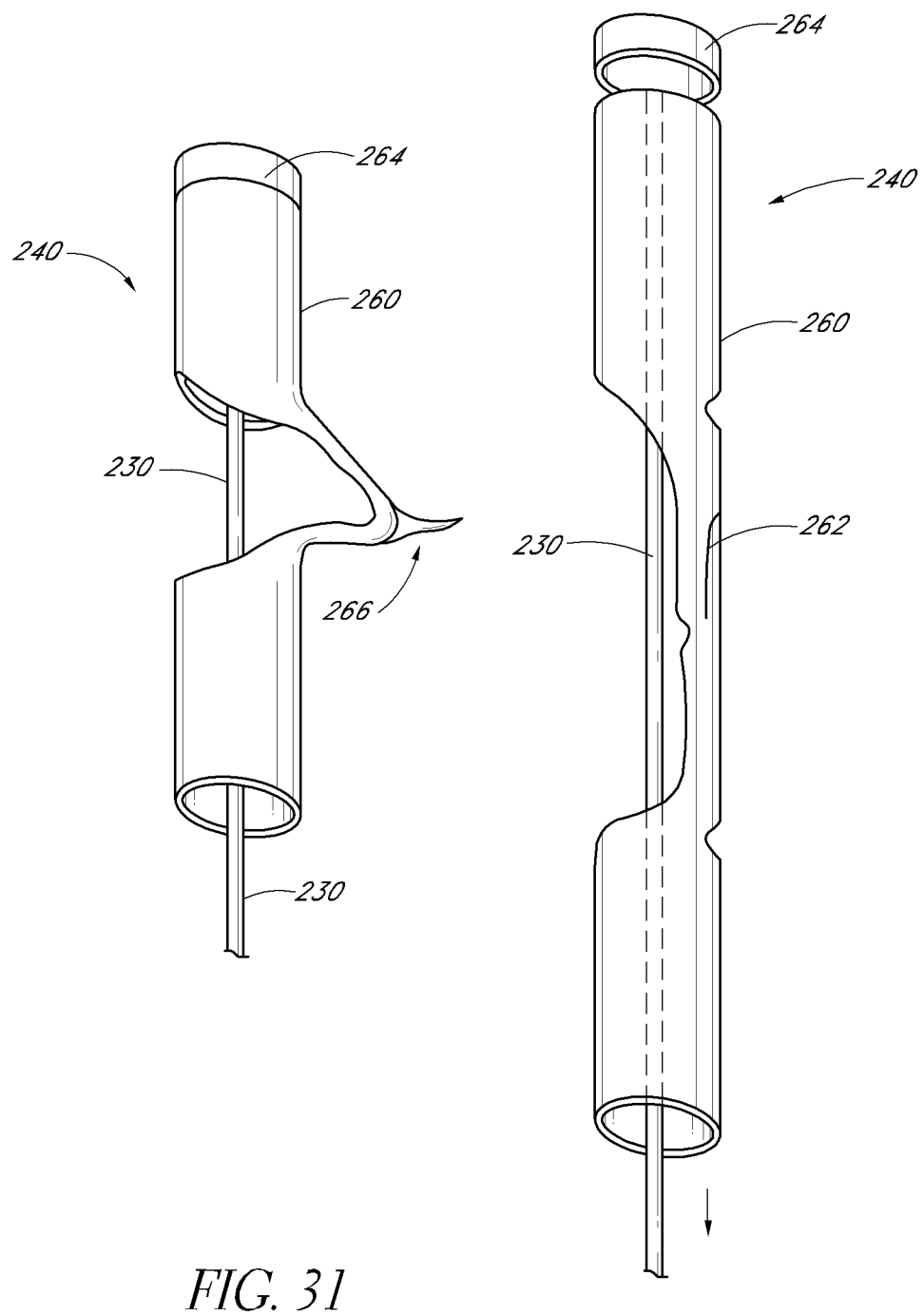
FIG. 31 is a side perspective view of another embodiment of an anchor for an implant valve in a deployed and un-deployed configuration.

FIG. 31 illustrates another embodiment of an actuated anchoring mechanism 240. In this embodiment, the anchor 240 comprises a tubular member 260, with a pattern 262 cut into the tubular member 260. The control wire 230 extends through the tubular member 260 and is attached to a distal stop 264. The tubular member 260 is attached to the cuff 102 by sutures, adhesives etc. By pulling on the control wire 230, longitudinal compression forces cause the tube to buckle exposes a hook or barb 266 to the tissue wall. The tube 260 may be made from a metallic material such as stainless steel or Nitinol. If the tube 260 is super-elastic it can be possible to recover the hook 266 when the force is released. If made from a stainless steel or the like, the anchor 240 can be plastically deformed and the exposure of the hook 266 would be set. The actuation of this anchor 240 generally requires a longitudinal force to buckle the tube 260 and may require a lock to hold the tension in the pull wire 230. This lock could be maintained by an interference fit such as a screw and nut.

In this embodiment, the hook 266 can be cut from a hypotube 260 of slightly larger inside diameter than the deployment control wire 230 outside diameter. Preferably these diameters are in the range of 0.01 to 0.03 inch. The hook 266 preferably extends from the device at an angle of 10 to 80 degrees, more preferably at an angle of 20 to 45 degrees.

Figure 32:
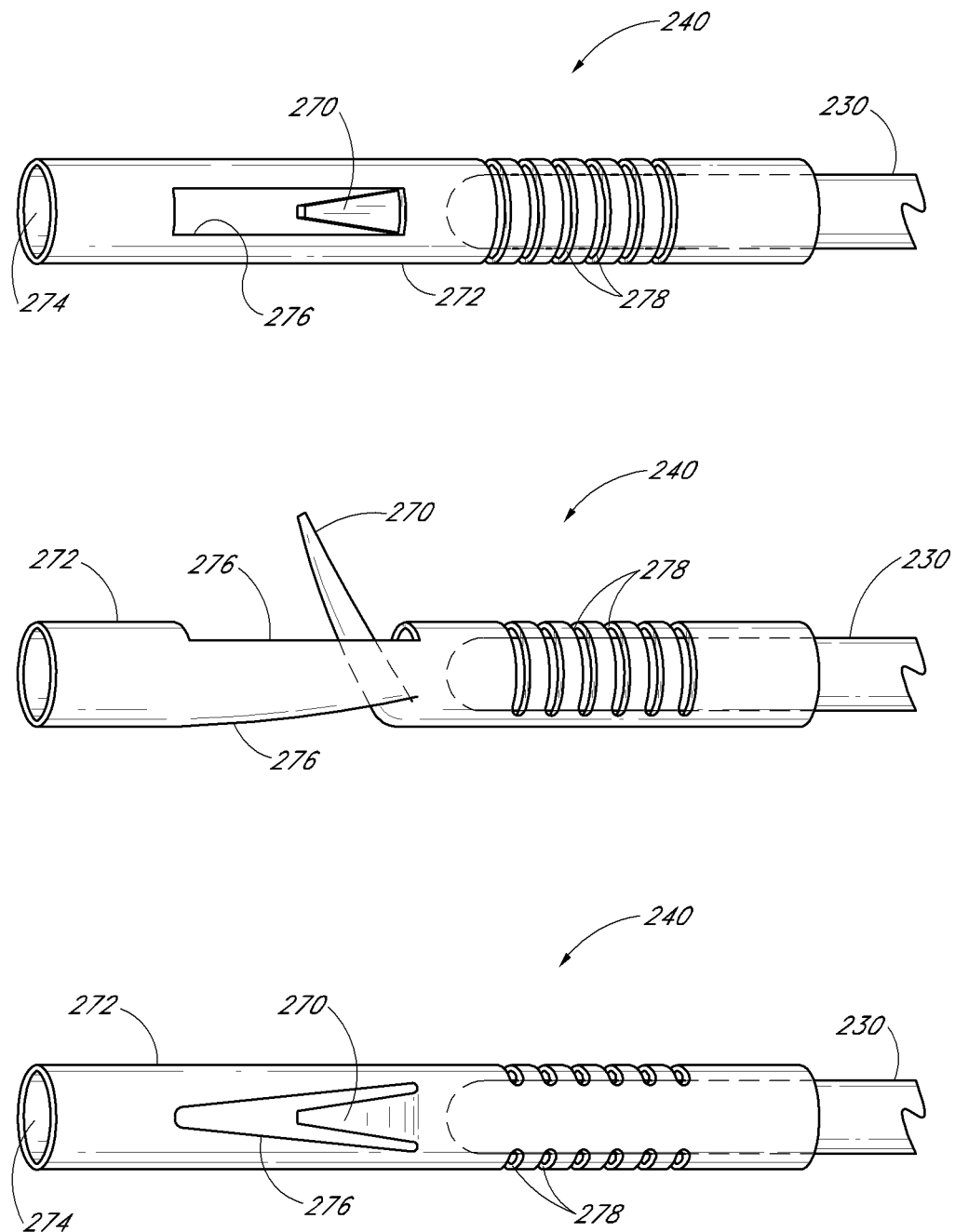
FIG. 32 is a top and side views of another embodiment of an anchor for an implant valve in a deployed and un-deployed configuration.

FIG. 32 illustrates another embodiment of an actuating anchor mechanism 240. In this embodiment, the anchor 240 comprises a pre-shaped finger 270 that was cut into a tube 272 and formed such that it would bend through the tubes inner diameter 274 and expose a point on the opposite side of the tube. A window 276 cut through both walls of the tube 272 would allow for this exposure of the hook 270. A wire 230 can be placed through the tube 272 to would interfere with the hook to hide it for delivery and recovery. This pivoting hook 272 could also be used on the same wall side if the attachment to the tube was in the center of the hook 272. Similar locking devices for the wire could be used if necessary described above. In the illustrated embodiment, the tube 272 includes slots 278 cut into the wall of the tube 272 to enhance the flexibility of the tube 272.

FIG. 32A illustrates yet another embodiment of an actuating anchor mechanism 240a. In this embodiment, the anchor 240a also comprises a pre-shaped finger 270a that was cut into a tube 272a and formed such that it would a first end 273a bend through the tube's inner diameter 274a and expose a point 273b on the opposite side of the tube 272a. A window 276a cut through both walls of the tube 272a would allow for this exposure of the hook 270a. A wire 230 can be placed through the tube 272 to would interfere with the side 272a of the hook 270 to deflect the point 273b for delivery and recovery.

FIG. 33 illustrates another embodiment of an actuating anchor 240. In this embodiment, a tubular member 280 is attached to the cuff 102. A coaxial member 282 (e.g., a distal end of the control wire 230) is positioned within the tubular member 280 and provided with a hook 284 that can be attached or integral to the coaxial member 282. When the coaxial member 282 is moved longitudinally within the tubular member 280 the hook 284 is exposed through a window or opening 286 in the tube 280. If pre-shaped Nitinol is used the hook 284 can be recoverable and hidden back into the tube 280 for removal. The hook 284 can face either proximal or distally or both directions for device stability.

Delivery Catheter

FIGS. 34-37 illustrate an exemplary embodiment of a delivery catheter 300 that can be used to deliver the valve 100 describe above. In general, the delivery catheter 300 can be constructed with extruded tubing using well known techniques in the industry. In some embodiments, the catheter 300 can incorporates braided or coiled wires and or ribbons into the tubing for providing stiffness and rotational torqueability. Stiffening wires may number between 1 and 64. More preferably, a braided configuration is used that comprises between 8 and 32 wires or ribbon. If wires are used the diameter can range from about 0.0005 inches to about 0.0070 inches. If a ribbon is used the thickness is preferably less than the width, and ribbon thicknesses may range from about 0.0005 inches to about 0.0070 inches while the widths may range from about 0.0010 inches to about 0.0100 inches. In another embodiment, a coil is used as a stiffening member. The coil can comprise between 1 and 8 wires or ribbons that are wrapped around the circumference of the tube and embedded into the tube. The wires may be wound so that they are parallel to one another and in the curved plane of the surface of the tube, or multiple wires may be wrapped in opposing directions in separate layers. The dimensions of the wires or ribbons used for a coil can be similar to the dimensions used for a braid.

Figure 34:
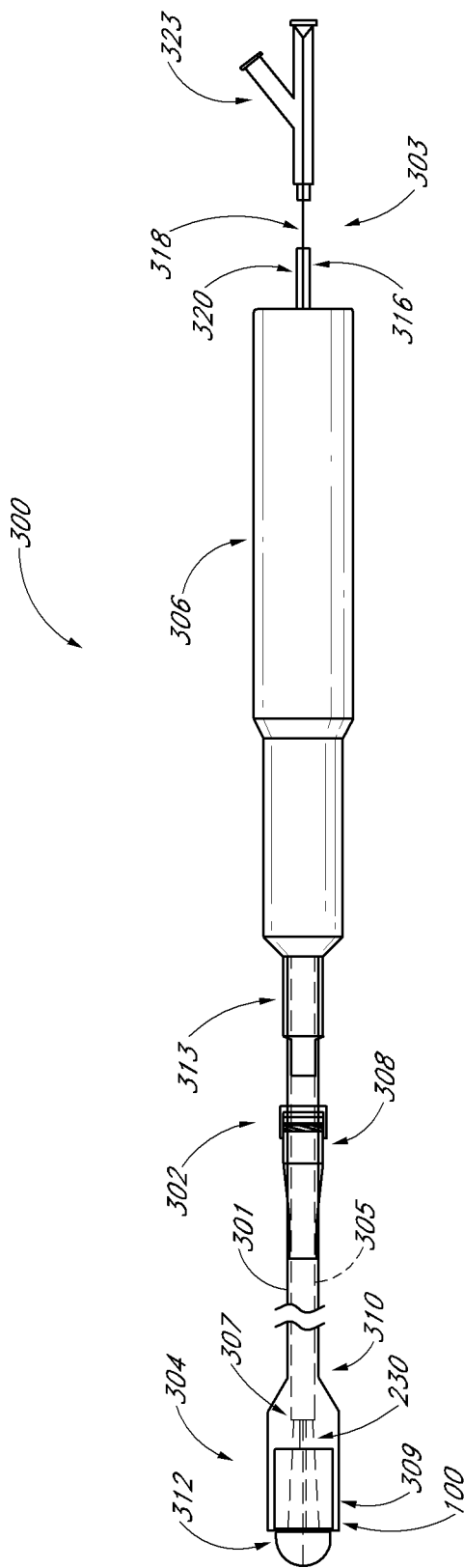
FIG. 34 is a side view of a deployment catheter.
Figure 35:
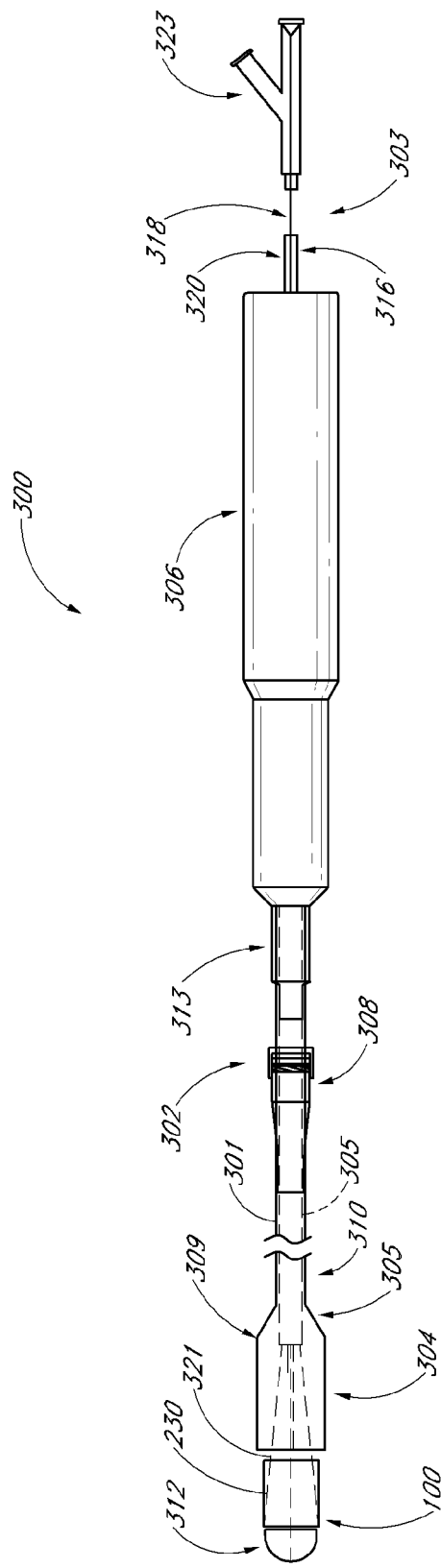
FIG. 35 is a side view of the deployment catheter of FIG. 34 with an outer sheath partially withdrawn.

With initial reference to FIG. 34, the catheter 300 generally comprises an outer tubular member 301 having a proximal end 302 and distal end 304 and an inner tubular member 305 also having a proximal end 303 and a distal end 307. The inner tubular member 305 extends generally through the outer tubular member 301, such that the proximal and distal ends 303, 307 of the inner tubular member 305 extend generally past the proximal end and distal ends 302, 304 of the outer tubular member 301. The proximal end 303 of the inner tubular member 305 includes a connection hub or handle 306 to mate other lab tools and to grasp and move the inner member 305 with respect to the outer member. A hemostasis valve 308 is preferably provided between the inner and outer members 301, 305 at the proximal end 302 of the outer tubular member 301. A strain relief 313 is preferably provided between the inner tubular member 305 and the handle 306 to limit strain on the inner member 305. The proximal end 302 of the outer tubular member 301 can include a grasping member or handle (not shown) for holding the outer tubular member 301 stationary with respect to the inner tubular member 305.

In one embodiment, the outer diameter of the catheter 300 measures generally about 0.030 inches to 0.200 inches with a wall thickness of the outer tubular member 301 being about 0.005 inches to about 0.060 inches. In another embodiment, the outer diameter ranges from about 0.15 inches to about 0.35 inches or from about 12 French to about 27 French. In this embodiment, the wall thickness of the outer tube 301 is between about 0.005 inches and about 0.030 inches. The overall length of the catheter 300 ranges from about 80 centimeters to about 320 centimeters.

As mentioned above, the catheter 300 includes a connection hub or handle 306 that is configured to allow wires, devices and fluid to pass as will be explained in more detail below. The connection hub 306 is preferably compatible with normal cath-lab components and can utilize a threaded end and a taper fit to maintain seal integrity. The inner diameter of the inner member 305 of the catheter 300 is configured allow for coaxial use to pass items such as guidewires, devices, contrast and other catheters. An inner lining material such as Teflon may be used to reduce friction and improve performance in tortuous curves. Additionally, slippery coatings such as DOW 360, MDX silicone or a hydrophilic coating from BSI Corporation may be added to provide another form of friction reducing elements.

Multidurometer materials in the catheter 300 can help to soften the transition zones and add correct stiffness for pushability. Transition zones may also be achieved through an extrusion process know as bump tubing, where the material inner and outer diameter change during the extrusion process. The entire catheter shafts 301, 305 can be produced in one piece. Another method for producing such a catheter shaft is to bond separate pieces of tubing together by melting or gluing the two components together and forming a single tube with multiple diameters and or stiffness. The application of heat can be applied by laser or heated air that flows over the shaft material or other methods of heat application sufficient to flow the materials together.

With continued reference to FIG. 34, the distal end 304 of the outer sheath 301 comprises an enlarged diameter section 309, which is configured to cover the implant 100. In one embodiment, the diameter of the enlarged diameter section 309 where the implant 100 is contained is between about 0.20 inches and about 0.32 inches in diameter with a length between about 0.5 in and about 5.0 inches. A second portion 310 of reduced diameter and increased flexibility is located proximal to the section 309 that covers the implant 100. This section ranges from about 0.10 inches to about 0.25 inches in diameter. In the preferred embodiment, the distal section 309 is about 0.29 inches diameter, and about 0.08 inches in length and the proximal section 310 has an outside diameter of about 0.19 inches. The enlarged distal portion 309 can be made from a material with a higher durometer than the proximal portion 310 of the catheter 300. In one embodiment, the material of the enlarged distal portion 309 is a biocompatible material. In another embodiment, the material is a metallic material such as stainless steel. In another embodiment, the material is a polymer such as FEP, PEEK or a polyimide. In another embodiment, the enlarged distal portion 309 of the device which covers the implant 100 is capable of transmitting light in the visible spectrum. This allows the orientation of the implant 100 to be visualized within the catheter 300. The distal end 304 may have a radiopaque marker (not shown) to locate the catheter 300 under fluoroscopy.

Figure 36:
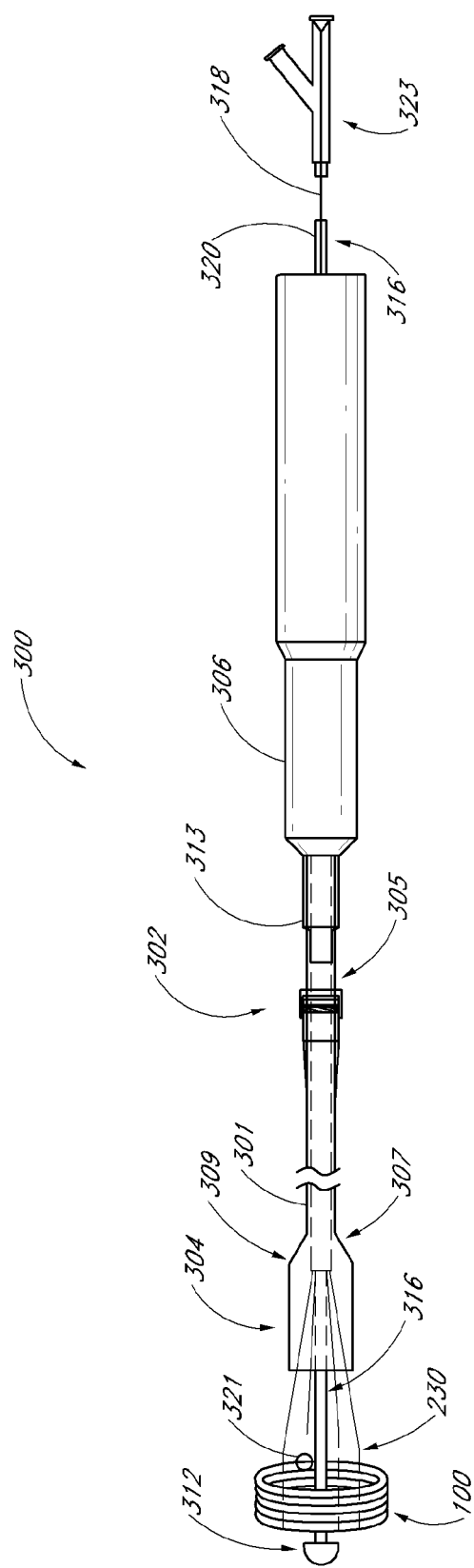
FIG. 36 is a side view of the deployment catheter of FIG. 35 with an outer sheath partially withdrawn and the implant deployed.
Figure 36A:
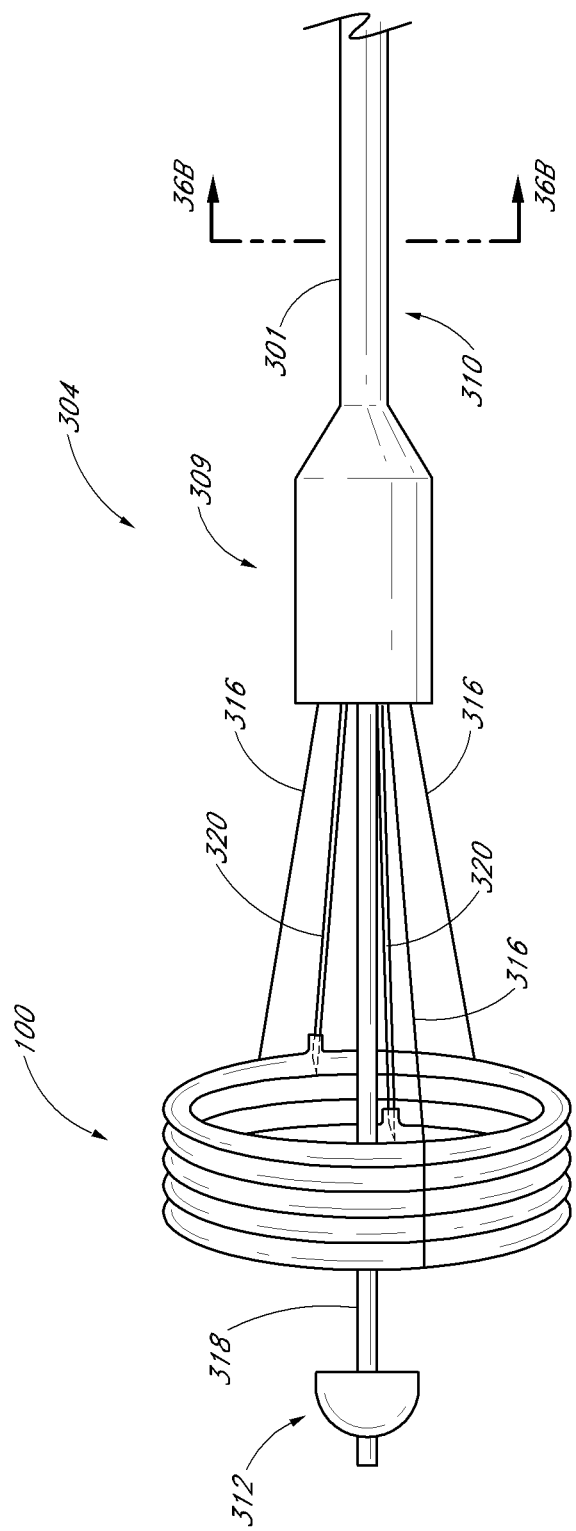
FIG. 36A is an enlarged view of the distal portion of the deployment catheter shown in FIG. 36.
Figure 36B:
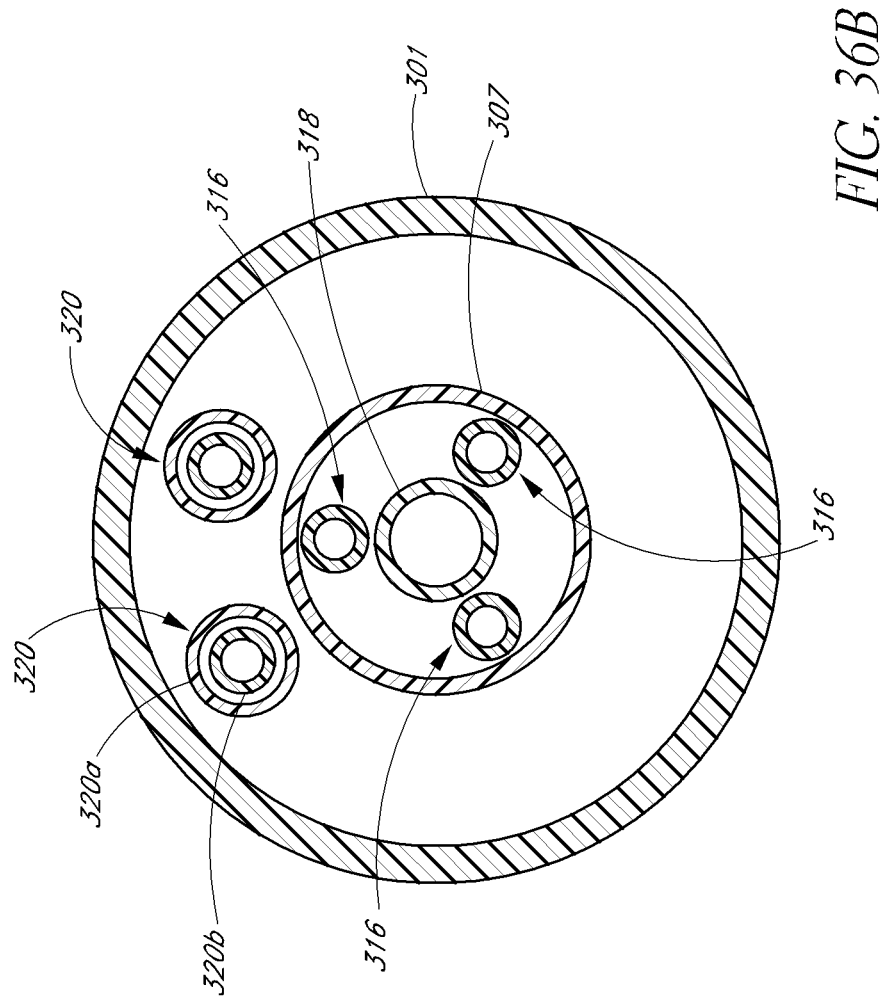
FIG. 36B is a cross-sectional view taken through line 36B-36B of FIG. 36A.

With continued reference to FIGS. 34-37 and in particular FIGS. 36A and 36B, multiple tubes extend through the inner member 305. Specifically, in illustrated embodiment, a guidewire tube 318, two inflation tubes 320 and three control wire tubes 316 extend from the proximal end 303 to the distal end 307 of the inner member 307. Of course, in modified embodiments, various other numbers and combinations of tubes 316, 318, 320 can be used depending upon the configuration of the implant 100 and the deployment procedure. These tubes may be extruded from materials such as polyethene, polypropylene, nylon, PEEK, polyimide or other accepted polymer materials. They may also combine metallic elements such as coils or braids for additional support or be made from metallic tubings such as Nitinol or stainless steel. As will be explained below, the guidewire tube 318 is configured to receive a guidewire. The inflation tubes 320 are configured to delivery inflation media to the implant 100 and the control wire tubes 316 receive the control wires 230, which are coupled to the implant 100. As will be explained in more detail below, the inflation tubes 320 can include inner and outer members 320a, 320b (see FIG. 36B) for providing an inflation disconnect mechanism as described below with reference to FIGS. 40A and 40B.

The inner member 305 material may also consist of stiffening members for transition zones or bump extrusions to reduced diameter and maintain correct pushability. Conventional guidewire passage through the catheter such as "over-the-wire" may be used or technology such as "rapid-exchange" may aid in procedure ease and catheter exchanges. Since multiple devices may be placed in a single catheterization, rapid-exchange may be preferred but not essential. Other features that may aid in ease of use include a slippery coating on the outer and or inner diameter such as mineral oil, MDX (silicone) or a hydrophilic layer to allow easy access to tortuous anatomy, or easier more controlled motion of one portion of the catheter relative to another portion of the catheter. It may be necessary or desirable to utilize a balloon to initiate radial contact of the device to its final position and location. In one embodiment, an inflation lumen and balloon placed distal to the hub is used. This balloon is used to pre-dilate the native valve annulus, vessel or ostium where the valve may be implanted. Elements to transmit signals externally could be imbedded into the catheter 300 for pressure and flow readings or Doppler information. These may include electro-mechanical sensors, such as piezo-electric devices, electrical sensors, wires, pressure portal or lumens or optical fibers.

As mentioned above, delivery of the implant 100 via catheterization of the implantation site can include a mechanism to deploy or expel the implant 100 into the vessel. This mechanism may include a push or pull member to transmit forces to the distal portion of the catheter 300. These forces may be applied externally to the body and utilize a handle at the proximal end of the catheter. Devices to transmit forces to the distal end may also include a rotational member to loosen or tighten, convert a torque into a translational force such as a threaded screw and nut or to add or subtract stiffness to the catheter or device, or to cause the device to assume a specific shape. The handle mechanism may also include a port for hydraulic pressures to be transmitted to the distal portion of the catheter or have the ability to generate hydraulic forces directly with the handle. These forces may include a pushing or pulling transmitted to the device or catheter, an exposure of the device to allow for implantation or to expel the device from the catheter. Further forces may include a radial or longitudinal expansion of the device or catheter to implant or size the location of implantation. The handle may also include connections to electrical signals to monitor information such as pressures, flow rates, temperature and Doppler information.

With reference to FIGS. 34 and 36, in the illustrated embodiment, the implant 100 is loaded between the distal portion 309 of the outer sheath 301 and the inner sheath 305. The distal portion 309 therefore forms a receptacle for the implant 100. A distal tip 312 can be coupled to the guidewire tube 318. The tip 312 can be used to close the receptacle when the catheter 300 is being advanced. The tip 312 can be distanced from the outer sheath 301 by proximally retracting the outer sheath 301, while holding the guidewire tube 318 stationary. Alternatively, the guidewire tube 318 can be advanced while holding the outer sheath 301 stationary. Control wires 230, which extend through the control wire tubes 316, can be coupled to implant 100 as described below and used to hold the implant 100 stationary as the implant outer sheath 301 is retracted. Alternatively the outer sheath 301 can be retracted with respect to the inner sheath 305, which acts as a pusher to push the implant 110 outer of the distal portion 309 of the outer sheath. The inflation channels 120 of the implant 100 are preferably connected to the inflation tubes 318 of the catheter by an inflation connection members 321 as will be described in more detail below.

With continued reference to FIG. 36, the inflation tubes 318, guidewire tube 320 and control wire tube 316 preferably extend to the proximal end 303 of the inner member 305. A connection hub 323 can be provided for connecting an inflation fluid source to the inflation tube 318. Various control mechanism (not shown) and sealing devices can also be provided for connecting to the control wires 230 and control wire tubes 316.

As will be described in more detail below, the control wires 230 and/or inflation lumen 318 can form part of a deployment mechanism for the implant 100. As the implant is navigated to the site, attachment between the implant 100 and catheter 300 is important. Many detachment mechanisms have been used to deploy devices such as stents and embolic coils through balloon expansion and simple pushable coils expelled from the distal end of a catheter. The implant 100 can utilize many different methods to implant 100 at the selected site such as an expulsion out the end of the catheter, a mechanical release mechanism such as a pin joint, unscrewing the device from the catheter delivery system, a tethered link such as a thread or wire, a fusible link as used in a GDC coil deployment, a cutting tool to sever a attachment of the device from the catheter, a threaded knot to tether the catheter to the device where the as the knot could be untied or cut, a hydraulic mechanism to deploy, expand or fracture a link between the catheter and the device. All above mentioned concepts can be enhanced by the utilization of the flexible tip 312 to allow acute articulation of the device and delivery catheter 300 to gain access to the implantation site.

As will be explained in more detail below, after the implant 100 has been temporarily deployed or positioned, it may be advantageous to recapture or reposition the implant for optimal results. This may include a rotation or translation of the implant 100 or a complete removal and exchange for a different diameter, length or style device. Capture of an implanted device may require a second catheter to reengage the device to remove or reposition to a proper location. This catheter may be constructed from polymer tubing as described above including coils, braids, etc. Additionally there may be a braided section at the distal most portion of the catheter to accept or capture the device for retrieval from the body.

As mentioned above, the guidewire tube 320 preferably extends through the inner sheath 305 and the tip 312. The guidewire tube 320 may have an inside diameter of 0.035 to 0.042 in so that the device is compatible with common 0.035 or 0.038 guide wires. A modified embodiment includes a lumen 0.014 to 0.017 inches in diameter for compatibility with 0.014 in diameter guide wires. In a third embodiment, the guidewire lumen 320 is 0.039 to 0.080 in diameter, so that the device may be delivered over a larger than standard guide wire, or a diagnostic catheter, such as a pig tail catheter. This provides the advantage of a stiffer support to facilitate easier delivery through calcified valves. If a diagnostic catheter is used as a guidewire it may also serve as a port for contrast injection.

The guidewire tube 320 can be made from a lubricious material such as Teflon, polypropylene or a polymer impregnated with Teflon. It may also be coated with a lubricious or hydrophilic coating. The tube 320 can be constructed of multiple layers of material, including a lubricious inner layer and an outer layer to facilitate bonding to other catheter components.

The catheter 300 may be delivered over a guide wire to aid in positioning. The guide wire may pass coaxially through the entire length of the catheter or in modified embodiments may pass coaxially though only a portion of the catheter in a configuration known as rapid exchange. This allows shorter guide wires to be used if devices are to be exchanged out.

In the illustrated embodiment, the catheter 300 comprises the outer catheter shaft 301 and the inner catheter shaft 305 which move relative to one another. In order to minimize the risk of guidewire damage in a rapid exchange design where the catheter must pass through the wall of two sheaths which move relative to one another, a slot feature is desirable. Either the inner or outer elongate tube may contain a longitudinal slot in the area where the guide wire passes from the inner diameter to the outer diameter of the catheter assembly. The other elongate tube preferably contains a hollow pin to engage the slot and prevent the excessive movement of the two elongate members. The guide wire passes through the opening in the hollow pin. The inner diameter of the hollow pin is preferably oriented at an acute angle to the central axis of the catheter.

Another design to enable rapid exchange like performance is for the guide wire to enter the catheter tip through a side hole distal to the location of the prosthetic valve. The guidewire exits the tip of the system near the center of the catheter tip. This design enables the catheter to follow the guide wire across the native valve, while still allowing multiple devices to be exchanged easily on a short length guide wire.

Figure 37:
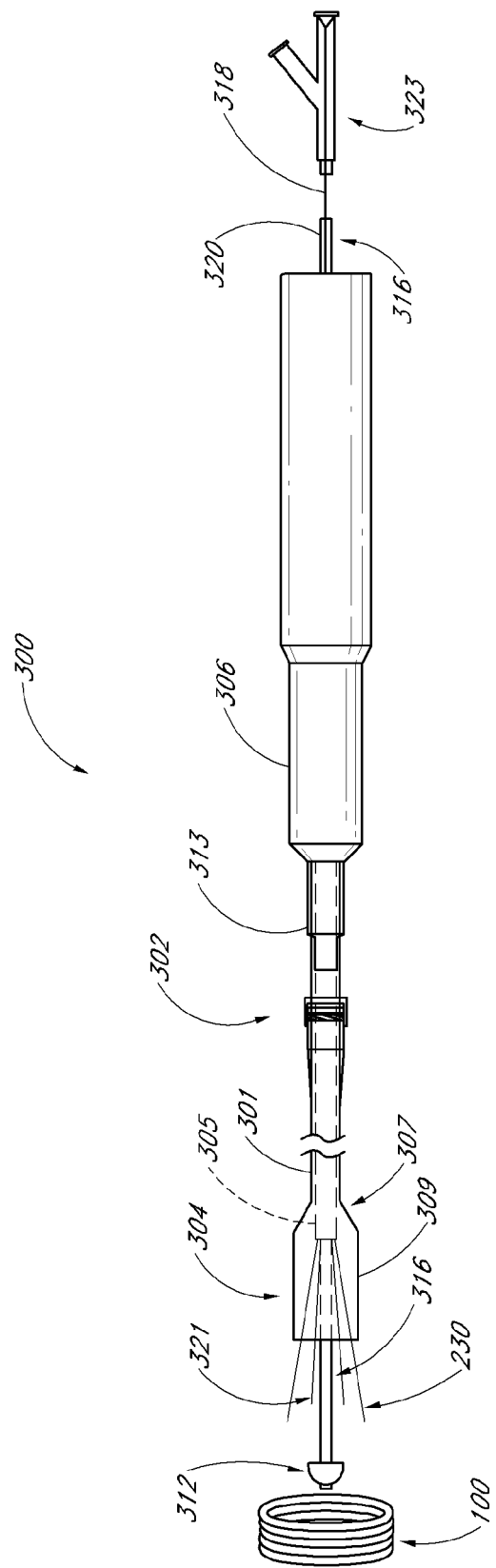
FIG. 37 is a side view of the deployment catheter of FIG. 35 with an outer sheath partially withdrawn and the implant deployed and detached.
Figure 37A:
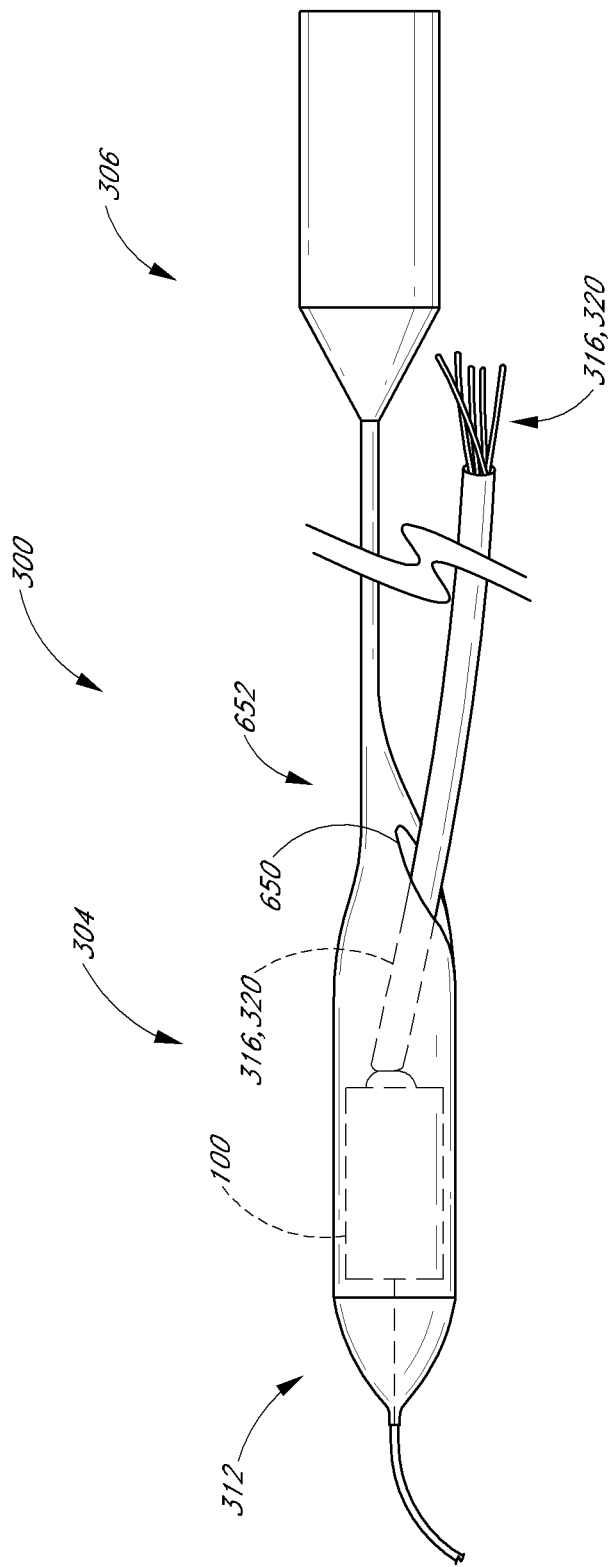
FIG. 37A is a side view of another embodiment of a deployment catheter.

As described above, the internal lumens of the catheter 300 can include the deployment control wires lumens 316, the inflation lumens 320, and an inner sheath 307 that encapsulates these lumens 316, 320. See e.g., FIG. 36B. With reference to FIG. 37A, in one embodiment of the delivery system 300, a portion of, or all, of the internal lumens 316, 320 are located within the delivery catheter 300 at the distal portion 304 of the catheter, and pass through a hole 650 in for example a middle portion 652 of the delivery catheter 300 so that they are located generally parallel to the delivery catheter 300 at the proximal end 306 of the catheter 300. In one embodiment, the hole through 650 which the lumens 316, 320 pass can be located between about 2 and about 20 cm from the distal end 304 of the device 300. The outside diameter of the delivery catheter 300 is substantially reduced proximal to the hole as shown in FIG. 37A, so that the entire device 300 may pass through most common introducers that are large enough to accept the distal portion 304 of the device 300.

This catheter configuration advantageously allows the operator to easily switch between the delivery sheath 300 and a recovery sheath (described herein) in the event that the device 100 needs to be recovered, because the delivery sheath 300 can be retracted out of the body over relatively short internal lumens 316, 320, while still maintaining a portion of the lumens 316, 320 outside the catheter so that the operator can manipulate them as necessary.

Because of its shorter length the recovery sheath may not require the exchange hole 650, and it may be possible to locate the internal lumens coaxially within the recovery sheath. However in the preferred embodiment the recovery sheath also includes a hole in a similar location allowing the internal lumens to pass coaxially through the distal portion of the sheath, through the hole, and be located generally parallel to the recovery sheath in the proximal portion.

In one embodiment contrast media is passed through a lumen (e.g., the guidewire tube 320) of the device, and the lumen passes through the prosthetic valve 100. This allows visual evaluation of valve function by angiography, without crossing the valve with an additional device. In the preferred embodiment the lumen crosses the valve while the valve is in the catheter. In the preferred embodiment the lumen also serves as the guidewire tube 320, where the device is delivered over a guide wire. The wire may be removed from the lumen to allow more cross sectional area for contrast injection. The proximal end of the lumen near the handle of the device attaches to a fitting to allow the injection of contrast media with a power injector tool. The inner diameter of the lumen may range from 0.014 to 0.100 inch. The diameter of the lumen may vary along the length of the catheter, for example, Preferably the portion of the lumen which passes through the prosthetic valve is of a minimum possible diameter to allow both sufficient flow and the use of an adequate sized guidewire. This portion is preferably in the range of diameters from 0.014 to 0.080. The portion of the lumen extending along the length of the catheter proximal to the implant may be of larger diameter, the larger diameter allows flow of contrast media at lower pressure gradients, and the corresponding larger outside diameter does not increase the profile of the complete device. This portion of the lumen is preferably in the inside diameter range of 0.035 to 0.100 in. The distal portion of the lumen may contain a diffuser or transition to a larger diameter to minimize the pressure required to inject a sufficient volume of contrast media through the lumen. Multiple exit ports positioned around a nose cone also facilitate the flow of contrast media.

Access for the catheter 300 may be gained through a major artery such as the femoral artery. This access site is particularly appropriate for aortic valve replacement. Alternative access methods may be better suited for other valves. For example the tricuspid valve and possibly the pulmonary valve could best be accessed through the venous system. In this case, access would be gained through either a femoral vein or a jugular vein. The catheter would then be passed into the right atrium through the superior or inferior vena cava. Some embodiment of the current invention utilize a relatively large diameter catheter, which may not be compatable with the diameter of all patients femoral arteries. In these patients it may be desirable to access the common iliac artery or to use a transeptal approach and access the heart through the venous system.

As mentioned above, the catheter 300 includes an atraumatic tip 312 to allow the device to be easily placed through the hemostasis valve of the introducer, and to easily cross the calcified aortic valve. The tip 312 may be cone shaped bullet shaped or hemispherical on the front end. The largest diameter of the tip 312 is preferably approximately the same as the distal portion 309 of the outer sheath 301. The tip 312 preferably steps down to a diameter slightly smaller than the inside diameter of the distal portion 309 of the outer sheath 301, so that the tip can engage the outer sheath 301 and provide a smooth transition. In the illustrated embodiment, the tip 312 is connected to the guide wire tube 320, and the guide wire lumen passes through a portion of the tip 312. The proximal side of the tip 312 also has a cone, bullet or hemispherical shape, so that the tip can easily be retraced back across the deployed valve 100, and into the deployment catheter 300. The tip 312 can be manufactured from a rigid polymer such as polycarbonate, or from a lower durometer material that allows flexibility, such as silicone. Alternatively, the tip 312 may be made from multiple materials with different durometers. For example, the portion of the tip 312 that engages the distal portion 309 of the outer sheath 301 can be manufactured from a rigid material, while the distal and or proximal ends of the tip are manufactured from a lower durmoter material.

With reference to FIGS. 35A and 35B, in a modified embodiment, the area where the tip 312 of the device is located to house a balloon 312a for dilatation. This balloon 312a could use the lumen where a guidewire passes through (as shown in the illustrated embodiment) or a separate lumen for inflation and deflation. Since the distal portion 309 is rather large (10-24 French) it can be advantageous place to locate a large diameter balloon that could be used to pre or post dilate the valve area. There may also be a stent or other structure mounted to this balloon 312a for device securement or anchor deployment. The balloon 312a could also be covered with a thin membrane material similar to the "SOX" device commercialized by Boston Scientific and seen in U.S. Pat. No. 6,280,412 Pederson Jr. et al. This covering would allow the device to be hidden during delivery and could be exposed when inflated. In another embodiment, a tear-away sheath that covered the balloon 312a for protection can be used.

Figure 38A:
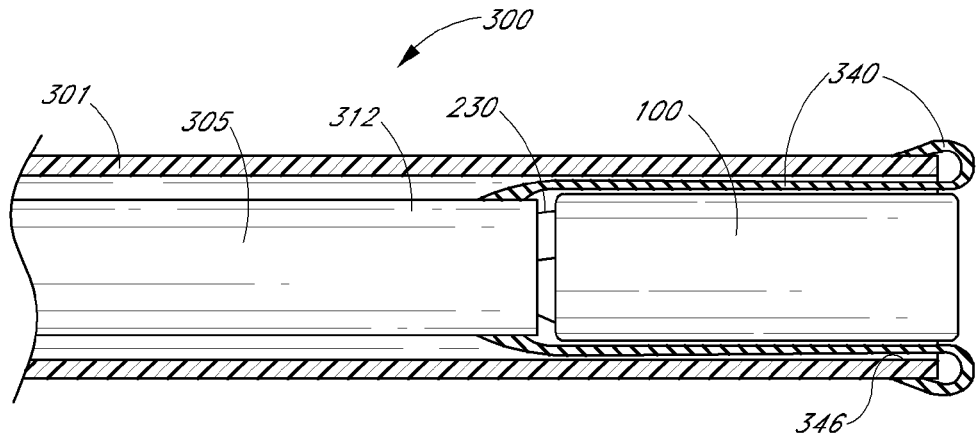
FIGS. 38A-C are schematic partial cross-sectional views of a modified embodiment of a deployment catheter with the implant in a stored, partially deployed and deployed position.
Figure 38B:
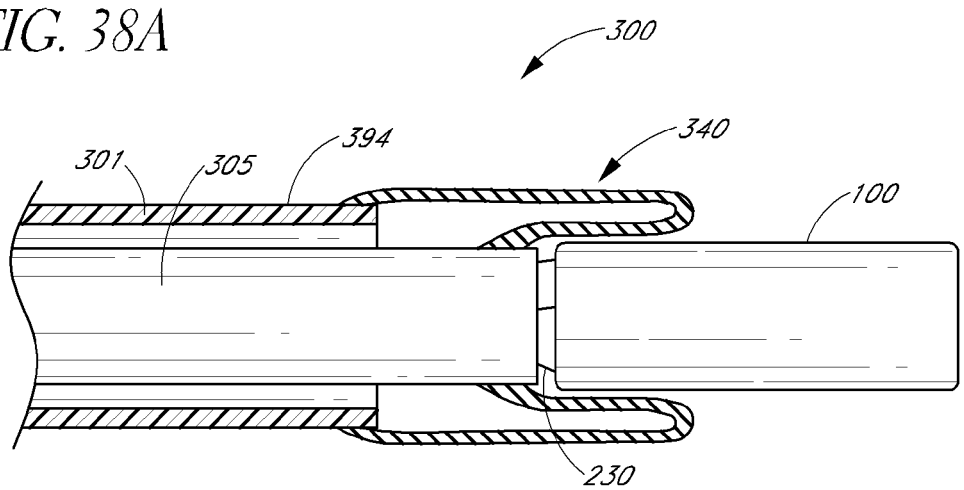
Figure 38C:
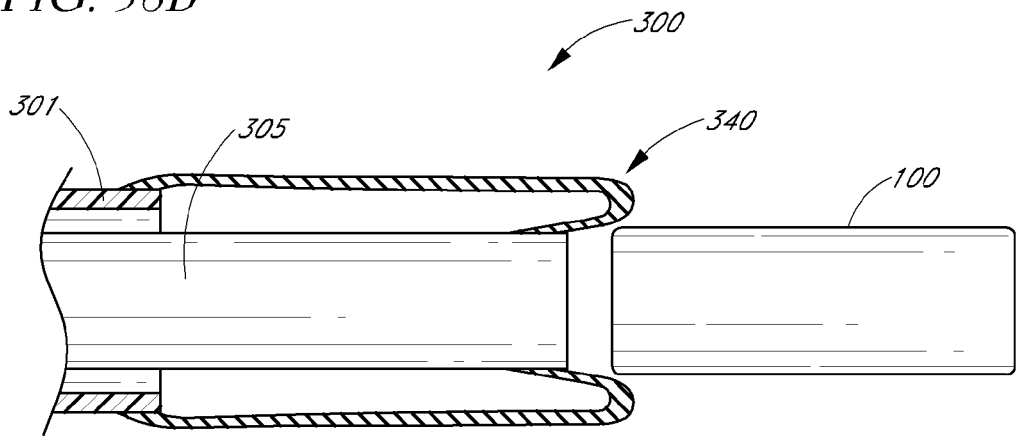

FIGS. 38A-38C illustrate one embodiment of a retractable sheath 340 that may be used in combination with the deployment catheter 300 described above. Many implantable medical devices have been delivered using retractable sheaths. For example, some devices include self-expanding stents, and grafts to percutaneously treat abdominal aortic aneurysms. On problem with this design is that the catheter must slide over the implant, resulting in a scraping and shear forces. For a delicate implant such as a tissue valve or abdominal aortic aneurism graft, this scraping or shearing may result in damage to the implant. In less fragile devices such as self-expanding stents the sheath material may be scraped off and embolized. Several medical devices have solved this problem using a radially expandable shear barrier, as described by Chobotov. This shear barrier in practice typically consists of a thin walled piece of tubing, slit along its length in several places. As the outer sheath is retracted, it slides along the slit tubing. Once the outer sheath has retracted past the slit tubing, it can expand radially allowing the device to be released.

The retractable sheath 340 of FIGS. 38A-C serves a similar function to the radially expandable shear barrier describe above, but provides several advantages. For example, as explained below, it does not have sharp edges and it can be made from a softer material, so it is less likely to cause trauma to the patient, or damage to the implant. In addition, it can be made from a thinner material allowing the device 340 to have a lower profile. And it does not protrude the full length of the implant 100 after the outer sheath 340 has been retracted.

As shown in FIGS. 38A-C, in the illustrated embodiment, the catheter 300 the outer sheath 301 is retracted to deploy the implant 100 and the inner sheath 305, which is stationary relative to the outer sheath 301, acts as a pusher and prevents the implant 100 from moving back with the outer sheath 301 during deployment. A thin flexible membrane 340 connects to the outer surface 342 of the pusher 305 and passes between the implant 100 and the outer sheath 301 and acts as a shear barrier. The flexible shear barrier 340 then attaches to the outer distal end 344 of the outer sheath 301. Preferably the membrane or shear barrier 340 extends out the tip of the outer sheath 301 and then is pulled inside out over the outer sheath 301 as shown in FIG. 28A. The membrane or shear barrier 340 is then bonded to the outer sheath 301 on its outer surface 342 near the tip of the outer sheath 301. In a modified embodiment, the flexible shear barrier 340 is bonded to the inner surface 346 of the outer sheath 301. The shear barrier 340 is preferably made from a polymer and has a thickness of about 0.0002 inches to about 0.0020 inches. In one embodiment, the polymer is nylon. The shear barrier 340 can be manufactured by an extrusion process or by a balloon blowing process where a polymer tubing is inflated inside a mold using heat and pressure.

As shown in FIGS. 38B and 38C, as the outer sheath 301 is pulled back the membrane 340 turns inside out and retracts from the implant 100, doubling over on its self. The sliding occurs between the flexible membrane 340 and the inner surface 346 of the outer, retractable sheath 301. Advantageously, little or no relative motion occurs between the implant 100 and the portion of the membrane 340 in contact with the implant 100. This minimizes any potential damage to the implant 100, and the risk of embolizing particles from the sheath 301. A lubricant can be applied between the outer sheath 301 and the membrane 340 and between the outer sheath 301 and the pusher 305. The membrane 340 advantageously serves to isolate the implant 100 and the patient from the lubricant. This embodiment reduces the force necessary to deploy the implant 100, and allows for a smoother more controlled deployment.

With reference back to FIG. 34, the hemostasis valve 308 is preferably is attached to the proximal end of the outer sheath 301 to prevent blood from leaking past the inner and outer sheaths 301, 305. In one embodiment, the valve 308 is a touhy-borscht design valve, or similar valve where the radial compression is easily adjustable. By adjusting the valve it is possible to lock the outer sheath 301 to the inner sheath 305 of the catheter 300 to prevent their accidental relative motion during delivery of the implant. At the proximal end 304 of the catheter 300, an additional hemostasis valve (not shown) is preferably provided to provide a seal for the multiple inflation lumens, and deployment control wires that must pass through the inner sheath 305. An additional port (not shown) can also be provided to allow the catheter 300 to be flushed to remove any trapped air before the catheter 300 is inserted into the patient.

Connection Between Implant and Inflation Lumens

As described above, in many embodiments, the implant 100 includes an inflatable structure 107, which defines inflation channels 120. In these embodiments, the inflation channels 120 are inflated with inflation media 122 to provide structure to the implant 100. As shown in FIGS. 34-37, the deployment catheter 300 includes at least one inflation tube 318 and in the illustrated embodiment two inflation tubes 318 that extend through from the proximal end 304 to the distal end of 302 of the catheter 300. The inflation tubes are placed in communication with the inflation channels 120 such that inflation media 122 can be supplied to the inflatable structure 107. It will be appreciated that after the inflatable structure 107 is inflated the inflation tubes 318 will need to be disconnected or uncoupled from the implant 100. Various devices and methods for uncoupling the implant 100 from the inflation tubes 318 will now be described.

In general, in embodiments in which the inflation media 122 is not self sealing the inflation channels 122 will need to be sealed as the inflation lumen 318 is disconnected from the implant 100. Sealing of these lumens could utilize many different techniques known to one skilled in the art. For example, as explained below, the inflation lumen can be placed through a valve, in such a way that it forces the valve into the open position. The valve could be one of a variety of normally closed or one way (check) valves.

Figure 39B:
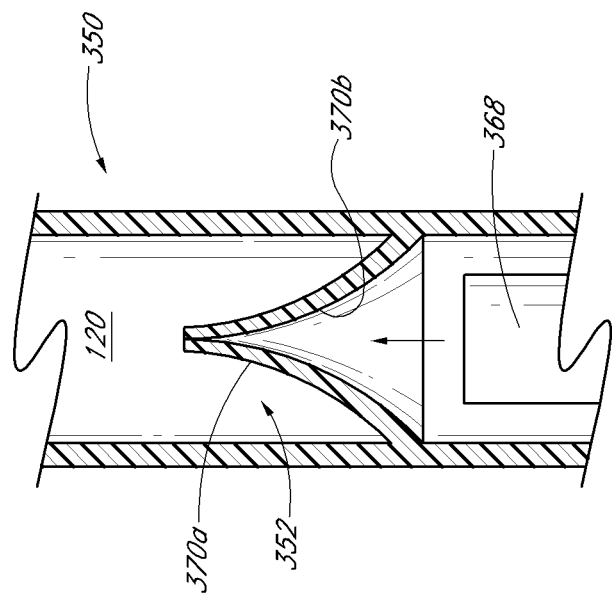
FIGS. 39A-D are cross-sectional side views of four embodiments of a sealing mechanism.
Figure 39A:
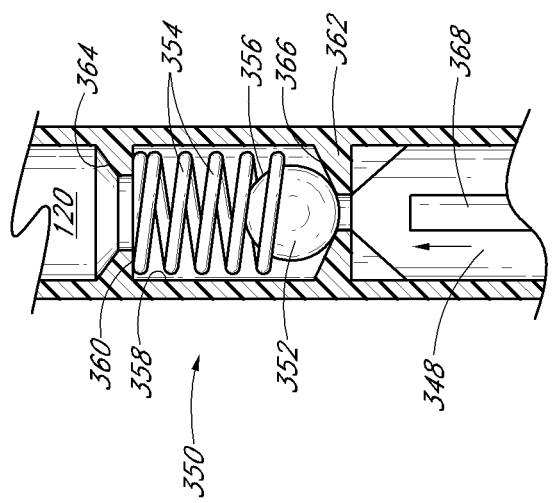

For example, FIG. 39A illustrates an embodiment of a connection mechanism 350 that includes a check valve 352 comprising a spring 354 and a ball member 356. The spring 354 and ball member 356 are positioned within a chamber 358 having a first open end 360 that is in communication with the inflation channels 120 and a second open end 362 that is in communication with the inflation tube 318. The spring 354 is supported by a narrowed portion 364 of the first open end 360. The spring 354 biases the ball 356 against a valve seat 366 formed by the second end 362 of the chamber 358. In the biased closed position, the ball 356 prevents inflation media 122 from exiting the inflation channels 120. When inflation media 122 is applied under pressure to the inflation channels 120, the pressure pushes the ball away from the valve seat 366 and into the chamber 358 allowing inflation media 122 to flow into the inflation channels 120. When the pressure is removed, the spring 354 forces the ball 356 against the valve seat 366 to prevent the inflation media 122 from escaping. A pin 368 can extend through the inflation lumen 318 and can be used to push against the ball 356, disabling the check valve 352 and allowing deflation of the inflation channels 120.

FIG. 39B illustrates another embodiment of a check valve 352. In this embodiment, check valve 352 comprises a duck-bill valve that includes at least two flanges or bills 370a, 370b that are biased towards each other to close the inflation channel 120. As with the ball valve described above, a pin 368 can be used to open the valve 325 and allow deflation of the inflation channels 120.

Figure 39D:
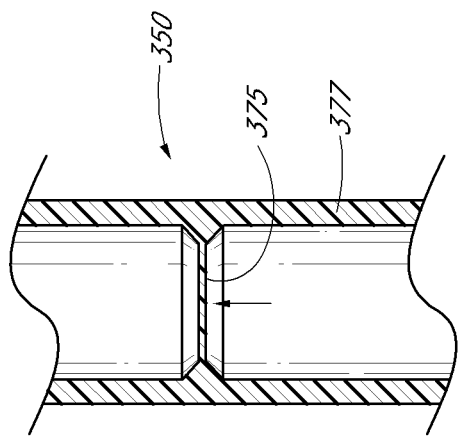
Figure 39C:
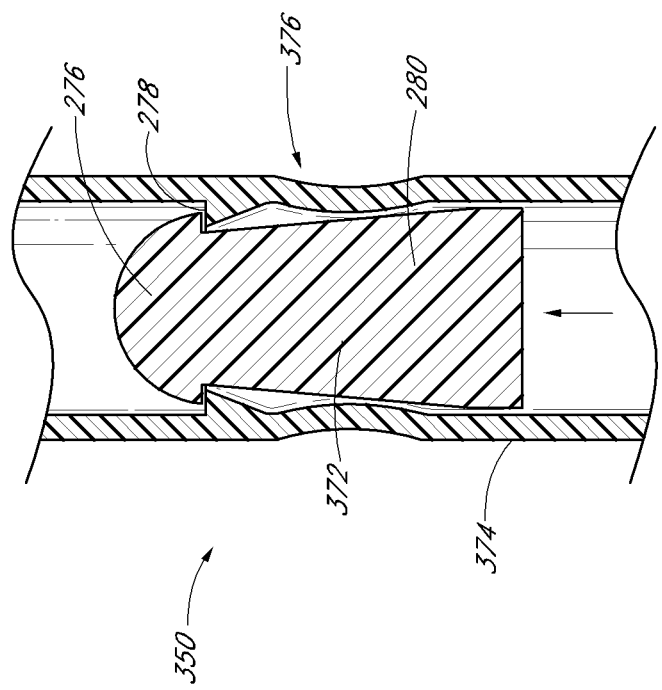

FIG. 39C illustrates another embodiment of a sealing mechanism 350. In this embodiment, the inflation lumens 120 are inflated using a needle (not shown) placed through a soft polymer plug 372 positioned between the inflation lumen 318 and the inflation channels 120. The needle is withdrawn from the plug 372 and the plug closes the hole formed by the needle, preventing the loss of fluid or pressure. In the preferred embodiment the plug 372 is silicone inside a nylon, PE or PET tube 374. After the silicone is cured and bonded to the tube the tube may optionally be necked 376 to place a compressive force on the silicone plug 372. The proximal and distal sections of the tube surrounding to the plug can be necked to an even smaller diameter, to prevent the migration of the plug. The diameter of the needle may range from 0.010 to 0.050 in with a diameter of about 0.020 in as the currently preferred diameter. The plug 372 diameter may range from 0.020 to 0.120 in. In the illustrated embodiment, the plug 372 also includes an enlarged distal section 376, which abuts against a distally facing ledge 378 provided within the tube 374 to secure the axial position of the plug 272. The proximal end 280 of the plug 372 can have an outward taper as shown to further secure the plug 372 within the tube 374.

FIG. 39D illustrates another embodiment in which the connection mechanism comprises a rupture disk 375, which is secured within an inside surface of a fluid tight chamber 377. The disk 375 is configured to rupture and allow the inflation of the inflation channels 120 when sufficient pressure is applied.

In some embodiments, it is advantageous to configure the deployment catheter 300 and the implant 100 such that the inflation tube 318 cannot disconnected unintentionally. For example, in one embodiment, the inflation tube 318 is connected to a deployment control wire 230 so that the inflation lumen 218 can not be removed from the implant 100 unless the deployment control wire 230 is also disconnected from the implant 100.

Figure 40A:
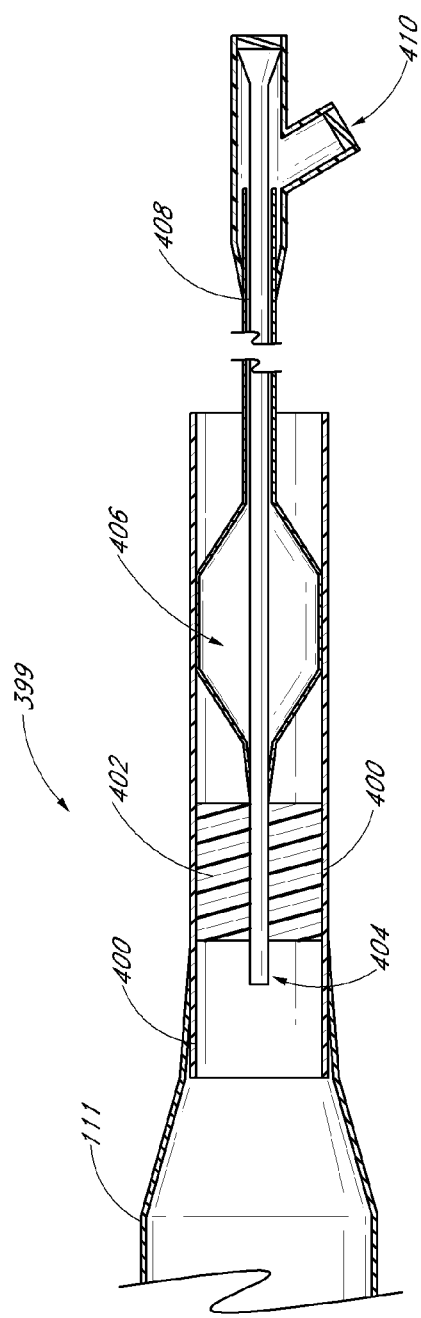
FIGS. 40A-B are cross-sectional side views of a sealing and connection mechanism in a connected and disconnected confirmation.
Figure 40B:
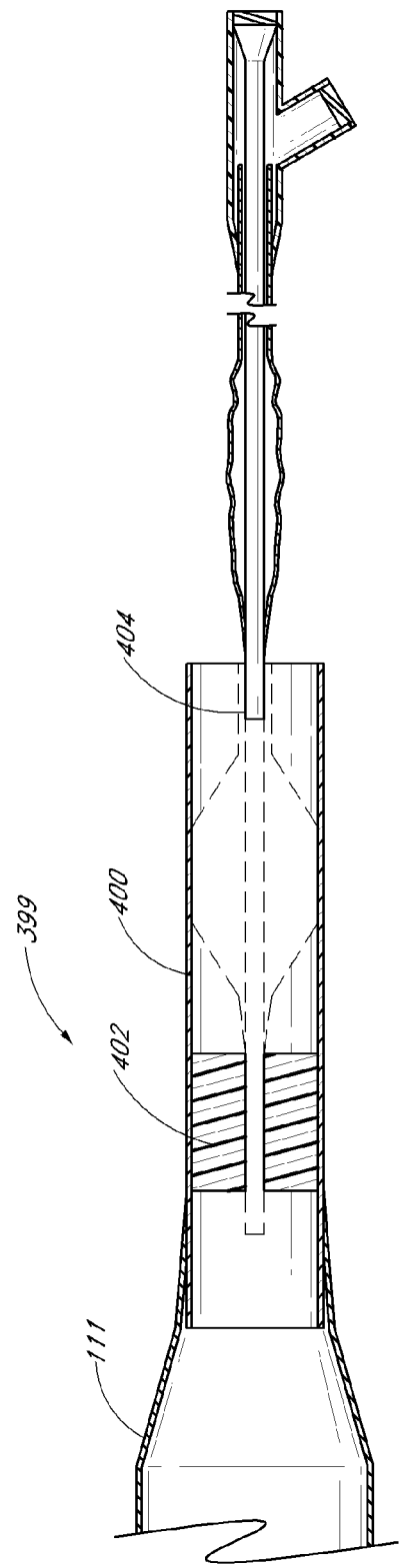

FIGS. 40A and 40B illustrates one embodiment of sealing and connection mechanism 399. In this embodiment, the balloon 111 is connected to a piece of tubing 400. Within the tubing 400, is positioned a seal-sealing plug 402, which can be configured as described above with reference to FIG. 39C. A tip 404 of the inflation lumen 318 is configured to be inserted through the plug 402 such that inflation media can be injected into the balloon 111. A connection balloon 406 is positioned generally around the tip 404 and proximally to the plug 402 within the tubing 400 A fluid channel 408 connects the connection balloon 406 to an inflation port 410 on the proximal end of the catheter 300. In use, the balloon 11 is inflated with inflation media provided through the tip 404. To disconnect the inflation lumen 318 from the tubing 400, the connection balloon 406 is deflated as shown in FIG. 40B allowing the inflation lumen 318 to be withdrawn with respect to the plug 402 and tubing 400. A stop or narrowed region (not shown) can be provided within the tubing 400 to enhance the connection between the inflated connection balloon 406 and tubing 400.

Figure 41:
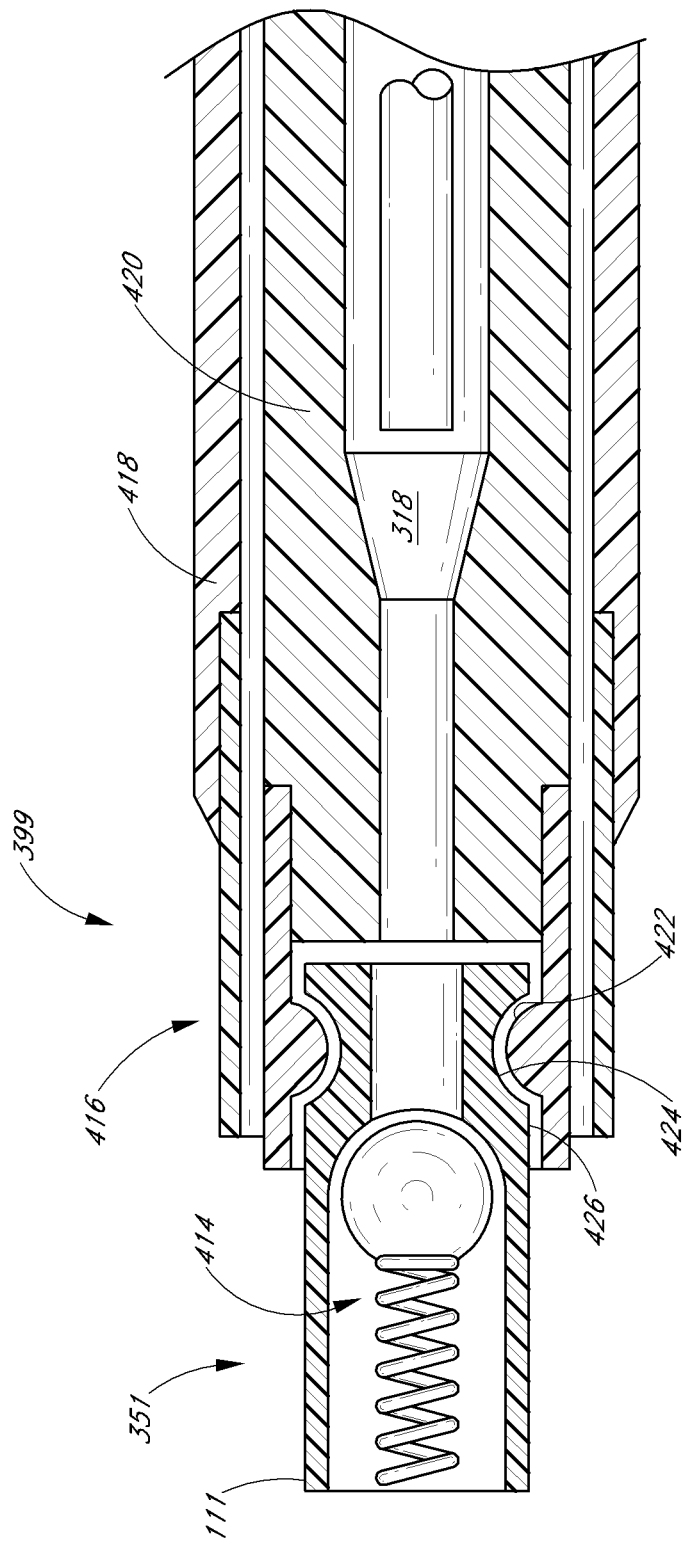
FIG. 41 is a cross-sectional side view of a sealing and connection mechanism.

FIG. 41 illustrates another embodiment of sealing and connection mechanism 399. In this embodiment, the mechanism 399 comprises a ball and spring type check valve 412, which can be arranged as described above with the connection portion 351 of the balloon 111. A connection mechanism 416 comprises an outer layer 418 and inner layer 420 of coaxial tubes. The inner layer 418 includes an engagement feature such as a bump 422 that engages a corresponding engagement feature 424 on an outer surface 426 of the balloon 111 or other portion of the implant 100. As shown in FIG. 41, the outer layer 418 extends over the engagement features 424, 426. The outer layer 418 is provided with a diameter that it forces the engagement feature 422 on the inner layer 420 to remain engaged in the engagement feature 424 on the balloon 411. As the outer layer 418 is retracted, the inner layer 410 in the area of the feature 422 is free to disengage from the engagement feature 424 on the balloon 422. In the illustrated embodiment, the inner layer 420 defines in part the inflation lumen 318. A push wire 368 can be provided as described above for deactivating the ball valve 414 and allowing deflation of the balloon 111.

Figure 42:
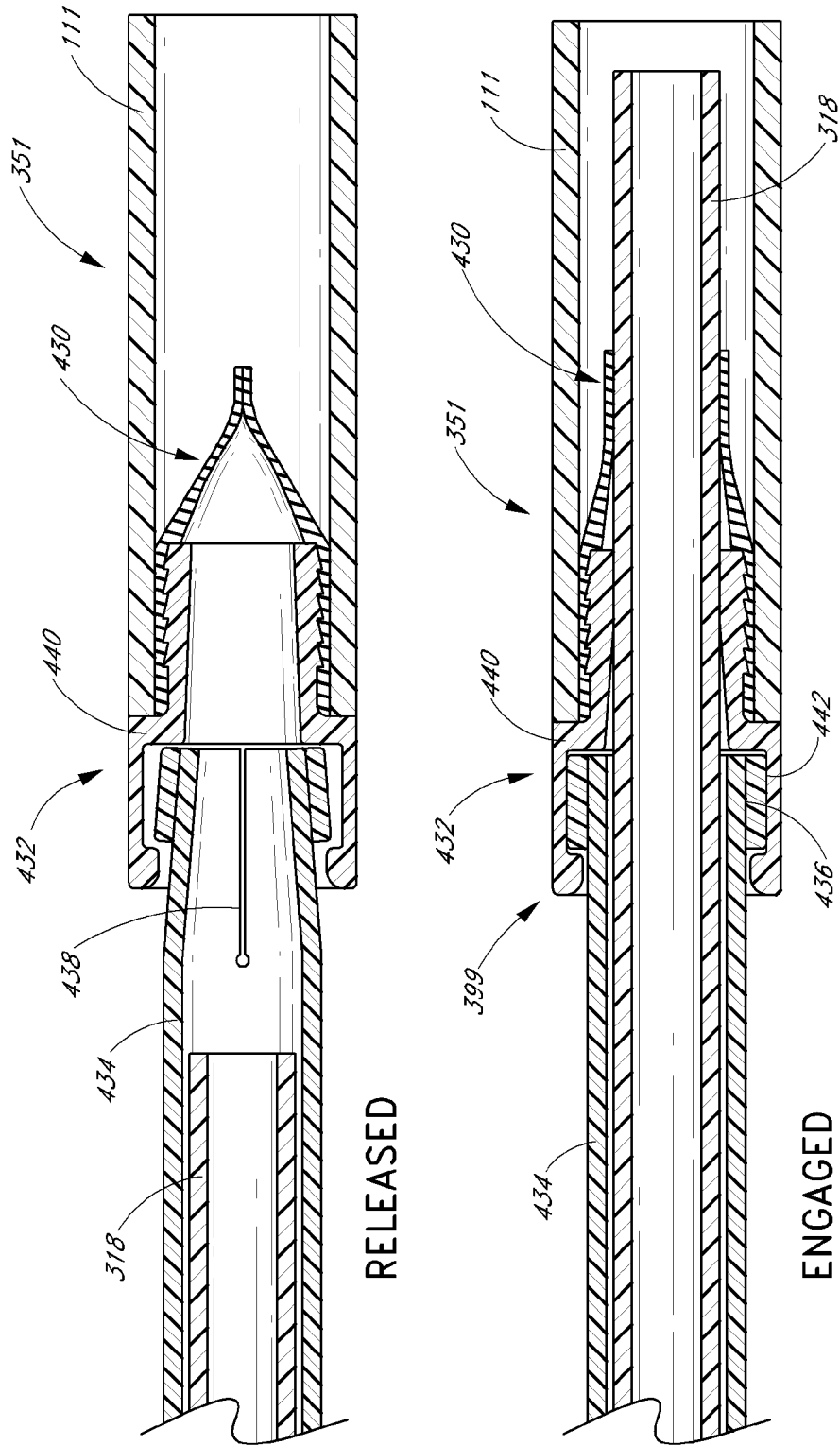
FIG. 42 is cross-sectional side view of a sealing and connection mechanism in a connected and disconnected confirmation.

FIG. 42 illustrates another embodiment of a sealing and connection mechanism 399. In this embodiment, the mechanism 250 comprises a duck valve 430 positioned in a connection portion 351 of the balloon 111. When the catheter 300 is engaged, the delivery tube 318 extends through the duckbill valve 420 allowing both inflation and deflation of the balloon 11. The tube 318 that extends through the valve 420 also extends through a lock mechanism 432, which holds the inflation lumen attached to the balloon. In the illustrated embodiment, the lock mechanism 432 comprises of a lock tubing 434 that extends approximately the length of the catheter 3000. The distal end of the lock tubing 434 has an enlarged ridge 436, and longitudinal slits 438 extending through the ridge 426. The distal end of the lock tubing 424 fits in an orifice plug 440, which is inserted into the connection portion 351 of the balloon 111 in line with the duckbill type valve 430. The orifice has a groove recess 442 to receive the enlarged ridge 436 of the lock tubing 434. The longitudinal slits 438 in the lock tubing 434 allow it to collapse sufficiently to easily engage and disengage from the groove 442 and the orifice 440. The inflation tube 318 extends through the lock tubing 434 preventing it from collapsing and releasing from the balloon 111.

After the balloon 111 has been inflated with the desired inflation media and the operator has chosen to disconnect the catheter 300 from the implant 100, the inflation tube 318 is withdrawn past the duckbill valve 430. At this time suction may be applied to remove as much inflation material as possible from the area past the valve 430. A rinse procedure could also be used to remove additional fluid. The inflation tube 318 is then withdrawn past the enlarged ridge 436 and the slit portion of the lock tubing 434. The lock tubing 434 can then be withdrawn from the orifice 440, and the implant 100 is separated from the catheter 300.

Figure 43:
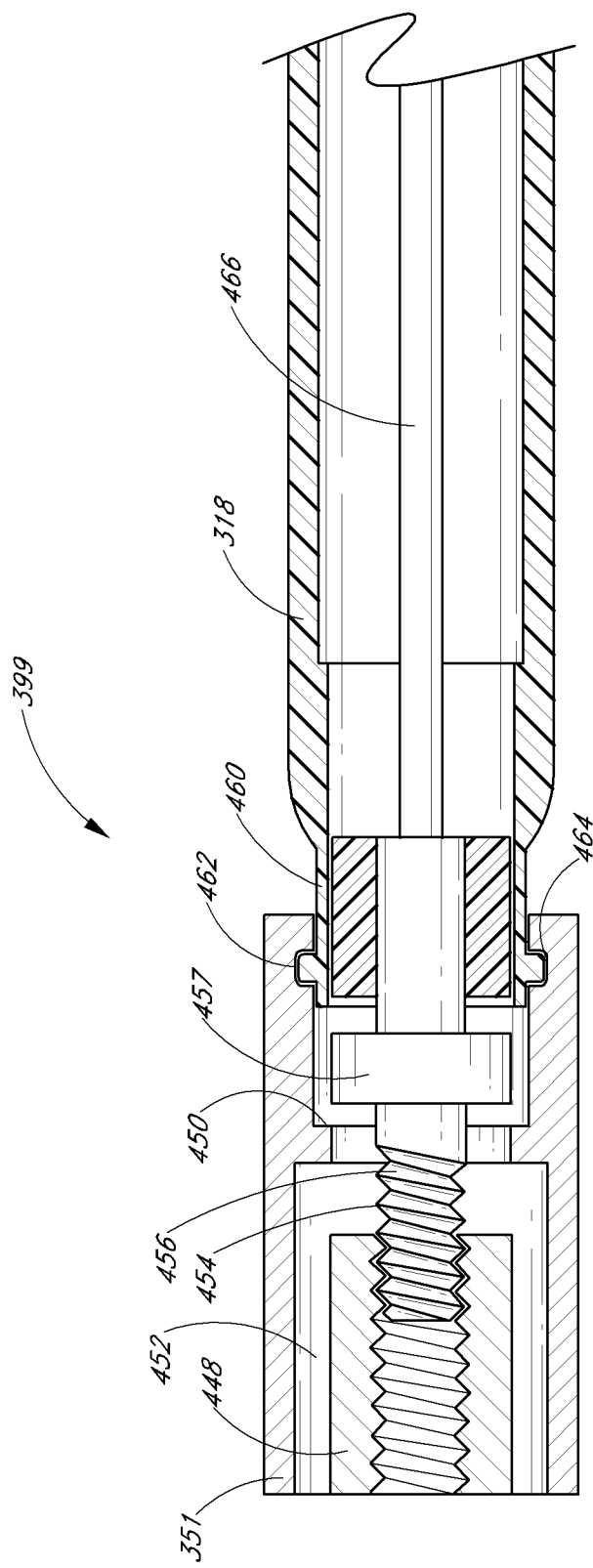
FIG. 43 is a cross-sectional side view of a sealing and connection mechanism.

FIG. 43 illustrates another embodiment of a sealing and connection mechanism 399. In this embodiment, connection portion 351 of the balloon 111 comprises a threaded bore 448 and a valve seat 450 positioned generally proximally of the threaded bore 448 within a fluid channel 452. A threaded portion 454 of a screw 456 is positioned within the bore 448. An enlarged, sealing portion 457 of the screw 456 is positioned within the fluid channel 452 proximal to the valve seat 450. As the screw 456 is threaded into the bore 448, the head 457 engages the seat 450 to seal the fluid channel 452 formed in the connection portion 351. The delivery or connection tube 318 includes a distal end 460 that can be inserted into the connection portion 351 of the balloon 111 to place the delivery lumen 318 in communication with the fluid channel 352. The distal end 460 can be provided with releasable tangs 462 that engage a corresponding groove 464 formed on the inner surface of the connection portion 351. The screw 458 is activated by a driver 466 that extends through the inflation tube 318 as shown in FIG. 43.

Control Wires

As discussed previously above, one advantage of many of the embodiments described herein is that the deployment of the implant 100 can be controlled. In one embodiment, the deployment of the implant is controlled via the use of control wires 230 that can be detachably coupled to the implant. Various mechanisms for detachably coupling the control wires 230 to the implant 10 will now be described.

With initial reference to FIG. 44, of the control wires 230 are attached to the cuff 102 of the implant 100 so that the implant 100 can be controlled and positioned after it is removed from the sheath or delivery catheter 300. The wires 230 are preferably stiff enough to prevent the implant 100 from rotating in a direction that would reduce the effectiveness or prevent the valve 104 from performing its function, of allowing blood flow only in a correct direction. Advantageously, the wires 230 would attach to the implant 100 in a proximal location and in a distal location. This would limit the degrees of freedom of the implant 100 relative to the wire 230, and minimize the possibility of the valve 104 or implant 100 of being damaged by the distal end of the wire 230.

With continued reference to FIG. 44, in the illustrated embodiment, the mechanism for coupling the wires 230 to the implant 100 incorporates a sheath 470 that extends over most of the length of the wire 230. The sheath is skived in at least one preferably two, locations to form skive(s) 272. At the skive or skives 472, a portion 474 of the cuff 102 or a portion of a member attached to the cuff 102 passes between the wire 230 and the sheath 470. With this method, the wire 230 may be released from the cuff 102 by withdrawing the wire 230 from the sheath 470 until the tip of the wire 230 extends past the skive or skives 472. In a preferred embodiment, the sheath 470 can be formed from part of the control wire tubes 316 that extend through the deployment catheter 300.

Preferably, three wires 230 are used, but any number between 1 and 10 can provide good results. The diameter of the wire 230 can range from about 0.002 inches to 0.020 inches. The wires 230 can be manufactured from a metal suitable for blood contact such as nitinol, stainless steel or one of many cobalt chrome nickel and/or iron based alloys. The wires 230 can also be made of a polymer that has the desired mechanical properties such as a polyimide. The sheath 472 can be manufactured from the many polymers suitable for blood contact including nylons Teflon PBX polyethylene polypropylene polyimides etc. The sheath 470 is preferably sufficiently rigid in the axial direction to prevent the accidental disconnection of the valve 100, so the dimensions of the sheath depend on the axial stiffness of the material. A polyimide sheath 470 with a 0.026 inches outside diameter and a 0.005 inch thick single wall has proven adequate, while a grillamid nylon sheath with a 0.030 inch outside diameter and a 0.007 inch thick single wall has also proven adequate. Preferably the polymer sheath 470 ranges in outside diameter from about 0.018 inches to 0.040 inches and in wall thickness from about 0.003 inches to about 0.010 inches. Additionally a stainless steel, nitinol or other metallic sheath cab be utilized. In this case, smaller diameters and thinner wall thicknesses are generally desirable. In one embodiment, the stainless steel sheath 470 has a 0.014 outer diameter with an inner diameter of about 0.011 inch and the wire 230 with a 0.009 inches outer diameter. With a metallic sheath 470, the preferred wall is about 0.0005 inch to about 0.0050 inch thick and the preferred outside diameter is about 0.007 inches to about 0.025 inches. The inside diameter of the sheath 470 should provide clearance to move freely over the wire 230. A clearance of 0.00 to about 0.007 inches should provide adequately free motion. A lubricant or hydrophilic coating may be applied to the inside diameter of the sheath 470, or the outside diameter of the wire 230. Different clearances may be required with less lubricious polymers. In addition, extrusion parameters may be adjusted to produce a surface finish on the inner diameter of the tube 470 that optimizes the motion of the sheath 470 relative to the wire 230. With some polymers a rougher surface may result in reduced friction. As mentioned above, the ideal wall thickness of the sheath 470 depends on the strength and stiffness of the particular material selected, but likely ranges between 0.002 and 0.020 inches, single wall thickness.

The proximal end of the deployment control wires 230 preferably contains a lock mechanism (not shown) to prevent the unintended relative motion of the wire relative to the sheath 470. The wires 230 may also be attached to a handle section that allows the relative movement of one wire individually or multiple wires together. In one embodiment the three wires 230 are attached to a ring, equally spaced around the edge of the ring. As the ring is moved proximal or distal relative to the main handle component the implant 100 moves proximal or distal relative to the catheter tip. As the ring is tilted off axis with the axis of the catheter handle, the implant 100 is tilted in a similar direction.

The deployment control mechanism can performs several functions. First as described above, during the initial deployment of the implant 100, it prevents the implant 100 from rotating off axis. Additionally the deployment control mechanism allows the implant 100 to be repositions after it has been removed from the sheath. The wires described above could be used to move the implant 100 proximally and distally.

Figure 45C:
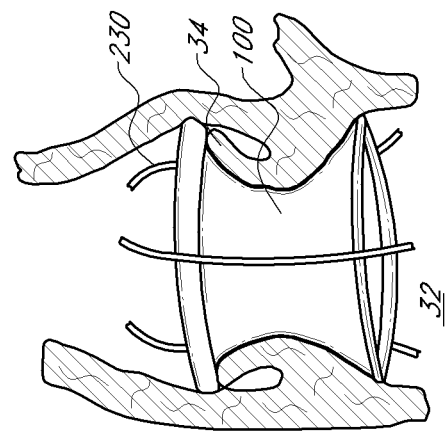
FIGS. 45A-C illustrates time sequence steps of partially deploying and positioning an artificial valve implant.
Figure 45B:
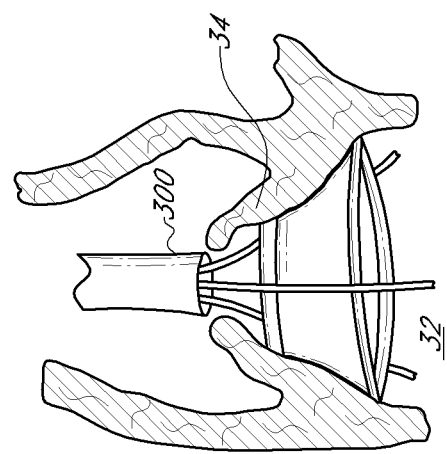
Figure 45A:
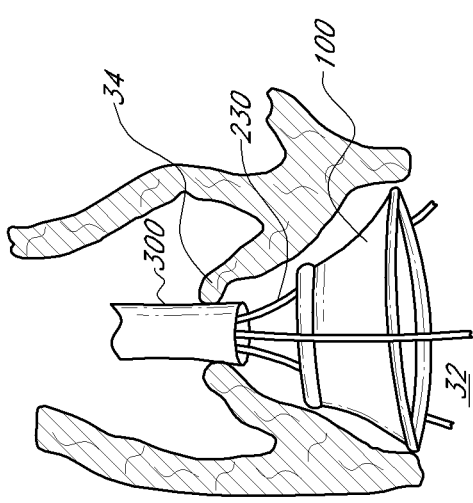

With reference to FIGS. 45A-C, in one embodiment, the implant 100 is initially deployed partially in the ventricle 32 (FIG. 45A) and then later pulled back into position at or near the native valve 34 annulus (FIG. 45B). Preferably, the valve 100 itself is placed just above the native valve annulus in the aortic root. The implant 100 can then be fully deployed (e.g., inflated) such that extends across the native valve annulus extending slightly to either side. See FIG. 45C. The deployment control wires 230 provide a mechanism for force transmission between the handle of the deployment catheter 300 and the implant 100. By moving all of the deployment control wires 230 together the device can be advanced or retracted in a proximal or distal direction. By advancing only a portion of the deployment control wires 230 relative to the other deployment control wires 230, the angle or orientation of the wires can be adjusted relative to the native anatomy. Radiopaque markers on the implant 100 or on the deployment control wires 230 or the radio-opacity of the wires 230 themselves, help to indicate the orientation of the implant 100 as the operator positions and orients the implant 100.

Figure 46C:
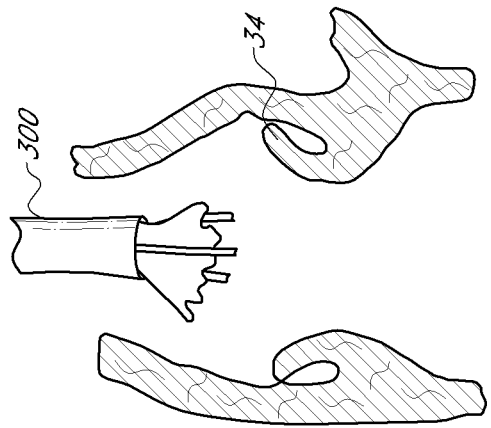
FIGS. 46A-C illustrates time sequence steps of deploying and withdrawing an artificial valve implant.
Figure 46B:
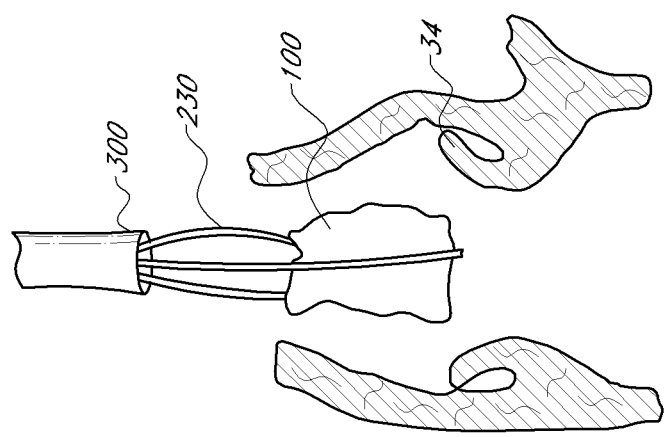
Figure 46A:
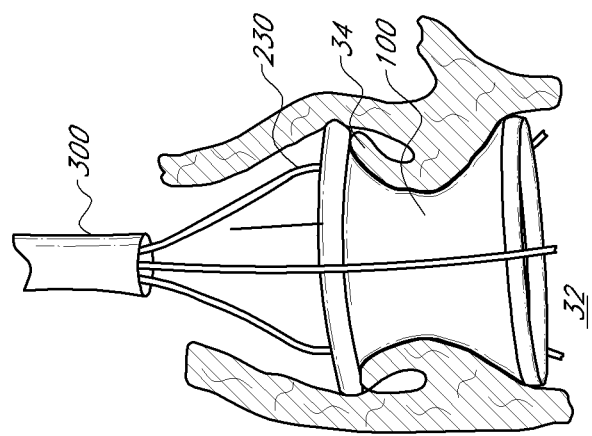

With reference to FIGS. 46A-C, the deployment control device also provides a method for retracting the implant 100 back into the deployment catheter 300 if the result is not satisfactory, or if the sizing of the implant could be optimized. Thus, after the implant 100 is fully or partially deployed (FIG. 46A), in addition to providing a mechanism to transmit axial force to the implant 100, the wires 230 described above provide a guide or ramp to pull the implant 100 back into the deployment catheter 300 as it is retracted as shown in FIGS. 46B and 46C. The implant 100 could be recovered into the deployment catheter 300, or a larger recovery sheath (see. e.g., FIG. 50 item 502) could be introduced over the deployment catheter 300 for recovery of the implant 100.

Figure 47A:
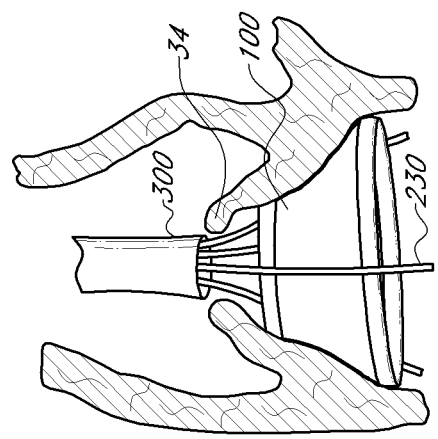
FIGS. 47A-E illustrates time sequence steps of deploying, testing and repositioning an artificial valve implant.
Figure 47B:
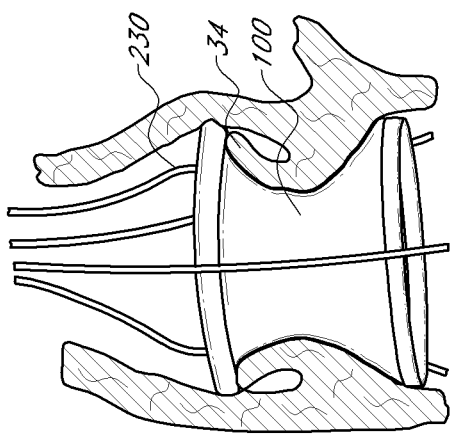
Figure 47C:
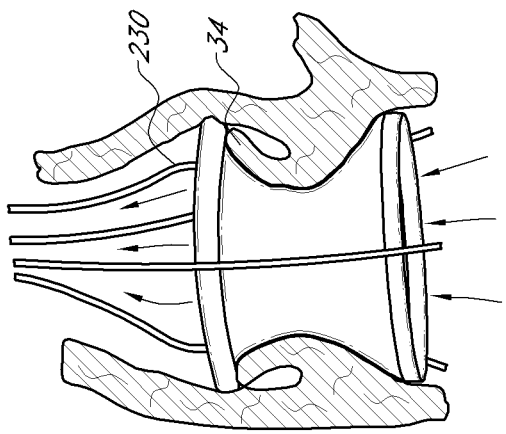
Figure 47E:
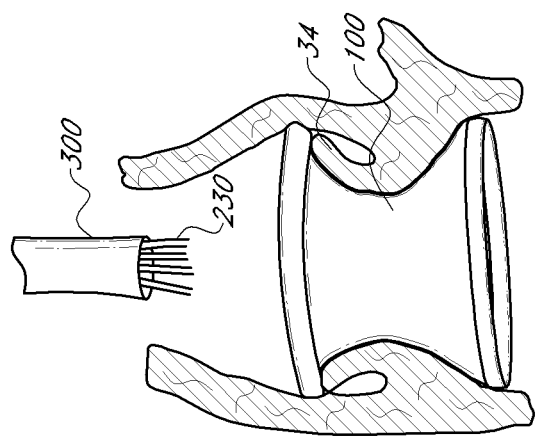
Figure 47D:
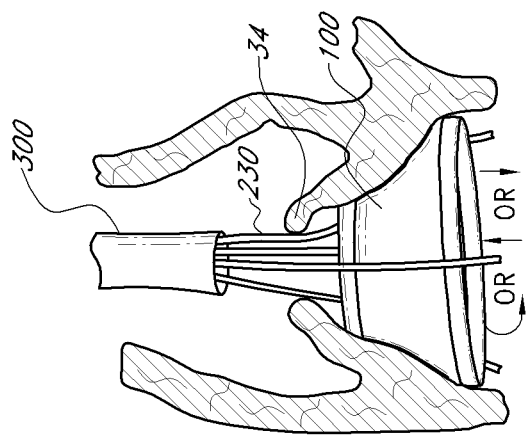

FIGS. 47A-E illustrate another advantage of the deployment control system. As shown in FIG. 47A, the implant 100 can be partially deployed and the wires used to seat the implant 100 against the native aortic valve 34. The implant 100 can then be fully deployed as in shown in FIG. 47B and then tested as shown in FIG. 47C. If justified by the test, the implant 100 can be deflated and moved as shown in FIG. 47D to a more optimum position. The implant 100 can then be fully deployed and released from the control wires as shown in FIG. 48E.

The deployment control systems described herein could be used with the cast in place support structure described in this application, or on a self expanding stent structure, or on a inflatable structure as described by herein. The deployment control device may also be used on other non-vascular devices such as stent grafts for aneurysm exclusion or self-expanding stents for treating stenosis.

Figure 48:
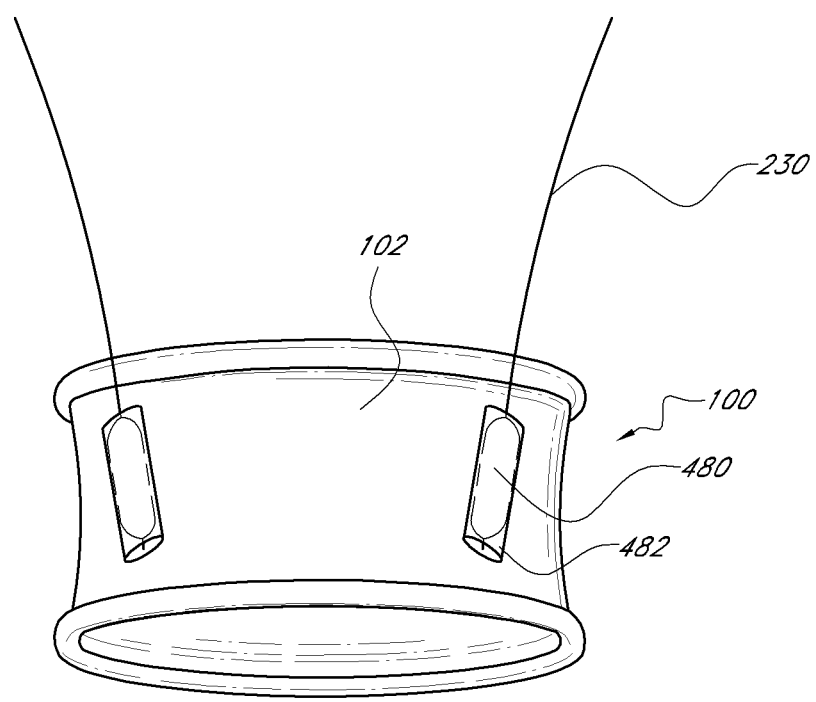
FIG. 48 is a side perspective view of an embodiment of connecting a control wire to a prosthetic valve implant.

FIG. 48 illustrates another embodiment of a deployment control system. In this embodiment, the control wires 230 include a small balloon 480 attached to the distal end of the wires 230. The balloons 480 are inserted through a small tube 482 provided on the implant 100. In one embodiment, the tube 482 is formed of a fabric and can be the same fabric used to form the cuff 102. The deployment control wires 230 are released by deflating the balloon 480. The balloon 480 is preferably about 0.02 to 0.12 inches diameter and the tube 482 preferably has a slightly smaller inner diameter than the outer diameter of the inflated balloon 480. The proximal and distal ends of the tube 482 may additionally have section(s) of reduced diameter, where the diameter is significantly smaller than the diameter of the inflated balloon 480.

As described above, the deployment control wires 230 can be used to allow the repositioning of the implant 100 after it has been unsheathed. The deployment control wires 230 are preferably rigid enough to allow the operator to reposition the implant 100 and to prevent the implant 100 from migrating due to the force of blood flow and pressure. Once the implant 100 is inflated, it is desirable for the wires 230 to be flexible and, in one embodiment, as flexible as the tip of a conventional guidewire. This flexibility allows the implant 100 to take the same shape and position that it will take after the wires 230 are removed. This allows both the securement and function of the implant 100 to be tested and evaluated before the operator commits to permanently implanting the implant 100. The increased flexibility is preferably provided in a plane tangent to the generally cylindrical shape defined by the vessel, where the valve 100 is implanted. Therefore, in a preferred embodiment, the control wires 230 will be particularly flexible at the tips allowing the device to be nearly free from forces exerted by the catheter 300, as it would be when disconnected.

Figure 49:
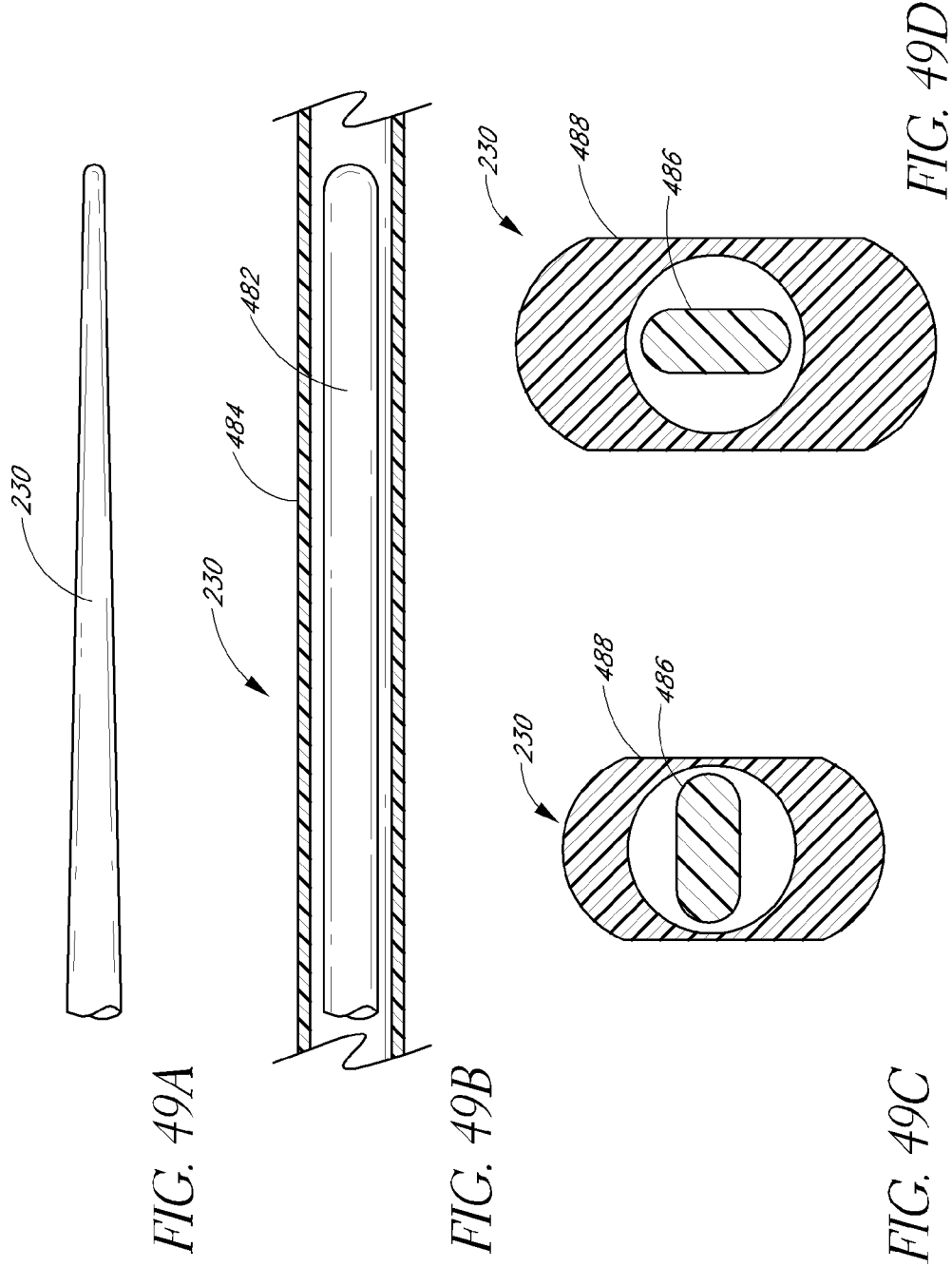
FIG. 49A is a side view of an embodiment of a control wire with controlled flexibility.
FIG. 49B is a side view of another embodiment of a control wire with controlled flexibility.
FIG. 49C is a cross-sectional front view of another embodiment of a control wire with controlled flexibility in a first position.
FIG. 49D is a cross-sectional front view the control wire of FIG. 49C in a second position.

Many embodiments of a wire that fulfills the requirements of flexibility and stiffness are possible. In one embodiment, the wires are manufactured to have a flexible tip and a less flexible proximal section. Techniques for manufacturing wires with these properties are widely known to those skilled in the art of guide wire design and manufacture. Techniques include grinding a tapered control wire as shown in FIG. 49A and or stepped shoulders to the diameter of the wires. In another embodiment, the wire is wrapped with coils of similar type or different materials to provide a soft feel to the distal section.

In another embodiment, which is illustrated in FIG. 49B, the deployment control wire 230 comprises of an inner wire 482 and an outer tube 484 over the inner wire 482. When a stiff system is desired, the inner wire 482 and tube 484 are used together. When a more flexible control wire 230 is desired, either the inner wire 482 or the tube 484 is used alone. In one embodiment, the inner wire 482 is preferably manufactured from a metal such as nitinol or stainless steel and the tube 484 can be metallic or polymeric. The tube 484 may be cut in a spiral pattern or have segments cut out of it or a skive cut in it to create the desired flexibility in the required areas. In another embodiment, patterns can be cut in the tube 484 as seen in U.S. Patent Publication 2002/0151961 A1 to Lashinski et al., which is hereby incorporated by reference herein. In this embodiment, there are patterns cut in the tube 484 to provide defined shape as the tube is deflected. In other embodiments, guidewires utilizing slots cut into a tube as seen by neurovascular products from Boston Scientific/Target Therapeutics can be used.

With reference to FIG. 49C and FIG. 49D, in another embodiment, deployment control wires with variable stiffness are created by utilizing a wire 486 and a sheath 488 as a system where each has a preferred bending plane. When the wire 486 and the sheath 488 are rotated so that their preferred bending planes align (see FIG. 49D) they have good flexibility in the plane where flexibility is required. When a stiffer system is desired, the wire 486 and sheath 484 are rotated so that their preferred bending planes are out of alignment (see FIG. 49C), preferably approximately 90 degrees out of alignment. In this configuration a less flexible system is produced. The wires 486 and sheath 495 cross sectional profile may be round with single or multiple flats to create a "D" shaped cross section, for example, as shown in the illustrated embodiment of FIGS. 49C and 49D. The Recovery Tools and Techniques Current valve systems are often deployed through a stent-based mechanism where the valve is sewn to the support structure. In the inflated embodiments described herein, the structure is added to the implant secondarily via the inflation fluid. This allows the user to inflate or pressurize the implant with any number of media including one that will solidify. As such, if the operator desires, the implant 100 can be moved before the inflation media is solidified or depressurization can allow for movement of the implant within the body. Since catheter based devices tend to be small in diameter to reduce trauma to the vessel and allow for easier access to entry, it often difficult to remove devices such as stents once they have been exposed or introduced into the vasculature. However, as will be explained below, a device described herein enables a percutaneous aortic valve to be recovered from the body and reintroduced retrograde to the introducer.

Figure 50:
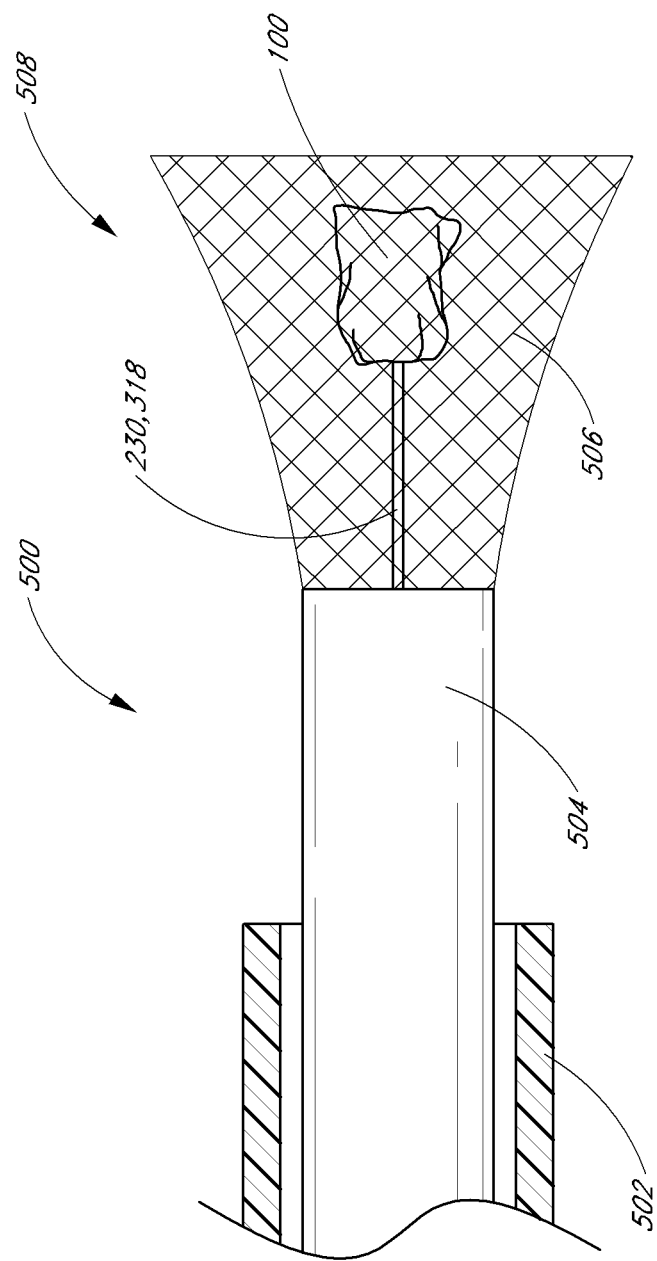
FIG. 50 is a side view of a distal end of a recapture device.

FIG. 50 illustrates one embodiment of a device 500 for recapturing an implant 100. As shown, the device 500 comprises an outer tubular sheath 502. A tubular recovery sheath 504 is inserted through the outer sheath 502. The recovery sheath 504 includes a sox or braided structure 506, which is coupled to the distal end of the sheath 504 and is configured to capture the implant into the device 500 without harm to the patient. Relative movement of the recovery sheath 504 with respect to the outer sheath 502 would expose the braid 506 when introduced into the body. By pulling a implant 100 into the braided section it may be safely reintroduced into a introducer or sheath. The braid 506 allows the implant to be guided into an introducer without harm or worry of the implant being tethered or compiled to a larger diameter where it may not fit into the inner diameter of a sheath.

A hemostasis valve (not shown) is preferably attached to the proximal end of the device 500. Also at the proximal end, a flush port and stop-cock can be provided for fluid introduction. In one embodiment, the inner shaft 504 would have a length of about 40 to 60 centimeters and a diameter of about 2 to 18 millimeters. In a modified embodiment, the distal end 508 of the braid section 506 could be attached to end of the outer coaxial sheath 502. This would allow relative motion between the two sheaths 502, 504 and allow the braided section 506 to be inverted upon it self. The braided section 506 can be formed or shaped into a funnel as shown in FIG. 50 so that it is in contact with the aortic wall when introduced into the body. The braid 506 may be constructed with materials such as polymeric strands or Nitinol, stainless steel or MP35N wire and attached by glue or thermal bonding techniques know in the industry. This wire, strand or ribbon may have a diameter or dimension of about 0.002 to 0.020 of an inch. The set or expanded shape would be about 1.00 to 1.50 inches and the length of the braid 506 would measure about 6 to 9 inches in length. It is also possible to have the inner sheath 504 and outer sheath 504 connected leaving the braid 506 fixed in length and diameter. The relative motion between the two sheaths 502, 504 would be limited or eliminated depending upon the construction of the device 500. Both configurations may require a capture sheath to collapse the braided section 506 while it is being inserted into the introducer. The diameter of this sheath would be about 24 F or similar in diameter to the introducer. Once inserted through the sheath, the device 500 is expelled out the introducer and exposed to the descending aorta. Hemostasis valves will prevent blood from leaking proximally out the catheter shaft.

In another embodiment the slit tubing is replaced by a fabric cone, where the fabric cone may contain a feature such as a preshaped wire or a balloon to facilitate its opening.

The braided cone 506 can be formed by heat setting or other manners into a cone shape with a free diameter slightly larger than the patients aorta. In another embodiment, the braided cone is manufactured from loops of wire so that the cut ends of the wire are all located at the proximal end of the cone. The wires used to manufacture the cone preferably have a diameter from 0.002 in to 0.020 in. The wires may also be replaced by ribbons having a thickness between 0.002 in and 0.020 in and a width between 0.003 in and 0.030 in. The diameter of the small end of the cone is preferably between 0.007 in and 0.3 in the cone is preferably be capable of collapsing to a diameter small enough to pass through the desired introducer size. The large end of the cone section preferably expands to a diameter similar to or slightly larger than the typical human aorta, or 0.75 in to 1.50 in.

In one embodiment, the separate recovery device 500 is supplied to facilitate the recapture of the implant in the event that the prosthetic valve did not produce the desired result in the patient. To recapture an inflatable aortic implant 100 as describe herein, the delivery catheter 300 for the device would be removed leaving inflation tubes 318 and or deployment control tubes 316 tethered to the implant 100. By inserting the retrieval catheter 500 over these connections the implant 100 is now coaxial to the retrieval system 500 and ready to be removed from the body. By advancing the retrieval catheter 500 over the implant 100 or by pulling the control lines 230, the implant 100 can be retracted into the braided section 506. The implant 100 is now covered and may safely be pulled into the sheath 502 and removed from the body.

Figure 51:
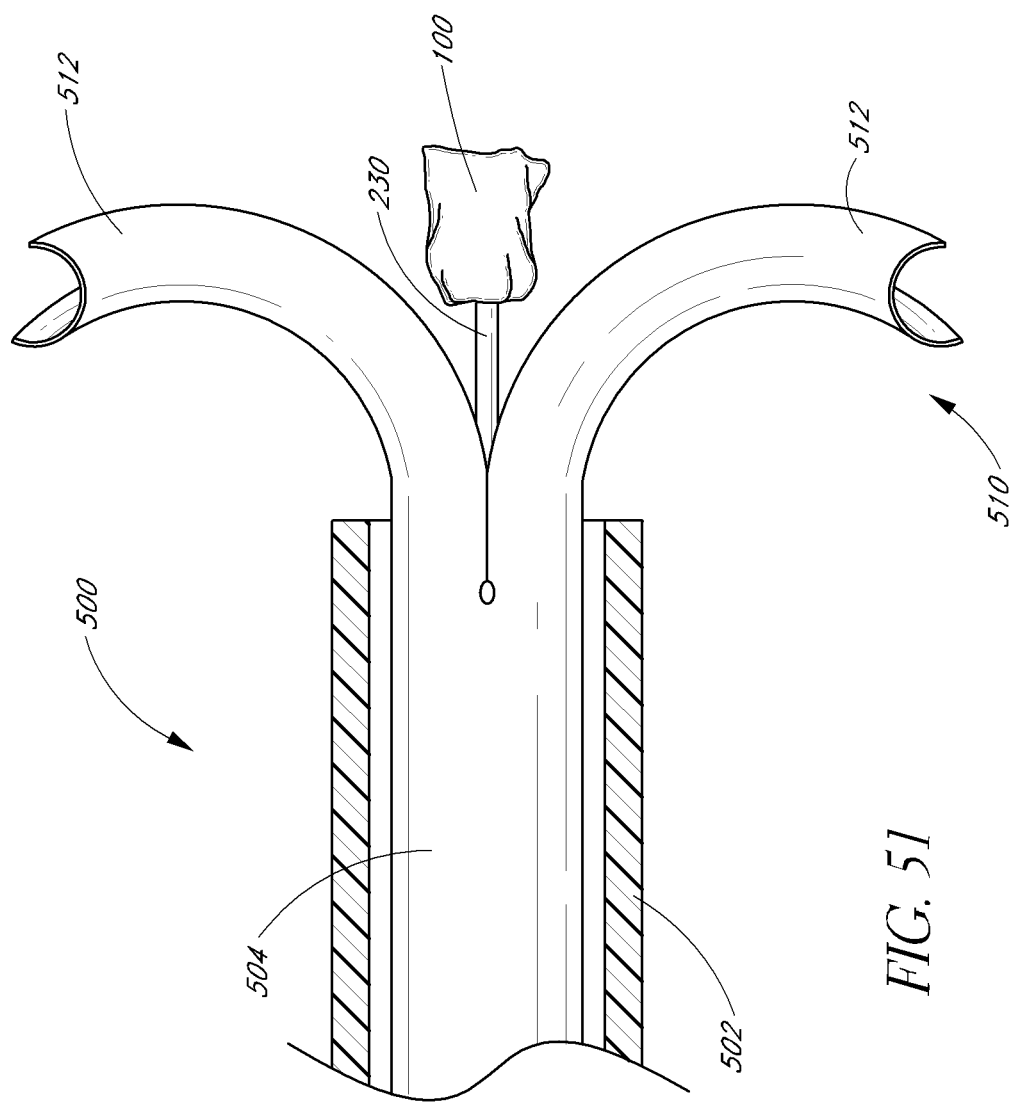
FIG. 51 is a side view of a distal end of another embodiment of a recapture device.

FIG. 51 illustrated another embodiment of a retrieval device/system. 500. In this embodiment, the distal end of the inner sheath 502 includes a spilt section 510 that is flared to funnel the implant into the device 500. In one embodiment, the distal end of the inner sheath 504 would be slit longitudinally about 1 to 2 inches in length and radially is 4 to 12 times. This would leave a series of narrow bands or strips 512 to be preshaped open or rolled back. In the illustrated embodiments, the strips 512 are curved outward away from the center line of the tube. This would require the retrieval outer sheath 502 to be advanced over the flairs 512 to capture the implant 100 to be removed. The implant 100 can include control wires 230 spaced radially to gather the device into in a similar manner as described above. The wires may be stainless steel, Nitinol or other suitable materials generally accepted in medical devices. Formation of this wires would allow them to be radially expandable to contact the aortic wall allowing the device to be pulled into the sheath.

Other applications for these recapturing systems may be advantageous for devices such as stents (coronary and peripheral), PFO and ASD closure devices, micro coils and other implantable devices that may need retrieval from the body. Currently snares and other tools are used to drag devices out of the body however, many devices will be hung up on catheters or introducers as they are removed. By creating a basket to protect the device from these events, removal becomes simpler and safer.

Another method for device recovery includes providing a string woven through the prosthetic valve 100. As tension is applied to the string the prosthetic valve 100 collapses back down, to a size small enough to be recovered into the delivery sheath, the introducer or a recovery sheath.

Excision and Debulking Devices

Figure 52A:
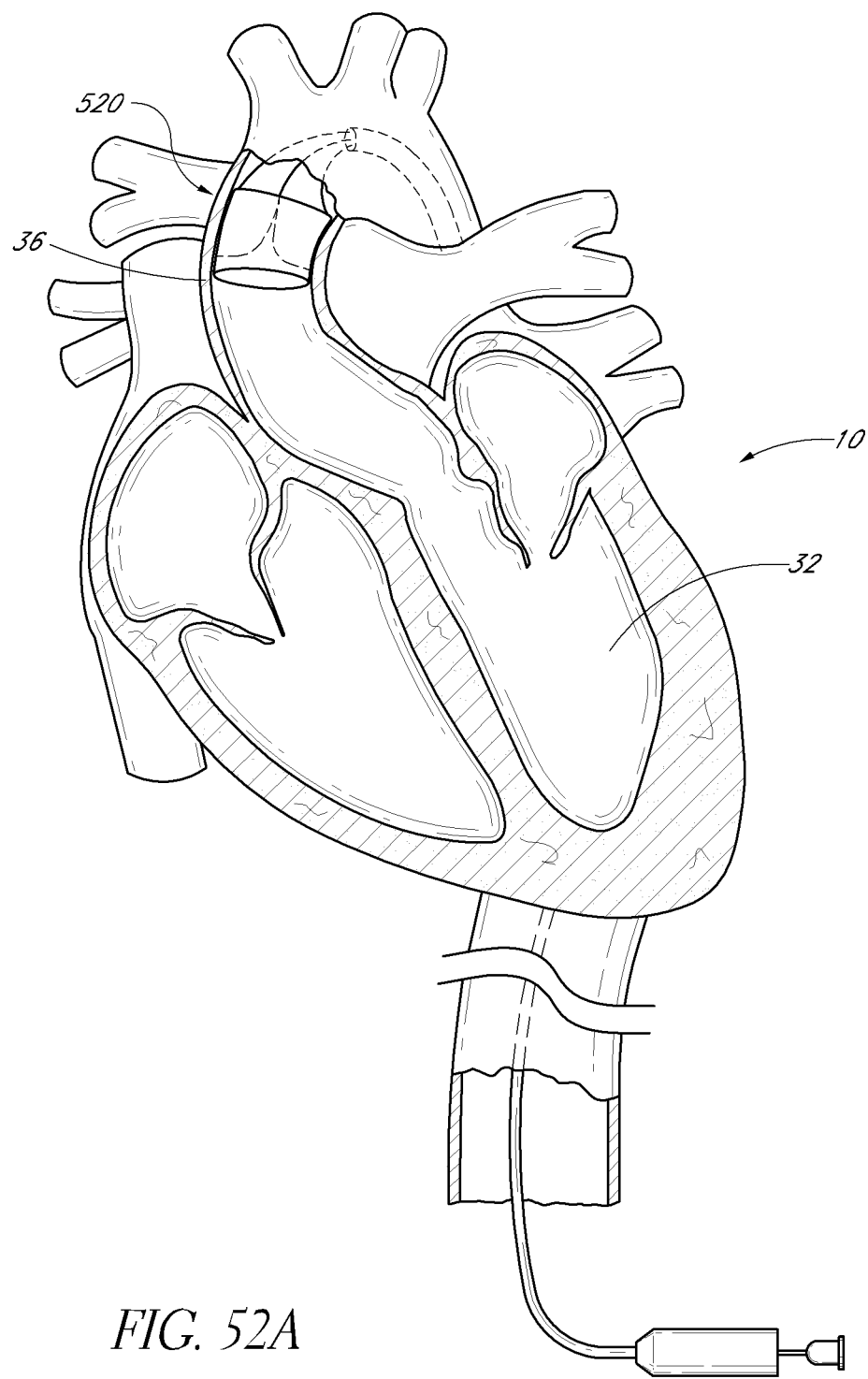
FIG. 52A is a partial cross-sectional view of the heart and the aorta with a temporary valve positioned therein.

The procedure of implanting a valve preferably begins with enlarging the valve annulus. This could be performed with a simple balloon valvuloplasty. However, in many instances this is not sufficiently. Thus, before a prosthetic valve is replaced in a surgical procedure, the surgeon often modifies or removes the native valve leaflets, and especially any calcification or vegetations in the area As will be explained in more detail below, in order to preserve outflow from the heart, between the time that the native aortic valve is excised or debulked and the time that a prosthetic valve is implanted, a temporary valve 520 (see FIG. 52A) can be installed. The temporary valve 520 can be placed in the aorta 36 in the arch or in the descending or ascending aorta. Examples of these types of valves are described in U.S. Pat. No. 3,671,979 and U.S. Pat. No. 4,056,854, which are hereby incorporated by reference herein. Many other temporary valve designs are possible; however, flexible polymer or tissue valves are the preferred valve type because they can be easily delivered via catheter. Several versions of flexible polymer valves are possible, for example, a "duck bill", tricuspid or bicuspid style valve can be used. Alternatively. an umbrella style valve or a windsock type valve could be used. The temporary valve 520 can be sealing and temporarily engaged to the wall of the aorta 36 by several methods including a self-expanding stent or an inflatable balloon like structure at the base of the valve. Additionally, the temporary 520 may be entirely inflatable or utilize combinations of polymers such as nylon, Teflon, Dacron or polypropylene with metallic elements including Nitinol, stainless steel, or other generally acceptable materials use in medical devices. There may be radiopaque markers attached to the temporary valve for proper placement and anchors deployable from the temporary valve or passively attached may aid the device in securment.

In one embodiment, the temporary valve 520 can be configured in a manner similar to the implant 100 described above. In such an embodiment, the temporary valve 520 would be delivered via catheterization technique by delivering a collapsed temporary valve and filling the valve body or cuff with fluid to provide structure or by compressing a valve assembly into a catheter for delivery and introducing the valve by removing a sheath to introduce the device to the targeted implantation site. It is also possible to unroll or unwrap a valve assembly from a catheter for delivery. Any method of delivery will suffice as long as the device can be safely removed once the removal and introduction of the new valve has been completed.

The temporary valve 520 should provide a manner for a catheter to pass across the temporary valve while still maintaining flow. The temporary valve 520 can be delivered with a guidewire advanced through the valve to allow guide wire compatible devices to be easily advanced across the valve. If an umbrella type valve is used blood flows between the device and the wall of the aorta. In this case the guidewire or catheter may pass around the valve rather than through the valve.

A modified method to using a temporary valve is to use a percutaneous bypass procedure. When this procedure is performed it is no longer necessary to maintain the flow through the aortic outflow tract. The aorta may be occluded during the excision step and the debris and fluid from the excised area may be aspirated after or during the excision step. In a percutaneous bypass procedure blood is oxygenated extracorporally and reintroduced into the body. A cardiopelegia solution is used to stop the heart-beat.

Figure 52B:
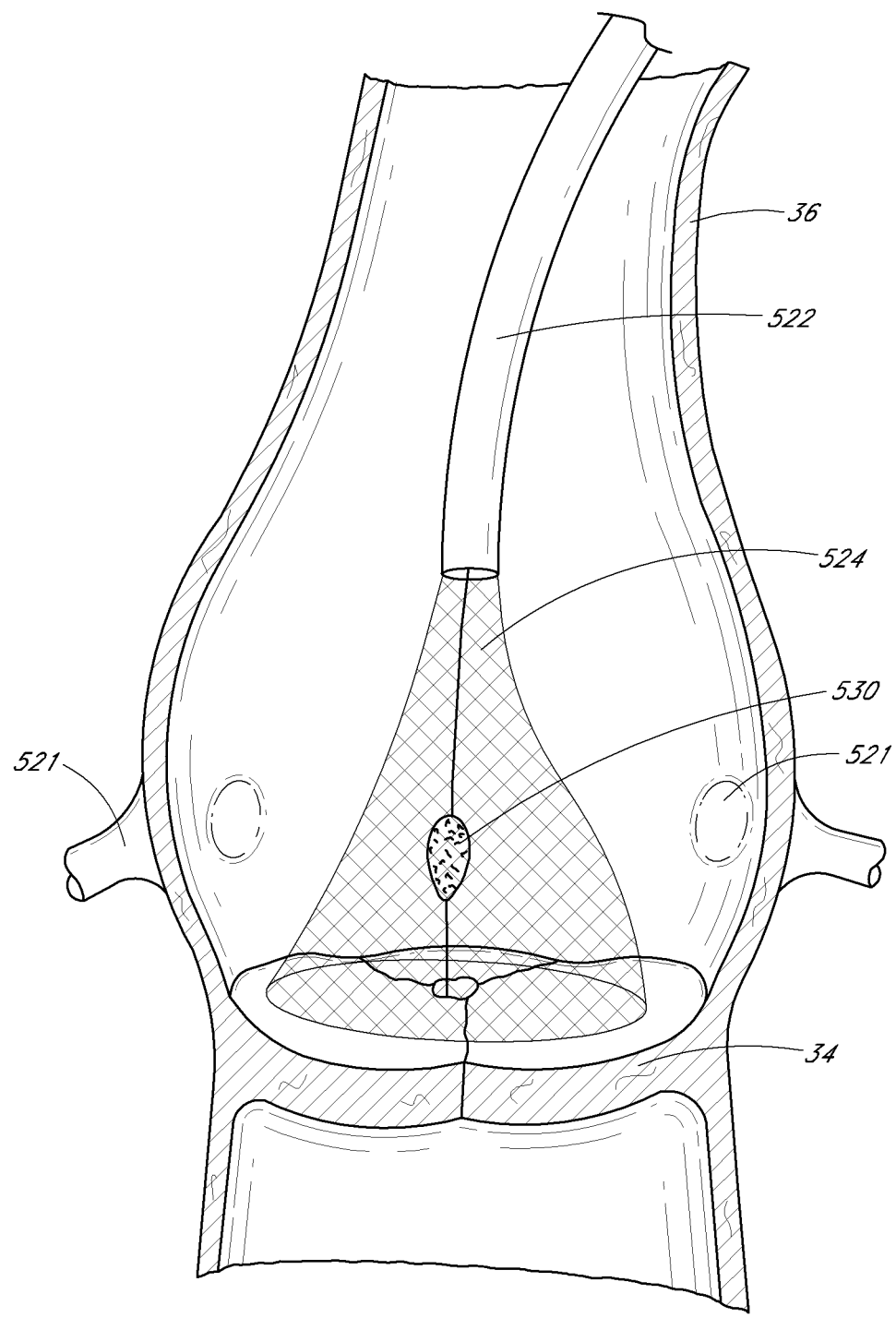
FIG. 52B is a partial cross-sectional view of the heart and the aorta with protection device positioned therein

With reference to FIG. 52B, an embolic protection device 522 is desirable, or necessary because as the calcified or diseased valve is removed or dissected embolic debris may likely be released. It may be desirable to locate the embolic protection device 522 downstream from the temporary valve 520 so that it will capture any embolized thrombosis and debris from the valve 34. It also may be desirable to locate the embolic protection device 522 below the ostia 521 of the coronary arteries. If this location is selected it may be difficult or impossible to locate the filter 522 downstream from the temporary valve 520. Filtration size can range from about 25 microns to 500 microns in size. The filter 524 of the protection device 522 may be made from Nitinol, MP35N, stainless steel or any acceptable polymeric material used in medical devices.

Many various tools are capable of removing portions of the aortic valve 34 or for removing calcification from the aortic valve 34. Examples of such tools that are known for surgical applications or for percutaneous applications include ultrasonic energy sources such as CUSA, hand tools such as cutters or knives and fluids that may dissolve or soften the tissue and or calcium to be removed. As shown in FIG. 52B, in one embodiment, the excise tool 530 is positioned generally within the filter 524.

In one embodiment, an ultrasound transducer may be positioned near a catheter tip and used as a tool to break up calcium and cause it to release from the valve tissue. This method was used for the surgical repair of calcified aortic valves. Unfortunately, the procedure can also damaged the healthy portions of the leaflets causing aortic insufficiency chronically. Typically, the aortic insufficiency would develop in one to two years. In some patients, the native valve was destroyed during the procedure. As a preparation for valve removal, a percutaneous adaptation of this technique may be appropriate. In addition to the ultrasound catheter, some method of collection the calcified tissue is often required. One method is the embolic protection filter described in this application. Alternatively, suction could be applied to the catheter tip, to remove the small particles. With either method, large nodules of calcium may be released from the native tissue. If the nodules are larger than the catheter they must be broken up before they can be safely removed percutaneously. Preferably, the ultrasound transducer can be manipulated to break up these large nodules into particles small enough that they can be removed. This technology is described in U.S. Pat. Nos. 4,827,911, 4,931,04, 5,015,227, 4,750,488, 4,750,901 and 4,922,902, which are hereby incorporated by reference herein. The frequency range for these devices is often about 10-50 KHz but seems to be optimal at about 35 Khz.

Another tool that can be used to excise the native valve 34 may comprise multiple external energy sources that are focused on the tissue to be removed from different directions. This technique can be used with several energy sources, for example ultrasound energy may be used in this way. Radiation energy may also be used in this way, by a method referred to as a gamma knife.

A heated wire system can also be used to cut the aortic valve out from the annulus. In such an embodiment, the wire may be mounted on a catheter and heated by means such as electric resistance or RF energy. The wire may be manipulated in the area of the valve to be removed, and located by balloons or wires. Wire sizes may range from 0.005-0.100 inches in diameter and are typically made from a Ni-chrome material.

In another embodiment, a laser can be used to cut the calcified tissue apart. The laser energy could be transmitted fiber optically through a catheter and applied to the calcified tissue at the catheter tip. The catheter tip may be manipulated by the operator to direct energy to the site-specific area causing ablation or cutting the tissue and or diseased material. It is important that the laser wavelength is correct and will couple to the material to be affected. There may be a need to adjust the wavelength, rep rate and energy density to customize the removal process.

In yet another embodiment, the calcified valve tissue may be broken up and removed using a cutting balloon, or an inflatable balloon with metal or rigid plastic blades along its length. An example of this is U.S. Pat. No. 5,616,149, which is hereby incorporated by reference herein. As the balloon is expanded the blades are forced into the tissue causing it to break apart. Mulitple inflations may be required to create a sufficiently large valve area. In one embodiment the balloon is mounted on a torquable catheter allowing a partially inflated balloon to be torqued scraping tissue away from the valve annulus. This balloon source may be used in the "hot-wire" application above to cut the tissue in a pie shaped pattern before removal or exclusion.

Several of the tools described for removing portions of the aortic valve may remove portions of valve or calcium that are larger than can pass through a catheter. In these cases a catheter with a provision to pulverize and extract the excised material may be needed. In one embodiment the catheter includes a rotating auger near its tip to break up the large particles and feed them back through the catheter shaft. Suction may also be applied to the catheter to prevent smaller particles from exiting the catheter tip. Examples of this may include the RotoBlader device produced by Boston Scientific but may be housed in a catheter to limit the escape of particles down stream.

FIGS. 53A-54C illustrate one embodiment of an excise device 530 which comprises a punch and die that can be used to punch out sections of tissue. The device 530 comprises a punch or cutter 532 with a sharp edge 534 that is moveably positioned within a channel or cavity 535 of a catheter body 540 to collect the removed sections of tissue. As will be explained below, the punch 532 can be actuated by pushing or pulling a wire 539 through the length of the catheter, by a hydraulic actuation, or by a screw device near the catheter tip that translates a rotational force transmitted through a flexible shaft into an axial or linear force that actuates the punch 532.

With continued reference to FIGS. 53A-54C, the cutting action is preferably from distal to proximal to move the material into a catheter's inner diameter. Although not shown, the device 530 can use a spring force to eject the material and a trap or door to retain the material once in the catheter shaft. As shown, a cutting edge 542 is formed in by a window 544 formed in the catheter body 540. The widow 544 forms a cutting edge that is generally perpendicular to the diameter of the catheter 540 or, in a modified embodiment, at an angle to provide a lower cutting force. The cutting edge 542 and or the puncher 532 can have any of a variety of shapes such as hyperboloid, triangular, diamond or serrated that would aid in cutting the material to be removed. The cutting edge 542 and/or punch 532 can also use a vibrating or ultrasonic energy to lower the forces required to cut the material. These can be delivered through the catheter 540 and may include transducers, motors or RF energy. In one modified embodiment, the punch 532 is replaced with a rotating blade. The entire device 530 is preferably flexible and configured to use normal catheterization tools including contrast, introducers, saline, guidewires etc/.

In the preferred embodiment, the cutting action is performed by pulling the punch 532 proximally into the cutting edge 542. The punch 532 is coupled to the wire 539, which extends through the catheter and is actuated by a handle 546 provided at the proximal end of the device 530. By cutting in this direction the excised tissue is pulled into the catheter 540, and the wire 539 which transmits the force is loaded in tension. An aspiration function is also incorporated into the lumen 535 into which the excised tissue is pulled. By maintaining a minimal fluid flow out through the catheter lumen 535 the risk of embolic events may also be minimized. A spring (not shown) can be provided at the distal end 552 of the device to pull the punch 532 distally after the wire 539 is released.

For a device such that described above or a DCA device, it is advantageous for the cutting portion of the device to be movable to engage the tissue. A balloon or forced wires which forces the cutting portion against tissue, is traditionally used with a DCA device, however this prevents perfusion. In the illustrated embodiment of FIGS. 54A-54C, a strap or straps 550 extend the length of the catheter 540 and aid the device 530 in engagement. The straps 550 are attached near the catheter tip 552 to the catheter 540 and on the opposing side of the cutting edge 542. A section 551 of the strap or straps 540 is free in the area near the cutting portion of the device 530. As the straps 550 are advanced relative to the catheter shaft 540, they are forced to bow out away from the cutting portion of the device 530. This forces the cutting portion of the device 530 into the tissue. The operator may rotate the device 530 to engage the desired tissue.

In a modified embodiment, the straps 550 extend axially across the portion of the catheter where the cutting takes place, and attach to an elongate member which is free to move axially relative to the elongate member that is attached to the cutting mechanism. The two elongate members are preferably located coaxially. In one embodiment both elongate members are polymer tubes.

FIGS. 55A and 55B illustrate another embodiment of the excise device. This embodiment is similar to the embodiment described above with reference to FIGS. 53A-54C in that it includes a catheter body 540, a cutting edge 542 and a tissue punch 532. In this embodiment, the tissue punch 532 is coupled to a return spring 554 and is actuated by pressurized fluid that is supplied through an inflation lumen 556 to a chamber 558 at the distal end 552 of the catheter body 540. A seal 560 is provided between the punch 532 and the catheter body 540 to seal the chamber 558. By increasing the pressure in the pressurized chamber 558, the punch 532 is moved proximally against the cutting edge 542. When the pressure is decreased, the punch 532 is moved distally by the spring 554. Barbs 560 can be provided in the catheter body 540 to retain tissue introduced through the window 544. The inflation lumen 556 can be attached to the catheter body 540 by an adhesive 564 as shown in FIG. 55B.

FIGS. 56A-C illustrate another modified embodiment of an excise device 530. In this embodiment, cutting wires 570 extend through lumens 572 provided in a catheter body 574. The cutting wires 570 can be mounted at their distal end to the distal portion of the catheter body 574. Most of the length of the cutting wires is encapsulated in the lumens 572 of the catheter body 574. A skive 576 is provided at the distal portion to expose a short portion 578 of the wires 570 just proximal to the point where the wires 570 are attached to the catheter body 574. In one embodiment, the skive 576 is between about 5 and 100 mm in length preferably between about 10 and 30 mm in length. As the proximal ends of the wires 570 are advanced relative to the catheter body 574 the distal portions 578 bow out away from the catheter body 574 through the skive 576. The wires 570 may have a cross section that provides a preferential bending plane and prevents their rotation within the lumen 572 of the catheter body 574. This may help the wires 570 deploy in a controlled orientation. The exposed portions 578 of the wire 570 can include cutting surfaces that are exposed to the tissue when the wires 570 are advanced. In another embodiment, this device 530 can be configured such that the wires 570 can be deployed, heated and then advanced or retracted through the valve annulus or it may be heated and then actuated within the valve annulus. The catheter body 574 can also include stiffening wires 580 positioned in lumens 582 as shown in FIG. 56B.

Figure 56D:
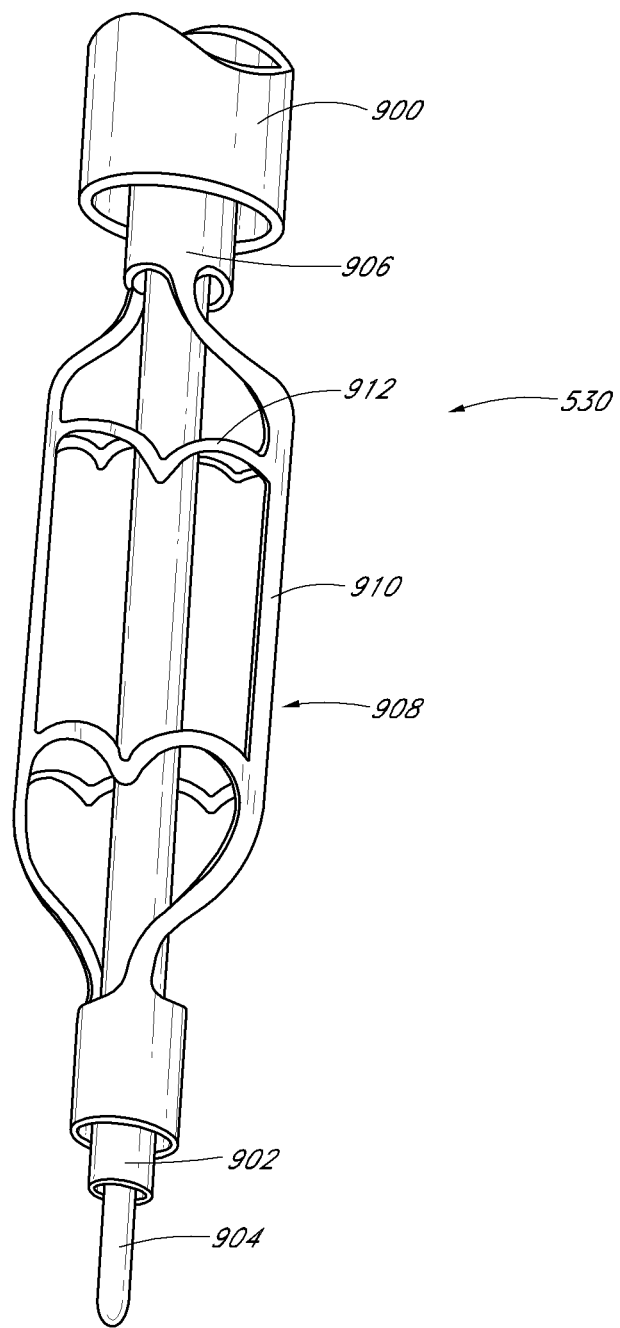
FIG. 56D is a side view of another embodiment of a debulking device.

FIG. 56D illustrates another modified embodiment of an excise device 530. In this embodiment, the device comprises an outer protective sheath 900, an inner sheath 902 that can track over a guidewire 904 and an intermediate member 906 positioned between the outer and inner sheaths 900, 902. The intermediate member 906 includes an cutting structure 908, which can expand as the outer sheath 900 is withdrawn to expose the cutting structure 908. In this embodiment, the cutting structure 906 comprises a plurality of elongated cutting members 910, which are supported by annular spring members 912. The device can be positioned within the valve and then the outer sheath 900 is withdrawn to expose the cutting members 910. The device can be rotated to provide a cutting action.

In yet another embodiment, an atherectomy catheter device (not shown) includes a housing at the distal end of a substantially round housing torque cable. A cutter torque cable is disposed within the housing and includes a rotatable and translatable cutter at its distal end. The housing includes a window into which an atheroma protrudes. The cutter severs the atheroma. A nose cone attached to the distal end of the housing collects and stores severed atheroma. A stabilizing member is attached to the exterior of the housing opposite the window. A stabilizing member can be provided and includes a balloon having an inflation lumen disposed within the housing. In a modified embodiment, a mechanical stabilizing member provided and includes a distal end attached to the distal end of the housing or to the nose cone, and a proximal end coupled to a stabilizing cable disposed within a cable lumen of the housing torque cable. The stabilizing cable can be advanced distally to bow the stabilizing member away from the housing and withdrawn proximally to flatten the stabilizing member against the housing, alternately urging the window side of the housing onto the atheroma and allowing it to retreat therefrom.

Another method for removing calcification and vegetation from the valve area is with a pharmacological agent. For example, an agent that dissolves calcium is secreted by osteoblasts. An agent similar to this could be utilized prior to the valve replacement procedure. Alternatively an agent like this could be coated on the valve leaflets or on another portion of the prosthesis so that it slowly elutes over the life of the valve. This would prevent or minimize the calcification that contributes to the deterioration of the valve. The agent could be contained in a polymer coating, in a porous metallic coating, or in the tissue itself To aid removal or debulking, the calcified tissue may be visualized by echocardiography and or fluoroscopy, ECHO, MRI, CT scan as is known in the art.

With reference back to FIG. 52B, an access sheath attached to the protection filter device 522 allows the excise device 530 or other tools to access the work area between the left ventricle 32 and the filter 530. The access catheter may be made of a flexible material which can be folded inside a delivery catheter. This allows the delivery catheter to be a low profile device while relatively large profile devices may be introduced through the access catheter. In one embodiment, a delivery catheter containing the temporary valve and embolic protection device and access catheter is advanced through the vasculature. The devices are deployed and the delivery catheter is removed completely from the patient. The access catheter then expands to an inside diameter large enough for the required devices for valve removal and replacement to pass through.

Many of the devices described above for removing or cutting the valve commissures could benefit from the use of a centering balloon to locate the catheter in the center of the native annulus while the cutting occurs. The centering balloon could be located proximal or distal to the valve, or balloons could be located both proximal and distal. The balloons could optionally contain perfusion lumens.

In a modified embodiment, the method of enlarging the annulus involves a process of shrinking tissue instead of or in addition to removing tissue. For example, it is possible to shrink collagen type tissue by the application of heat. In such an embodiment, the tissue is preferably heated to a temperature of 50 to 65 C. More preferably the tissue is heated to 55 to 60 C in one embodiment the tissue is heated to a temperature of 59 C. The heating may be accomplished from a variety of energy sources, one particularly advantageous energy source for a percutaneous application is RF energy. Accordingly, a catheter with a heated element on the tip may be used to heat specific portions of the valve.

In one embodiment, the catheter incorporates a needle near the heated portion. The portion of the catheter intended to transfer heat to the leaflet tissue is positioned below the surface of the leaflet. This minimizes the transmission of heat into the bloodstream, while maximizing the transmission of heat to the leaflet tissue.

In another embodiment the heating step is applied by a tool that also dilates the annulus. This tool may be a balloon inflated with a heated solution or a dilation device that contains heating elements, such as those described in this application using deflected straps.

In general, the application of heat is intended to affect the portions of the leaflets nearest to the center of the valve. Excessive shrinking of the outer portion of the valve annulus may cause the effective orifice area to be reduced. Shrinking an area near the tip or free edge of each leaflet will cause the effective orifice area to be increased. It may additionally release the calcium deposits within the valve tissue thus providing a large effective orifice area to implant a new valve.

Procedures for Deploying the Implant

Various procedures and methods for deploying an implant 100 in the aortic position will now be described. In one embodiment, the method generally comprises gaining access to the aorta, most often through the femoral artery. A balloon valvuloplasty may optionally be performed in the case of aortic stenosis, or another method may be used to remove or debulk the native valve as described above. A delivery sheath or catheter is advanced over the aortic arch and past the aortic valve. The outer sheath of the catheter is retracted exposing the valve and cuff. Fluid is used to inflate the valve and a second inflation fluid may be used to partially form the implant. This allows the distal portion of the implant to open to its full diameter. The proximal portion of the implant may be slightly restricted by the deployment control mechanism. In general, the amount that the deployment-control mechanism restricts the diameter of the proximal end of the device depends on the length of the wires extend past the outer sheath, which an be adjusted by the operator. Alternatively, in some embodiments, the implant contains multiple inflation ports to allow the operator to inflate specific areas of the implant different amounts. In another embodiment, burst discs or flow restricters are used to control the inflation of the proximal portion of the implant 100. The implant is then pulled back into position. The distal ring seats on the ventricular side of the aortic annulus. A balloon may be used to dilate or redilate the device if necessary. At this time, the deployment control wires may act to help separate fused commissures by the same mechanism a cutting balloon can crack fibrous or calcified lesions. Additional casting material may be added to inflate the implant fully. The inflation lumen is then disconnected, and the deployment control wire(s) are then disconnected, and the catheter is withdrawn leaving the device behind. In modified embodiments, these steps may be reversed or their order modified if desired.

The above-describe method generally describes an embodiment for the replacement of the aortic valve. However, similar methods could be used to replace the pulmonary valve or the mitral or tricuspid valves. For example, the pulmonary valve could be accessed through the venous system, either through the femoral vein or the jugular vein. The mitral valve could be accessed through the venous system as described above and then trans-septaly accessing the left atrium from the right atrium. Alternatively, the mitral valve could be accessed through the arterial system as described for the aortic valve, additionally the catheter can be used to pass through the aortic valve and then back up to the mitral valve.

For mitral valve replacement, the implant may require a shorter body length (e.g., 1-4 cm) and would mount in the native mitral valve area. It may be delivered from the right side of the heart from the femoral vein up through the inferior vena cava and into the right atrium. From there, a transeptal-puncture may be made for entry into the left atrium and access to the mitral valve. Once in the left atrium, the implant would be delivered with the valve pointing down to allow flow from the left atrium to the left ventrical. A similar shape would allow the device to be deployed in the left atrium and advanced into the left ventrical. The proximal ring may require inflation to hold the device in the left ventrical by creating a diameter difference between the mitral orifice and the proximal cuff diameter. Here as with the aortic replacement, the mitral valve may require partial removal or cutting of the valve or chorde to allow the native valve to be excluded and provide room for the replacement valve to be implanted. This may be achieved by balloon valvuloplasty, cutting techniques such as a cutting balloon or by utilizing a hot-wire or knife to cut slits in the native valve to allow for exclusion. Once the native valve has been prepared for the new valve, the mitral valve orifice may be crossed with the distal portion of the implant and the distal portion may be inflated for proper shape and structure. At this time, the native valve will have been excluded and the replacement valve will be fully operational.

Other methods of mitral replacement would include a transapical delivery where the patent would receive a small puncture in the chest cavity where the operator could access the apex of the heart similar to a ventricular assist device implantation. Once access is gained to the left ventrical, the aortic and mitral valves are a direct pathway for implantation of the replacement valve. In this case, the aortic valve would be delivered with the flow path in the same direction as the catheter. For the mitral valve, the flow path would be against the direction of implantation. Both may still utilize the base of the implant to anchor the device using diameter differences to secure the device. It may be desirable to also use a hook or barb that could protrude from the cuff either passively or actively as the cuff is filled with fluid. The barb could be singular or a plurality of barbs or hooks could be used where the length could be between 1-5 millimeters in length depending upon the tissue composition. Where a longer barb may be required if the tissue is soft or flexible. It may be desired to have shorter lengths if the tissue is a stiffer more fibrous structure where the barbs could hold better.

For the pulmonary and tricuspid valve placement, the operator could access the femoral vein or internal jugular (IJ) vein for insertion of the delivery system. As with the transeptal mitral valve approach the delivery system and device would be introduced either superiorly or inferiorly to the vena cava and to the right atrium and right ventrical where the pulmonary and tricuspid valves are accessible. The femoral approach is preferable due to the acute bends the delivery system would be required to make from a superior or IJ access. Once in the right ventrical the device could be delivered similarly to the aortic method where the cuff utilizes the base of the pulmonary valve for a positive anchor with a diameter difference holding it from migrating distally. It may be desirable to also use a hook or barb that could protrude from the cuff either passively or actively as the cuff is filled with fluid. The barb could be singular or a plurality of barbs or hooks could be used where the length could be between 1-5 millimeters in length depending upon the tissue composition. Where a longer barb may be required if the tissue is soft or flexible. It may be desired to have shorter lengths if the tissue is a stiffer more fibrous structure where the barbs could hold better.

In any placement, the proper valve configuration would be chosen by the performance of each required application. For instance the aortic valve may require a two or three-leaflet valve that will require a high degree of resistance to stress and fatigue due to the high velocities and movement. The pulmonary valve may require a lesser valve due to the more passive nature or the lower pressure that the valve is required to support. Lengths may vary and will be dependant upon the valve and structure surrounding them. A shorter valve (1-4 centimeters) may be required for the mitral but the aortic may allow for a longer valve (1-8 centimeter) where there is more room to work. In any application, the maximum orifice size is generally desired since the cross sectional area helps determine the outflow volume. The aortic cross sectional area may vary from nearly 0.00 square centimeters in a heavily calcified valve to about 5 square centimeters in a healthy valve. Most cases the desire in replacement is to increase a cross sectional area for additional flow.

During the procedure or during patient selection, or follow-up, various imaging techniques can be used. These include fluoroscopy, chest x-ray, CT scan and MRI. In addition, during the procedure or during patient selection, or follow-up, various flows and pressures may be monitored, for example echocardiography may be used to monitor the flow of blood through the relevant chambers and conduits of the heart. Pulmonary wedge pressure, left atrial pressure and left ventricular pressures may all be recorded and monitored. It may be desirable to use a measurement tool to determine the size of valve required or to determine if the anatomy provides enough room to allow implantation of a valve. In the past, marker-wires have been used to measure linear distance and a similar technique could be used in this application to measure a distance such as the distance from a coronary artery to the annulus of the aortic valve. To measure the diameter of a valve, a balloon with a controlled compliance could be used. Ideally, the balloon would be very compliant and inflated with volume control, but a semi compliant balloon could also be used and inflated with a normal interventional cardiology inflation device. The compliance curve of the balloon could then be used to relate the pressure to the diameter. The diameter range of valves in the heart may range from 10-50 mm in diameter and 2-40 mm in length. A similar sizing balloon has been used for sizing septal defects.

In one embodiment, implantation of a prosthetic valve includes the step of dilating the valve after it is positioned and functioning within the native anatomy. If the dilation step is used to replace a balloon valvuloplasty prior to the inflation of the balloon the cuff will minimize the embolization from the dilation. The dilation of the functional implant step may also be used in patients where a valvuloplasty is performed prior to implantation of the device, but where the outflow area is not as large as desired. Certain embodiments of the implantable prosthetic valve include deployment control wires or stiffening wires. If these features are present in the implant at the time of post dilation, then the features may act to concentrate the force from the deployment of the balloon in a mechanism similar to the function of a cutting balloon commonly known in interventional cardiology.

To gain access to the aortic valve the femoral arteries (radial, brachial, carotid) can be used to introduce tools into the vascular system. Once in the arterial conduits, catheters may be advanced to the aortic arch and the native aortic valve. As discussed above, it may be necessary to install a temporary valve to allow gating of the blood flow while the work is being completed on the native valve. This will provide time for the interventional cardiologist to prepare for removal and installation of a new aortic valve. The placement of the temporary valve could be between the native valve and the coronary arteries, or the valve could be placed in a location between the coronary arteries and the location where the great vessels branch off from the aorta or at any other location within the patients aorta. Placing a valve in these non native locations to treat aortic insufficiency has been proven effective in clinical experience by the use of the Huffnagel valve. Placing a temporary valve in these locations has been described by Moulolupos and Boretos. A guidewire or pig-tail catheter may be used to pass a stiffer catheter through the stenotic hole in the aortic valve. It may be necessary to install a filtration device to protect any vessels including the coronary tree from debris as the valve is loosened and removed. This filter may be placed in the region of the aortic valve just before the coronary ostia or distal to the sinus and just before the great vessels. Once through the valve opening a balloon may be passed into the aortic valve to predilate the region and loosen any calcium. This may aid in the removal of the tissue that may be calcified and or fibrosed. The use of a catheter to deliver energy such as ultrasonic, RF, heat or laser may additionally break or loosen the tissue including the calcification in and on the leaflets. There are chemical treatments that have shown some promise in dissolving the calcium such as Corazon Inc. of California (see U.S. Pat. No. 6,755,811).

The ultrasonic energy device is described in detail through U.S. Pat. No. 4,827,911 and has a proven track record known as CUSA to remove calcium in a surgical suite from valve tissue. This has shown promise acutely but will denature the collagen tissue and result in a degeneration of the valve tissue remaining in about a year leaving a poorly functioning valve. After a filter has been installed and the valve tissue has been softened, a template may be used to define the area to be removed. This template will define the hole and prevent the removal of healthy tissue. At this time the valve is ready to be removed with adequate time since the temporary valve will be functioning when the native valve is removed. This will be important to not allow the patient to go from aortic stenosis to aortic insufficiency. The removal tool may now be passed through the stenotic valve and begin the removal process of the native valve. As mentioned above and in patents and US applications such as 20040116951 Rosengart there are many ways to remove tissue from this region.

The embodiments described above provide a technique that lends itself well to delivering a catheter based valve removal tool. Through a pushing and pulling force the pin and die set as seen in the drawings will allow the valve to be removed in a controlled manner while leaving the material in a catheter shaft for removal. It is asserted that this is the first that allows the aortic outflow track to be gated or valve temporarily. Though an aortic balloon pump may function as a temporary or supplementary valve in some conditions, the balloon pump is ineffective and dangerous in patients with aortic insufficiency. A removed or partially removed aortic valve constitutes severe aortic stenosis.

Figure 57A:
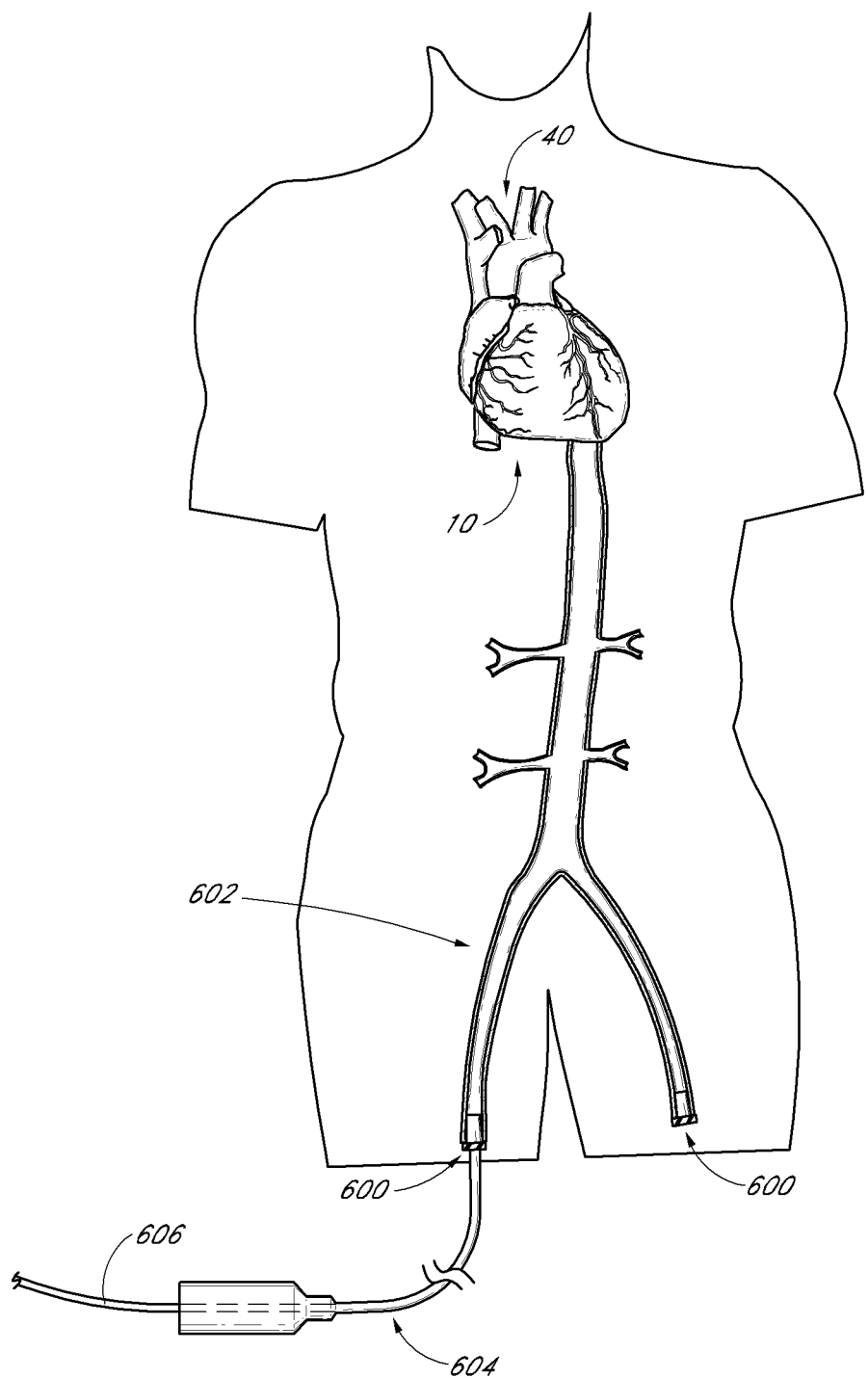
FIGS. 57A-O are time sequenced steps of an embodiment of a method for deploying a temporary valve, an excise device and a prosthetic valve implant.
Figure 57B:
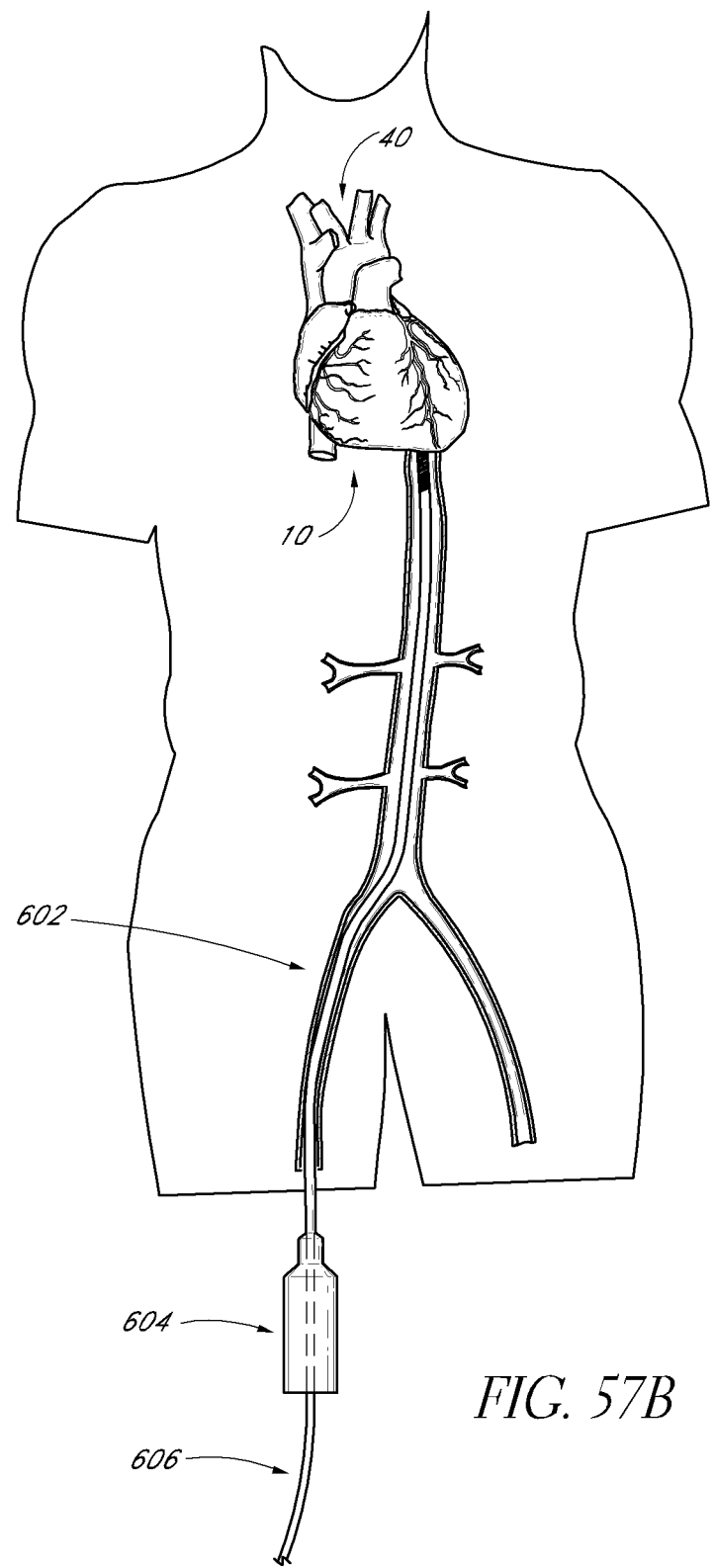
Figure 57C:
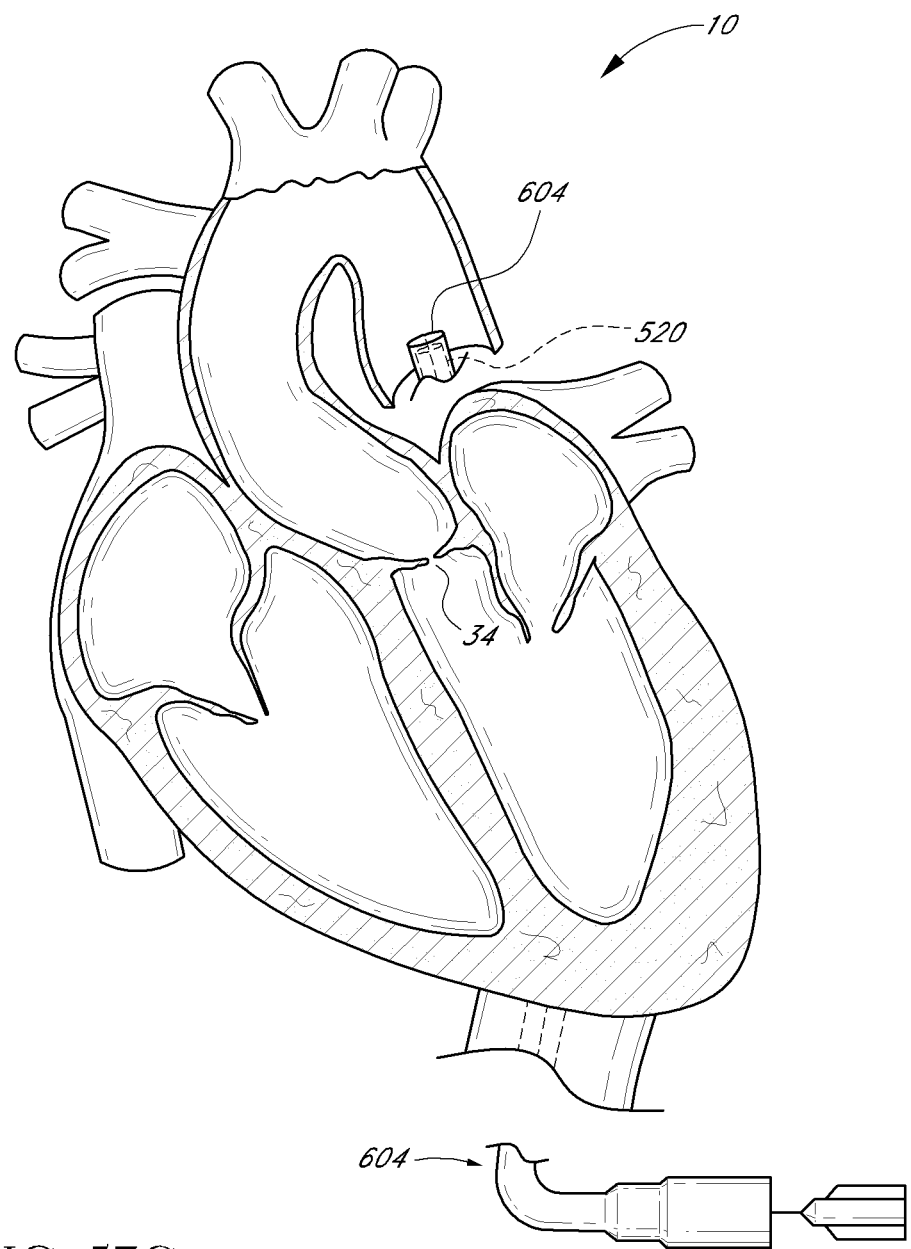
Figure 57D:
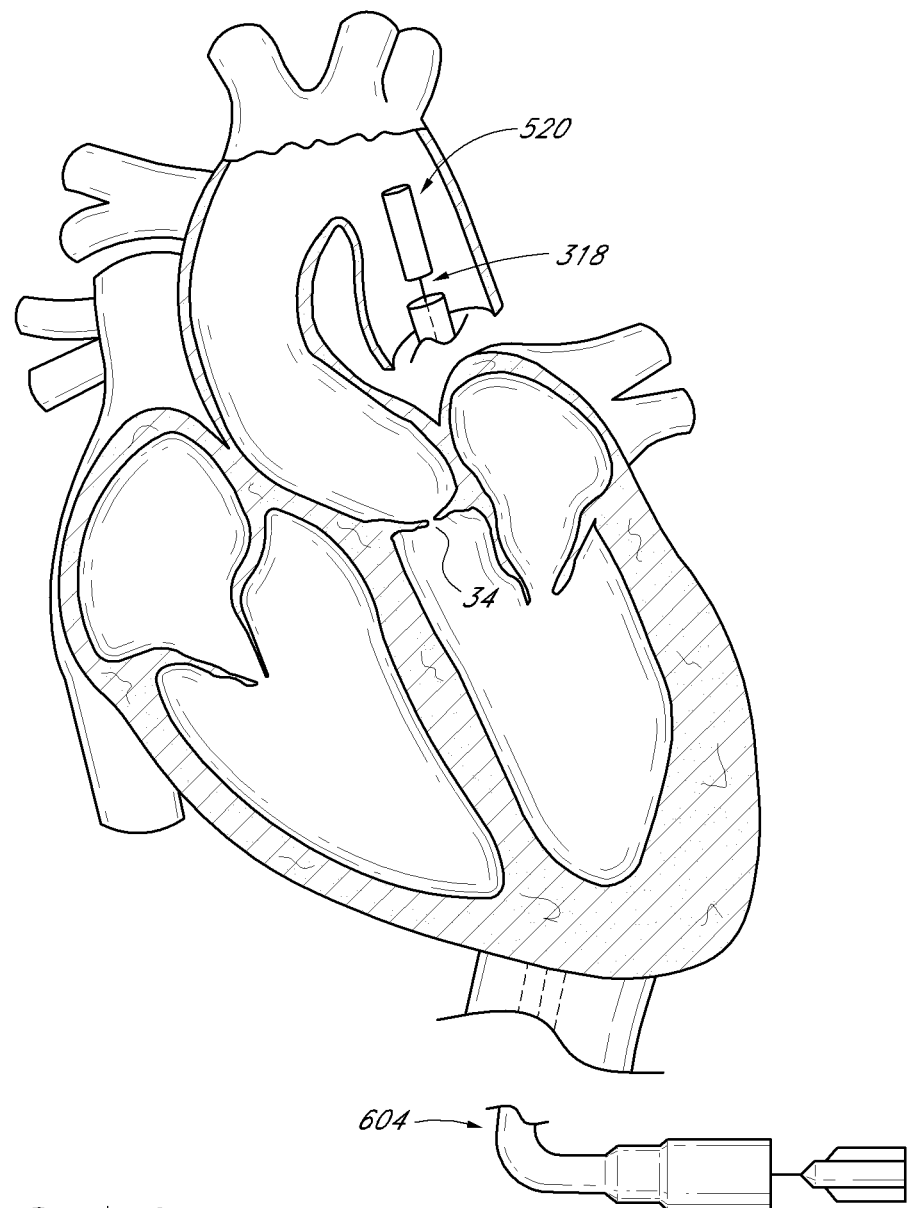
Figure 57E:
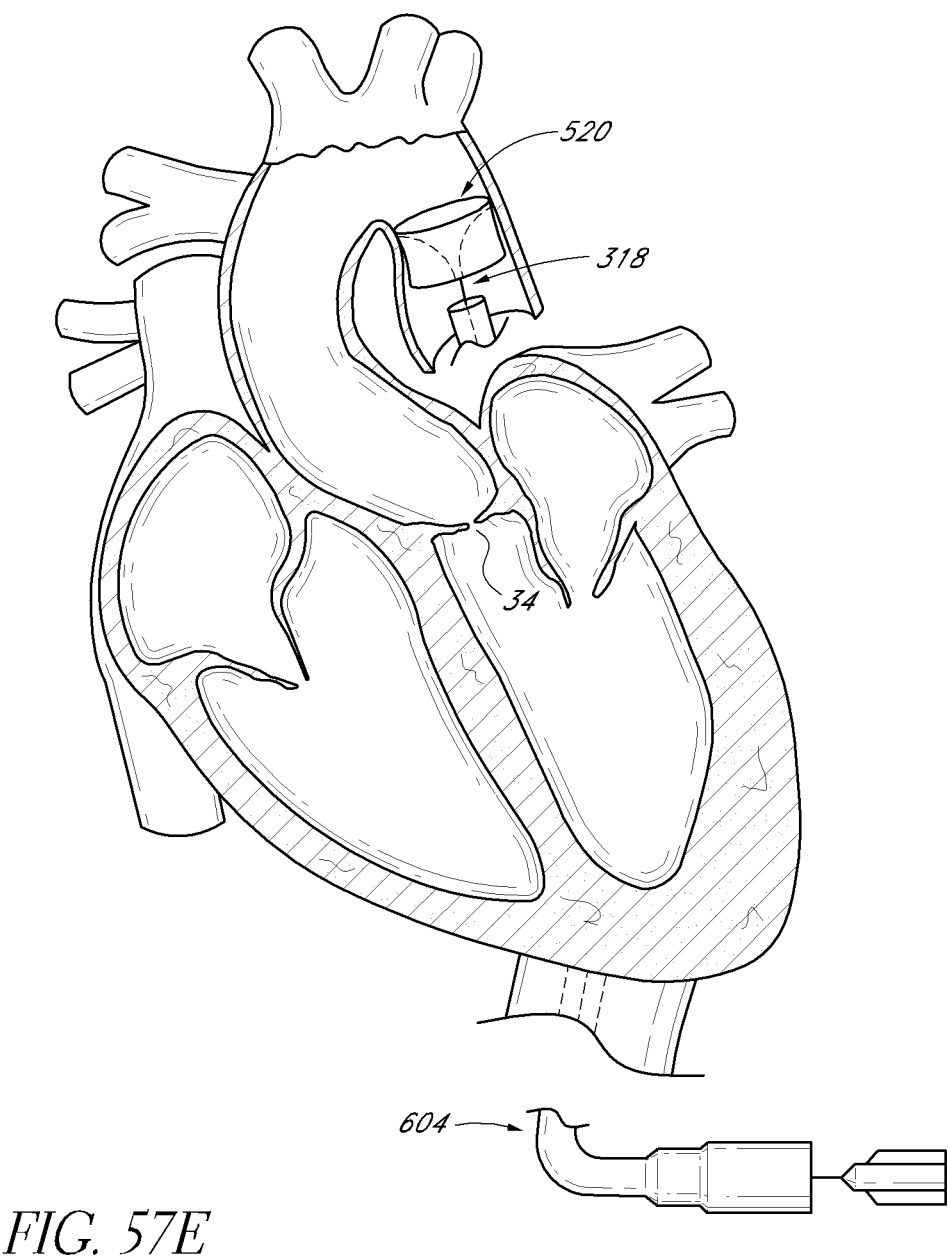
Figure 57F:
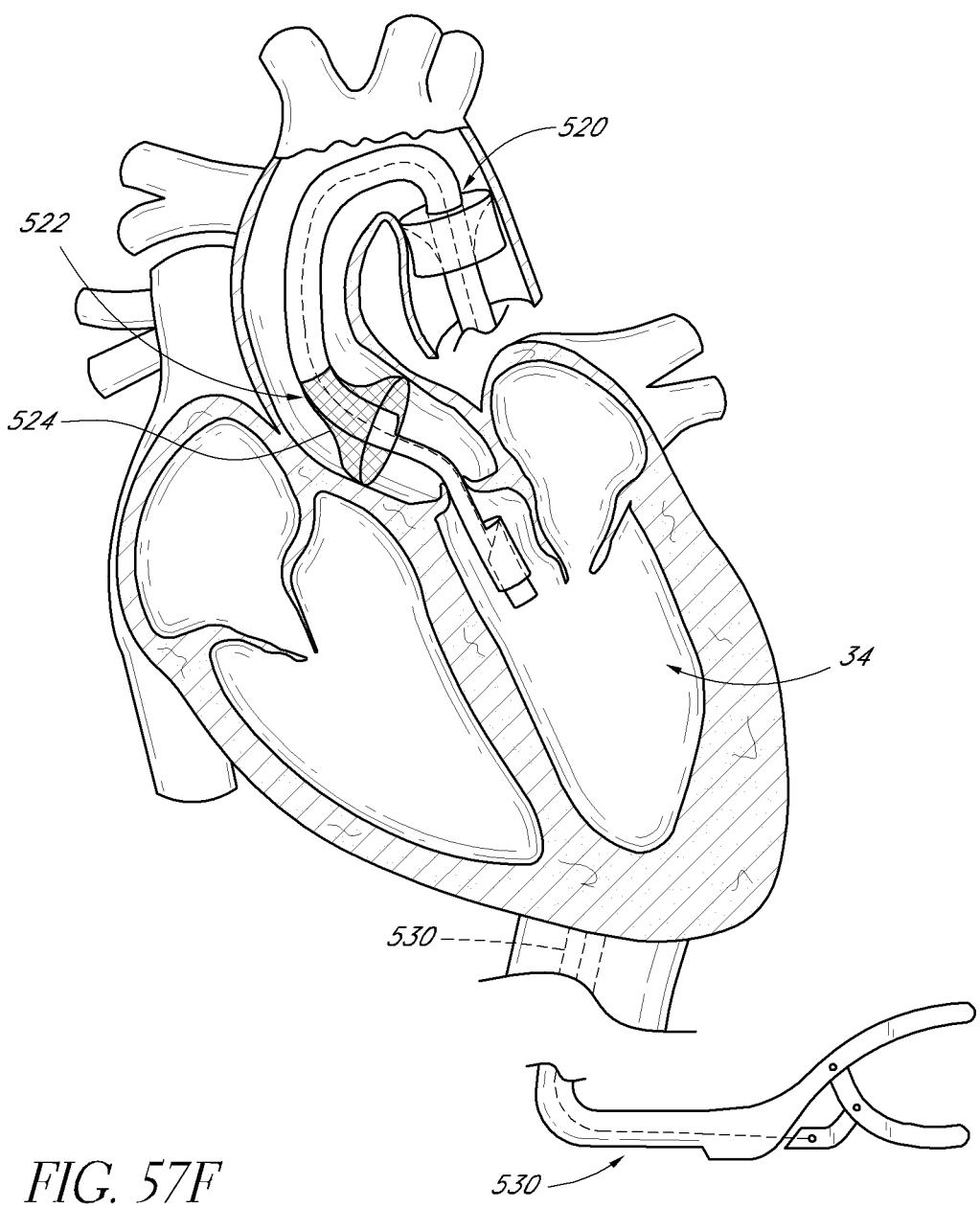
Figure 57G:
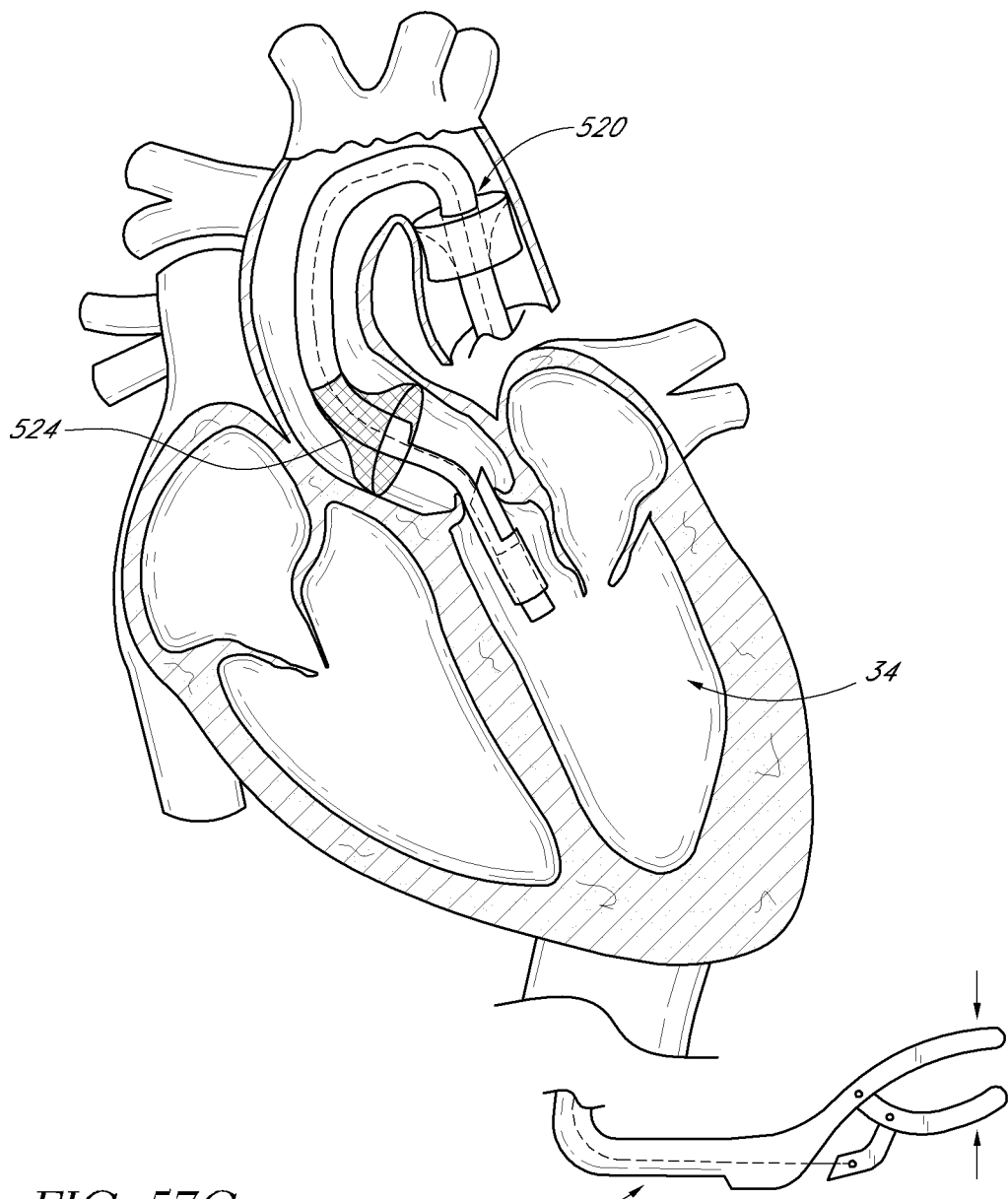
Figure 57H:
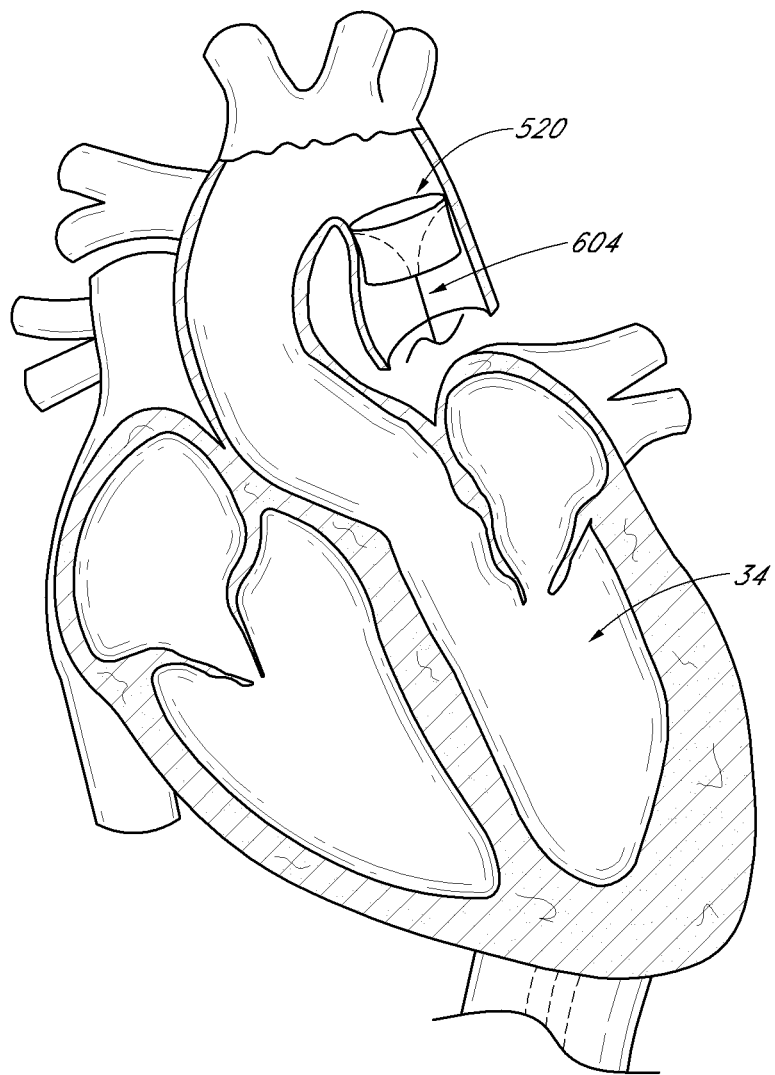
Figure 57I:
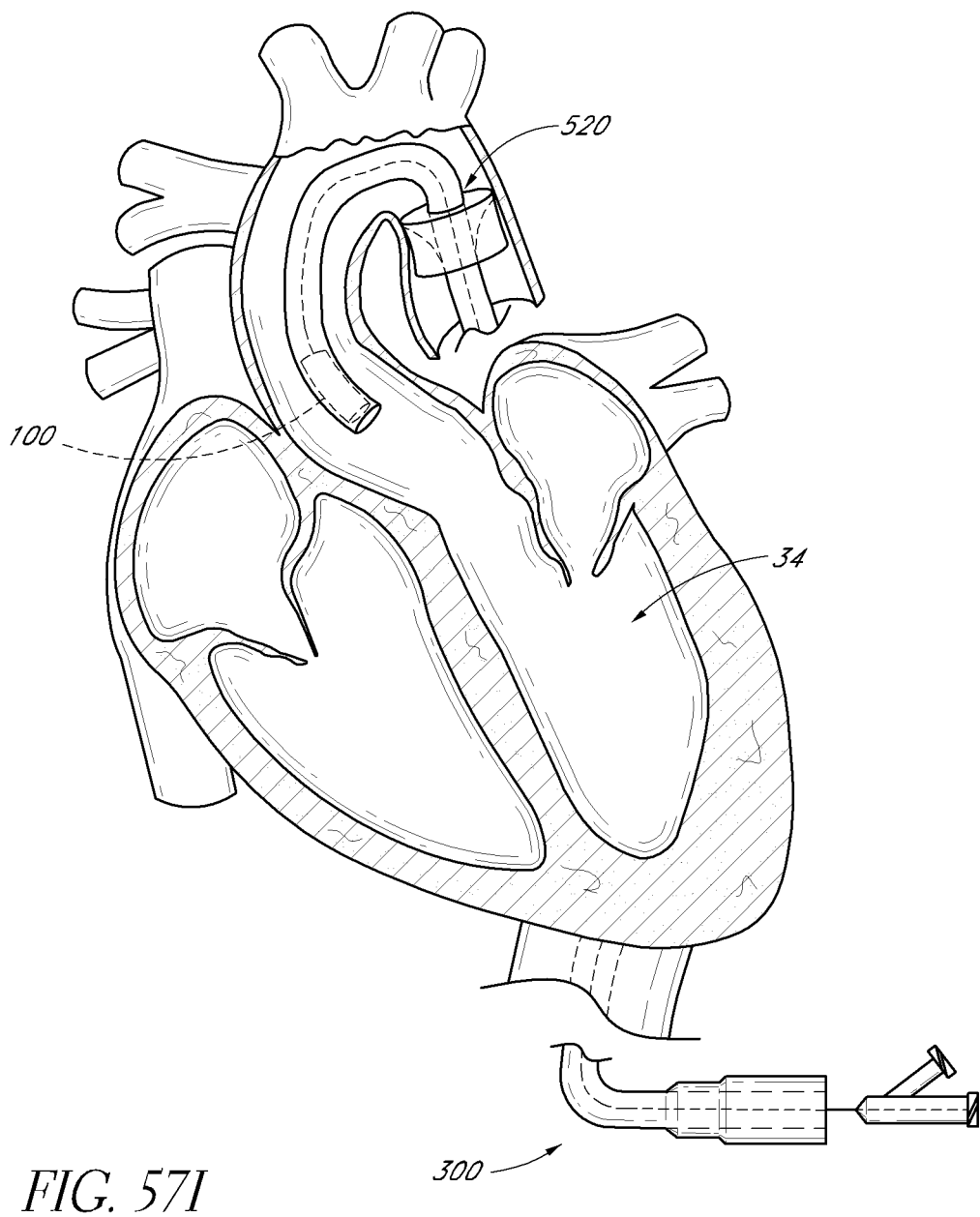
Figure 57J:
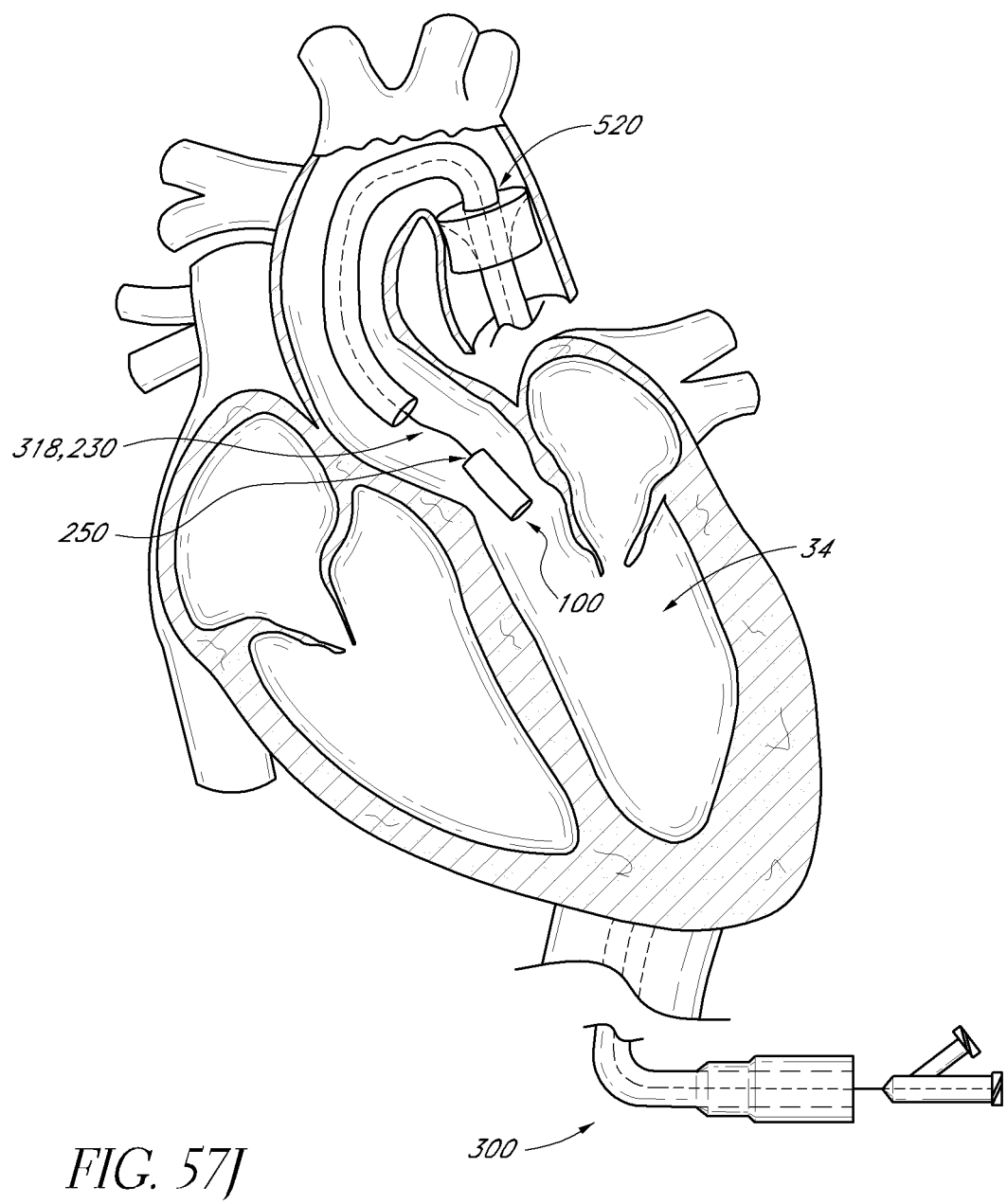
Figure 57K:
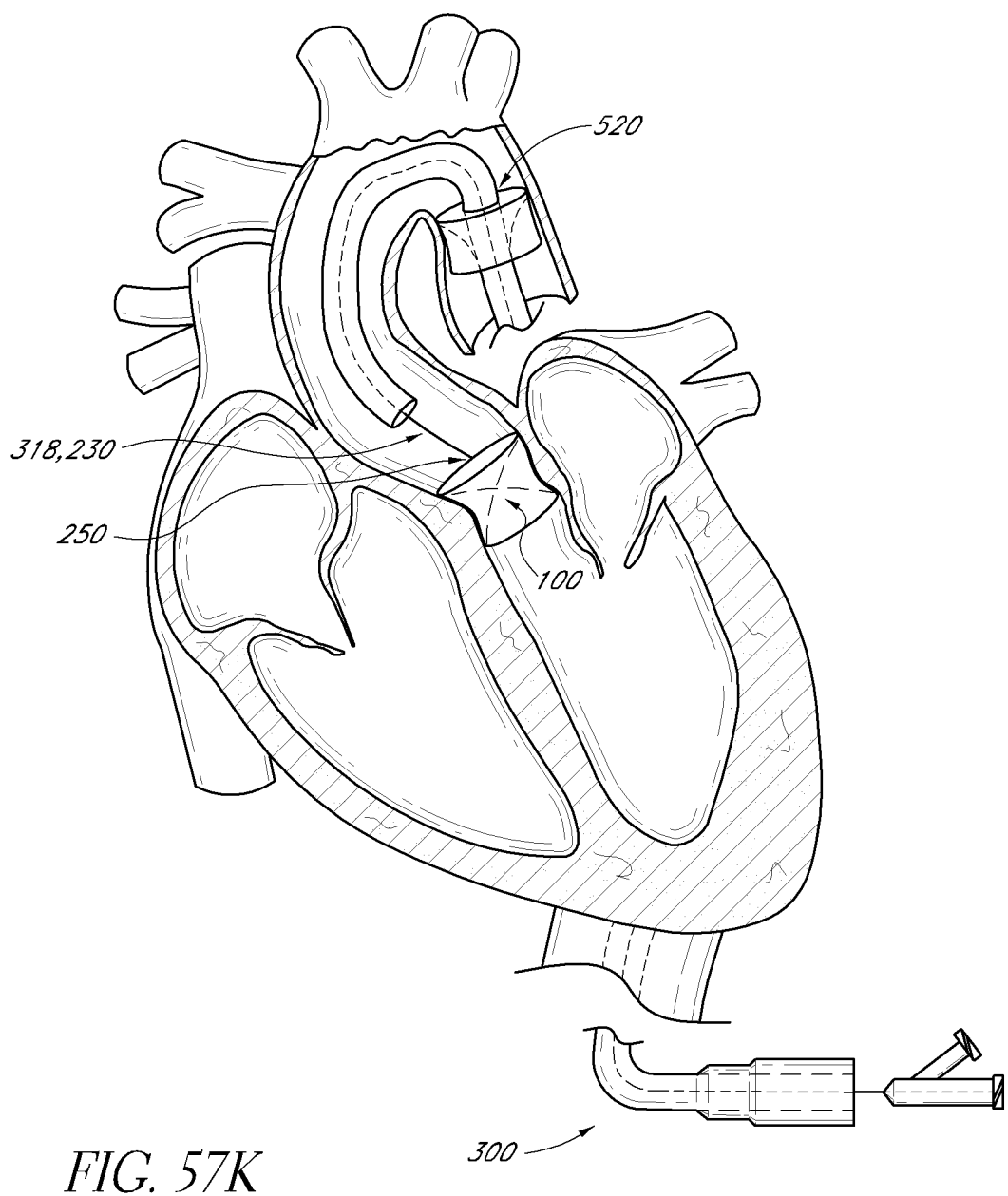
Figure 57L:
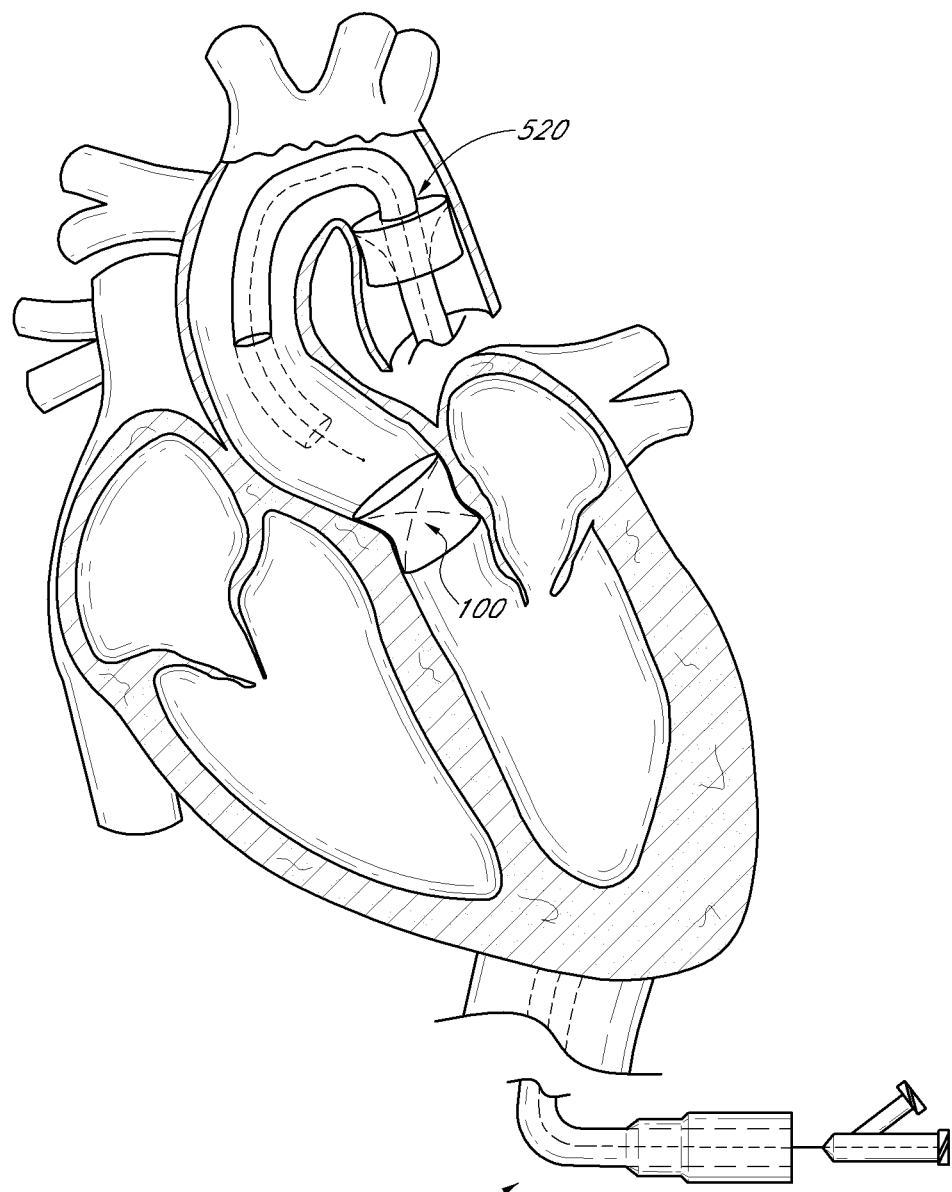
Figure 57M:
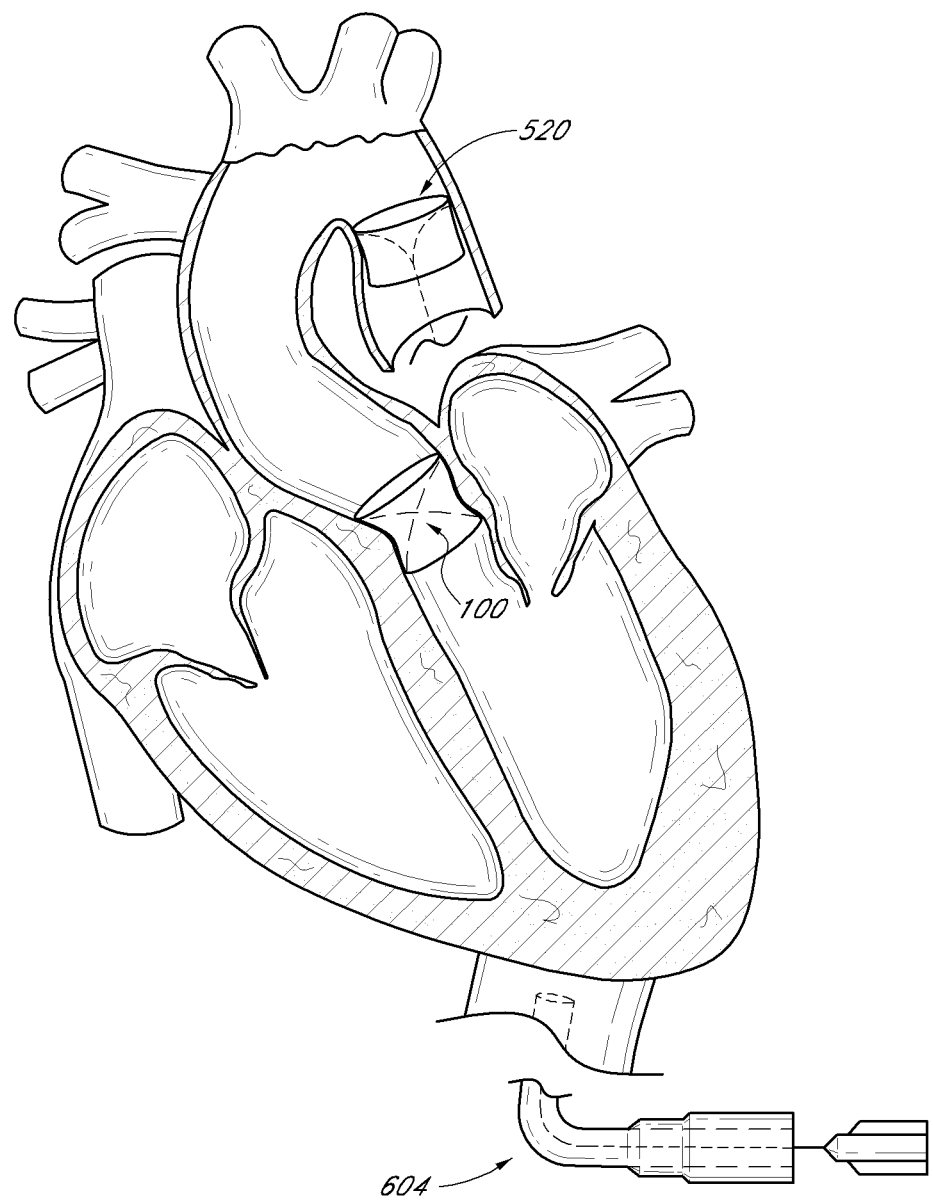
Figure 57N:
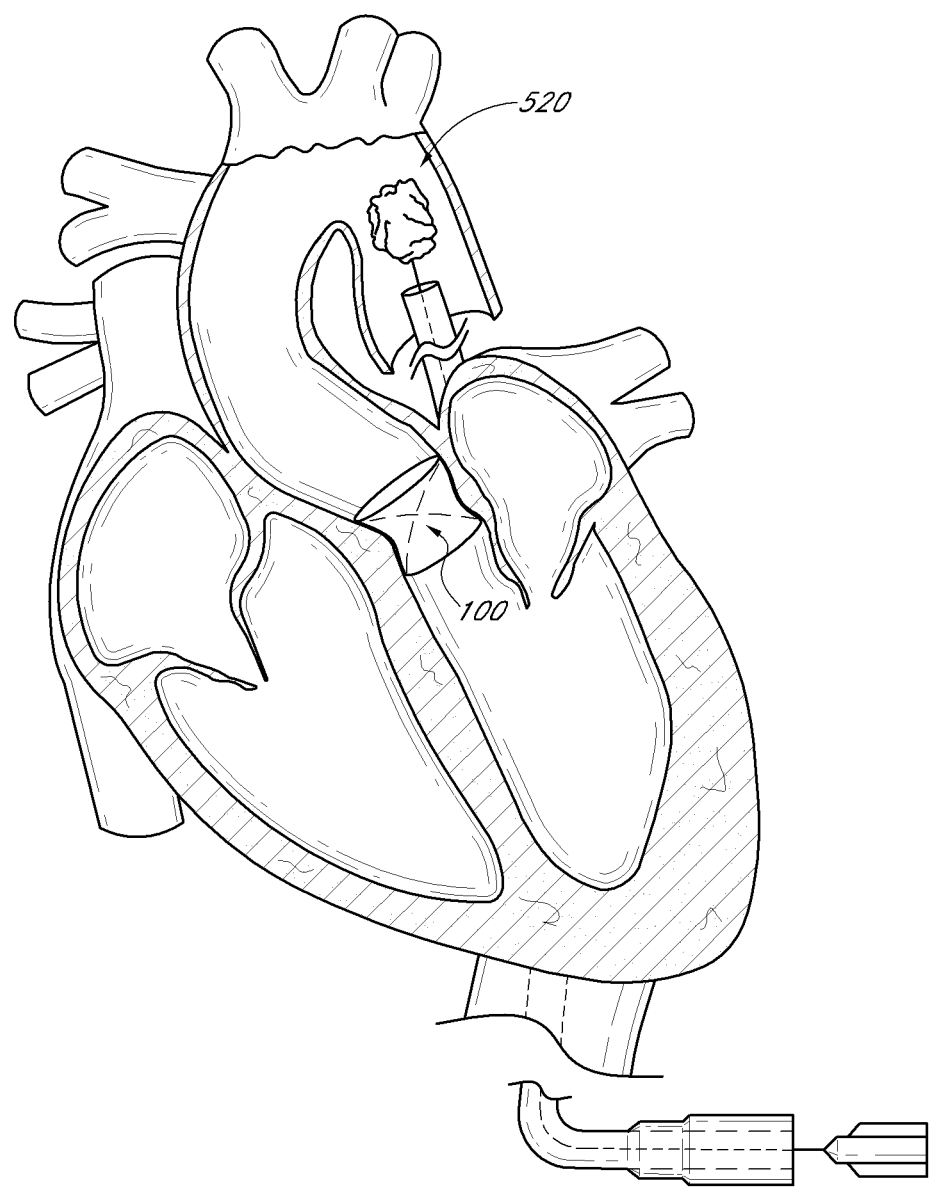
Figure 57O:
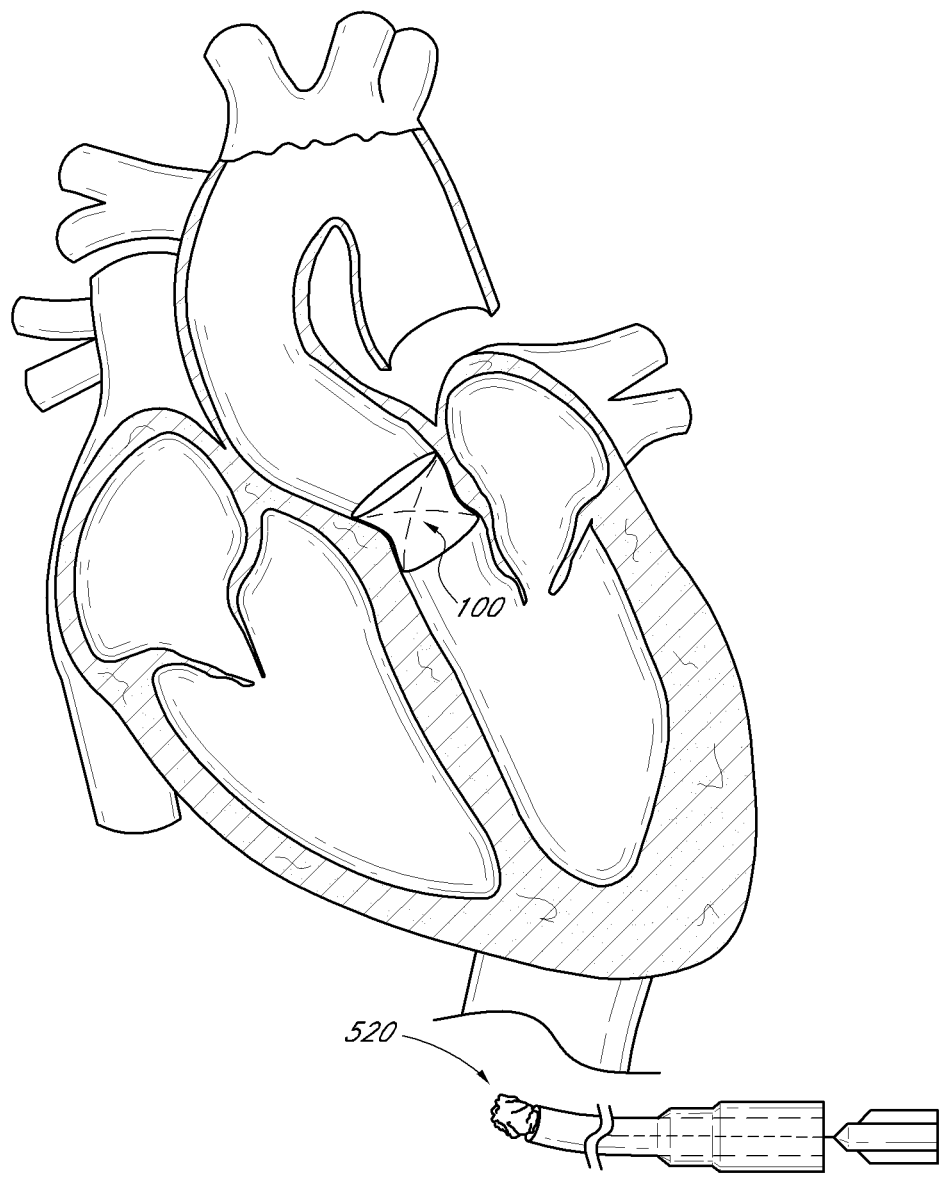

FIGS. 57A-57O will now be used to describe a embodiment of procedure for installing an prosthetic aortic valve 100, which utilizes some of the procedures described above. In particular, the illustrate embodiment includes the steps of placing a temporary valve, optionally placing an embolic protection device, removing or debulking or destroying all or part of the stenotic valve, implanting a permanent prosthetic valve, and then removing the temporary valve and embolic protection device. Of course those of skill in the art will recognize that not all of these steps are required and/or that the order of certain steps can be changes. In addition, those of skill in the art will recognize various modified embodiments of the steps described herein.

As shown in FIG. 57A, access to the aorta can be provided by an access sheath 600 through the femoral artery 602. A deployment catheter 604 is advanced over guidewires 606 through the access sheath and through the femoral artery toward the aortic arch 10 (FIG. 57B) The deployment catheter 620 is used to implant a temporary valve 520, as described above with reference to FIG. 52A. The temporary valve 520 is implanted preferably as a first step, although an embolic protection filter may also be implanted as a first step. For the treatment of a stenosed aortic valve 34, the temporary valve 520 is placed in the aorta 36. The valve 520 may be placed in the ascending or descending aorta. A valve 520 in this position has been proven moderately effective by experience with the Hufnagel valve, and was described in similar designs disclosed by Moulolupos U.S. Pat. No. 3,671,979 and Boretos U.S. Pat. No. 4,056,854. Although a valve placed beyond the coronary arteries does not provide ideal performance as a long term implant, the function of the valve in this location has been proven sufficient for short-term use. In a healthy patient, the coronary arteries fill during diastole, however in a patient with severe aortic insufficiency the pressure required to fill the coronaries in diastole is not present. These patients are able to perfuse the coronary arteries sufficiently for survival.

Alternatively, the temporary valve 520 may be placed so that it acts between the native aortic valve and the coronary arteries although its physical position would likely extend well above the coronary arteries. In this embodiment the inlet side of the temporary valve would seal to the aortic wall just below the coronary arteries. The outlet side of the valve would extend up beyond the coronary arteries. The mid portion of the valve and the outlet side of the valve would have an outside diameter smaller than the inside diameter of the patients aorta. This would allow blood flow from the outlet of the valve, around the outside of the valve back towards the ostia of the coronary arteries. In this embodiment the valve would have a sealing portion on the inlet side of the valve, the sealing portion would have an outside diameter to match the patients aortic root diameter. This diameter would range from about 18 mm to about 38 mm. Multiple sized valves are required to accommodate differing patient anatomies. The sealing portion of the valve may be expandable or compliant to improve sealing and best conform to a wide range of patient anatomies. The length of the sealing portion is limited by the position of the valve and the position of the coronary arteries, the length of the sealing portion may range from about 1 mm to about 5 mm, preferably about 3 mm. The mid and outlet portions of the valve are preferably between 30% and 90% the diameter of the native aorta. This allows sufficient room for blood to flow back around the valve and perfuse the coronary arteries. The valve may also incorporate a secondary retaining mechanism, securing the outlet or mid portion of the valve beyond the coronary arteries Alternatively, the valve can be replaced by a pump similar to a device designed by Medtronic known as a Hemo Pump, which is placed in the aorta. The pump moves blood out from the ventricle into the aorta, serving the function of both the native aortic valve and the contracting left ventricle. The pump may consist of a screw type pump actuated by a rotating shaft, where the motor is located outside the body. The inlet of the pump located on the distal end of the catheter may optionally be isolated from the outlet of the pump by a balloon. The balloon inflates between the outside diameter of the pump and the inner diameter of the aorta, in a location between the pump inlet and the pump outlet. Alternatively a pump using two occlusion balloons, both between the inlet and the outlet of the pump could isolate an area between the balloons for treatment. The valve removal procedure could take place in this area.

The temporary valve designs described by Moulolupos and Boretos in U.S. Pat. Nos. 3,671,979 and 4,056,854 respectively, include umbrella valve designs that allow the blood to flow in one direction between the valve and the wall of the aorta. The valves prevent flow in an opposite direction as the valve seals against the wall of the aorta. These valves can be attached to a temporary valve catheter and adapted for use with the present invention.

Other valve designs are also possible for a temporary valve including a ball and cage valve, a tilting leaflet valve, bi-leaflet valve a reed type valve, a windsock style valve, a duckbill valve, or a tricuspid valve. In addition to these valves made from synthetic materials including polyurethane or tissue valve may also be utilized. Commonly used in permanent valve replacements valves constructed from bovine pericardium or porcine aortic valves, are adequate. To produce a low profile percutaneous device the preferred embodiment is a thin flexible polymer valve of either a duckbill design or umbrella valve design.

The temporary valve should be placed in such a way that it can be easily removed at the end of the procedure and also in such a way that the operator has access across the valve for performing the remaining steps. A guidewire or catheter lumen placed through the valve or around the valve before the valve is positioned in the body allows the required access for downstream procedures.

Alternatively an inflatable structure may be used. The inflatable structure provides the advantage of improved sealing characteristics with the vessel wall, and the inflatable structure may produce a lower profile device with some valve designs. The inflatable valve structure could be designed to be recoverable using wires as described in previous direct flow disclosures for permanent valve replacement devices, an inflatable prosthetic valve was first described by Block in U.S. Pat. No. 5,554,185 and is also described herein. The inflatable structure preferably inflates to an outside diameter between about 18 mm and about 35 mm.

In another embodiment, the temporary valve structure is a recoverable self-expanding stent. The stent could be a Z-stent formed from wires segments shaped into rings or a coil. Alternatively the Z-stent could be cut from a tube using a process like laser cutting. With a Z-type stent careful design of the stent shape is required to make the stent recoverable. It must be ensured that no crown hangs up on the recovery sheath. One method to accomplish this is to attach each crown to the crown of the next stent segment by welding, fusing or other joining techniques. Or the stent could be braided from wires in a design similar to a Wall Stent as produced by Boston Scientific. The material for the stent is preferably a superelastic material such as nitinol. Alternatively a material with a relatively high yield strength and/or a relatively low modulus of elasticity, such as a cobalt chrome alloy, or titanium, could be used. These non superelastic materials are most appropriate for use in a stent manufactured by a braiding process.

In another embodiment, the structure for the temporary valve 520 consists of an unwrapable structure, similar to the structure described by Yang in U.S. Pat. No. 6,733,525 or as described herein. The structure is delivered in its wrapped position. After the structure is positioned the structure is unwrapped and expanded to its final diameter.

In general, any of a wide variety of valve structures may be utilized for the temporary valve in accordance with the present invention. Since the temporary valve is only intended to remain functional at an intraluminal site for a relatively short period of time (e.g. less than a few hours), the temporary valve of the present invention is not plagued by many of the deficiencies of prior permanent implantable valves (thrombogenicity, efficiency, durability, etc.). Thus, valve design can be selected to minimize the initial crossing profile and optimize removal.

For example, in the example described previously in which a valve is supported by a Z-stent structure, each of the proximal apexes of the stent may be attached to a pull wire, which merge into a common axially moveable control wire which runs the length of the temporary valve deployment catheter. Following transluminal navigation to the desired temporary valve site, an outer sheath may be proximally retracted relative to the control wire, thereby enabling the stent and valve to be deployed from the distal end of the catheter. Following completion of the procedure, the temporary valve may be removed by applying proximal traction to the control wire and/or distal force on the outer sheath. The plurality of control filaments will cause the Z-stent to collapse, as it is drawn back into the tubular sheath.

Thus, the temporary valve of the present invention is preferably permanently attached to its deployment catheter. In this regard, the term "deployment" refers to the conversion of the temporary valve from a reduced cross sectional profile such as for transluminal navigation, to an enlarged cross sectional profile for functioning as a valve in a vascular environment. However, at no time does the valve become detached from the deployment catheter. This eliminates the complexity of snaring or otherwise recapturing the temporary valve, for retraction into a catheter. Alternatively, the present invention may be practiced by the use of a detachable temporary valve, which must be captured prior to removal.

The preferred temporary valve is therefore preferably carried by an elongate flexible catheter body, having a proximal control for advancing the valve into a functional configuration, and retracting the valve into a collapsed configuration for transluminal navigation into or away from the temporary valve site. Activation of the control to retract the valve back into the temporary valve catheter does not necessarily need to preserve the functionality of the valve. Thus, proximal retraction of the valve into the temporary valve catheter may involve a disassembly, stretching, unwinding, or other destruction of the valve if that is desirable to facilitate the step of removing the temporary valve.

Although tissue valves may be used for the temporary valve in accordance with the present invention, due to the short duration of the intended working life of the valve, any of a variety of polymeric valves may be adapted for use in the present context. Polymeric membranes may be configured to mimic the leaflets on a normal heart valve, or may be configured in any of a wide variety of alternative forms, as long as they are moveable between a first, open configuration and a second, closed configuration for permitting blood flow and essentially only a single direction. Thus, polymeric membranes may be formed into any of a wide variety of flapper valves, duck bill valves, or other configurations.

Regardless of the valve leaflet construction, the temporary valve may be supported by an inflatable cuff as has been disclosed elsewhere herein. The temporary valve deployment catheter is provided with an inflation lumen extending between a proximal source of inflation media and a distal point of attachment to the inflatable cuff. Once positioned at the desired site, the temporary valve may be released such as by proximal retraction of an outer delivery sheath. Inflation media may thereafter be expressed from the source to inflate the cuff to enable the valve and provide a seal with the vessel wall. Following the procedure, the inflation media is aspirated out of the cuff by way of the inflation lumen 318 to deflate the cuff, and the temporary valve is withdrawn from the patient.

Alternatively, the temporary valve may take the form of an inflatable balloon, with an inflation cycle which is synchronized to the heart beat so that it is deflated to permit forward flow but inflated to inhibit reverse flow in the artery.

An embolic protection filter may be mounted to the temporary valve or to the temporary valve structure. The filter may be attached to the outlet section of a duckbill type valve. Alternatively the filter may be mounted on its own support structure.

With the temporary valve deployed as shown in FIGS. 57D and 57E, a filter or embolic protection device 522 may be used during the procedure of implanting a percutaneous valve. Several methods of embolic protection are possible as described above. In the illustrated embodiment of FIG. 57F, a filtering basket 524 is placed down stream of the temporary valve 520 as shown, the basket 524 catches any debris that is embolized or cut from the native valve (see FIG. 57G) and the basket 524 is then recovered.

A trapping size of about 35 to 250 micron and may be treated with an anti-thrombogenic coating to prevent clotting. A basket of similar design could be mounted to the catheter shaft of a device designed for percutaneous treatment of a coronary valve, in a case where the valve is approached from a retrograde direction. In an application where the device is placed in an antegrade direction, a larger version of a conventional wire based embolic protection device could be used.

In an application for aortic valve treatment it may be desirable to place the embolic protection very close to the annulus of the valve because the ostia of the coronary arteries are very close to the area being treated. In a balloon, valvuloplasty used as a pretreatment for valve replacement or alone as an independent therapy, the embolic protection filter may be attached to the proximal end of the balloon or to the catheter shaft very near the proximal end of the balloon, specifically within 1 cm of the proximal end of the balloon. The filter could be positioned similarly on a catheter for the delivery of a percutaneous prosthetic valve, this configuration is especially beneficial for a balloon expandable prosthetic valve.

An alternative method of embolic protection applicable to a balloon valvuloplasty or implantation of a percutaneous prosthetic valve by means that prevent flow through the aortic valve is described as follows. Flow is occluded in a position at the treatment site or, preferably beyond the treatment site, in either a retrograde or antegrade direction. The treatment is performed. The treatment site is disengaged from the device. The treatment area is aspirated. Because the flow is prevented by the occlusion the embolic material does not travel. The occlusion is then removed. The preferred embodiment for an aortic application is a valvuloplasty balloon with dual balloons. A larger distal balloon is inflated within the ventricle. The balloon is pulled back so that the aortic outflow is obstructed, the balloon is sized so that it is significantly larger than the aortic valve. The second smaller diameter balloon located immediately proximal to the first balloon is then inflated to dilate the valve annulus. The second balloon is then deflated and the entire area aspirated with an aspiration catheter. The first balloon is then deflated to restore aortic outflow. Alternatively, there may be a tube central to these balloons providing flow while this operation in occurring. This would be a limited by-pass of oxygenated blood around the area being decalcified. During this by-pass, a cutting mechanism may be introduced where as the valve and calcium may be mechanically removed. Examples of cutting mechanisms would include a rotating burr, an oscillating pin and die to punch the material out in segments or ultrasound energy to fragment the material free for aspiration removal. It may be necessary to additionally canulate the coronary arteries to continue flow to these critical vessels.

The system could further contain a perfusion lumen to reintroduce the left ventricular outflow in a location that does not cause the movement of blood in the area of the aortic root. For example blood could be reintroduced in the coronary arteries or in the aortic arch or in the carotid arteries.

It may also be possible to have the filter device 522 mounted to the delivery catheter and actuated by the handle to open and close the filter to the vessel wall. This device would be placed between the aortic valve and the great vessels in the arch. A secondary catheter system could also be used to filter debris from the aorta and delivered from another vessel to the arch. This filter could also be attached to the temporary valve assembly providing filtration protection with valve support as the native valve is removed or decalcified. A filter could also be mounted to the excision tool protecting the down stream vessels from emboli. By protecting each individual vessel such as the carotids, great vessels, and the aorta separately, devices would be required in each of these vessels to protect them from emboli. These filters could be a simple windsox style as seen by EPI (Boston Scientific) and could recover the emboli through a catheter. Other systems for filtration include the Percusurge device sold by Medtronic where balloons protect the area of interest and aspiration withdrawals the emboli.

Filtration devices may be set directly on the calcified aortic valve to prevent any material from escaping. This filtration device may be made from a woven or braided wire such as Nitinol or stainless steel, MP35N, polymeric fibers or other suitable material commonly used in medical devices. The materials may be composed of round, oval or flat ribbon material. This may provide benefits when designing low profile device. These wire would be have cross sectional diameters ranging from 0.001-0.030 inches. These wires may be supported by larger extension wires to hold the filter material open as seen in. The filter may require a support structure such as a stent or series of struts to provide dimensional integrity. This stent structure could be a common Z-stent or an inflatable structure to hold the filter open and sealed to the valve base or vessel wall. The support structure would be expanded or deployed by exposing the device from a sheath or by actively providing a force to move the structure from a beginning shape to a final shape. Housed in a catheter for delivery, the device would be constrained to a small cross section and expand to a larger cross sectional diameter or area as allowed. The deployed device would have a general conical shape with the open large diameter facing down or toward the valve. The opposite end would come together at the catheter and be retrievable by the introduction catheter or a second retrieval catheter to remove any debris captured. These catheters may have a diameter of about 8-24 French. The filtration material could be located inside or outside the support structure depending upon what flow characteristics were required. For instance, if the filter material was located on the outside of the support structure the filter may be in contact with the coronary ostia. It may be more desirable to have the filter material on the inside of the support structure holding it away from the ostia of the coronary arteries. The filtration would trap particles from about 35-250 microns in size and allow adequate flow through the aorta. The distal portion of the filter may have a ring or template at the distal end to allow for a patterned removal of the native aortic valve. The distal portion would fit between the aortic wall of the sinus and the calcium deposits to be removed. The template would provide a pattern that may be traced by a removal tool as described in paragraphs above. By using a template the pattern would be close to the native healthy orifice. An acceptable cross sectional area would be about 2-3 $cm^2$. This would provide adequate room to place a new valve and provide the patient good hemodynamic flow. This template could be as simple as a guide provided by a wire ring or a pattern with three arches as seen in a healthy valve similar to a clover. It may however be simpler to provide a round hole than a complex shape to begin. This template may be above or below the native valve and may require more than one shape and or size.

Another design for a filter is to utilize a braided Nitinol stent that will provide support to the filter material but is still recoverable inside the catheter. In this embodiment, the filter material would be inside the braided structure and the braid would be in contact with the aortic wall. This would provide a seal between the filter device and the vessel directing flow through the filter element and allowing the coronary arteries to be patent After the temporary valve 520 and embolic protection filter 524 are in place, a debulking or valve removal step is performed as shown in FIGS. 57F-H. If possible, a guidewire may be advanced across the native valve. In some severely calcified native valves it may not be possible or practical to advance a wire across the valve. In these cases a new lumen may be formed through the valve. This can be done using a sharp wire needle or a heated wire cutting tool, or a rotating drill type cutting tool. A centering device may be used to ensure that the new lumen is created near the center of the native valve. Designs for centering devices known in interventional cardiology for the treatment of chronically occluded arteries may be used. These devices typically include a centering balloon. Alternatively an expandable wire basket may be used to center the wire while maintaining flow. An expandable basket could be cut from a superelastic hypotube such as a nitinol hypotube. One basket design includes a short uncut section of tube at both the proximal and distal ends this tube segment is about 1 to about 3 mm in length. The proximal and distal tube sections are connected by at least three struts. The struts are from about 30 to about 60 mm in length, and may be stabilized to each other by one ore more connectors along their length. The tube is then heat set or otherwise formed so that the middle portion is expanded to between 18 mm and 35 mm. The proximal and distal uncut hypotube sections support a central lumen for guidewire access, while the struts push out against the vessel walls to center the device.

After wire access has been gained it still may be difficult or impossible to pass some embodiments of the cutting device across the stenossed native valve. If necessary a preliminary cutting step may be performed to enlarge the valve opening sufficiently that a second cutting device may be inserted. In one embodiment the primary cutting device includes a rotating burr centered on a guidewire. The burr is mounted to a small flexible hypotube or solid shaft, which is spun by a motor outside the body. Preferably the hypotube has an inside diameter of 0.014 to 0.040 in and the shaft has a diameter of about 0.010-0.030 inches. The rotating burr preferably has an outside diameter slightly larger than the secondary cutting tool this is preferably in a range of 2 to 6 mm diameter. A similar rotating burr device is marketed by Boston Scientific, under the trade name Rotoblader, for the treatment of stenotic arteries.

A cutting device of this design could also be used to open the calcified valve to the desired diameter. In this case a larger burr may be used ranging in diameter from about 3 to about 9 mm in diameter. A steerable catheter may be required to center the newly enlarged opening in the native anatomy. A steerable catheter may consist of a flexible elongate tube with a pull wire located off center in at least a portion of the elongate tube. When tension is applied to the pullwire, it causes the catheter to bend in the direction to which the wire is offset. Multiple pullwires may be used to allow the catheter to be steered in multiple areas or directions. The catheter my also be manufactured with a preferred bending plane, allowing even a centered pullwire to steer the catheter, and providing more precise control of the catheter shape. The catheter is preferably of an outside diameter between 3 mm and 9 mm.

Several embodiments of cutting devices are possible some of which are describe above. In one embodiment, the cutting device 530 consists of a tool that pushes or pulls a sharpened punch into a die as described with reference to FIG. 53A. This cuts segments of calcified tissue away from the valve annulus and pulls them back into the catheter shaft. From there suction may optionally be applied to extract the calcified tissue from the body through a catheter. This design has the advantage of producing a minimum of embolic debris, because most of the tissue is forced into the catheter shaft. Preferably the cutting die is manufactured from a hardened pin ground at an angle so that the cutting forces are primarily piercing the material first with a high force per square inch. The cutter is preferably ground at an angle between 20 and 80 degrees from the axial direction of the pin. Secondary angles may also be ground on the pin near the pint formed by the primary grinding angle. This minimizes the force required to start the cut. Preferably the pin diameter is between 3 mm and 10 mm.

Alternatively a similar cutting device could be used where the cutting portion consists of a rotating cutter. The cutter is pulled back through the die portion forcing the material into the catheter shaft in a similar manner to the device described above. The rotating edge of the cutter may be sharpened to an edge to minimize embolic material as much as possible or may be serrated to maximize the cutting ability of the device. This device is very similar in function to devices commonly used for DCA or directional coronary atherectomy. Typically DCA devices cut in a push mode, capturing the cut out section in a cavity near the distal tip of the device. The devices described above operate in a pull mode, which allows the cut out material to be evacuated out the catheter shaft or fill a larger area within the catheter shaft. However either cutting device described could be manufactured to operate in a push mode rather than a pull mode. It may be desired to have the helix direction pull the material back or proximally to the catheter handle. This would allow for convenient removal of the debris from the body.

The cutting device may include a device to engage the cutting portion of the device to the tissue. In one embodiment a balloon possibly a perfusion balloon is attached to the non-cutting side of the device. As the balloon is inflated the cutter is moved laterally to engaged into the tissue. To maintain flow out of the heart the balloon inflation and cutting may be accomplished during the time that the aortic valve would be closed. This could be synchronized to the patients heart rate by echocardiography or similar sensing techniques or the patient could be placed on a temporary pace maker and the pacemaker output could be used to time the inflation of the balloon. The inflation media could be a liquid or a gas. A gas such as helium or CO2 would allow the quickest inflation time through a small lumen. Helium would provide an even quicker inflation time than CO2, however CO2 may be better dissolved in the blood in the event of a balloon burst.

Preferably the engagement method allows flow to pass around the engagement device as shown in FIG. 53A. One way to accomplish this is with a single or plurality of metal straps as described above with reference to FIG. 53A that expand out from the catheter against the native valve. The straps may be made to bow out from the catheter shaft by moving the mounting points of the straps towards each other, or by sliding the straps through the proximal section of the catheter. Alternatively the straps may be made self expanding and be constrained by a sheath or other means, during delivery. A self expanding sheathed device may consist of other geometries besides a simple strap. For example the expanding device could be formed from a braided mesh similar to a recoverable self expanding stent. These straps would be about 0.005-0.020 inches in cross section and have a length of about 40-80 mm.

Another engagement method that allows flow past the catheter includes a steerable catheter mechanism. The device can be bent in such a way that the window of the cutting device is pushed against the tissue, while this force is opposed by a section of the catheter bushed against tissue in an opposite direction. A DCA device marketed by the company Foxhollow uses this mechanism to engage tissue.

The engagement means may be adjustable to a predetermined range of sizes from the catheter handle. The cutting tool is advanced or retracted into the annulus and successive cuts are made by the operator. The catheter may be rotated slightly between each cut. Once the new annulus is cut out large enough for the engagement means to pass through the annulus the operator knows that the annulus has been enlarged to a size that corresponds with the adjustment, or size of the engagement means. If this is a sufficiently large cross sectional area for adequate flow after the permanent prosthetic valve is implanted, then the cutting device may be removed. If a larger annulus is desired the engagement means may be adjusted or replaced with a larger size, and the process repeated. If the distal end of wire straps are attached at the distal end of the cutting device and the proximal end of the wire straps are attached to the distal end of a sheath mounted over the cutting tool shaft, then the advancement of the sheath will cause the wire straps to bow out and engage the tissue. The distance that the sheath is advanced corresponds to the diameter that the engagement mechanism will pass through. Markings on the cutter shaft show the operator what diameter the engagement means is expanded to. Preferably the engagement means is expandable to at least about 2 cm. This provides an effective orifice area over 3 $cm^2$.

The cutting device 530 may include a lumen for contrast or therapeutic agent injection. The injection of contrast allows the operator to visualize the size and position of the cut out area relative to the aortic root and the ventricle, under fluoroscopy, MRI, NMR or other imaging techniques used in interventional cardiology. The injection of a therapeutic agent may be used to have any desired effect on the heart or ventricle. Certain therapeutic agents such as antibiotics may aid in reducing the risk of endocarditis or in the treatment of a valve damaged by endocarditis. Other therapeutic agents may increase or decrease the heart rate or hearts output as desired by the physician. The diameter of the inflation lumen is preferably between 0.010 and 0.060 in. in diameter.

As the valve 34 is being removed imaging the procedure is important. The operator must be able to visualize the position of the cutout relative to the aortic wall and the aortic root. Two-dimensional imaging techniques such as fluoroscopy need to be performed on multiple axis to allow the cutting procedure to be performed safely. The operator must be careful not to cut through the aortic wall or through the ventricle. Electrical conduction paths near the annulus such as the bundle of his may require special attention and care. The area between the anterior leaflet of the mitral valve and the aortic valve must not be damaged, and the mitral leaflets and chordae must be avoided. To visualize these and other obstacles during the procedure any number of common imaging techniques may be employed either during the procedure or prior to the procedure in a road-mapping step. Echocardiography may be employed in one of several forms to image the necessary areas. TEE or trans esophageal echocardiography may be particularly useful in imaging the valve area before the procedure begins and during the procedure as well. TTE may also be used with the benefit of being less invasive to the patient, but it is limited by a reduced image quality and the fact that the operator's hand must be near the patient's chest. This makes the simultaneous use of fluoroscopy and other imaging techniques unsafe for the operator. During the procedure fluoroscopy or MRI or NMR or similar imaging techniques may be used to visualize the size and shape of the newly cut out opening and the position of the opening relative to all the relevant structures of the native anatomy.

The cutting device 830 could be actuated by a simple lever type handle moving the cutter in either a proximal or a distal direction as the handle is squeezed. In addition the handle could contain a rotational swivel or union that allows the catheter to be rotated while the handle is held in a fixed position. Further, the function of the catheter rotation could be incorporated into the actuation of the handle. The handle mechanism could be designed or adjusted sot that the catheter rotates a predetermined amount each time the cutter is actuated. This could be accomplished with a simple cam and sprag mechanism, or using a stepper motor. The actuation of the cutting mechanism could also be powered electronically or pneumatically to minimize operator fatigue and to prevent the overloading of the device. In this case the operator would simply depress a button to actuate the cutting function. The handle may also contain an aspiration lumen to assist in the removal of debris from within the catheter shaft, and an injection lumen to inject contrast media or a therapeutic agent, or a fluid such as saline. Other means of providing energy to the device include an impact or momentum drive where a high velocity rate would contact the area to be removed providing a high degree of force to the calcific valve. Drive or propulsion methods may include a gaseous discharge or chemical reaction to generate a hydraulic force to drive an object into or through the calcified valve. Other predictiable forces may include preloading a spring mechanism and releasing the energy stored to drive an object into or through the calcified valve.

The valve could also be cut out in sections using a laser or heated wire. Severely calcified areas could be broken up with Cavitation Ultrasound energy, prior to removal with a cutting tool or the calcified areas may be broken up with ultrasound and the debris captured in a filter. Similarly a chemical compound could be used to dissolve or break up the calcium.

With reference to FIGS. 57I-57L, the valve implantation step includes the installation of an inflatable valve 100 as described above or any stent based valve such as Edwards/PVT, CoreValve's self-expanding system. This step is described in previous filings by Lashinski from Direct Flow Medical and by Anderson from PVT/HeartPort both of California.

With reference now to FIGS. 57M-57O, as a final step in the illustrated embodiment, the two items to be removed after successful implantation of the new valve are the filtration device 522 which may hold emboli or debris and it's delivery catheter. This step may require aspiration and or suction to capture any items not trapped within the filter. Once the filter moved through the temporary valve 520, the filter 524 may need to be redeployed to capture any particles that the temporary valve 520 may hold or dislodge during removal. Once the temporary valve 520 is either deflated or drawn back into the sheath, the filter 524 and it's delivery system may be removed leaving the new valve 100 functioning properly.

The illustrated embodiment provides a method of implanting a percutaneous prosthetic valve assembly, where the outflow tract is not blocked at any time during the implantation process. In heart failure patients, blocking the aortic output can have serious consequences, such as death. Another less significant problem with blocking aortic output is the contracting ventricle can exert significant pressure on the device, making positioning very difficult, and possibly forcing the device away from the desired location before it is completely deployed or anchored. To overcome this issue in some cases patients have been rapidly paced. By increasing the patients heart rate to such an extent that the heart does not effectively pump blood. This may not be required during the implantation of this inflatable device.

In contrast, devices such as those disclosed in Andersen family of US patents (U.S. Pat. Nos. 5,411,552 6,168,614 6,582,462) result in the complete or nearly complete obstruction of the aortic valve during deployment. For example as a balloon expandable valve structure is expanded the balloon blocks the aortic output. In one embodiment Andersen describes the use of multiple balloons to deploy the valve, as was common with a balloon valvuloplasty. Using multiple balloons would provide a very small path for fluid to flow between the balloons when the balloons are fully inflated to a pressure high enough that they take on their natural generally round cross section. However when the balloons are partially inflated or during the inflation process the multiple balloons conform to and occlude the lumen, resulting in complete or nearly complete blockage of the outflow tract.

The self-expanding valve support structures disclosed in Andersen and Leonhardt (U.S. Pat. Nos. 6,582,462 and 5,957,949) also block aortic outflow as they are deployed. As the sheath is retracted from the distal portion of the device the device opens and begins to conform to the native vessel. The portion of the valve structure designed to seal to the valve annulus or other portion of the native anatomy comes in contact with the native anatomy. At the same time, the proximal portion of the device is still restrained within the deployment catheter, preventing the valve from opening. At this stage of deployment the devices effectively block all aortic output.

The simplest extension of existing technology to allow implantation of a prosthetic valve without blocking flow is the use of a perfusion balloon with a balloon expandable support structure. The perfusion balloon would have a lumen through the balloon large enough to allow significant perfusion through the balloon during deployment. Perfusion balloon technology is well developed, and known. Wasicek et al describe a perfusion balloon catheter is U.S. Pat. No. 6,117,106

Using a self-expanding valve support structure it would be possible to maintain flow past the valve using a tube section placed through the affected valve, outside the self expanding support structure. After the self-expanding support structure is completely deployed the tube section could be withdrawn. The tube section is longer than at least the sealing portion of the self-expanding valve support structure, and preferably attached to an elongate member to allow its withdrawal. Alternatively the tube section could be located inside the valve support structure. In this case the tube section would allow fluid (usually blood) to flow into the deployment catheter. Perfusion holes in the deployment catheter would allow blood to flow out into the native conduit.

Relating to the current inflatable prosthetic valve or cast in place support structure described herein, a different deployment procedure is used which allows outflow to be maintained. This deployment method could also be used with some self-expanding percutaneous valves. The deployment method is described as follows for an aortic valve replacement. The procedure could be easily adapted to any other coronary valve. The deployment catheter is advanced across the aortic valve. The prosthetic valve and inflatable cuff are unsheathed in the ventricle, but remain attached to the deployment control wires. The distal end of the inflatable cuff is inflated. The sheath is retracted far enough that the deployment control wires allow the prosthetic valve to function. The device is then withdrawn across the native valve annulus. The device is then fully inflated. The valve function may be tested using various diagnostic techniques. If the valve function is sufficient the inflation media may be exchanged for the permanent inflation media. The deployment control wires and the inflation lumens are then disconnected and the catheter withdrawn. In this procedure the key to maintaining the outflow tract is the use of deployment control wires. The deployment control wires allow the device to be moved an appreciable distance from the deployment sheath before the device is permanently positioned in the desired location. Other deployment control devices could be used to have similar effect. For example a sheath used as a shear barrier between the retractable sheath and the implant having longitudinal slots could be configured to produce a similar function. It may be desirable to predilate the native valve annulus with a balloon before device implantation. This may allow for a larger effective orifice area to implant the device and precondition the valve area. Secondarily, an additional dilatation may be desired after implantation to ensure the device is apposed to the wall of the annulus and seated properly.

The current percutaneous valve replacement devices do not provide a means for testing the function of the valve before committing to the position of the valve. These devices are deployed at a location and if the location was a wrong location or if the valve does not have a good effect, the valves can-not be removed. The present invention includes a method of valve implantation consisting of the steps of positioning the valve, enabling the valve, testing the function of the valve, and finally deploying the valve.

Relating to the current inflatable prosthetic valve or cast in place cuff, a unique deployment procedure is used, consisting of the steps of position, enable, test, and reposition or deploy. This deployment method could also be adapted to a valve with a self-expanding support structure or to other implantable devices. The deployment method is described as follows for an aortic valve replacement. The procedure could be easily adapted to any other coronary valve. The deployment catheter is advanced across the aortic valve. The prosthetic valve and inflatable cuff are unsheathed in the ventricle, but remain attached to the deployment control wires. The distal end of the inflatable cuff is inflated. The sheath is retracted far enough that the deployment control wires allow the prosthetic valve to function. The device is then withdrawn across the native valve annulus. The device is then fully inflated, enabling the valve to function. The valve function may be tested using various diagnostic techniques. If the valve function, sizing or securement is not sufficient or ideal the valve may be partially deflated, and advanced or retracted, and then reinflated or the valve may be fully deflated and retracted into the deployment catheter or another slightly larger catheter, and removed. Once a valve is positioned, sized and secured acceptably or ideally the inflation media may be exchanged for a permanent inflation media, which may jell, set or cure. The inflation catheters and deployment control wires are then disconnected and the catheter removed, fully deploying the valve.

If the technology from a known self-expanding recoverable stent is adapted to a valve support structure, the stent is only recoverable from a partially deployed state. A self-expanding support structure of a length sufficient only to support and retain the valve would not allow testing of the valve function, until the valve was fully deployed. This is because the proximal portion of the support structure contained within the device would prevent normal function of the valve. A proximal extension of the support structure could be added to act as a deployment control device allowing the valve function to be tested in a configuration where it is still possible to remove or reposition the valve. The proximal extension could be a continuation of the braided or laser cut stent structure, provided that the cell structure is open enough to allow blood flow through the stent. In an aortic valve application the required length of the proximal extension would most likely extend beyond the ostia of the coronary arteries. In this case the shape of the stent structure may be designed to permit unobstructed flow to the coronary arteries or to permit adequate flow to the coronary arteries. Another possibility is to design the proximal extension so that it acts as multiple individual wires. This could be done by laser cutting or by changing a braid pattern. This would also allow the proximal portion of the implant to act as a deployment control device.

A method for recapturing a self-expanding stent is described by Johnson et al in U.S. Pat. No. 5,817,102, as follows.

There is provided an apparatus for deploying a radially self-expanding stent within a body lumen. The apparatus includes a stent confining means for elastically compressing a radially self-expanding stent into a delivery configuration in which the self-expanding stent has a reduced radius along its entire axial length. The apparatus includes an elongate and flexible stent delivery device having a proximal end, a distal end and a distal region near the distal end. The distal region is used in delivering the radially self-expanding stent into a body lumen, and in positioning at a treatment site within the body lumen with the stent surrounding the delivery device along the distal region. The proximal end of the delivery device remains outside of the body. An axial restraining means is disposed along the distal region of the delivery device. A control means is operable associated with the delivery device and the confining means. The control means moves the confining means axially relative to the delivery device toward and away from a confinement position in which the confining means compresses the self-expanding stent into the delivery configuration, and urges the stent into a surface engagement with the axial restraining means. The restraining means, due to the surface engagement, tends to maintain the self-expanding stent axially aligned with the deployment device as the confining means is moved axially away from the confinement position to release the stent for radial self-expansion.

Preferably the stent delivery device is an elongate and flexible length of interior tubing, with a central lumen for accommodating a guidewire. The stent confining means can be an elongate and flexible length of tubing, having a lumen for containing the interior tubing. The second (or outer) tubing surrounds the stent to confine it.

The preferred axial restraining means is a low durometer sleeve surrounding the interior tubing along the distal region. If desired, an adhesive can be applied to an exterior surface of the sleeves. Alternatively, the axial restraining means can consist of several elongate strips disposed along the distal region, with adhesive applied to radially outward surfaces of the strips, if desired.

In either event, so long as the exterior tubing surrounds the stent to radially compress the stent, it also maintains the stent in surface engagement with the sleeve or strips. As the exterior tubing is axially withdrawn to allow part of the stent to radially self-expand, the rest of the stent remains confined against the sleeve or the strips. As a result, the stent does not travel axially with the exterior tubing. Rather, the stent remains substantially fixed in the axial direction with respect to the interior tubing. This structure affords several advantages. First, the interior tubing can be used as a means to positively maintain the radially self-expanding stent in the desired axial position during deployment. The interior tubing can itself be employed as a reliable indicator of stent position, both prior to and during deployment. Further, should the need arise to retract the stent after a partial deployment, the outer tubing can be moved back into the confinement position, without tending to carry the stent along with it.

The current percutaneous valve replacement devices are not removable or repositionable. These devices are deployed at a location and if the location was a wrong location or if the valve does not have a good effect, the valves can not be removed, recaptured or repositioned percutaneously. The present invention includes a method of implantation facilitating percutaneously repositioning, recapturing and/or removing, a prosthetic valve A balloon expandable support structure is more difficult to make recapturable, repositionable or removable. One method would be to use a shape memory alloy, such as Nitinol. In this case if Nitinol was used it would be in the martensitic phase at body temperature. Martensitic Nitinol is not superelastic, but soft and conformable. It would be somewhat suitable as a balloon expandable support structure material, except the yield strength is very low. This requires relatively thick cross sections to be used. The balloon expandable support structure is deployed in any way desired, such as by the methods described in Andersen. If the location or performance of the valve is not acceptable the support structure may be caused to contract by changing its temperature, causing it to return to its preset "remembered" shape, which in this case is a smaller, radially collapsed shape. The temperature controlling media could be a fluid such as saline, and could be delivered while a catheter or balloon is inserted through the support structure. This would cause the valve and valve support structure to collapse down on the balloon or catheter allowing removal or possibly redeployment. Other shape memory materials are available, and may have more desirable mechanical properties for use as a balloon expandable support structure. In some cases the biocompatibility of these alloys is not known.

It would be possible to construct a self-expanding valve that would be capable of being recaptured. This could be done using technology from recapturable self-expanding stents. Typically these devices are braided from a superelastic or high strength alloy and have relatively low radial strength. As they are pulled back into a sheath they collapse on their diameter and lengthen facilitating recapturability. Not all braided self-expanding structures are recapturable. To our knowledge this technology has not yet been applied to valve support structures.

Relating to the current inflatable prosthetic valve or cast in place support structure, a different deployment procedure is used which allows the device to be repositionable recapturable, and removable. This deployment method could also be used with some self-expanding percutaneous valve support structures. The deployment method is described as follows for an aortic valve replacement. The procedure could be easily adapted to any other coronary valve. The deployment catheter is advanced across the aortic valve. The prosthetic valve and inflatable cuff are unsheathed in the ventricle, but remain attached to the deployment control wires. The distal end of the inflatable cuff is inflated. The sheath is retracted far enough that the deployment control wires allow the prosthetic valve to function. The device is then withdrawn across the native valve annulus. The device is then fully inflated. The valve function may be tested using various diagnostic techniques. If the valve function, sizing or securement is not sufficient or ideal the valve may be partially deflated, and advanced or retracted, and then reinflated or the valve may be fully deflated and retracted into the deployment catheter or another slightly larger catheter, and removed. Once a valve is positioned, sized and secured acceptably or ideally the inflation media may be exchanged for a permanent inflation media which may jell, set or cure. The inflation catheters and deployment control wires are then disconnected and the catheter removed. This deployment method provides many advantages including the ability to reposition recapture and remove the device.

In an alternative delivery method (surgical) transapical access would allow for the device to be placed in a less invasive surgical procedure. This may still be a beating-heart procedure but would limit the access incision area. Through the apex of the heart a tube may be inserted to introduce the device to the aortic valve from a antigrade approach. This would allow the device to be placed and or moved in the same manner previously described in a catheter delivery.

The prosthetic valve with inflatable cuff may also be delivered surgically. The inflatable cuff aids in sealing the valve to the native anatomy. A valve of this design may be placed in any coronary valve position as well as in a vein, lung, ureter, or any area of the body known to benefit from the implantation of a valve or flow control device. In one embodiment the native valve is sutured in place similar to known coronary prosthetic valves. The inflatable cuff is then expanded to form a tight seal with the native anatomy. In another embodiment the valve is placed in the desired location and the valve is expanded. The valve is held in place by physical interference with the native anatomy. The geometry of the implant may be similar to the percutaneous applications for the inflatable prosthetic valve described in previously.

The valve may be further secured by additional methods such as sutures or staples. The surgical procedure may also be performed in a less invasive manner, for example a smaller opening in the atrium or aorta could be used to implant the valve, because the valve attachment process is less critical. In another embodiment the valve may be implanted with a minimally invasive surgical device. A device of this design for an aortic valve application punctures the chest wall and the ventricular wall near the apex of the heart. The device is then advanced across the native valve annulus and implanted in a manner consistent with the percutaneous embodiments of the invention. This procedure may be guided by echocardiography, angiography, thorascopy or any other appropriate visualization method commonly known.

One Step Implantation

By deploying the device at the site in one step the native valve may be excluded while the new valve is being placed. It is conceived that the device may have a shape similar to a tubular hyperbola to exclude the old valve by trapping it under the new structure during deployment. This may aid in patient comfort and safety if the vessel is not occluded during implantation by a balloon deployed stent system. As the sheathed device is delivered via catheter through the vessel past the aortic valve, it may be reveled or exposed by removing the sheath partially or completely and allowing proper placement at or beneath the native valve. Once in the vessel, the device may be moved proximal or distal and the fluid may be introduced to the cuff providing shape and structural integrity. It may be necessary to add or retract the fluid for proper positioning or removal. Once the cuff is positioned properly and the fluid is added creating the structure and sealing the device to the vessel wall, the delivery catheter may be disconnected and removed leaving the now functioning valve device as a permanent implant. The disconnection method may included cutting the attachments, rotating screws, withdrawing or shearing pins, mechanically decoupling interlocked components, electrically separating a fuse joint, removing a trapped cylinder from a tube, fracturing a engineered zone, removing a collecting mechanism to expose a mechanical joint or many other techniques known in the industry.

Two Step Implantation

It may be desirable to implant the valve structure in two steps. It is desirable to attach the valve to the native tissue securely and without leaks. Also it is desirable to avoid blocking the flow of blood for a long period of time. For these reasons it may be desirable to first implant a retention-sealing device as a first step and then as a second step implant the cuff with the valve attached. The retention-sealing device could be a stent like structure expanded in place or a ring shaped support structure where the valve is secondarily attached. The ring shaped structure could utilize the fluid inflation method as mentioned above and could be a separate system and catheter. It could incorporate barbs for anchoring. It could also incorporate a sealing material to help prevent blood from leaking around the valve. The device could incorporate a mechanism to attach the support structure to. The retention mechanism could be a shoulder or a channel that the support registers in. Once in position, the deployment of the valve could take place as mentioned in the One Step Implantation description above In an alternative embodiment a support structure, such as a stent is delivered in one step and the valve is delivered in a later step. The valve is then attached to the support structure. The support structure may be an expandable scaffold or stent designed to produce a physical interference with the native vessel. The support structure could also use the geometry of the native anatomy as described in other embodiments, for Deflate Balloons after Anchoring In another embodiment the balloon inflation step is used to enable the device and the support structure and anchoring device are delivered in a later step. In one embodiment the support structure is a balloon expandable stent. The stent is placed inside the inflated cuff. The stent may also extend proximal or distal from the cuff. More than one stent can be used. Preferably a stent is placed proximal to the valve portion of the implant and a stent is placed distal to the valve portion of the implant, or a portion of the stent extends across the valve. In one embodiment the balloons are left as part of the implant in a deflated state. The balloons are disconnected from the catheter by a mechanism described in this application with the exception that the sealing feature is not required. Other detachment mechanisms are also possible. In another embodiment the balloon is removed from the device after it is deflated. The balloon may be placed in a channel in the cuff and simply retracted after deflation. Alternatively the balloon may be attached to the implant with sutures designed to break as the balloon is inflated. After the balloon is inflated and deflated the balloon can be retracted.

Stent on Device

A method of delivering a valve attached to a cuff as a first step, and delivering an expandable structure as a second step. The structure may be a stent or an unwrapable band, engaged coaxially inside the cuff. The cuff may be positioned using an inflatable cuff, where the cuff remains inflated after the device is disconnected from the catheter. In this case the inflation serves the function of temporary securement and of permanent sealing. Alternatively the cuff may contain a removable balloon. In this embodiment the inflation provides a means of temporary support until the permanent support structure is deployed. Yet another alternative involves a valve and cuff assembly that contains no inflation provision. The cuff is held in place using deployment control wires that are shaped in a way to cause the expansion of the prosthesis. The stent or expandable support structure is then delivered to a position located coaxially within the cuff. The stent is then deployed, securing the device.

Creating Support Structure In Vivo

The present invention includes a method of creating a support structure inside the body of a patient. The preferred embodiment includes manufacturing the support structure by a casting method. In this method fluid is injected into a mold or cuff that is attached to the valve and delivered percutaneously. The fluid then jells hardens or solidifies forming the support structure.

There are other methods of manufacturing a support structure in vivo. In one embodiment the support structure can be assembled from many small solid particles. The particles can be attached to one another by various means, including a thread woven through the particles, in such a way that when the thread is tensioned the thread and the particles form a rigid structure. The particles could be attached to one another by a sintering process, with an adhesive or by another method. The support structure could also be manufactured in place from wire, which is woven and inserted into the shape of a support structure in vivo.

The support structure could also be manufactured in place using a biological reaction such as forming calcium deposits on the appropriate portion of the valve. The support structure could be assembled by nanomachines.

The support structure could also be manufactured from a fluid that solidifies jells or hardens that is not contained inside a mold. The fluid could be applied to an area on the outer surface of the valve or the inner surfaces oft the area where the valve is to be applied, in vivo. The support structure could be manufactured from a material that solidifies hardens or becomes more rigid by the addition of a catalyst, heat, cold or other energy source. The material could be applied to the outer surface of the prosthetic valve before the valve is installed and then activated in vivo. The support structure could be excited or activated by an electronic energy. This source could also be activated by magnets through a suspension fluid that solidifies in a magnetic field.

Attachment of Valve to Non-Structural Element

In the embodiments described above, the valve can be attached only to a nonstructural element. In the preferred embodiment the nonstructural element is the sewing cuff or mold. The support structure is later manufactured within the mold. Other examples of valves permanently attached only to nonstructural elements are possible. A valve could be attached to an unsupported tubular section of fabric. After the fabric graft and valve are positioned in the patient a stent or other support structure could be deployed within the graft anchoring the graft in place. The stent could utilize barbs or fangs to puncture the graft and anchor the devices solidly to the native tissue. The stent could also be placed so that it only partially overlaps the graft. In this way barbs or fangs could be placed that do not puncture the graft. In another embodiment, rigid structural elements such as commissural support posts or barbs or anchors are attached to the cuff and delivered with the nonstructural element.

Radially Moveable and/or Flexible Tissue Supports

In accordance with another aspect of present invention, there is provided an inflatable or formed in place support for a translumenally implantable heart valve, in which a plurality of tissue supports are flexible and/or movable throughout a range in a radial direction. As used herein, a radial direction is a direction which is transverse to the longitudinal axis of the flow path through the valve.

Valve and valve support design preferably accomplish a variety of objectives, including long term durability of the valve. The inflatable valve support of the present embodiment can be optimized in a variety of ways, to enhance valve life. For example, except at its point of attachment to the annulus, the wall and coaptive edges of the tissue leaflet preferably will not contact any structural components of the implant or other tissue of the valve or surrounding environment. Such contact may result in premature wear and ultimately valve failure. In addition, upon valve closure, the tissue supporting elements of the formed in place support preferably allow for a controlled deceleration of the motion of the leaflets. This lessens the stress seen by the connection points of the tissue to the structural elements. In many valve designs, these support elements are referred to as commissural supports.

The most common valve is a three cusp leaflet configuration where support posts extend axially from the base of the valve in a downstream direction to support the tissue, creating a tricuspid valve. Preferably, under pressure, the leaflets will open and close with the stresses being distributed evenly about the structural element. In this tricuspid design, the forces upon closure of the valve are in an upstream axial direction and radially inwardly on the valve. By allowing the commissural supports to flex inward, the forces seen by the connection between the tissue and the support element will drop and the longevity of the valve may be increased. In conventional surgical valves, deceleration or dampening of the closure force is accomplished by a wire formed stent or a polymer cast or machined to distribute the forces evenly about the stent.

Forces experienced by the valve upon valve closure are on the order of about 15 grams per support post, and prosthetic valve testing may be accomplished up to about 45 grams per support post, for a safety factor of about 300 percent. The supports are preferably movable in a radial direction upon closure of the valve through a range, as is discussed below, to dampen the impact stresses on the valve.

Bending of the tissue supports may include not only flexure of the supports but also flexure of the hoop or base of the valve support. This maximizes the distribution of stresses over the structural element, thereby lessening the stress concentrations at any one point or area.

Figure 58:
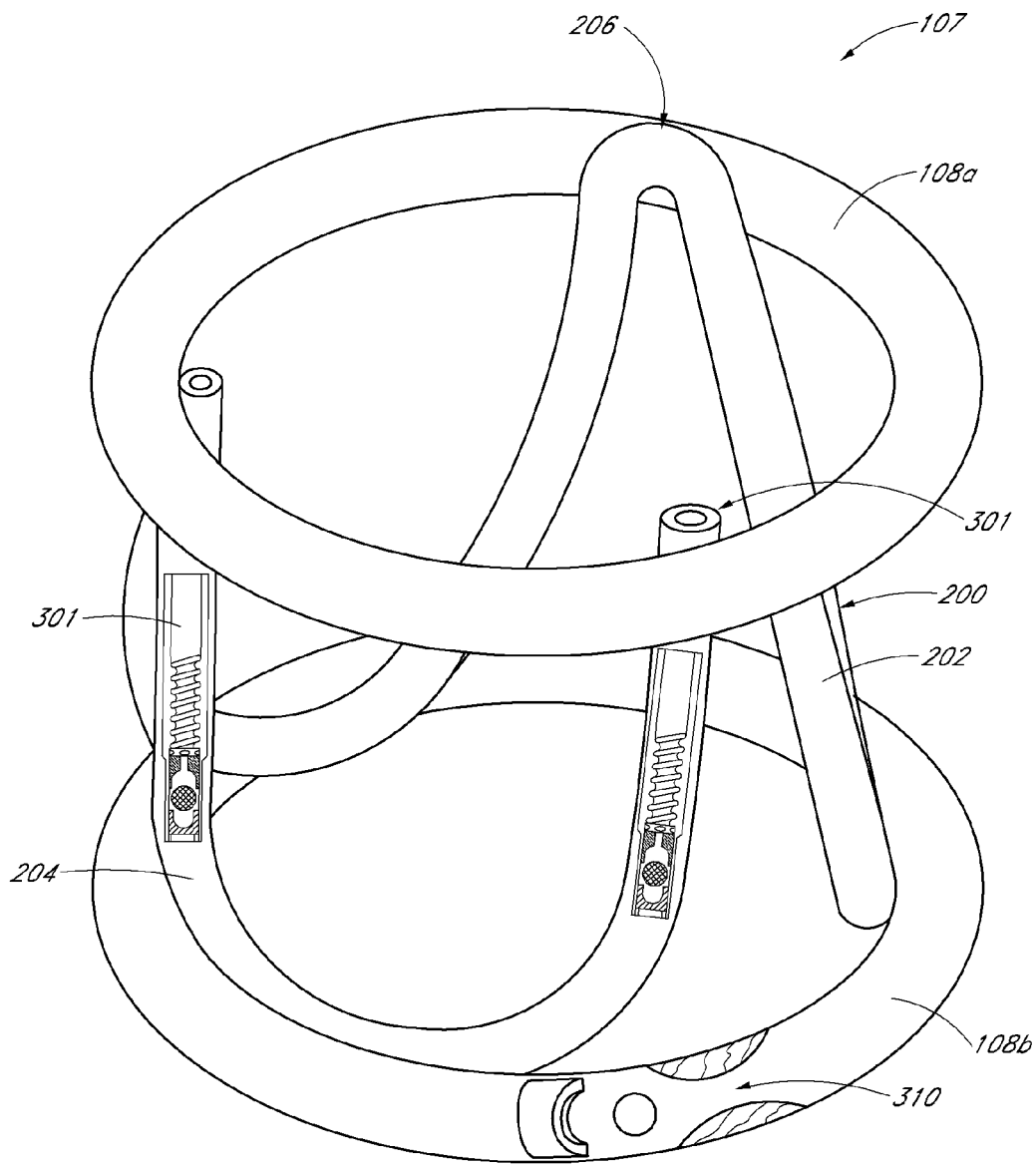
FIG. 58 is a side perspective view of another embodiment of a valve.

The tissue supports (i.e., commissural supports) on the inflatable valve support of the present arrangement may be provided with a range of radial direction motion in a variety of ways. Referring to FIG. 58, an inflatable support 107 is schematically illustrated, and has been described in greater detail elsewhere herein. The illustrated inflatable support 107 has been simplified somewhat to illustrate the radial range of motion feature. For example, the illustrated inflatable support 107 comprises a downstream support ring 108a, and an upstream support ring 108b, but structure for maintaining the spacing between the support rings and related inflation lumen have been omitted for simplicity.

The illustrated inflatable support 107 is configured for supporting a valve having a three cusp leaflet configuration, as has been discussed. Accordingly, the support 107 is provided with three tissue supports 200. Each tissue support 200 comprises a first inflatable strut 202 which is joined with a second inflatable strut 204 at a downstream apex 206. As will be apparent to those of skill in the art, the first inflatable strut 202 and second inflatable strut 204 may be separate components, or may be a unitary tube, which is bent at an angle to form apex 206. As may be seen in FIG. 58, the apex 206 resides in contact with or adjacent the radially inwardly-facing (lumenal) side of the downstream support ring 108a.

Figure 59:
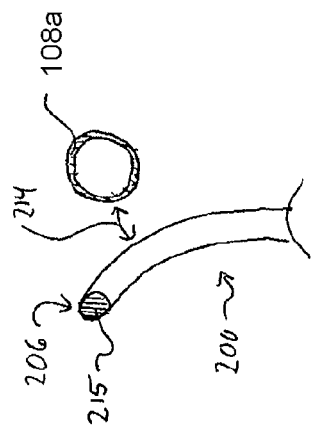
FIG. 59 is a top plan view of the valve of FIG. 58.

Referring to FIG. 59, there is illustrated a top plan view of the inflatable support 107 of FIG. 58. As seen therein, each apex 206 comprises a lumenal side 208 facing the center of the lumen and an ablumenal side 210 facing radially outwardly from the center of the blood flow lumen. The downstream support ring 108a may also be considered to have a lumenal side 212, facing radially inwardly. In FIG. 59, the apex 206 is illustrated in a resting position, in which the ablumenal side 210 of apex 206 is positioned in contact with or in close proximity to the lumenal side 212 of the downstream support 108a. This may be further seen in FIG. 59A.

Figure 59A:
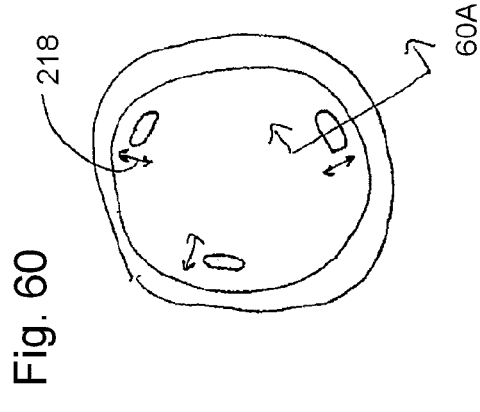
FIG. 59A is a partial cross-sectional view of a portion of the valve of FIG. 58.
Figure 60:
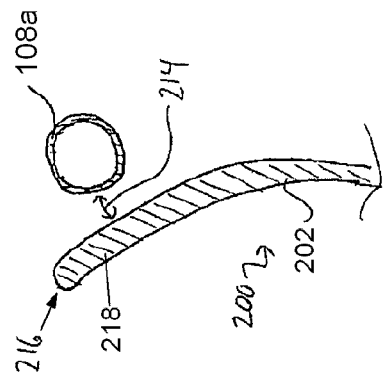
FIG. 60 is another top plan view of the valve of FIG. 58.

As discussed briefly above, each apex 206 is capable of movement in a radial direction through a limited range of motion. As illustrated in FIG. 60, each apex 206 has been advanced radially inwardly away from the lumenal side 212 of the downstream support ring 108a through a range of motion 218. The range of motion 218 may be engineered into the valve to have a variety of limits, depending upon the desired valve performance. In general, apex 206 will be permitted to travel through a range of no greater than about 3 mm, often no greater than about 2 mm, and, in certain embodiments, no greater than about 1 mm. The apex 206 is preferably biased such that it is in contact with or in close proximity to the lumenal side 212 of downstream support ring 108a as illustrated in FIGS. 59 and 59A, such that the downstream support ring 108a serves as a limit on the range of travel for apex 206 in a radially outwardly-facing direction.

In operation, forward flow of blood (systole) opens the leaflets in a downstream direction and may press the apex 206 against its outer limit of motion which may be contact with the downstream support ring 108a. Upon valve closure, and under diastolic pressure, the apex 206 is forced radially inwardly through the range of motion 218, to provide a spacing which may be seen in FIG. 60 or 60A. Upon valve opening, the apex 206 is allowed to flex radially outwardly, back into the position illustrated in FIGS. 59 and 59A. This configuration permits distribution of force experienced during normal valve operation, in a manner that may enhance valve life.

The tissue support 200 may be configured in a variety of ways, to accomplish a range of radial motion. For example, although the tissue support 200 is illustrated in FIG. 58 as having a first inflatable strut 202 and a second inflatable strut 204, a third or fourth or more inflatable struts may be joined at a single apex 206 to provide a commissural support 200. Alternatively, the tissue support 200 may comprise only a single inflatable strut 202.

Alternatively, the tissue support 200 may comprise a non-inflatable component, such as one or two or three or four or more axially-extending support elements. The support elements may be solid elements, such as wire, ribbon, solid rod, or tubing stock which does not require inflation for its structural integrity. Such support elements may be movably connected or rigidly connected to the upstream support ring 108b in any of a variety of ways, depending upon the construction materials and other design choices.

Figure 60A:
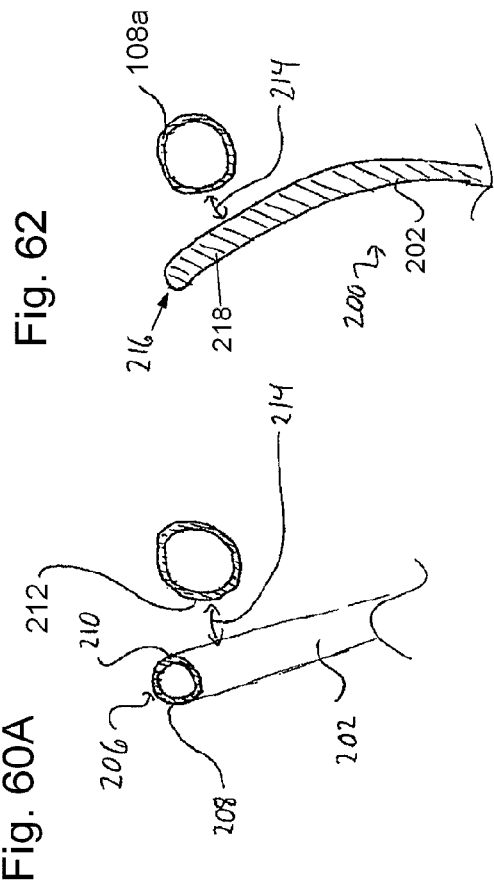
FIG. 60A is another partial cross-sectional view of a portion of the valve of FIG. 58.

As an independent variable, the tissue support 200, whether inflatable or not, may permit a range of radial motion, either by flexing about a discrete hinge point, or flexing about a force distribution, or by bending, or all of the above. Referring to FIG. 60A, there is illustrated a fragmentary cross-sectional view through the apex 206 of a first inflatable strut 202. The apex 206 and strut 202 are illustrated as spaced apart from the downstream support ring 108a by a distance 214, such as during valve closure. In the illustrated embodiment, the first inflatable strut 202 remains substantially linear, indicating that the strut 202 has achieved movement by distributing torsional or bending forces along its length and particularly in the vicinity of the upstream support ring 108b. This may be accomplished by using an inflation media for the first inflatable strut 202 which cures to a relatively rigid state.

Figure 61:
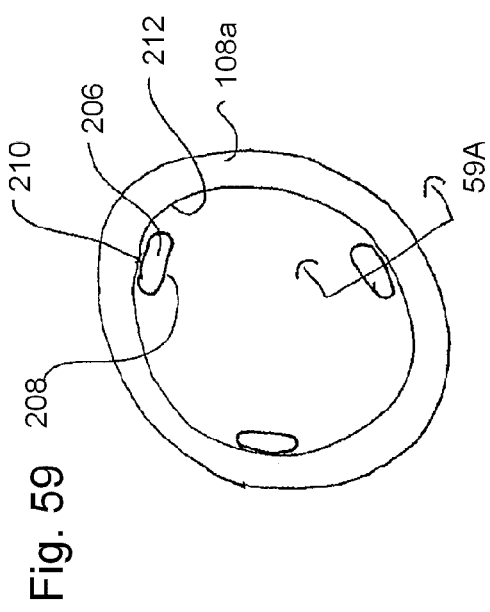
FIG. 61 is another partial cross-sectional view of a portion of the valve of FIG. 58.

Alternatively, referring to FIG. 61, there is illustrated a cross-sectional view similar to FIG. 60A, in which the strut is instead formed from a single strand solid element 215, such as a wire, or polymeric extrusion, which may be configured in a sinusoidal pattern much like that illustrated in FIG. 58. In this configuration, the metal or polymeric strut is flexible, although biased in the linear orientation, such that, as illustrated in FIG. 61, the strut bends along its length to provide the range of motion 214.

Figure 62:
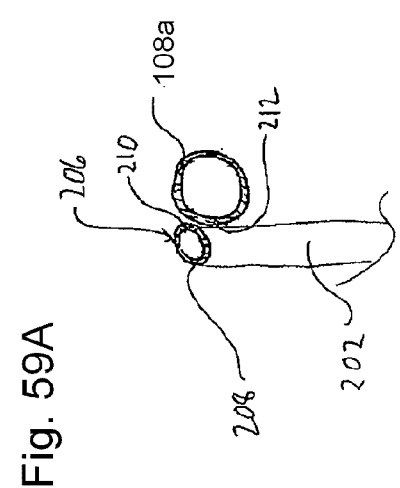
FIG. 62 is another partial cross-sectional view of a portion of the valve of FIG. 58.

As a further alternative, the tissue supporting strut 202 may be a single element 218 extending in a downstream direction from the upstream support ring 108b, to a distal (downstream) end 216. In this construction the tissue support 200 is only a single element, as opposed to an apex 206 at the junction of a first and second strut. The upstream end of the tissue support 200 may be connected to the upstream support ring 108b or to an inflatable tissue support. As illustrated in FIG. 62, the single element strut 218 may also be configured from a material such as a metal or polymer and with a design that permits flexibility along its length. Thus, upon valve closure, as illustrated in FIG. 61, the strut 202 bends radially inwardly along its length to provide a distribution of the closure forces on the valve.

The tissue support 200 may extend in an axial direction such that the apex 206 or downstream end 216 is positioned approximately at the level of the downstream support ring 108a, as has been illustrated, for example, in FIG. 58. Alternatively, referring to FIG. 19, the apex 206 may be positioned in between the upstream support ring 108b and the downstream support ring 108a. As with FIG. 58, FIGS. 63, 64 and 64A have been simplified by omitting inflatable elements, fabric sleeves or other structure for associating the upstream and downstream support rings. In this embodiment, the apex 206 may be positioned within the range of from about 0.5 cm to about 2.0 cm from upstream support ring 108b.

Figure 63:
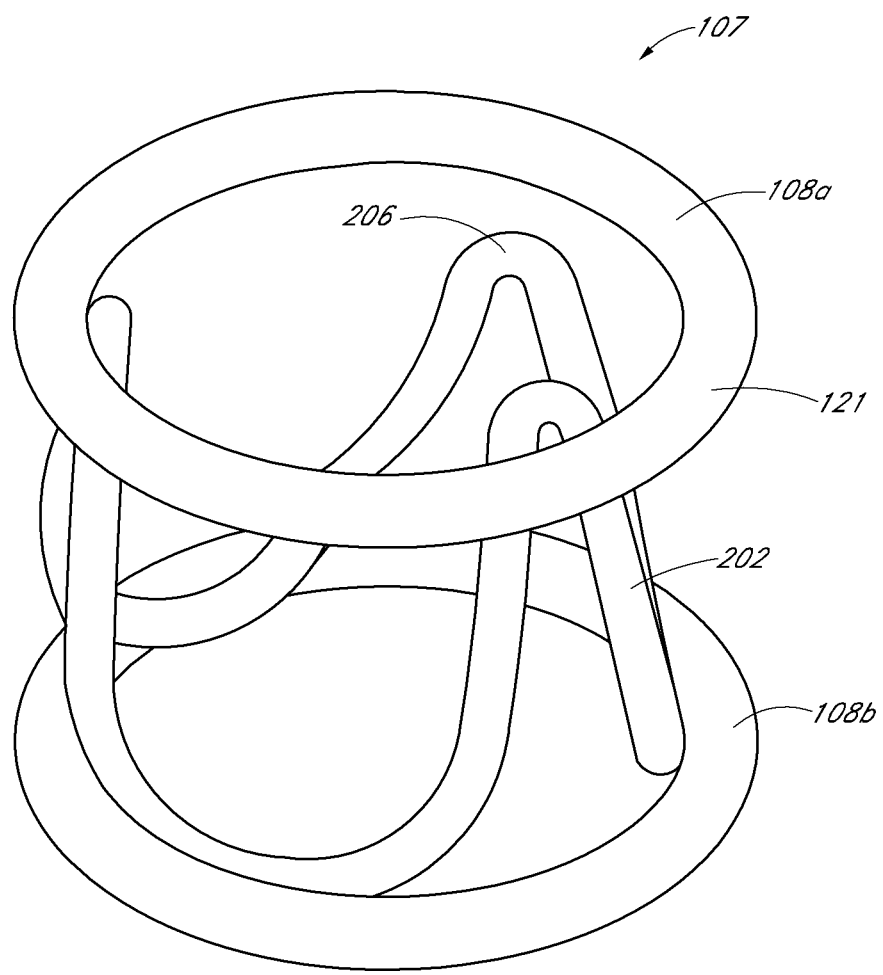
FIG. 63 is side perspective view of another embodiment of a valve.
Figure 64:
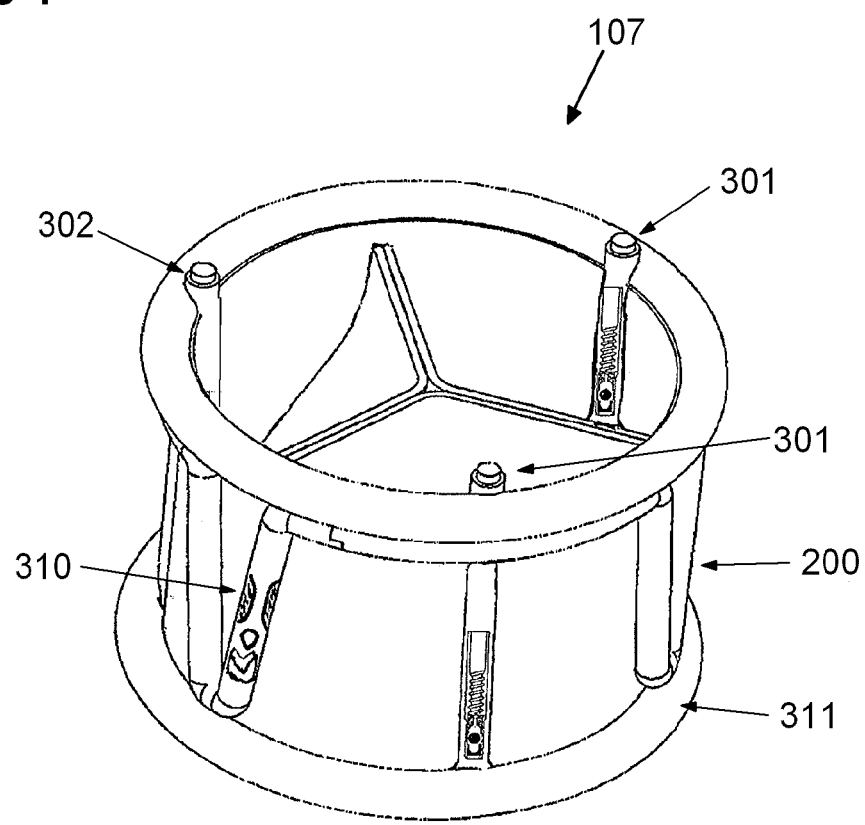
FIG. 64 is side perspective view of another embodiment of a valve.
Figure 64A:
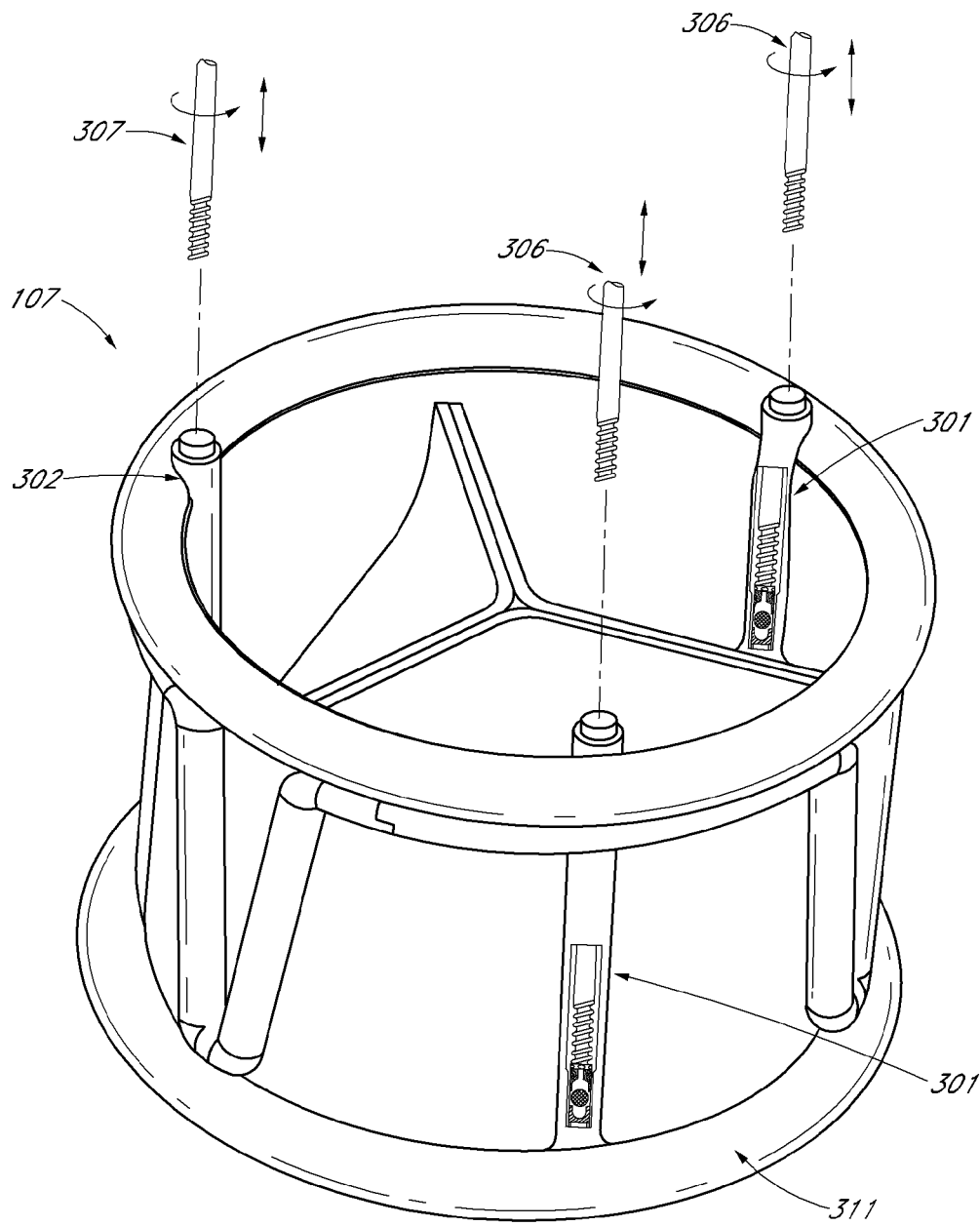
FIG. 64A is side perspective view of another embodiment of a valve.
Figure 68:
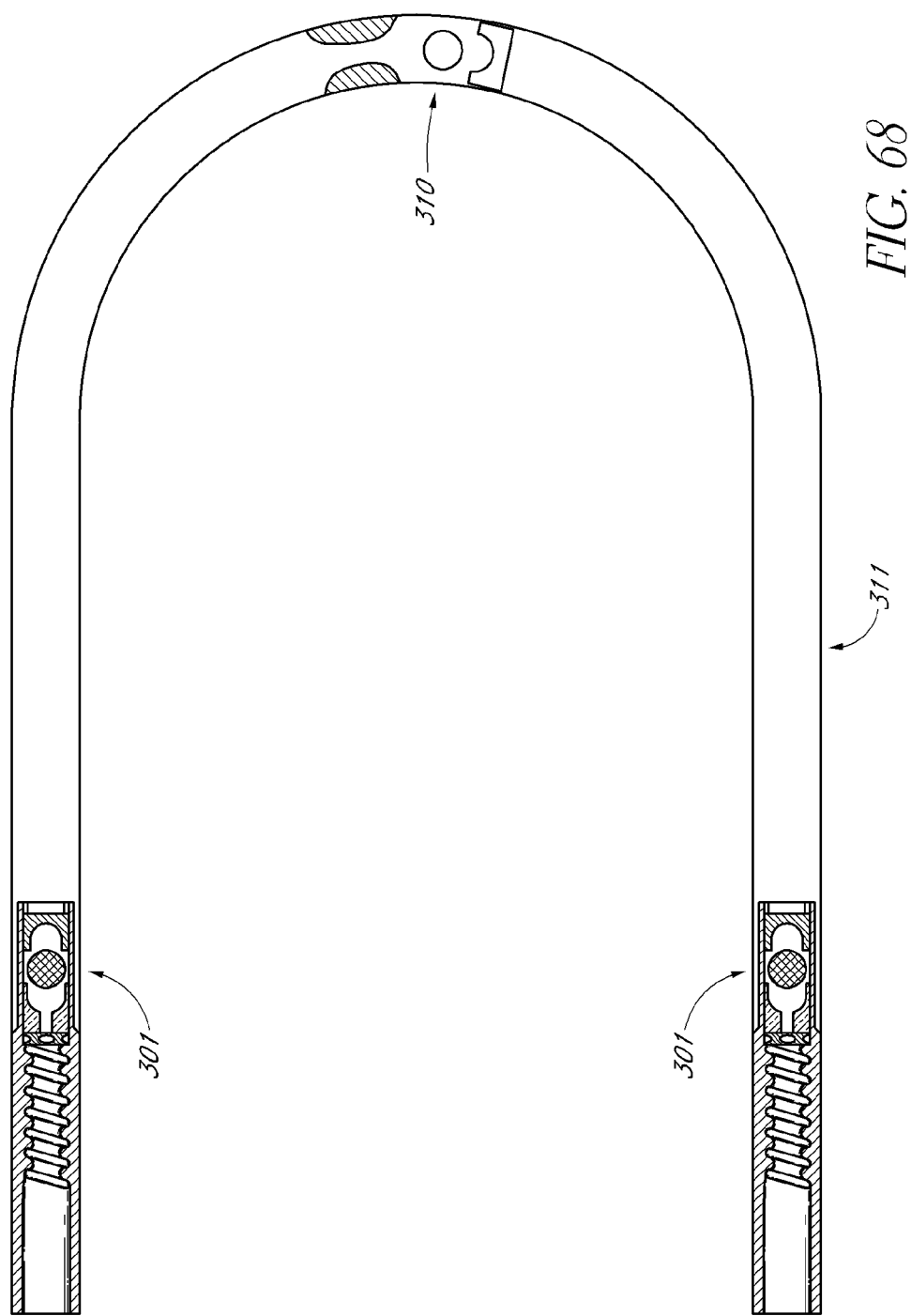

Alternatively, the apex 206 or downstream end 216 may be positioned downstream from the downstream support ring 108a, as illustrated in FIG. 63. The apex 206 may be positioned at least about 0.2 cm, and, in certain embodiments, between about 0.7 cm and about 1.0 cm downstream of the downstream support ring 108a.

In any of the foregoing embodiments, the tissue support 200 may be connected with respect to the downstream support ring 108a in any of a variety of ways, such as through the use of sutures, glue, welding, or other tethered structures. The connection between the tissue support 200 and the downstream support ring 108a may either be rigid, or permit a degree of radial flexibility as has been discussed.

In one implementation, the tissue support 200 is secured with respect to the downstream support ring 108a using a bioabsorbable suture or adhesive, which will maintain the structural orientation of the valve during implantation, inflation and curing of the inflation media. After a period of from about a few hours to 2 or 3 or more days, depending upon the inflation media and the suture materials, the connection between the tissue support 200 and the downstream support ring 108a would dissipate, allowing the tissue support 200 to move radially throughout its predetermined range of motion.

In any of the foregoing embodiments, the geometry of the tissue support 200 may take any of a variety of forms, depending upon the desired performance characteristics. For example, although illustrated in FIGS. 58 and 63 as a circular cross section inflatable tube, the tissue support 200 may also be inflatable to a noncircular, such as an oval or elliptical configuration. This allows optimization of the minimum luminal diameter through the valve support, while maintaining the structural integrity of the inflatable strut. The inflatable strut may also be a substantially constant cross section throughout its length, or may change in cross section, such as by decreasing from a relatively large upstream cross section to a relatively smaller downstream cross section. This may enable a distribution of bending forces, throughout the radial range of motion for the tissue support 200, as has been discussed. In the context of noninflatable tissue supports 200, circular, oval, elliptical, rectangular, or other cross sectional configurations may be used, depending upon the desired performance. Rectangular (e.g. ribbon) cross sectional struts may be desirable for minimizing the wall thickness and maximizing MLD within the valve structure. With noninflatable tissue supports 200, or tissue support components, any of a variety of progressively flexible designs may be utilized to distribute forces along the length of the tissue support 200. This may include, for example, decreasing the cross sectional area of the strut in a downstream direction, or increasing the density of perforation, score lines, or other surface modifications or aperture patterns to increase the flexibility in a downstream direction.

The cross sectional dimension of the 108a and 108b rings may measure about 2.0 mm to about 4.0 mm in diameter but may also measure 1.0 mm in diameter where the apex inflation channels may measure about 0.7 mm to about 3.0 mm in diameter but preferably about 2.0 mm in diameter. Within these inflation channels are also housed valving systems that allow for pressurization without leakage or passage of fluid in a single direction. The two valves at each end of the inflation channel are utilized to fill and exchange fluids such as saline, contrast and inflation media. The length of this inflation channel 311 may vary depending upon the size of the device and the complexity of the geometry but measures about 10 to 30 cm in length and has a diameter of about 2 to 4 mm with a wall thickness of about 0.0002 to 0.010 inches. The inflation channel material may be blown using heat and pressure from materials such as nylon, polyethylene, Pebax, polypropylene or other common materials that will maintain pressurization. The fluids that are introduced are used to create the support structure where without them the implant is an undefined fabric and tissue assembly. In one embodiment the inflation channels 311 are filled with saline and contrast for radiopaque visualization under fluoroscopy. This fluid is introduced from the proximal end of the catheter with the aid of an inflation device such as an endoflator or other means to pressurize fluid in a controlled manner. This fluid is transferred from the proximal end of the catheter through two inflation tubes 306 which are connected to the implant at the end of each inflation channel 311. With reference to FIGS. 64A-68, in the illustrated embodiment, the inflation channel 311 can have a valve 301 at each end whereby they can be separated from the inflation tube 306 thus disconnecting the catheter from the implant. This connection can be a screw or threaded connection, a collecting system, an interference fit or other means of reliable securement between the two components. Under pressurization the two components may be separated whereby the implant will remain pressurized. The pressure is maintained in the implant by the integral valve (i.e., end valve) at each end of the inflation channel 311. In the illustrated embodiment, this valve has a ball 303 and seat to allow for fluid to pass when connected and seal when disconnected. In between the ends of the inflation channel 311 is an additional directional valve 310 to allow fluid to pass in a single direction. This allows for the filling of each end of the inflation channel 311 and displacement of fluid in a single direction. Once inflated with saline and contrast this fluid can be displaced by a fill media that solidifies from the proximal end of the catheter where the saline and contrast is pushed out one end of the inflation channel 311 and replaced with the new inflation media fluid and the inflation tubes 306 are then disconnected from the implant. In some case the implant has one or more inflation tube 306 connections but it is preferred to have two inflation connections and a third or forth for additional steering control. These (non-fluid) connections 307 may use the same attachment means such as a screw or threaded element but may not have a fluid port since they are not used for communication with the device and its filling.

The end valve system 301 consists of a tubular section 312 with a soft seal 304 and spherical ball 303 to create a sealing mechanism 313. The tubular section 312 is about 0.5 to 2 cm in length and has an outer diameter of about 0.010 to 0.090 inches with a wall thickness of 0.005 to 0.040 inches. The material may include a host of polymers such as nylon, polyethylene, Pebax, polypropylene or other common materials such as stainless steel, Nitinol or other metallic materials used in medical devices. The soft seal material may be introduced as a liquid silicone or other material where a curing occurs thus allowing for a through hole to be constructed by coring or blanking a central lumen through the seal material. The soft seal 304 is adhered to the inner diameter of the wall of the tubular member 312 with a through hole for fluid flow. The spherical ball 303 is allowed to move within the inner diameter of the tubular member 312 where it seats at one end sealing pressure within the inflation channels and is moved the other direction with the introduction of the inflation tube 306 but not allowed to migrate too far as a stop ring or ball stopper 305 retains the spherical ball 303 from moving into the inflation channel 311. As the inflation tube 306 is screwed into the inflation channel check valve (i.e., end valve) 301 the spherical ball 303 is moved into an open position to allow for fluid communication between the inflation channel 311 and the inflation tube 306. When disconnected the ball 303 is allowed to move against the soft seal 304 and halt any fluid communication external to the inflation channel 311 leaving the implant pressurized. Additional embodiments may utilize a spring mechanism to return the ball to a sealed position and other shapes of sealing devices may be used rather than a spherical ball. A duck-bill style sealing mechanism or flap valve would additionally suffice to halt fluid leakage and provide a closed system to the implant.

The various methods and techniques described above provide a number of ways to carry out the invention. Of course, it is to be understood that not necessarily all objectives or advantages described may be achieved in accordance with any particular embodiment described herein. Thus, for example, those skilled in the art will recognize that the methods may be performed in a manner that achieves or optimizes one advantage or group of advantages as taught herein without necessarily achieving other objectives or advantages as may be taught or suggested herein.

Furthermore, the skilled artisan will recognize the interchangeability of various features from different embodiments disclosed herein. Similarly, the various features and steps discussed above, as well as other known equivalents for each such feature or step, can be mixed and matched by one of ordinary skill in this art to perform methods in accordance with principles described herein. Additionally, the methods which is described and illustrated herein is not limited to the exact sequence of acts described, nor is it necessarily limited to the practice of all of the acts set forth. Other sequences of events or acts, or less than all of the events, or simultaneous occurrence of the events, may be utilized in practicing the embodiments of the invention.

Although the invention has been disclosed in the context of certain embodiments and examples, it will be understood by those skilled in the art that the invention extends beyond the specifically disclosed embodiments to other alternative embodiments and/or uses and obvious modifications and equivalents thereof. Accordingly, the invention is not intended to be limited by the specific disclosures of preferred embodiments herein

We claim:

1. A method of implanting a prosthetic heart valve, the method comprising the steps of:
   translumenally advancing a catheter carrying a prosthetic valve that comprises an inflatable support structure to a position proximate a native valve of a patient, wherein the inflatable support structure comprises at least two valves positioned at ends of the inflatable support structure;
   inflating a first chamber of the inflatable support structure with a contrast media wherein a directional valve is located between the at least two valves positioned at ends of the inflatable support structure, and wherein the directional valve is configured to inflate the first chamber in a first axial direction and to inhibit flow in a second axial direction opposite to the first axial direction;
   visualizing the prosthetic valve under fluoroscopy;
   displacing the contrast media in the first chamber of the inflatable support structure with a new inflation media, and wherein the directional valve is configured to displace the contrast media in the first chamber with the new inflation media in the first axial direction and to inhibit flow in the second axial direction opposite to the first axial direction; and removing the catheter from the patient, leaving the prosthetic valve and the inflated first chamber of the inflatable support structure within the patient.

2. The method of claim 1, further comprising allowing the new inflation media to solidify within the first chamber of the inflatable support structure.

3. The method of claim 1, further comprising proximally retracting the valve after the first chamber is at least partially inflated.

4. The method of implanting a prosthetic valve as in claim 1, additionally comprising the step of removing the native valve prior to the removing the catheter step.

* * * * *